United States Patent
Gross et al.

(10) Patent No.: US 12,232,984 B2
(45) Date of Patent: Feb. 25, 2025

(54) INTELLIGENT JOINT PROSTHESIS

(71) Applicant: CANARY MEDICAL INC., Vancouver (CA)

(72) Inventors: Jeffrey M. Gross, Carlsbad, CA (US); Peter J. Schiller, San Marcos, CA (US); William L. Hunter, Vancouver (CA); Fred Cushner, New York, NY (US); Patrick M. Aubin, Seattle, WA (US)

(73) Assignee: Canary Medical Inc., Vancouver (CA)

( * ) Notice: Subject to any disclaimer, the term of this patent is extended or adjusted under 35 U.S.C. 154(b) by 774 days.

(21) Appl. No.: 17/399,499

(22) Filed: Aug. 11, 2021

(65) Prior Publication Data

US 2021/0369198 A1    Dec. 2, 2021

Related U.S. Application Data

(63) Continuation of application No. 17/424,058, filed as application No. PCT/US2020/036516 on Jun. 6, 2020.
(Continued)

(51) Int. Cl.
*A61F 2/46* (2006.01)
*A61B 5/00* (2006.01)
(Continued)

(52) U.S. Cl.
CPC ............ *A61F 2/468* (2013.01); *A61B 5/0004* (2013.01); *A61B 5/076* (2013.01); *A61B 5/4504* (2013.01);
(Continued)

(58) Field of Classification Search
CPC ...... A61F 2/468; A61F 2/30721; A61F 2/482; A61F 2/12; A61F 2/24; A61F 2/30942;
(Continued)

(56) References Cited

U.S. PATENT DOCUMENTS 4,161,782 A    7/1979  McCracken
4,894,728 A    1/1990  Goodman
(Continued)

FOREIGN PATENT DOCUMENTS

AT    513434 B1    2/2015
CA    1212501 A    10/1986
(Continued)

OTHER PUBLICATIONS

Bergmann, Georg; Bender, Alwina; Graichen, Friedmar; Dymke, Jorn; Rohlmann, Antonius; Trepczynski, Adam; Heller, Markus O; Kutzner, Ines. Standardized Loads Acting in Knee Implants. PLoS One 9.1: e86035. Public Library of Science. (Jan. 23, 2014)) (Year: 2014).*
(Continued)

*Primary Examiner* — Linh Giang Le

(57) ABSTRACT

Medical devices coupled to a sensor, and systems including such devices, can generate data and analysis based on that data, which may be used to identify and/or address problems associated with the implanted medical device, including incorrect placement of the device, unanticipated degradation of the device, and undesired movement of the device. Also provided are medical devices coupled to a sensor, and devices and methods to address problems that have been identified with an implanted medical device.

23 Claims, 61 Drawing Sheets

Related U.S. Application Data

(60) Provisional application No. 62/858,277, filed on Jun. 6, 2019.

(51) Int. Cl.

| | | |
|---|---|---|
| *A61B 5/07* | (2006.01) | |
| *A61F 2/30* | (2006.01) | |
| *A61F 2/48* | (2006.01) | |
| *G06Q 40/08* | (2012.01) | |
| *G16H 20/10* | (2018.01) | |
| *G16H 20/30* | (2018.01) | |
| *G16H 20/40* | (2018.01) | |
| *G16H 40/67* | (2018.01) | |
| *H04W 12/037* | (2021.01) | |
| *H04W 84/18* | (2009.01) | |
| *H04W 88/08* | (2009.01) | |
| *A61B 5/11* | (2006.01) | |
| *A61F 2/12* | (2006.01) | |
| *A61F 2/24* | (2006.01) | |
| *A61F 2/32* | (2006.01) | |
| *A61F 2/38* | (2006.01) | |
| *A61F 2/40* | (2006.01) | |
| *H04L 67/12* | (2022.01) | |

(52) U.S. Cl.
CPC ............ *A61B 5/4851* (2013.01); *A61B 5/686* (2013.01); *A61B 5/6878* (2013.01); *A61F 2/30721* (2013.01); *A61F 2/482* (2021.08); *G06Q 40/08* (2013.01); *G16H 20/10* (2018.01); *G16H 20/30* (2018.01); *G16H 20/40* (2018.01); *G16H 40/67* (2018.01); *H04W 12/037* (2021.01); *H04W 84/18* (2013.01); *H04W 88/08* (2013.01); *A61B 5/112* (2013.01); *A61B 2562/0219* (2013.01); *A61F 2/12* (2013.01); *A61F 2/24* (2013.01); *A61F 2002/30331* (2013.01); *A61F 2002/30507* (2013.01); *A61F 2002/3067* (2013.01); *A61F 2002/30884* (2013.01); *A61F 2/30942* (2013.01); *A61F 2002/30985* (2013.01); *A61F 2/32* (2013.01); *A61F 2/389* (2013.01); *A61F 2/40* (2013.01); *A61F 2250/0002* (2013.01); *A61F 2250/0096* (2013.01); *H04L 67/12* (2013.01)

(58) Field of Classification Search
CPC .... A61F 2/32; A61F 2/389; A61F 2/40; A61F 2002/30331; A61F 2002/30507; A61F 2002/3067; A61F 2002/30884; A61F 2002/30985; A61F 2250/0002; A61F 2250/0096; A61F 2002/30324; A61F 2002/30957; A61F 2002/30878; A61F 2/48; A61B 5/0004; A61B 5/076; A61B 5/4504; A61B 5/4851; A61B 5/686; A61B 5/6878; A61B 5/112; A61B 2562/0219; G06Q 40/08; G16H 20/10; G16H 20/30; G16H 20/40; G16H 40/67; H04W 12/037; H04W 84/18; H04W 88/08; H04L 67/12

See application file for complete search history.

(56) References Cited

U.S. PATENT DOCUMENTS

| | | |
|---|---|---|
| 5,019,794 A | 5/1991 | Letessier et al. |
| 5,042,504 A | 8/1991 | Huberti |
| 5,245,109 A | 9/1993 | Kaminsky et al. |
| 5,312,216 A | 5/1994 | Hogg |
| 5,358,202 A | 10/1994 | Tse et al. |
| 5,383,874 A | 1/1995 | Jackson |
| 5,413,604 A | 5/1995 | Hodge |
| 5,626,581 A | 5/1997 | Staehlin et al. |
| 5,672,954 A | 9/1997 | Watanabe |
| 5,716,981 A | 2/1998 | Hunter et al. |
| 5,833,603 A | 11/1998 | Kovacs et al. |
| H1765 H | 12/1998 | O'Phelan |
| 5,906,643 A | 5/1999 | Walker |
| 6,019,794 A | 2/2000 | Walker |
| 6,206,835 B1 | 3/2001 | Spillman, Jr. et al. |
| 6,245,109 B1 | 6/2001 | Mendes et al. |
| 6,358,202 B1 | 3/2002 | Arent |
| 6,374,097 B1 | 4/2002 | Kudou |
| 6,447,448 B1 | 9/2002 | Ishikawa et al. |
| 6,610,096 B2 | 8/2003 | Macdonald |
| 6,610,101 B2 | 8/2003 | Herr et al. |
| 6,620,168 B1 | 9/2003 | Lombardo et al. |
| 6,706,071 B1 | 3/2004 | Wolter |
| 6,712,778 B1 | 3/2004 | Jeffcoat et al. |
| 6,805,667 B2 | 10/2004 | Christopherson |
| 7,009,511 B2 | 3/2006 | Mazar et al. |
| 7,097,662 B2 | 8/2006 | Evans, III et al. |
| 7,127,300 B2 | 10/2006 | Mazar et al. |
| 7,130,695 B2 | 10/2006 | Czygan et al. |
| 7,141,026 B2 | 11/2006 | Aminian et al. |
| 7,190,273 B2 | 3/2007 | Liao et al. |
| 7,195,645 B2 | 3/2007 | DiSilvestro et al. |
| 7,328,131 B2 | 2/2008 | Donofrio et al. |
| 7,333,013 B2 | 2/2008 | Berger |
| 7,347,874 B2 | 3/2008 | DiSilvestro |
| 7,383,071 B1 | 6/2008 | Russell et al. |
| 7,450,332 B2 | 11/2008 | Pasolini et al. |
| 7,463,997 B2 | 12/2008 | Pasolini et al. |
| 7,553,923 B2 | 6/2009 | Williams et al. |
| 7,559,951 B2 | 7/2009 | DiSilvestro et al. |
| 7,603,894 B2 | 10/2009 | Breed |
| 7,613,497 B2 | 11/2009 | Govari et al. |
| 7,813,808 B1 | 10/2010 | Doron et al. |
| 7,819,808 B2 | 10/2010 | Oonuki |
| 7,874,673 B2 | 1/2011 | Cleveland |
| 7,889,070 B2 | 2/2011 | Reeves |
| 7,922,771 B2 | 4/2011 | Otto et al. |
| 7,924,267 B2 | 4/2011 | Sirtori |
| 8,029,566 B2 | 10/2011 | Lozier et al. |
| 8,080,064 B2 | 12/2011 | Dietz et al. |
| 8,109,890 B2 | 2/2012 | Kamiar et al. |
| 8,176,922 B2 | 5/2012 | Sherman et al. |
| 8,241,296 B2 | 8/2012 | Wasielewski |
| 8,244,368 B2 | 8/2012 | Sherman |
| 8,245,583 B2 | 8/2012 | Stein |
| 8,283,793 B2 | 10/2012 | Pless |
| 8,311,632 B2 | 11/2012 | Pless et al. |
| 8,317,869 B2 | 11/2012 | Cloutier et al. |
| 8,372,420 B2 | 2/2013 | Hunter et al. |
| 8,491,569 B1 | 7/2013 | Anderson |
| 8,551,023 B2 | 10/2013 | Sherman et al. |
| 8,556,888 B2 | 10/2013 | Nields et al. |
| 8,634,928 B1 | 1/2014 | O'Driscoll et al. |
| 8,721,643 B2 | 5/2014 | Morgan et al. |
| 8,761,859 B2 | 6/2014 | Roche |
| 8,876,739 B2 | 11/2014 | Salarian et al. |
| 8,996,892 B1 | 3/2015 | Chu et al. |
| 9,019,098 B2 | 4/2015 | Okano |
| 9,307,932 B2 | 4/2016 | Mariani et al. |
| 9,364,659 B1 | 6/2016 | Rao |
| 9,368,105 B1 | 6/2016 | Freed et al. |
| 9,390,724 B2 | 7/2016 | List |
| 9,393,433 B2 | 7/2016 | Parramon et al. |
| 9,424,840 B1 | 8/2016 | Hart et al. |
| 9,445,930 B2 | 9/2016 | Chen et al. |
| 9,451,919 B2 | 9/2016 | Roche |
| 9,456,915 B2 | 10/2016 | Chen et al. |
| 9,549,742 B2 | 1/2017 | Berend et al. |
| 9,603,649 B2 | 3/2017 | Matyas et al. |
| 9,629,583 B2 | 4/2017 | Gradel et al. |
| 9,820,858 B2 | 11/2017 | Harris et al. |
| 10,070,973 B2 | 9/2018 | Sherman et al. |
| 10,219,699 B2 | 3/2019 | Wilder et al. |

(56) References Cited

U.S. PATENT DOCUMENTS

| | | |
|---|---|---|
| 10,285,637 B1 | 5/2019 | Hnat et al. |
| 10,492,686 B2 | 12/2019 | Hunter et al. |
| 10,499,855 B2 | 12/2019 | Hunter |
| 10,582,896 B2 | 3/2020 | Revie |
| 10,596,009 B2 | 3/2020 | Mines et al. |
| 11,071,279 B2 | 7/2021 | Singh et al. |
| 11,191,479 B2 | 12/2021 | Bailey et al. |
| 2001/0032059 A1 | 10/2001 | Kelly et al. |
| 2001/0050087 A1 | 12/2001 | Weissman et al. |
| 2002/0024450 A1 | 2/2002 | Townsend et al. |
| 2002/0026224 A1 | 2/2002 | Thompson et al. |
| 2002/0107576 A1 | 8/2002 | Meyers et al. |
| 2002/0113685 A1 | 8/2002 | Izaki et al. |
| 2002/0147416 A1 | 10/2002 | Zogbi et al. |
| 2003/0004403 A1 | 1/2003 | Drinan et al. |
| 2003/0069644 A1 | 4/2003 | Kovacevic et al. |
| 2003/0204267 A1 | 10/2003 | Hazebrouck et al. |
| 2004/0011137 A1 | 1/2004 | Hnat et al. |
| 2004/0019382 A1 | 1/2004 | Amirouche et al. |
| 2004/0019384 A1 | 1/2004 | Kirking et al. |
| 2004/0083003 A1 | 4/2004 | Wasielewski |
| 2004/0113790 A1 | 6/2004 | Hamel |
| 2004/0138757 A1 | 7/2004 | Nadzadi et al. |
| 2004/0204635 A1 | 10/2004 | Scharf et al. |
| 2004/0204766 A1 | 10/2004 | Siebel |
| 2004/0211580 A1 | 10/2004 | Wang et al. |
| 2004/0243148 A1 | 12/2004 | Wasielewski |
| 2004/0243244 A1 | 12/2004 | Otto et al. |
| 2004/0249464 A1 | 12/2004 | Bindseil et al. |
| 2004/0249471 A1 | 12/2004 | Bindseil et al. |
| 2005/0010299 A1 | 1/2005 | Disilvestro |
| 2005/0010301 A1 | 1/2005 | Disilvestro et al. |
| 2005/0012610 A1 | 1/2005 | Liao et al. |
| 2005/0021126 A1 | 1/2005 | Machan et al. |
| 2005/0027192 A1 | 2/2005 | Govari et al. |
| 2005/0065408 A1 | 3/2005 | Benderev |
| 2005/0165317 A1 | 7/2005 | Turner et al. |
| 2005/0171594 A1 | 8/2005 | Machan et al. |
| 2005/0181005 A1 | 8/2005 | Hunter et al. |
| 2005/0181009 A1 | 8/2005 | Hunter et al. |
| 2005/0228410 A1 | 10/2005 | Berreklouw |
| 2005/0242666 A1 | 11/2005 | Huscher et al. |
| 2005/0245992 A1 | 11/2005 | Persen et al. |
| 2005/0288563 A1 | 12/2005 | Feliss et al. |
| 2006/0009856 A1 | 1/2006 | Sherman et al. |
| 2006/0030771 A1 | 2/2006 | Levine et al. |
| 2006/0030945 A1 | 2/2006 | Wright |
| 2006/0036246 A1 | 2/2006 | Carl et al. |
| 2006/0047283 A1 | 3/2006 | Evans, III et al. |
| 2006/0069403 A1 | 3/2006 | Shalon et al. |
| 2006/0111777 A1 | 5/2006 | Chen |
| 2006/0116744 A1 | 6/2006 | Von Arx et al. |
| 2006/0142670 A1 | 6/2006 | Disilvestro et al. |
| 2006/0152377 A1 | 7/2006 | Beebe et al. |
| 2006/0165317 A1 | 7/2006 | Gzybowski |
| 2006/0184067 A1 | 8/2006 | Clark et al. |
| 2006/0224088 A1 | 10/2006 | Roche |
| 2006/0229711 A1 | 10/2006 | Yan et al. |
| 2006/0229730 A1 | 10/2006 | Railey et al. |
| 2006/0271112 A1 | 11/2006 | Martinson et al. |
| 2006/0271199 A1 | 11/2006 | Johnson |
| 2006/0282168 A1 | 12/2006 | Sherman et al. |
| 2007/0004994 A1 | 1/2007 | Sherman |
| 2007/0005141 A1 | 1/2007 | Sherman |
| 2007/0032749 A1* | 2/2007 | Overall ............... A61B 5/02444 600/595 |
| 2007/0034013 A1 | 2/2007 | Moon et al. |
| 2007/0060955 A1 | 3/2007 | Strother et al. |
| 2007/0067018 A1 | 3/2007 | Miller |
| 2007/0088442 A1 | 4/2007 | Cima et al. |
| 2007/0089518 A1 | 4/2007 | Ericson et al. |
| 2007/0126696 A1 | 6/2007 | Boillot |
| 2007/0151884 A1 | 7/2007 | Thoes et al. |
| 2007/0161884 A1 | 7/2007 | Black |
| 2007/0167809 A1 | 7/2007 | Dala-Krishna |
| 2007/0179628 A1 | 8/2007 | Rochetin |
| 2007/0179739 A1 | 8/2007 | Donofrio et al. |
| 2007/0211022 A1 | 9/2007 | Boillot |
| 2007/0211023 A1 | 9/2007 | Boillot |
| 2007/0233065 A1 | 10/2007 | Donofrio et al. |
| 2007/0233267 A1 | 10/2007 | Amirouche et al. |
| 2007/0234819 A1 | 10/2007 | Amirouche |
| 2007/0238984 A1 | 10/2007 | Maschke et al. |
| 2007/0238992 A1 | 10/2007 | Donofrio et al. |
| 2007/0239282 A1 | 10/2007 | Caylor et al. |
| 2007/0265662 A1 | 11/2007 | Ufford |
| 2007/0288194 A1 | 12/2007 | Boillot |
| 2008/0020012 A1 | 1/2008 | Ju et al. |
| 2008/0027679 A1 | 1/2008 | Shklarski |
| 2008/0033527 A1 | 2/2008 | Nunez et al. |
| 2008/0048878 A1 | 2/2008 | Boillot |
| 2008/0065225 A1 | 3/2008 | Wasielewski |
| 2008/0076972 A1 | 3/2008 | Dorogusker et al. |
| 2008/0088436 A1 | 4/2008 | Reeves et al. |
| 2008/0114270 A1 | 5/2008 | DiSilvestro et al. |
| 2008/0139954 A1 | 6/2008 | Day et al. |
| 2008/0214903 A1 | 9/2008 | Orbach |
| 2008/0215609 A1 | 9/2008 | Cleveland et al. |
| 2008/0235621 A1 | 9/2008 | Boillot |
| 2008/0275350 A1 | 11/2008 | Liao et al. |
| 2008/0300597 A1 | 12/2008 | Morgan et al. |
| 2008/0300659 A1 | 12/2008 | Matos |
| 2008/0306325 A1 | 12/2008 | Burnett et al. |
| 2008/0309481 A1 | 12/2008 | Tanaka et al. |
| 2009/0005708 A1 | 1/2009 | Johanson et al. |
| 2009/0005876 A1 | 1/2009 | Dietz et al. |
| 2009/0012372 A1 | 1/2009 | Burnett et al. |
| 2009/0048524 A1 | 2/2009 | Wildau et al. |
| 2009/0076358 A1 | 3/2009 | Reggiardo et al. |
| 2009/0088756 A1 | 4/2009 | Anderson |
| 2009/0099570 A1 | 4/2009 | Paradis et al. |
| 2009/0119222 A1 | 5/2009 | O'Neil et al. |
| 2009/0149964 A1 | 6/2009 | May et al. |
| 2009/0157146 A1 | 6/2009 | Linder et al. |
| 2009/0192533 A1 | 7/2009 | Dlugos, Jr. et al. |
| 2009/0253587 A1 | 10/2009 | Fernandez |
| 2009/0264894 A1 | 10/2009 | Wasielewski |
| 2009/0299228 A1 | 12/2009 | Lozier et al. |
| 2010/0014626 A1 | 1/2010 | Fennell et al. |
| 2010/0057046 A1 | 3/2010 | Stevens et al. |
| 2010/0100011 A1 | 4/2010 | Roche |
| 2010/0145337 A1 | 6/2010 | Janna et al. |
| 2010/0152621 A1 | 6/2010 | Janna et al. |
| 2010/0164705 A1 | 7/2010 | Blanchard |
| 2010/0191100 A1 | 7/2010 | Anderson et al. |
| 2010/0204551 A1 | 8/2010 | Roche |
| 2010/0204802 A1 | 8/2010 | Wilson et al. |
| 2010/0204955 A1 | 8/2010 | Roche et al. |
| 2010/0249533 A1 | 9/2010 | Pierce et al. |
| 2010/0249787 A1 | 9/2010 | Roche |
| 2010/0249790 A1 | 9/2010 | Roche |
| 2010/0250284 A1 | 9/2010 | Roche et al. |
| 2010/0262160 A1 | 10/2010 | Boyden et al. |
| 2010/0285082 A1 | 11/2010 | Fernandez |
| 2010/0287422 A1 | 11/2010 | Miyazaki |
| 2010/0312188 A1 | 12/2010 | Robertson et al. |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |

(56) References Cited

U.S. PATENT DOCUMENTS

| | | |
|---|---|---|
| 2010/0331734 A1 | 12/2010 | Stein |
| 2010/0331738 A1 | 12/2010 | Stein et al. |
| 2010/0331894 A1 | 12/2010 | Stein |
| 2010/0331932 A1 | 12/2010 | Stevenson et al. |
| 2010/0332152 A1 | 12/2010 | Stein |
| 2011/0004076 A1 | 1/2011 | Janna et al. |
| 2011/0015693 A1 | 1/2011 | Williamson |
| 2011/0019595 A1 | 1/2011 | Magar et al. |
| 2011/0054272 A1 | 3/2011 | Derchak |
| 2011/0060220 A1 | 3/2011 | Roche et al. |
| 2011/0063094 A1 | 3/2011 | Meiertoberens et al. |
| 2011/0077736 A1 | 3/2011 | Rofougaran |
| 2011/0077865 A1 | 3/2011 | Chen et al. |
| 2011/0087306 A1 | 4/2011 | Goossen |
| 2011/0092860 A1 | 4/2011 | Salarian et al. |
| 2011/0092948 A1 | 4/2011 | Shachar et al. |
| 2011/0098576 A1 | 4/2011 | Hollstien |
| 2011/0158206 A1 | 6/2011 | Shrestha et al. |
| 2011/0160572 A1 | 6/2011 | Mcintosh et al. |
| 2011/0160583 A1 | 6/2011 | Roche et al. |
| 2011/0160616 A1 | 6/2011 | Stein et al. |
| 2011/0184740 A1 | 7/2011 | Gruenstein et al. |
| 2011/0196501 A1 | 8/2011 | Michelson |
| 2011/0200052 A1 | 8/2011 | Mungo et al. |
| 2011/0213221 A1 | 9/2011 | Roche |
| 2011/0213413 A1 | 9/2011 | Brown et al. |
| 2011/0224564 A1 | 9/2011 | Moon et al. |
| 2011/0288436 A1 | 11/2011 | Stone |
| 2011/0288805 A1 | 11/2011 | Dejnabadi et al. |
| 2011/0319755 A1 | 12/2011 | Stein et al. |
| 2012/0029316 A1 | 2/2012 | Raptis et al. |
| 2012/0035868 A1 | 2/2012 | Roche et al. |
| 2012/0095526 A1 | 4/2012 | Roche |
| 2012/0116310 A1 | 5/2012 | Forsell |
| 2012/0123498 A1 | 5/2012 | Gross |
| 2012/0123716 A1 | 5/2012 | Clark |
| 2012/0130687 A1 | 5/2012 | Otto et al. |
| 2012/0152017 A1 | 6/2012 | Stein et al. |
| 2012/0157839 A1 | 6/2012 | Stein |
| 2012/0157884 A1 | 6/2012 | Stein et al. |
| 2012/0166680 A1 | 6/2012 | Masoud et al. |
| 2012/0190940 A1 | 7/2012 | Stein et al. |
| 2012/0191206 A1 | 7/2012 | Stein et al. |
| 2012/0216611 A1 | 8/2012 | Stein et al. |
| 2012/0220839 A1 | 8/2012 | Stein et al. |
| 2012/0226360 A1 | 9/2012 | Stein et al. |
| 2012/0226364 A1 | 9/2012 | Kampas et al. |
| 2012/0232834 A1 | 9/2012 | Roche et al. |
| 2012/0283600 A1 | 11/2012 | Stein |
| 2012/0313760 A1 | 12/2012 | Okano |
| 2012/0323333 A1 | 12/2012 | Metzger |
| 2012/0330367 A1 | 12/2012 | Roche et al. |
| 2013/0011008 A1 | 1/2013 | Ikezoye et al. |
| 2013/0023794 A1 | 1/2013 | Stein et al. |
| 2013/0023795 A1 | 1/2013 | Stein et al. |
| 2013/0027186 A1 | 1/2013 | Cinbis et al. |
| 2013/0079668 A1 | 3/2013 | Stein et al. |
| 2013/0079669 A1 | 3/2013 | Stein et al. |
| 2013/0079670 A1 | 3/2013 | Stein et al. |
| 2013/0079671 A1 | 3/2013 | Stein et al. |
| 2013/0079672 A1 | 3/2013 | Stein et al. |
| 2013/0079674 A1 | 3/2013 | Stein et al. |
| 2013/0079675 A1 | 3/2013 | Stein et al. |
| 2013/0079679 A1 | 3/2013 | Roche et al. |
| 2013/0079790 A1 | 3/2013 | Stein et al. |
| 2013/0079884 A1 | 3/2013 | Stein et al. |
| 2013/0109998 A1 | 5/2013 | Swoboda et al. |
| 2013/0110008 A1 | 5/2013 | Bourget et al. |
| 2013/0123684 A1 | 5/2013 | Giuffrida et al. |
| 2013/0144379 A1 | 6/2013 | Najafi et al. |
| 2013/0179110 A1 | 7/2013 | Lee |
| 2013/0197656 A1 | 8/2013 | Conrad |
| 2013/0215979 A1 | 8/2013 | Yakovlev et al. |
| 2013/0225949 A1 | 8/2013 | Roche |
| 2013/0225982 A1 | 8/2013 | Mcintosh et al. |
| 2013/0226034 A1 | 8/2013 | Stein et al. |
| 2013/0226035 A1 | 8/2013 | Stein et al. |
| 2013/0252610 A1 | 9/2013 | Kim |
| 2013/0261450 A1 | 10/2013 | Stein et al. |
| 2013/0268081 A1 | 10/2013 | Stein et al. |
| 2013/0281839 A1 | 10/2013 | Yan et al. |
| 2013/0317367 A1 | 11/2013 | Shuler |
| 2013/0325019 A1 | 12/2013 | Thomas et al. |
| 2013/0338455 A1 | 12/2013 | Gradel et al. |
| 2013/0338770 A1 | 12/2013 | Boyden et al. |
| 2014/0009262 A1 | 1/2014 | Robertson et al. |
| 2014/0025338 A1 | 1/2014 | Blount et al. |
| 2014/0031063 A1 | 1/2014 | Park et al. |
| 2014/0058289 A1 | 2/2014 | Panken et al. |
| 2014/0085102 A1 | 3/2014 | Mccormick |
| 2014/0094715 A1 | 4/2014 | Stein et al. |
| 2014/0107796 A1 | 4/2014 | Stein et al. |
| 2014/0135589 A1 | 5/2014 | Osorio |
| 2014/0135616 A1 | 5/2014 | Stein et al. |
| 2014/0135624 A1 | 5/2014 | Stein et al. |
| 2014/0135655 A1 | 5/2014 | Stein et al. |
| 2014/0135773 A1 | 5/2014 | Stein et al. |
| 2014/0136143 A1 | 5/2014 | Stein et al. |
| 2014/0148676 A1 | 5/2014 | Stein et al. |
| 2014/0163645 A1 | 6/2014 | Dinsmoor et al. |
| 2014/0171754 A1 | 6/2014 | Stein et al. |
| 2014/0180697 A1 | 6/2014 | Torok et al. |
| 2014/0188007 A1 | 7/2014 | Stein et al. |
| 2014/0194707 A1 | 7/2014 | Stein et al. |
| 2014/0200584 A1 | 7/2014 | Stein et al. |
| 2014/0213867 A1 | 7/2014 | Pletcher et al. |
| 2014/0256324 A1 | 9/2014 | Mohanty |
| 2014/0257047 A1 | 9/2014 | Sillay et al. |
| 2014/0275815 A1 | 9/2014 | Stein et al. |
| 2014/0275849 A1 | 9/2014 | Acquista |
| 2014/0275861 A1 | 9/2014 | Kroh et al. |
| 2014/0276240 A1 | 9/2014 | Stein et al. |
| 2014/0276241 A1 | 9/2014 | Stein et al. |
| 2014/0276885 A1 | 9/2014 | Stein et al. |
| 2014/0276887 A1 | 9/2014 | Stein et al. |
| 2014/0277542 A1 | 9/2014 | Stein et al. |
| 2014/0288464 A1 | 9/2014 | Stein |
| 2014/0296663 A1 | 10/2014 | Boyden et al. |
| 2014/0303739 A1 | 10/2014 | Mentink et al. |
| 2014/0322935 A1 | 10/2014 | Filman et al. |
| 2014/0328253 A1 | 11/2014 | Lee |
| 2014/0330105 A1 | 11/2014 | Roche |
| 2014/0378872 A1 | 12/2014 | Hong et al. |
| 2015/0032215 A1 | 1/2015 | Slamin et al. |
| 2015/0032217 A1 | 1/2015 | Bojarski |
| 2015/0039093 A1 | 2/2015 | Mctighe et al. |
| 2015/0057775 A1 | 2/2015 | Dong |
| 2015/0080901 A1 | 3/2015 | Stein |
| 2015/0088253 A1 | 3/2015 | Doll et al. |
| 2015/0124675 A1 | 5/2015 | Farmer et al. |
| 2015/0164401 A1 | 6/2015 | Toth et al. |
| 2015/0202494 A1 | 7/2015 | Hollenbach et al. |
| 2015/0238304 A1 | 8/2015 | Lamraoui |
| 2015/0238691 A1 | 8/2015 | Boyden et al. |
| 2015/0335290 A1 | 11/2015 | Hunter |
| 2016/0025978 A1 | 1/2016 | Mallinson |
| 2016/0029952 A1* | 2/2016 | Hunter .................. A61F 2/4657 600/595 |
| 2016/0029998 A1 | 2/2016 | Brister et al. |
| 2016/0038087 A1 | 2/2016 | Hunter |
| 2016/0051823 A1 | 2/2016 | Maile et al. |
| 2016/0081762 A1 | 3/2016 | Stein et al. |
| 2016/0101281 A1 | 4/2016 | Chen |
| 2016/0106533 A1 | 4/2016 | Galstian et al. |
| 2016/0128573 A1 | 5/2016 | Wilder et al. |
| 2016/0166201 A1 | 6/2016 | Stein et al. |
| 2016/0192878 A1 | 7/2016 | Hunter |
| 2016/0199658 A1 | 7/2016 | Nassif et al. |
| 2016/0232322 A1 | 8/2016 | Mensinger et al. |
| 2016/0258779 A1 | 9/2016 | Hol et al. |
| 2016/0302721 A1 | 10/2016 | Wiedenhoefer et al. |
| 2016/0310077 A1 | 10/2016 | Hunter et al. |
| 2016/0338644 A1 | 11/2016 | Connor |
| 2016/0340177 A1 | 11/2016 | Takada |

(56) References Cited

U.S. PATENT DOCUMENTS

| | | |
|---|---|---|
| 2016/0374566 A1 | 12/2016 | Fung et al. |
| 2017/0035593 A1 | 2/2017 | Chen et al. |
| 2017/0049963 A1 | 2/2017 | Varsavsky et al. |
| 2017/0119316 A1 | 5/2017 | Herrmann et al. |
| 2017/0119472 A1 | 5/2017 | Herrmann et al. |
| 2017/0119566 A1 | 5/2017 | Chen et al. |
| 2017/0138986 A1 | 5/2017 | Kern |
| 2017/0156288 A1 | 6/2017 | Singh |
| 2017/0156632 A1 | 6/2017 | Swiston et al. |
| 2017/0181825 A1 | 6/2017 | Hunter |
| 2017/0189553 A1 | 7/2017 | Hunter |
| 2017/0189752 A1 | 7/2017 | Mohrman et al. |
| 2017/0196478 A1 | 7/2017 | Hunter |
| 2017/0196499 A1 | 7/2017 | Hunter |
| 2017/0196507 A1 | 7/2017 | Singh et al. |
| 2017/0196508 A1 | 7/2017 | Hunter |
| 2017/0196509 A1 | 7/2017 | Hunter |
| 2017/0252187 A1 | 9/2017 | Chapman et al. |
| 2017/0294949 A1 | 10/2017 | Zhang et al. |
| 2017/0328931 A1 | 11/2017 | Zhang et al. |
| 2017/0333080 A1 | 11/2017 | Roschak et al. |
| 2018/0000380 A1 | 1/2018 | Stein et al. |
| 2018/0028824 A1 | 2/2018 | Pivonka et al. |
| 2018/0055443 A1 | 3/2018 | Stein et al. |
| 2018/0064335 A1 | 3/2018 | Rutschman et al. |
| 2018/0125365 A1 | 5/2018 | Hunter et al. |
| 2018/0177607 A1 | 6/2018 | Trabish et al. |
| 2018/0177611 A1 | 6/2018 | Trabish et al. |
| 2018/0177612 A1 | 6/2018 | Trabish et al. |
| 2018/0228428 A1 | 8/2018 | Anker et al. |
| 2018/0235546 A1 | 8/2018 | Hunter |
| 2019/0038361 A1 | 2/2019 | Wasielewski |
| 2019/0038425 A1 | 3/2019 | Otto et al. |
| 2019/0076033 A1 | 3/2019 | Sweeney et al. |
| 2019/0076273 A1 | 3/2019 | Goodchild et al. |
| 2019/0192072 A1 | 6/2019 | Bailey et al. |
| 2019/0231555 A1 | 8/2019 | Neubardt |
| 2019/0247197 A1 | 8/2019 | Jagannathan et al. |
| 2019/0290451 A1 | 9/2019 | Trabish et al. |
| 2019/0350518 A1 | 11/2019 | Bailey et al. |
| 2019/0350519 A1 | 11/2019 | Bailey et al. |
| 2019/0350520 A1 | 11/2019 | Bailey et al. |
| 2019/0350521 A1 | 11/2019 | Bailey et al. |
| 2019/0350522 A1 | 11/2019 | Bailey et al. |
| 2019/0350523 A1 | 11/2019 | Bailey et al. |
| 2020/0054215 A1 | 2/2020 | Roche |
| 2020/0093430 A1 | 3/2020 | Bailey et al. |
| 2020/0093431 A1 | 3/2020 | Bailey et al. |
| 2020/0155327 A1 | 5/2020 | Suh et al. |
| 2021/0077241 A1 | 3/2021 | Hunter |

FOREIGN PATENT DOCUMENTS

| | | |
|---|---|---|
| CA | 2620247 A1 | 3/2007 |
| CA | 3017932 A1 | 9/2017 |
| CN | 2580920 Y | 10/2003 |
| CN | 1806776 A | 7/2006 |
| CN | 1899222 A | 1/2007 |
| CN | 101060815 A | 10/2007 |
| CN | 101254103 A | 9/2008 |
| CN | 101257860 A | 9/2008 |
| CN | 101273925 A | 10/2008 |
| CN | 101287408 A | 10/2008 |
| CN | 101296673 A | 10/2008 |
| CN | 101426453 A | 5/2009 |
| CN | 101484085 A | 7/2009 |
| CN | 101495025 A | 7/2009 |
| CN | 101536938 A | 9/2009 |
| CN | 101573085 A | 11/2009 |
| CN | 101773387 A | 7/2010 |
| CN | 101849865 A | 10/2010 |
| CN | 202036215 U | 11/2011 |
| CN | 101773387 B | 12/2011 |
| CN | 102688097 A | 9/2012 |
| CN | 102740803 A | 10/2012 |
| CN | 102885626 A | 1/2013 |
| CN | 102905649 A | 1/2013 |
| CN | 103313661 A | 9/2013 |
| CN | 103458830 A | 12/2013 |
| CN | 103735303 A | 4/2014 |
| CN | 103957992 A | 7/2014 |
| CN | 105283150 A | 1/2016 |
| CN | 109310324 A | 2/2019 |
| DE | 4322619 C1 | 9/1994 |
| DE | 19924676 A1 | 11/2000 |
| DE | 10342823 A1 | 4/2005 |
| EP | 1528902 B1 | 11/2006 |
| EP | 2018825 A1 | 1/2009 |
| EP | 1814471 B1 | 3/2010 |
| EP | 2967879 B1 | 1/2022 |
| JP | 2001046411 A | 2/2001 |
| JP | 2003527926 A | 9/2003 |
| JP | 2005520630 A | 7/2005 |
| JP | 2005288172 A | 10/2005 |
| JP | 2006055629 A | 3/2006 |
| JP | 2006102498 A | 4/2006 |
| JP | 2007083019 A | 4/2007 |
| JP | 2007535372 A | 12/2007 |
| JP | 2008501488 A | 1/2008 |
| JP | 2008510584 A | 4/2008 |
| JP | 2011514812 A | 5/2011 |
| JP | 2013039444 A | 2/2013 |
| JP | 2016525389 A | 8/2016 |
| JP | 2017023436 A | 2/2017 |
| JP | 2017510307 A | 4/2017 |
| JP | 2022128381 A | 9/2022 |
| KR | 101274641 B1 | 6/2013 |
| KR | 20140133419 A | 11/2014 |
| WO | 9733513 A1 | 9/1997 |
| WO | 02064019 A2 | 8/2002 |
| WO | 2004016204 A1 | 2/2004 |
| WO | 2004091419 A2 | 10/2004 |
| WO | 2005120203 A2 | 12/2005 |
| WO | 2006089069 | 8/2006 |
| WO | 2006105098 A2 | 10/2006 |
| WO | 2006108065 A2 | 10/2006 |
| WO | 2006113394 A2 | 10/2006 |
| WO | 2008032316 A2 | 3/2008 |
| WO | 2008035089 A1 | 3/2008 |
| WO | 2008103181 A1 | 8/2008 |
| WO | 2008152549 A2 | 12/2008 |
| WO | 2009145633 A1 | 12/2009 |
| WO | 2009148847 A2 | 12/2009 |
| WO | 2010111678 A2 | 9/2010 |
| WO | 2012006066 A1 | 1/2012 |
| WO | 2012061825 A2 | 5/2012 |
| WO | 2012095784 A1 | 7/2012 |
| WO | 2012103549 A1 | 8/2012 |
| WO | 2013022890 A1 | 2/2013 |
| WO | 2013044117 A1 | 3/2013 |
| WO | 2013044127 A1 | 3/2013 |
| WO | 2013044157 A1 | 3/2013 |
| WO | 2013044160 A2 | 3/2013 |
| WO | 2013044165 A2 | 3/2013 |
| WO | 2013044174 A2 | 3/2013 |
| WO | 2013044165 A3 | 5/2013 |
| WO | 2014053956 A1 | 4/2014 |
| WO | 2014100795 A1 | 6/2014 |
| WO | 2014144070 A1 | 9/2014 |
| WO | 2014144107 A1 | 9/2014 |
| WO | 2014144707 A1 | 9/2014 |
| WO | 2014209916 A1 | 12/2014 |
| WO | 2015021807 A1 | 2/2015 |
| WO | 2015038979 A1 | 3/2015 |
| WO | 2015092747 A2 | 6/2015 |
| WO | 2015188867 A1 | 12/2015 |
| WO | 2015200704 A1 | 12/2015 |
| WO | 2015200707 A1 | 12/2015 |
| WO | 2015200718 A1 | 12/2015 |
| WO | 2015200720 A2 | 12/2015 |
| WO | 2015200722 A2 | 12/2015 |
| WO | 2015200723 A1 | 12/2015 |
| WO | 2016044651 A1 | 3/2016 |
| WO | 2016065205 A1 | 4/2016 |

(56) References Cited

FOREIGN PATENT DOCUMENTS

| WO | 2016174612 | A1 | | 11/2016 | | |
|---|---|---|---|---|---|---|
| WO | 2016180653 | A1 | | 11/2016 | | |
| WO | 2016180654 | A1 | | 11/2016 | | |
| WO | 2017152153 | A1 | | 9/2017 | | |
| WO | 2017165717 | | | 9/2017 | | |
| WO | WO-2017165717 | A1 | * | 9/2017 | ........... | A61B 5/0002 |
| WO | 2018119360 | A1 | | 6/2018 | | |

OTHER PUBLICATIONS

U.S. Appl. No. 17/424,058, pending (Not yet published).
U.S. Appl. No. 17/394,751, pending (Patent Application Pub. No. 2021/0366610, cited herein).
U.S. Appl. No. 17/401,098, pending (Patent Application Pub. No. 2021/0369471, cited herein).
U.S. Appl. No. 17/401,110, pending (Patent Application Pub. No. 2021/0369199, cited herein).
U.S. Appl. No. 17/469,596, pending (Not yet published).
USAN U.S. Appl. No. 17/477,345, pending (Not yet published).
U.S. Appl. No. 17/483,309, pending (Not yet published).
U.S. Appl. No. 17/490,400, pending (Not yet published).
Angers-Goulet, Mathieu et al., "Up to seven years' follow-up of short cemented stems in complex primary total knee arthroplasty: A prospective study", The Knee24 (2017), pp. 1166-1174.
Cushner, Fred MD et al., "Feasibility and Compliance of Monitoring Post-Operative Activity Levels in TKA Patients using Wireless Technology", Lenox Hill Hospital ppt presentation.
D'Apuzzo, Michele R. et al., "Morbid Obesity Independently Impacts Complications, Mortality, and Resource Use After TKA", Clin Orthop Relat Res (2014) 473, pp. 57-63.
Malin, Andrew S. MD et al., "Routine Surveillance of Modular PFC TKA Shows Increasing Failures after 10 Years", Clin Orthop Relat Res (2010), 468, pp. 2469-2476.
Parratte, Sebastien MD et al., Do Stemmed Tibial Components in Total Knee Arthroplasty Improve Outcomes in Patients with Obesity?, Clin Orthop Relat Res, Jan. 2017, vol. 475, No. 1, pp. 137-145.
Patil, Shantanu et al., "How Do Knee Implants Perform Past the Second Decade? Nineteen- to 25-year Followup of the Press-fit Condylar Design TKA", Clin Orthop Relat Res (2015) 473 pp. 135-140.
Ries, Christian MD et al., "Shortkeeled Cemented Tibial Components Show an Increased Risk for Aseptic Loosening", Clin Orthop Relat Res (2013) 471 pp. 1008-1013.
Ries, Michael D., "Endosteal Referencing in Revision Total Knee Arthroplasty," The Journal of Arthroplasty, vol. 13, No. 1, pp. 85-91. (1998).
Yoon, Chan MD et al., "Medial Tibial Periprosthetic Bone Resorption and Its Effect on Clinical Outcomes after Total Knee Arthroplasty: Cobalt-Chromium versus Titanium Implants", The Journal of Arthroplasty, Accepted Manuscript Apr. 16, 2018, pp. 1-43.
Zimmer® NexGen® RH Knee Brochure 8 pp.
Zimmer® Persona® The Personalized Knee Systems Brochure 12 pp.
PCT International Search Report and Written Opinion dated Oct. 30, 2020, for PCT/US2020/036516.
Old, AB et al., "Revision of Total Knee Arthroplasties Performed in Young, Active Patients with Posttraumatic Arthritis and Osteoarthritis", J Knee Surg, Nov. 2017, vol. 30, No. 9, pp. 905-908.
Park, Min-Ho, MD et al., "Using a Tibial Short Extension Stem Reduces Tibial Component Loosening After Primary Total Knee Arthroplasty in Severely Varus Knees: Long-term Survival Analysis with Propensity Score Matching," The Journal of Arthroplasty, vol. 33, 2018, pp. 2512-2517.
Simoncini, Matteo; "Design and integration of an instrumented knee prosthesis", Thesis No. 6379 (2014), École Polytechnique Fédérale de Lausanne.
Ai-Fakih E., et al., "The Use of Fiber Bragg Grating Sensors in Biomechanics and Rehabilitation Applications: The State-of-the-Art and Ongoing Research Topics," Sensors, Sep. 25, 2012, vol. 12, No. 10, pp. 12890-12926.
Almouahed S., et al., "New Trends in Instrumented Knee Prostheses," International Conference on Information and Communication Technologies: From Theory to Applications, Apr. 7-11, 2008, 6 Pages.
Arami A., et al., "Accurate Measurement of Concurrent Flexion-Extension and Internal-External Rotations in Smart Knee Prostheses," IEEE Transactions on BioMedical Engineering, Sep. 2013, vol. 60, No. 9, pp. 2504-2510.
Arami A., et al., "Instrumented Prosthesis for Knee Implant Monitoring," IEEE International Conference on Automation Science and Engineering, Trieste, Italy, Aug. 24-27, 2011, pp. 828-835.
Bosch Press Release: "Bosch Sensortec Launches First IMU with Sub 1mA Current Consumption", Jun. 25, 2014, 3 Pages.
Bosch Sensortec: Bosch for BMI160 Small, Low—Power Inertial Measurement Unit, Jan. 15, 2015, 2 Pages.
Bosch Sensortec: "Data Sheet for BMI160 Small, Low Power Inertial Measurement Unit," Document Revision 0.8, Release Date Feb. 10, 2015, No. BST-BMI160-DS000-07, 110 Pages.
Chandrakasan A.P., et al., "Next Generation Micro-Power Systems," Symposium on VLSI Circuits Digest of Technical Papers, 2008, pp. 1-5, 04 pages.
European Search Report in European Patent Application No. 23177756. 6, dated Nov. 8, 2023, 8 Pages.
Extended European Search Report for European Application No. 14762269.0, mailed Oct. 24, 2016, 08 Pages.
Extended European Search Report for European Application No. 14762650.1, mailed Jul. 21, 2017, 10 Pages.
Extended European Search Report for European Application No. 14817352.9, mailed Jun. 13, 2017, 15 Pages.
Extended European Search Report for European Application No. 15812631.8, mailed Nov. 12, 2018, 17 Pages.
Extended European Search Report for European Application No. 15842678.3, mailed Feb. 5, 2019, 13 Pages.
Extended European Search Report for European Application No. 17771204.9, mailed Feb. 28, 2020, 09 Pages.
Extended European Search Report for European Application No. 20214094.3, mailed May 28, 2021, 07 Pages.
Extended European Search Report for European Application No. 22153300.3, mailed Jul. 18, 2022, 07 Pages.
Forchelet D., et al., "Enclosed Electronic System for Force Measurements in Knee Implants," Sensors, Aug. 14, 2014, vol. 14, pp. 15009-15021.
Graichen F., et al., "Hip Endoprosthesis for in Vivo Measurement of Joint Force and Temperature," Journal of biomechanics, 1999, vol. 32, No. 10, pp. 1113-1117.
Heinlein B., et al., "Design, Calibration and Pre-clinical Testing of an Instrumented Tibial Tray," Journal of biomechanics, 2007, vol. 40, pp. S4-S10.
International Preliminary Report on Patentability for International Application No. PCT/US2014/028381, mailed Sep. 24, 2015, 13 Pages.
International Preliminary Report on Patentability for International Application No. PCT/US2014/043736, mailed Jan. 7, 2016, 11 Pages.
International Preliminary Report on Patentability for International Application No. PCT/US2015/050789, mailed Mar. 30, 2017, 07 Pages.
International Preliminary Report on Patentability for International Application No. PCT/US2017/023916, mailed Oct. 4, 2018, 20 Pages.
International Preliminary Report on Patentability for International Application No. PCT/US2020/036516, mailed Dec. 16, 2021, 10 Pages.
International Search Report and Written Opinion for International Application No. PCT/US2014/028381, mailed Jul. 7, 2014, 15 Pages.
International Search Report and Written Opinion for International Application No. PCT/US2014/043736, mailed Oct. 15, 2014, 15 Pages.

(56) References Cited

OTHER PUBLICATIONS

International Search Report and Written Opinion for International Application No. PCT/US2015/050789, mailed Feb. 1, 2016, 10 Pages.

International Search Report and Written Opinion for International Application No. PCT/US2017/023916, mailed Aug. 2, 2017, 23 Pages.

Jacq C., et al., "Investigation of Polymer Thick-Film Piezoresistors for Medical Wrist Rehabilitation and Artificial Knee Load Sensors," Procedia Engineering, 2014, vol. 87, pp. 1194-1197.

Kroft S., "The Data Brokers: Selling your Personal Information," Extracted from Google on Sep. 4, 2014 is a script from "The Data Brokers" Aired on Mar. 9, 2014 on 60 Minutes CBS, pp. 1-8.

Loh N.C., et al., "Sub-10 cm3 Interferometric Accelerometer with Nano-g Resolution," Journal of Microelectromechanical Systems, vol. 11, No. 3, Jun. 2002, pp. 182-187.

Partial Supplementary European Search Report for European Application No. 14762650.1, mailed Apr. 13, 2017, 08 Pages.

Partial Supplementary European Search Report for European Application No. 14762650.1, mailed Mar. 17, 2017, 08 Pages.

Partial Supplementary European Search Report for European Application No. 14817352.9, mailed Feb. 14, 2017, 09 Pages.

Partial Supplementary European Search Report for European Application No. 15842678.3, mailed Oct. 16, 2018, 15 Pages.

Polla D.L., et al., "Microdevices in Medicine," Annual Review Of Biomedical Engineering, 2000, vol. 02, pp. 551-576.

Singh U.K., et al., "Piezoelectric Power Scavenging of Mechanical Vibration Energy," Australian Mining Technology Conference, Oct. 2-4, 2007, pp. 111-118.

Xiang X., et al., "A Review of the Implantable Electronic Devices in Biology and Medicine," China Academic Journal Electronic Publishing House, vol. 32 (3), Mar. 3, 2004, pp. 462-467.

Yeh R., et al., "Single Mask, Large Force, and Large Displacement Electrostatic Linear Inchworm Motors," Journal of Microelectromechanical Systems, Aug. 4, 2002, vol. 11, No. 4, pp. 330-336, XP011064780.

Yiming L., et al., "Application of Wireless Sensor Networks in Healthcare," Chinese Journal of Medical Instrumentation, vol. 37, No. 5, Dec. 31, 2013, pp. 351-354 and Figure 1.

Yun K-S., et al., "A Surface-Tension Driven Micropump for Low-voltage and Low-Power Operations", Journal of Microelectromechanical Systems, Oct. 5, 2002, vol. 11, No. 5, pp. 454-461, DOI:10.1109/JMEMS.2002.803286, XP001192816.

Laqua, D. "Intelligent Power Management enables Autonomous Power Supply of Sensor Systems for Modern Prostheses." Biomedical Engineering—Biomedizinische Technik. suppl. 1 57 : 247-250. Walter De Gruyter Gmbh. (Sep. 2012) ( Year: 2012).

\* cited by examiner

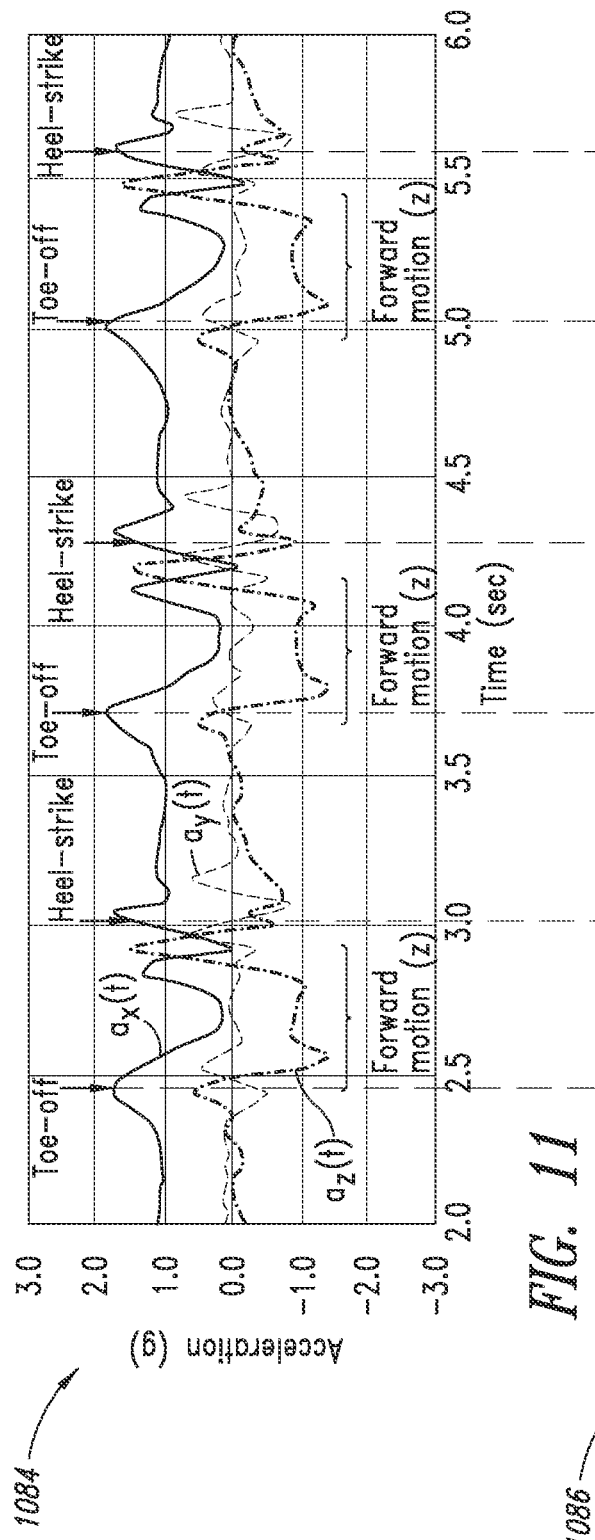
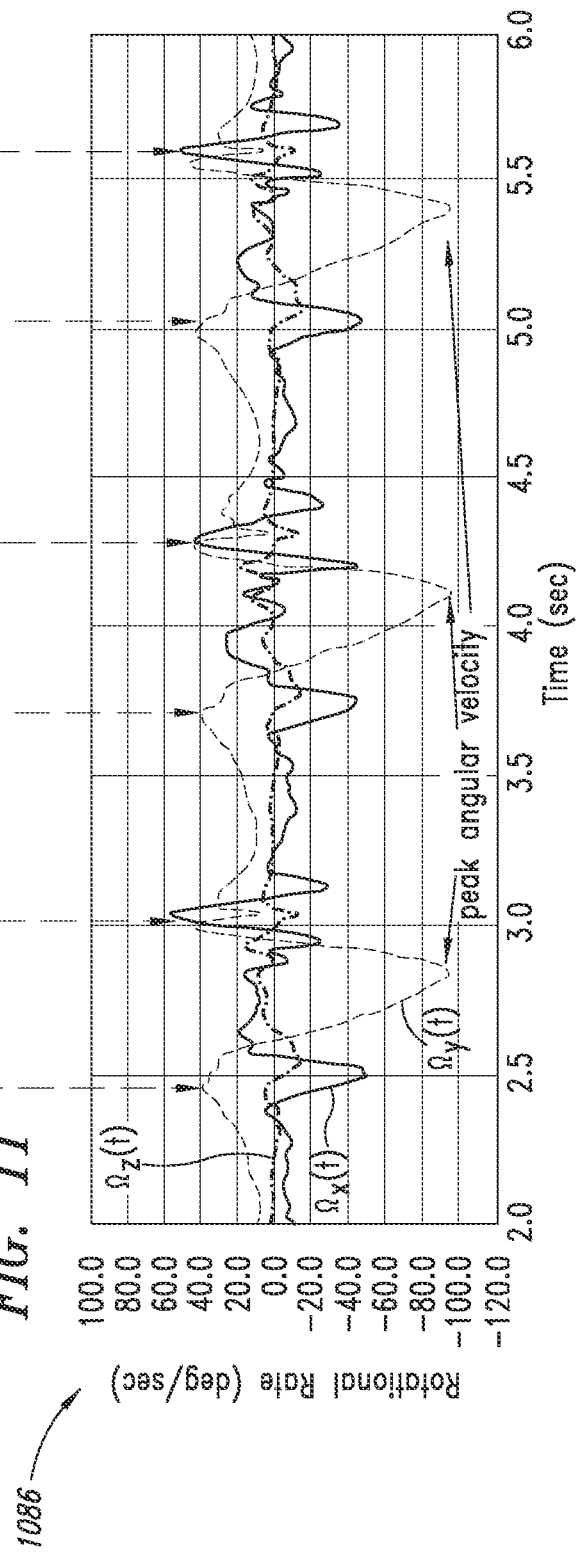
FIG. 11
FIG. 12

$$r_h - r_1 = \underbrace{(\cos(t) + .5\sin(t), \sin(t), 0)}_{2316 \quad 2320}$$

$$\tilde{X} = \begin{bmatrix} \tilde{x}_{1,1} & \tilde{x}_{1,2} & \tilde{x}_{1,3} & \cdots & \tilde{x}_{1,p} \\ \tilde{x}_{2,1} & \tilde{x}_{2,2} & \tilde{x}_{2,3} & \cdots & \tilde{x}_{2,p} \\ \vdots & & & & \vdots \\ \tilde{x}_{N,1} & \tilde{x}_{N,2} & \tilde{x}_{N,3} & \cdots & \tilde{x}_{N,p} \end{bmatrix}$$ — 2402 j=2

$\dfrac{\sum_{i=1}^{N} \tilde{x}_{i,j}}{N}$ → $\mu_j$ = mean of column j — 2406

$\dfrac{\sum_{i=1}^{N}(\tilde{x}_{i,j}-\mu_j)^2}{N}$ → $\sigma_j^2$ = mean of column j — 2408

$\sqrt{\sigma_j^2} = \sigma_j$ = standard division of column j — 2410

2404

$x_{i,j} = \dfrac{\tilde{x}_{i,j} - \mu_j}{\sigma_j}$ — 2412

$$X = \begin{bmatrix} x_{1,1} & x_{1,2} & x_{1,3} & \cdots & x_{1,p} \\ x_{2,1} & x_{2,2} & x_{2,3} & \cdots & x_{2,p} \\ \vdots & & & & \vdots \\ x_{N,1} & x_{N,2} & x_{N,3} & \cdots & x_{N,p} \end{bmatrix}$$ — 2414

FIG. 32C $$A = \begin{bmatrix} a_{11} & a_{12} & a_{13} \\ a_{21} & a_{22} & a_{23} \\ a_{31} & a_{32} & a_{33} \end{bmatrix} \phantom{xx} 2422$$

$$u = \begin{bmatrix} u_1 \\ u_2 \\ u_3 \end{bmatrix} \phantom{xx} 2424$$

$Au = \lambda u$ —— 2426

$$\begin{bmatrix} a_{11} & a_{12} & a_{13} \\ a_{21} & a_{22} & a_{23} \\ a_{31} & a_{32} & a_{33} \end{bmatrix} \begin{bmatrix} u_1 \\ u_2 \\ u_3 \end{bmatrix} = \begin{bmatrix} a_{11}u_1 + a_{12}u_2 + a_{13}u_3 \\ a_{21}u_1 + a_{22}u_2 + a_{23}u_3 \\ a_{31}u_1 + a_{32}u_2 + a_{33}u_3 \end{bmatrix} = \begin{bmatrix} \lambda u_1 \\ \lambda u_2 \\ \lambda u_3 \end{bmatrix}$$

2428

$Au - \lambda u = 0$ —— 2430

$(A - \lambda I)u = 0$ —— 2432

$u = (A - \lambda I)^{-1} 0$ —— 2434

$|A - \lambda I| = 0$ —— 2436

FIG. 32D $$\begin{vmatrix} a_{11}-\lambda & a_{12} & a_{13} \\ a_{21} & a_{22}-\lambda & a_{23} \\ a_{31} & a_{32} & a_{33}-\lambda \end{vmatrix} = a_{11}-\lambda \begin{vmatrix} a_{22}-\lambda & a_{23} \\ a_{32} & a_{33}-\lambda \end{vmatrix} + a_{12} \begin{vmatrix} a_{23} & a_{21} \\ a_{33}-\lambda & a_{31} \end{vmatrix} + a_{13} \begin{vmatrix} a_{21} & a_{22}-\lambda \\ a_{31} & a_{32} \end{vmatrix} \quad \text{— 2442}$$

$$0 = a\lambda^3 + b\lambda^2 + c\lambda + d \quad \text{— 2444}$$

$$AU = \Lambda U, \text{ where } U = \begin{bmatrix} u_1 & u_2 & u_3 \end{bmatrix} \text{ and } \Lambda = \begin{bmatrix} \lambda_1 & 0 & 0 \\ 0 & \lambda_2 & 0 \\ 0 & 0 & \lambda_3 \end{bmatrix} \quad \text{— 2453}$$

$A = U\Lambda U^{-1}$ — 2450

$A = X^T X \implies \lambda_i \geq 0; \; u_i \cdot u_j = 0 \text{ when } \lambda_i \neq \lambda_j; \; U^{-1} = U^T$ — 2451

$A = U\Lambda U^T$ — 2452

*FIG. 32E*

PCA($\dot{\theta}_x, \dot{\theta}_y, \dot{\theta}_z$) ⟶ $zx = y$ principle axis

PCA($a_x, a_y, a_z$) ⟶ $x$ = principle axis, $z$ secondary axis $$y = f(x) \quad \text{—2490}$$

$$\text{2492} \text{—} F = f(x) = F(u) = \int_{-\infty}^{\infty} f(x)e^{-i2\pi ux} dx \quad \text{—2494}$$

$$\text{2496} \text{—} F^{-1}F(u) = f(x) = \int_{-\infty}^{\infty} F(u)e^{i2\pi ux} dx \quad \text{—2498}$$

$$F(u) = R(u) + iI(u) \quad \text{—2499}$$

$$F(u) = |F(u)|e^{j\theta(u)} \quad \text{—2500}$$

$$\text{where } |F(u)| = (R^2(u) + I^2(u))^{\frac{1}{2}} j \text{ and}$$

$$\theta(u) = \tan^{-1}\frac{I(u)}{R(u)}$$

$$P(u) = |F(u)|^2 \quad \text{—2502}$$

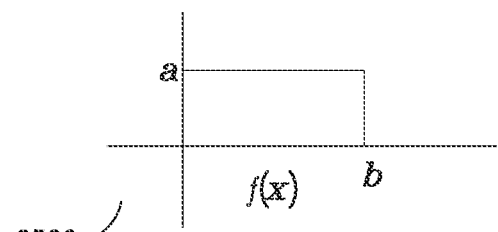

$$2504 \text{—} \sum_{x=1}^{4} e^{-i2\pi ux} = \begin{array}{l} \cos(2\pi u) - i\sin(2\pi u) + \\ \cos(4\pi u) - i\sin(4\pi u) + \\ \cos(6\pi u) - i\sin(6\pi u) + \\ \cos(8\pi u) - i\sin(8\pi u) \end{array} \quad \text{—2506}$$

$$f(x) = \begin{cases} 0 \leq x \leq b, & 1 \\ \text{otherwise}, & 0 \end{cases} \quad \text{—2508}$$

$$2510 \begin{cases} F(u) = \int_{-\infty}^{\infty} f(x)e^{-i2\pi ux} dx \\ = a\int_{0}^{b} e^{-i2\pi ux} dx \\ = \frac{a}{i2\pi u}\left[e^{-i2\pi ux}\right]_{0}^{b} \\ = \frac{a}{2u}\sin(\pi ub)e^{-i\pi ub} \end{cases}$$

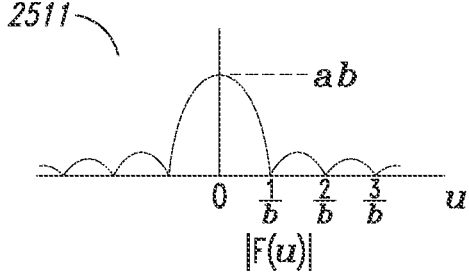

*FIG. 34A*

$$2512 \begin{cases} z = f(x,y) \quad \text{---} 2514 \\ \mathsf{F}(f(x,y)) = \mathsf{F}(u,v) = \int_{-\infty}^{\infty} \int_{-\infty}^{\infty} f(x,y) e^{-i2\pi(ux+uy)} dx dy \\ \mathsf{F}^{-1}(\mathsf{F}(u,v)) = \int_{-\infty}^{\infty} \int_{-\infty}^{\infty} \mathsf{F}(u,v) e^{i2\pi(ux+uy)} du dv \end{cases}$$

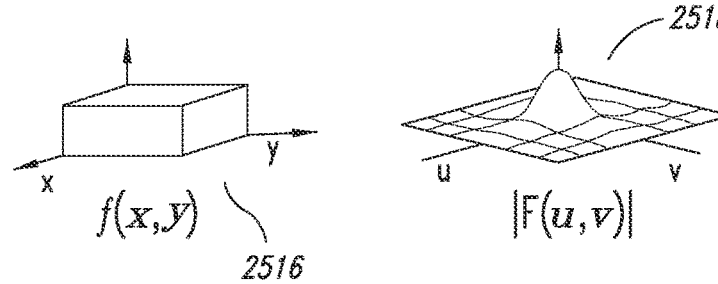

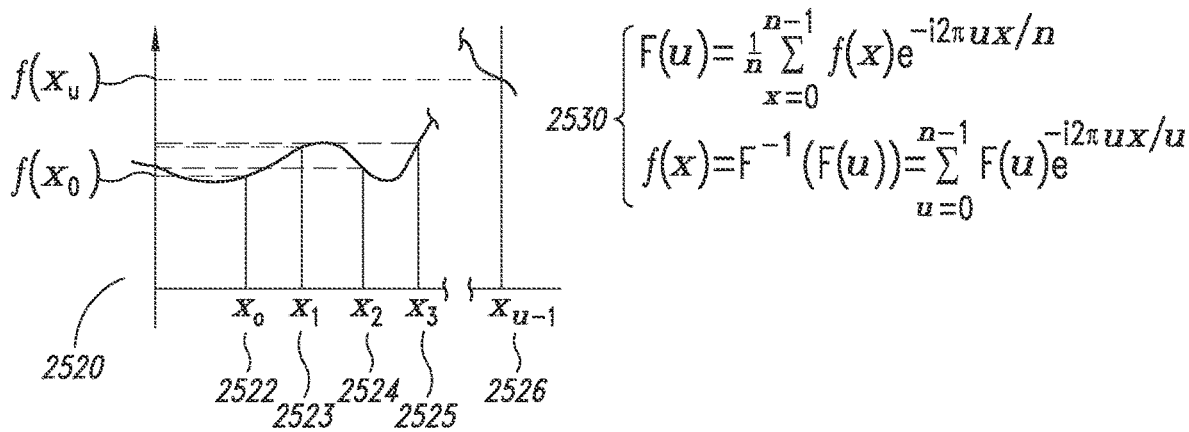

$$2530 \begin{cases} \mathsf{F}(u) = \frac{1}{n} \sum_{x=0}^{n-1} f(x) e^{-i2\pi ux/n} \\ f(x) = \mathsf{F}^{-1}(\mathsf{F}(u)) = \sum_{u=0}^{n-1} \mathsf{F}(u) e^{-i2\pi ux/u} \end{cases}$$

$$\left. \begin{array}{l} \mathsf{F}(u,v) = \frac{1}{mn} \sum_{x=0}^{m-1} \sum_{y=0}^{n-1} f(x,y) e^{-i2\pi(ux/m+vy/n)} \\ f(x,y) = \sum_{u=0}^{m} \sum_{v=0}^{n} \mathsf{F}(u,v) e^{i2\pi(ux/m+vy/n)} \end{array} \right\} 2532$$

*FIG. 34B*

INTELLIGENT JOINT PROSTHESIS

CROSS-REFERENCE TO RELATED APPLICATION

This application is a Continuation of U.S. application Ser. No. 17/424,058, filed Jul. 19, 2021, which is a national phase under 35 U.S.C. § 371 of International Application No. PCT/US2020/036516, filed Jun. 6, 2020, which claims the benefit under 35 U.S.C. § 119(e) of U.S. Provisional Patent Application No. 62/858,277 filed Jun. 6, 2019, which applications are incorporated herein by reference in their entirety for all purposes.

FIELD OF THE INVENTION

The present invention relates generally to medical devices with a sensor, systems including such devices, methods of using such devices and systems and the data generated therefrom, and devices and methods to address problems associated with an implanted medical device with a sensor.

BACKGROUND

Medical devices and implants have become commonplace in modern medicine. Typically, medical devices and implants are manufactured to replace, support, or enhance an anatomical or biological structure. When the medical device is located on the surface of the patient, the device is readily viewable by the patient and the attending health care professional. However, when the medical device is designed to be implanted in a patient, i.e., is an implantable medical device or a medical implant, it is typically not readily viewable.

Examples of medical implants include orthopedic implants such as hip, shoulder and knee prosthesis; spinal implants (spinal cages and artificial discs) and spinal hardware (screws, plates, pins, rods); intrauterine devices; orthopedic hardware used to repair fractures and soft tissue injuries (casts, braces, tensor bandages, plates, screws, wires, dynamic hip screws, pins and plates); cochlear implants; aesthetic implants (breast implants, fillers); and dental implants.

Using the knee as a specific example, current prosthetic systems for a total knee arthroplasty (TKA) typically consist of up to five components: a femoral component, a tibial component, a tibial insert, a tibial stem extension and a patella component, where collectively these five components may be referred to as a total knee implant (TKI). These components are designed to work together as a functional unit, to replace and provide the function of a natural knee joint. The femoral component is attached to the femoral head of the knee joint and forms the superior articular surface. The tibial insert (also called a spacer) is often composed of a polymer and forms the inferior articulating surface with the metallic femoral head. The tibial component consists of a tibial stem that inserts into the marrow cavity of the tibia and a base plate, which is sometimes called either a tibial plate, a tibial tray, or a tibial base plate that contacts/holds the tibial insert. Optionally, and particularly where the proximal tibial bone quality and/or bone quantity is compromised, a tibial stem extension can be added to the tibial stem of the tibial component, where the tibial stem extension serves as a keel to resist tilting of the tibial component and increase stability. Commercial examples of TKA products include the Persona™ knee system (I113369) and associated tapered tibial stem extension (K133737), both by Zimmer Biomet Inc. (Warsaw, Indiana, USA). The surgery whereby these four components are implanted into a patient is also referred to as a total knee replacement (TKR). Similar prosthetic devices are available for other joints, such as total hip arthroplasty (THA) and shoulder arthroplasty (TSA), where one articular surface is metallic, and the opposing surface is polymeric. Collectively, these devices and procedures (TKA, THA and TSA) are often referred to as total joint arthroplasty (TJA).

For a TKA, the tibial component and the femoral component are typically inserted into, and cemented in place within, the tibia bone and femoral bone, respectively. In some cases, the components are not cemented in place, as in uncemented knees. Regardless of whether they are cemented in place or not, once placed and integrated into the surrounding bone (a process called osteointegration), they are not easy to remove. Accordingly, proper placement of these components during implantation is very important to the successful outcome of the procedure, and surgeons take great care in implanting and securing these components.

Current commercial TKA systems have a long history of clinical use with implant duration regularly exceeding 10 years and with some reports supporting an 87% survivorship at 25 years. Clinicians currently monitor the progress of TKA patients post implant using a series of physical exams at 2-3 weeks, 6-8 weeks, 3 months, 6 months, 12 months, and yearly thereafter.

After the TKI has been implanted, and the patient begins to walk with the knee prosthesis, problems may occur and are sometimes hard to identify. Clinical exams are often limited in their ability to detect failure of the prosthesis; therefore, additional monitoring is often required such as CT scans, MRI scans or even nuclear scans. Given the continuum of care requirements over the lifetime of the implant, patients are encouraged to visit their clinician annually to review their health condition, monitor other joints, and assess the TKA implant's function. While the current standard of care affords the clinician and the healthcare system the ability to assess a patient's TKA function during the 90-day episode of care, the measurements are often subjective and lack temporal resolution to delineate small changes in functionality that could be a pre-cursor to larger mobility issues. The long-term (>1 year) follow up of TKA patients also poses a problem in that patients do not consistently see their clinicians annually. Rather, they often seek additional consultation only when there is pain or other symptoms.

Currently, there is no mechanism for reliably detecting misplacement, instability, or misalignment in the TKA without clinical visits and the hands and visual observations of an experienced health care provider. Even then, early identification of subclinical problems or conditions is either difficult or impossible since they are often too subtle to be detected on physical exam or demonstratable by radiographic studies. Furthermore, if detection were possible, corrective actions would be hampered by the fact that the specific amount movement and/or degree of improper alignment cannot be accurately measured or quantified, making targeted, successful intervention unlikely. Existing external monitoring devices do not provide the fidelity required to detect instability since these devices are separated from the TKA by skin, muscle, and fat—each of which masks the mechanical signatures of instability and introduce anomalies such as flexure, tissue-borne acoustic noise, inconsistent sensor placement on the surface, and inconsistent location of the external sensor relative to the TKA.

Implants other than TKA implants may also be associated with various complications, both during implantation and post-surgery. In general, correct placement of a medical implant can be challenging to the surgeon and various complications may arise during insertion of any medical implant (whether it is an open surgical procedure or a minimally invasive procedure). For example, a surgeon may wish to confirm correct anatomical alignment and placement of the implant within surrounding tissues and structures. This can however be difficult to do during the procedure itself, making intraoperative corrective adjustments difficult.

In addition, a patient may experience a number of complications post-procedure. Such complications include neurological symptoms, pain, malfunction (blockage, loosening, etc.) and/or wear of the implant, movement or breakage of the implant, inflammation and/or infection. While some of these problems can be addressed with pharmaceutical products and/or further surgery, they are difficult to predict and prevent; often early identification of complications and side effects, although desirable, is difficult or impossible.

The present disclosure is directed to identifying, locating and/or quantifying these problems, particularly at an early stage, and providing methods and devices to remedy these problems.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

Briefly stated, the present disclosure relates to intelligent implants, systems including intelligent implants, methods of using the implants/systems to do at least one of detect, locate, quantify and/or characterize problems associated with the implant, and methods and devices to address the problems that have been identified. As provided in more detail below, the present disclosure provides medical devices coupled to a sensor, and systems including such devices, which can generate data as well as analysis based on that data, which may be used to identify and/or address problems associated with the implanted medical device. In one embodiment the medical device is an artificial joint (TJA) and the data is kinematic data reflecting movement of the artificial joint. Problems that may be identified include incorrect placement of the TJA device, incorrect alignment of the device, unanticipated degradation or wear of the device, instability of the device (and the associated joint), and undesired movement of the device. Also provided are medical devices coupled to a sensor, and devices and methods to address problems that have been identified with an implanted medical device.

The medical device coupled to a sensor may be referred to as an intelligent implant, where the intelligent implant will include a sensor that can detect and/or measure the functioning of the implant and/or the immediate environment around the implant and/or the activity/movement of the implant as well as the activity and movement of the patient. The implant may alternatively be referred to herein as a prosthesis, where an intelligent implant and an intelligent prosthesis have the same meaning. In one embodiment, the coupling of the sensor to the medical device, e.g., to the prosthesis/implant, is to have the sensor located entirely within the medical device such that the sensor is totally enclosed by the exterior surface of the medical device, so that no part of the sensor physically contacts any tissue of a patient into whom the medical device has been implanted. In embodiments of the present disclosure, reference herein to a medical device, or to an implant or a prosthesis may be understood to be a reference to an intelligent medical device or implant/prosthesis having a sensor that is located entirely within the medical device or implant/prosthesis as disclosed herein. In embodiments of the present disclosure, reference herein to a medical device, or to an implant or a prosthesis having a sensor is to be understood to be a reference to an intelligent medical device or implant/prosthesis wherein the sensor is located entirely within the medical device or implant/prosthesis. In embodiments of the present disclosure, reference herein to a medical device, or an implant/prosthesis having a sensor is to be understood to be a reference to an intelligent medical device or implant/prosthesis wherein the sensor is one accelerometer or more than one accelerometer (e.g., two, three, four, five, six, seven, etc. accelerometers) located entirely within the medical device or implant/prosthesis. In embodiments of the present disclosure, reference herein to a medical device, or an implant/prosthesis having a sensor is to be understood to be a reference to an intelligent medical device or implant/prosthesis wherein the sensor is one or more accelerometers (e.g., two, three, four, five, six, seven, etc. accelerometers) located entirely within a tibial extension of the medical device, implant/prosthesis, such that the medical device or implant/prosthesis is, e.g. a component of a TKA.

The systems will include the intelligent implant and one or more of a memory that stores data from that detection and/or measuring, an antenna that transmits that data; a base station that receives the data generated by the sensor and may transmit the data and/or analyzed data to a cloud-based location; a cloud-based location where data may be stored and analyzed, and analyzed data may be stored and/or further analyzed; and a receiving station that receives output from the cloud-based location, where that receiving station may be accessed, e.g., by a health care professional or an insurance company or the manufacturer of the implant, and the output may identify the status of the implant and/or the functioning of the implant and/or the status of the patient who has received the implant, and may also provide recommendations for addressing any concerns raised by analysis of the original data.

For example, instability in the total joint arthroplasty (e.g. TKA, THA and TSA) hardware may lead to bone erosion and accelerated fatigue of the implant components. Left untreated or uncorrected, bone erosion and accelerated fatigue will typically lead to pain and inflammation. By the time pain and inflammation prompt a total joint arthroplasty (TJA) patient to seek medical care, the extent of bone erosion and TJA fatigue may leave the health care professional with only one-choice: a highly invasive and expensive surgery with reduced probability of "successful" outcome. The present disclosure provides devices, systems and methods which provide that the instability in the TJA hardware can be detected early before bone erosion and implant fatigue damage. This instability can be detected, quantified and characterized, and the results communicated to a health care provider to allow for early treatment and/or more effective treatment of the problem, i.e., the health care provider may take advantage of corrective treatments that are far less invasive, less expensive, and more likely to succeed. The present disclosure also provides devices and/or methods to address the instability problem.

The present disclosure refers to TJA (total joint arthroplasty) which term includes reference to the surgery and associated implanted hardware such as a TJA prosthesis of the present disclosure. Features of methods, devices and systems of the present disclosure may be illustrated herein by reference to a specific intelligent TJA prosthesis, however, the disclosure should be understood to apply to any one or more TJA prosthesis, including a TKA (total knee arthroscopy) prosthesis, such as a TKI (total knee implant) which may also be referred to as a TKA system; a TSA (total shoulder arthroscopy) prosthesis, such as a TSI (total shoulder implant) which may also be referred to as a TSI system; and a THA (total hip arthroscopy) prosthesis, such as a THI (total hip implant) which may also be referred to as a THA system. In one embodiment the TJA prosthesis is an intelligent TJA, also referred to as an intelligent TJA prosthesis, having at least one sensor at disclosed herein.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The following are some exemplary numbered embodiments of the present disclosure:

1. A tibial insert for an implantable knee prosthesis, comprising a tibial insert that is 1, 2, 3, 4, 5, 6, 7, 8, 9, or, 10 mm thicker on the medial side of the implant, as compared to the lateral side.

2. A tibial insert for an implantable knee prosthesis, comprising a tibial insert that is 1, 2, 3, 4, 5, 6, 7, 8, 9, or, 10 mm thicker on the lateral side of the implant, as compared to the medial side.

3. A tibial insert for an implantable knee prosthesis, comprising a tibial insert that is 1, 2, 3, 4, 5, 6, 7, 8, 9, or, 10 mm thicker on the anterior side of the implant, as compared to the posterior side.

4. A tibial insert for an implantable knee prosthesis, comprising a tibial insert that is 1, 2, 3, 4, 5, 6, 7, 8, 9, or, 10 mm thicker on the posterior side of the implant, as compared to the anterior side.

5. A tibial insert/articular spacer/for an implantable knee prosthesis, comprising a tibial insert that is 1, 2, 3, 4, 5, 6, 7, 8, 9, or, 10 mm thicker on the medial, lateral, anterior and/or posterior side of the implant.

6. The tibial insert according to any one of embodiments 1-5, wherein said tibial insert is composed of polyethylene, or polyetheretherketone (PEEK).

7. The tibial insert according to any one of embodiments 1-6 wherein said tibial insert is customized to a patient.

8. The tibial insert according to any one of embodiments 1 to 7 wherein said insert is manufactured by 3-D printing, or, by molding.

9. An implantable medical device, comprising:
a circuit configured to be fixedly attached to an implantable prosthetic device; a power component; and a device configured to uncouple the circuit from the power component.

10. An implantable medical device, comprising: a circuit configured to be fixedly attached to an implantable prosthetic device; a battery; and a fuse coupled between the circuit and the battery.

11. A method, comprising electrically opening a fuse that is disposed between a circuit and a battery, at least the fuse and the circuit being disposed on an implanted prosthetic device.

12. An implantable medical device, comprising: at least one sensor configured to generate a sensor signal; and a control circuit configured to cause the at least one sensor to generate the sensor signal at a frequency that is related to a telemedicine code.

13. An implantable medical device, comprising: at least one sensor configured to generate a sensor signal; and a control circuit configured to cause the at least one sensor to generate the sensor signal at a frequency that allows a doctor to qualify for payment under a telemedicine insurance code.

14. An implantable medical device, comprising: at least one sensor configured to generate a sensor signal; and a control circuit configured to cause the at least one sensor to generate the sensor signal at a frequency that allows a doctor to qualify for full payment under a telemedicine insurance code.

15. A method, comprising, generating a sensor signal that is related to an implanted medical device at a frequency that allows a doctor to qualify for payment available under a telemedicine insurance code.

16. A method, comprising, generating a sensor signal that is related to an implanted medical device at a frequency that allows a doctor to qualify for full payment available under a telemedicine insurance code.

17. An implantable prosthesis, comprising:
a housing; and
an implantable circuit disposed in the housing and configured
to generate at least one first signal representative of a movement;
to determine whether the signal meets at least one first criterion; and
to send the signal to a remote location in response to determining that the signal meets the at least one first criterion.

18. A base station, comprising:
a housing; and
a base-station circuit disposed in the housing and configured
to receive, from an implantable prosthesis, at least first signal representative of a movement;
to send the at least one first signal to a destination;
to receive at least one second signal from a source; and
to send the at least one second signal to the implantable prosthesis.

19. A method, comprising opening a fuse disposed on an implantable prosthesis between a power source and an implantable circuit in response to a current through the fuse exceeding an overcurrent threshold.

20. A method, comprising opening a fuse disposed on an implantable prosthesis between a power source and an implantable circuit in response to a current through the fuse exceeding an overcurrent threshold for at least a threshold time.

21. A method, comprising opening a fuse disposed on an implantable prosthesis between a power source and an implantable circuit in response to a voltage across the fuse exceeding an overvoltage threshold.

22. A method, comprising opening a fuse disposed on an implantable prosthesis between a power source and an implantable circuit in response to a voltage across the fuse exceeding an overvoltage threshold for at least a threshold time.

23. A method, comprising opening a fuse disposed on an implantable prosthesis between a power source and an implantable circuit in response to a temperature exceeds an overtemperature threshold.

24. A method, comprising opening a fuse disposed on an implantable prosthesis between a power source and an implantable circuit in response to a temperature exceeding an overtemperature threshold for at least a threshold length of time.

25. A method, comprising: generating a sensor signal in response to a movement of a subject in which a prosthesis is implanted; and transmitting the sensor signal to a remote location.

26. A method, comprising: generating a sensor signal in response to a movement of a subject in which a prosthesis is implanted; sampling the sensor signal; and transmitting the samples to a remote location.

27. A method, comprising: generating a sensor signal in response to a movement of a subject in which a prosthesis is implanted; determining whether the sensor signal represents a qualified event; and transmitting the signal to a remote location in response to determining that the sensor signal represents a qualified event.

28. A method, comprising: generating a sensor signal in response to a movement of a subject in which a prosthesis is implanted; receiving a polling signal from a remote location; and transmitting the sensor signal to the remote location in response to the polling signal.

29. A method, comprising: generating a sensor signal in response to a movement of a subject in which a prosthesis is implanted; generating a message that includes the sensor signal or data representative of the sensor signal; and transmitting the message to a remote location.

30. A method, comprising: generating a sensor signal in response to a movement of a subject in which a prosthesis is implanted; generating a data packet that includes the sensor signal or data representative of the sensor signal; and transmitting the data packet to a remote location.

31. A method, comprising: generating a sensor signal in response to a movement of a subject in which a prosthesis is implanted; encrypting at least a portion of the sensor signal or data representative of the sensor signal; and transmitting the encrypted sensor signal to a remote location.

32. A method, comprising: generating a sensor signal in response to a movement of a subject in which a prosthesis is implanted; encoding at least a portion of the sensor signal or data representative of the sensor signal; and transmitting the encoded sensor signal to a remote location.

33. A method, comprising: generating a sensor signal in response to a movement of a subject in which a prosthesis is implanted; transmitting the sensor signal to a remote location; and entering an implantable circuit associated with the prosthesis into a lower-power mode after transmitting the sensor signal.

34. A method, comprising: generating a first sensor signal in response to a movement of a subject in which a prosthesis is implanted; transmitting the first sensor signal to a remote location; entering at least one component of an implantable circuit associated with the prosthesis into a lower-power mode after transmitting the sensor signal; and generating a second sensor signal in response to a movement of the subject after an elapse of a low-power-mode time for which the implantable circuit is configured.

35. A method, comprising: receiving a sensor signal from a prosthesis implanted in a subject; and transmitting the received sensor signal to a destination.

36. A method, comprising: sending an inquiry to a prosthesis implanted in a subject, receiving a sensor signal from a prosthesis after sending the inquiry; and transmitting the received sensor signal to a destination.

37. A method, comprising: receiving a sensor signal and at least one identifier from a prosthesis implanted in a subject; determining whether the identifier is correct; and transmitting the received sensor signal to a destination in response to determining that the identifier is correct.

38. A method, comprising: receiving a message including a sensor signal from a prosthesis implanted in a subject; decrypting at least a portion of the message; and transmitting the decrypted message to a destination.

39. A method, comprising: receiving a message including a sensor signal from a prosthesis implanted in a subject; decoding at least a portion of the message; and transmitting the decoded message to a destination.

40. A method, comprising: receiving a message including a sensor signal from a prosthesis implanted in a subject; encoding at least a portion of the message; and transmitting the encoded message to a destination.

41. A method, comprising: receiving a message including a sensor signal from a prosthesis implanted in a subject; encrypting at least a portion of the message; and transmitting the encrypted message to a destination.

42. A method, comprising: receiving a data packet including a sensor signal from a prosthesis implanted in a subject; decrypting at least a portion of the data packet; and transmitting the decrypted data packet to a destination.

43. A method, comprising: receiving a data packet including a sensor signal from a prosthesis implanted in a subject; decoding at least a portion of the data packet; and transmitting the decoded data packet to a destination.

44. A method, comprising: receiving a data packet including a sensor signal from a prosthesis implanted in a subject; encoding at least a portion of the data packet; and transmitting the encoded data packet to a destination.

45. A method, comprising: receiving a data packet including a sensor signal from a prosthesis implanted in a subject; encrypting at least a portion of the data packet; and transmitting the encrypted data packet to a destination.

46. A method, comprising: receiving a sensor signal from a prosthesis implanted in a subject; decrypting at least a portion of the sensor signal; and transmitting the decrypted sensor signal to a destination.

47. A method, comprising: receiving a sensor signal from a prosthesis implanted in a subject; decoding at least a portion of the sensor signal; and transmitting the decoded sensor signal to a destination.

48. A method, comprising: receiving a sensor signal from a prosthesis implanted in a subject; encoding at least a portion of the sensor signal; and transmitting the encoded sensor signal to a destination.

49. A method, comprising: receiving a sensor signal from a prosthesis implanted in a subject; encrypting at least a portion of the sensor signal; and transmitting the encrypted sensor signal to a destination.

50. An implantable circuit for an implantable prosthesis.

51. An implantable prosthesis including an implantable circuit.

52. An implantable prosthesis including a fuse.

53. A base station for communication with an implantable prosthesis.

54. A monitoring-session-data collection, analysis, and status-reporting system implemented as a component of one or more computer systems, each computer system having one or more processors, one or more memories, one or more network connections, and access to one or more mass-storage devices, the one or more the monitoring-session-data collection, data-analysis, and status-reporting system comprising:
a monitoring-session-data-receiving component that receives monitoring-session-data, including acceleration data generated by sensors within or proximal to a prosthesis attached or implanted within a patient, from an external monitoring-session-data source and that stores the received monitoring-session-data in one or more of the one or more memories and one or more mass-storage devices;
a monitoring-session-data-processing component that prepares the monitoring-session-data for processing, determines component trajectories representing motion modes and additional metric values from the monitoring-session-data; and
a monitoring-session-data-analysis component that
determines a prosthesis status and a patient status from the motion modes and additional metric values,
distributes the determined prosthesis status and patient status to target computer systems through the network connections, and
when indicated by the determined prosthesis status and patient status, distributes one or more alarms and events to target computer systems through the network connections.

55. The monitoring-session-data collection, analysis, and status-reporting system of embodiment 54 wherein the monitoring-session-data includes: a patient identifier; a device identifier; a timestamp; device-configuration data; and an ordered set of data.

56. The monitoring-session-data collection, analysis, and status-reporting system of embodiment 55 wherein the ordered set of data comprises one of:
a time sequence of data vectors, each data vector including numerical values related to linear-accelerations with respect to three coordinate axes of an internal device coordinate system; and
a time sequence of data vectors, each data vector including numerical values related to linear-accelerations with respect to three coordinate axes of a first internal device coordinate system and including numerical values related to angular velocities, numerical values related to angular velocities relative to the first internal device coordinate system or to a second internal device coordinate system.

57. The monitoring-session-data collection, analysis, and status-reporting system of embodiment 54 wherein the monitoring-session-data-processing component prepares the monitoring-session-data for processing by:
receiving a time sequence of data vectors, each data vector including three numerical values related to linear-accelerations in the directions of three coordinate axes of a first internal device coordinate system and including three numerical values related to angular velocities about each axis of the first or a second internal device coordinate system;
when rescaling of the data-vector sequence is needed, rescaling the numerical values of the data vectors;
when normalization of the data-vector sequence is needed, normalizing the numerical values of the data vectors;
when transformation of one or more of the numerical values related to linear-acceleration and the numerical values related to angular velocities is needed to relate the numerical values related to linear-acceleration and the numerical values related to angular velocities to a common internal coordinate system, transforming one or more of the numerical values related to linear-acceleration and the numerical values related to angular velocities to relate to the common internal coordinate system; and
when the time sequence of data vectors needs to be synchronized with respect to a fixed-interval time sequence, synchronizing the data vectors with respect to a fixed-interval time sequence.

58. The monitoring-session-data collection, analysis, and status-reporting system of embodiment 54 wherein the monitoring-session-data-processing component determines component trajectories representing motion modes and additional metric values from the monitoring-session-data by:
orienting the prepared monitoring-session-data, comprising data vectors, each data vector including three numerical values related to linear-accelerations in the directions of three coordinate axes of an internal device coordinate system and including three numerical values related to angular velocities about each axis of the internal device coordinate system, with respect to a natural coordinate system;
bandpass filtering the oriented data vectors to obtain a set of data vectors for each of multiple frequencies, including a normal-motion frequency;
determining, from the data vectors for each of the non-normal-motion frequencies, a spatial amplitude in each of the coordinate-axis directions of the natural coordinate system;
determining, from a basis trajectory for the patient and the data vectors for the normal-motion frequency, a spatial amplitude in each of the coordinate-axis directions of the natural coordinate system; and
determining, from the basis trajectory for the patient and the data vectors for the normal-motion frequency, current normal-motion characteristics.

59. The monitoring-session-data collection, analysis, and status-reporting system of embodiment 58 wherein determining, from the data vectors for a frequency, a spatial amplitude in each of the coordinate-axis directions of the natural coordinate system further comprises: generating a spatial trajectory from the data vectors; projecting the spatial frequency onto each of the coordinate axes; and determining the lengths of the protections of the spatial frequency onto each of the coordinate axes.

60. The monitoring-session-data collection, analysis, and status-reporting system of embodiment 54 wherein the monitoring-session-data-analysis component determines a prosthesis status and a patient status from the motion modes and additional metric values by:
submitting the motion modes and additional metric values to a decision tree that generates a diagnosis-and-suggestions report; and
packaging the diagnosis-and-suggestions report together with amplitudes generated for the motion modes, metrics generated from a normal-motion-frequency trajectory and a base trajectory, and additional metric values to generate one or both of an output report and output data values that characterize the prosthesis status and the patient status.

61. The monitoring-session-data collection, analysis, and status-reporting system of embodiment 54 wherein the monitoring-session-data-analysis component wherein the one or more alarms and events distributed to target computer systems include:

an alarm that notifies a medical practitioner or medical facility of the need, by the patient, of immediate assistance or intervention; and an event that indicates additional services and/or equipment needed by the patient that may be handled by various external computer systems to automatically provide the additional services and/or equipment to the patient or inform the patient of the additional services and/or equipment and provide the patient with information regarding procurement of the additional services and/or equipment.

62. A method, carried out by a monitoring-session-data collection, analysis, and status-reporting system implemented as a component of one or more computer systems, each computer system having one or more processors, one or more memories, one or more network connections, and access to one or more mass-storage devices, the method comprising:

receiving monitoring-session-data, including acceleration data generated by sensors within or proximal to a prosthesis attached or implanted within a patient, from an external monitoring-session-data source;

storing the received monitoring-session-data in one or more of the one or more memories and one or more mass-storage devices;

determining a prosthesis status and a patient status from the motion modes and additional metric values, distributing the determined prosthesis status and patient status to target computer systems through the network connections, and when indicated by the determined prosthesis status and patient status, distributing one or more alarms and events to target computer systems through the network connections.

63. The method of embodiment 62 wherein determining a prosthesis status and a patient status from the motion modes and additional metric values further comprises:

preparing the monitoring-session-data for processing, determines component trajectories representing motion modes and additional metric values from the monitoring-session-data;

submitting the motion modes and additional metric values to a decision tree that generates a diagnosis-and-suggestions report; and packaging the diagnosis-and-suggestions report together with amplitudes generated for the motion modes, metrics generated from a normal-motion-frequency trajectory and a base trajectory, and additional metric values to generate one or both of an output report and output data values that characterize the prosthesis status and the patient status.

64. The method of embodiment 62 wherein preparing the monitoring-session-data for processing further comprises receiving a time sequence of data vectors, each data vector including three numerical values related to linear-accelerations in the directions of three coordinate axes of a first internal device coordinate system and including three numerical values related to angular velocities about each axis of the first or a second internal device coordinate system;

when rescaling of the data-vector sequence is needed, rescaling the numerical values of the data vectors;

when normalization of the data-vector sequence is needed, normalizing the numerical values of the data vectors;

when transformation of one or more of the numerical values related to linear-acceleration and the numerical values related to angular velocities is needed to relate the numerical values related to linear-acceleration and the numerical values related to angular velocities to a common internal coordinate system, transforming one or more of the numerical values related to linear-acceleration and the numerical values related to angular velocities to relate to the common internal coordinate system; and when the time sequence of data vectors needs to be synchronized with respect to a fixed-interval time sequence, synchronizing the data vectors with respect to a fixed-interval time sequence.

65. The method of embodiment 62 wherein determining component trajectories representing motion modes and additional metric values from the monitoring-session-data by:

orienting the prepared monitoring-session-data, comprising data vectors, each data vector including three numerical values related to linear-accelerations in the directions of three coordinate axes of an internal device coordinate system and including three numerical values related to angular velocities about each axis of the internal device coordinate system, with respect to a natural coordinate system;

bandpass filtering the oriented data vectors to obtain a set of data vectors for each of multiple frequencies, including a normal-motion frequency;

determining, from the data vectors for each of the non-normal-motion frequencies, a spatial amplitude in each of the coordinate-axis directions of the natural coordinate system;

determining, from a basis trajectory for the patient and the data vectors for the normal-motion frequency, a spatial amplitude in each of the coordinate-axis directions of the natural coordinate system; and determining, from the basis trajectory for the patient and the data vectors for the normal-motion frequency, current normal-motion characteristics.

66. The method of embodiment 54 wherein determining, from the data vectors for a frequency, a spatial amplitude in each of the coordinate-axis directions of the natural coordinate system further comprises:

generating a spatial trajectory from the data vectors;

projecting the spatial frequency onto each of the coordinate axes; and determining the lengths of the protections of the spatial frequency onto each of the coordinate axes.

67. The method of embodiment 54 wherein determining a prosthesis status and a patient status from the motion modes and additional metric values further comprises:

submitting the motion modes and additional metric values to a decision tree that generates a diagnosis-and-suggestions report; and packaging the diagnosis-and-suggestions report together with amplitudes generated for the motion modes, metrics generated from a normal-motion-frequency trajectory and a base trajectory, and additional metric values to generate one or both of an output report and output data values that characterize the prosthesis status and the patient status.

68. The method of embodiment 54 wherein the one or more alarms and events distributed to target computer systems include:

an alarm that notifies a medical practitioner or medical facility of the need, by the patient, of immediate assistance or intervention; and an event that indicates additional services and/or equipment needed by the patient that may be handled by various external computer systems to automatically provide the additional services and/or equipment to the patient or inform the patient of the additional services and/or equipment and provide the patient with information regarding procurement of the additional services and/or equipment.

69. A physical data-storage device encoded with computer instructions that, when executed by one or more processors within one or more computer systems of a monitoring-session-data collection, analysis, and status-reporting system, each computer system having one or more processors, one or more memories, one or more network connections, and access to one or more mass-storage devices, control the monitoring-session-data collection, analysis, and status-reporting system to:
  receive monitoring-session-data, including acceleration data generated by sensors within or proximal to a prosthesis attached or implanted within a patient, from an external monitoring-session-data source.

70. A method for determining joint loosening in a patient having an implanted artificial joint, comprising a) analyzing movement of an implanted artificial joint, and b) comparing said movement vs. previous/standardized norms.

71. A method for determining loosening of an implanted prosthesis in a patient having the implanted prosthesis, comprising:
  a. obtaining a standardized norm of movement by analyzing movement of an implanted prosthesis during one or more first monitoring sessions,
  b. obtaining a current description of movement by analyzing movement of an implanted prosthesis during one or more second monitoring sessions that occur subsequent to the one or more first monitoring sessions; and
  c. comparing said current description of movement to said standardized norm of movement, to thereby identify loosening of an implanted prothesis in a patient having the implanted prosthesis.

72. A method for identifying a clinical or subclinical condition associated with an implant in a patient, the method comprising:
  a. monitoring a first motion of the implant during a first monitoring session using a sensor which is directly coupled to the implant, to provide a first monitoring-session data for the first motion;
  b. monitoring a second motion of the implant during a second monitoring session using the sensor, to provide a second monitoring-session-data for the second motion; and
  c. comparing the first monitoring-session data or a product thereof to the second monitoring-session-data or a product thereof, to provide a comparison that is indicative of a clinical or subclinical condition associated with the implant.

73. The method of embodiment 72 wherein the clinical or subclinical condition is a loosening of the implant (motion of prosthesis within the surrounding bone or cement, e.g., the implant becomes separated from the host bone due, e.g., to periprosthetic lucency or periprosthetic osteolysis).

74. The method of embodiment 72 wherein the clinical or subclinical condition is a malalignment (sub-optimal positioning of a prosthetic component) or a realignment of the implant (change in alignment of prosthetic component).

75. The method of embodiment 72 wherein the clinical or subclinical condition is deformation (wear) of the implant.

76. The method of embodiment 72 wherein the patient is asymptomatic for the condition, and the comparison of the first and second data or products thereof indicate that the condition has occurred between the first and second monitoring sessions.

77. The method of embodiment 72 wherein the patient is asymptomatic for loosening of the implant, and the comparison of the first and second data or products thereof indicate that the implant has loosened between the first and second monitoring sessions.

78. The method of embodiment 72 wherein the patient is asymptomatic for realignment of the implant, and comparison of the first and second data or products thereof indicate that the implant has changed alignment between the first and second monitoring sessions.

79. The method of embodiment 72 wherein the patient is asymptomatic for deformation of the implant, and comparison of the first and second data or products thereof indicate that the implant has deformed between the first and second monitoring sessions.

80. A method for treating a clinical or subclinical condition associated with an implant in a patient, comprising:
  a. identifying an implant in a patient, where the implant has a clinical or subclinical condition; and
  b. attaching corrective external bracing to patient to restore proper alignment and/or enhanced stability to the implant.

81. The method of embodiment 80 wherein the corrective external bracing has been specifically tailored to the patient and the subclinical condition.

82. A method for treating a clinical or subclinical condition associated with an implant in a patient, comprising:
  a. identifying an implant in a patient, where the implant has a clinical or subclinical condition; and
  b. contacting the implant with a fixation system to retard progression of the subclinical condition.

83. The method of embodiment 82 wherein the fixation system comprises hardware selected from a K-wire, pin, screw, plate and intramedullary device.

84. The method of embodiment 82 wherein a screw is located through a bone that holds the implant, where a terminus of the screw pushes against a surface of the implant to retard movement of the implant, where a screw is selected from one, two, three, four, five, six, seven, eight, nine, ten, eleven, twelve, thirteen, fourteen, fifteen, sixteen, seventeen, eighteen, nineteen and twenty screws.

85. The method of embodiment 82 wherein the fixation system comprises bone cement.

86. A method for treating a clinical or subclinical condition associated with an implant in a patient, comprising:
  a. identifying an implant in a patient, where the implant has a clinical or subclinical condition; and
  b. contacting the implant with a tamp, where the contacting changes a location of the implant within the patient; and optionally
  c. applying a cement around the implant having the changed location.

87. The method of embodiment 86 wherein the subclinical condition is a realignment of the implant.

88. A method for treating a clinical or subclinical condition associated with an implant in a patient, comprising:
  a. identifying an implant in a patient, where the implant has a clinical or subclinical condition; and
  b. implanting an insert adjacent to a component of the implant, where the insert modifies forces acting on the component of the implant.

89. The method of embodiment 88 wherein the insert is a tibial insert.

90. The method of embodiment 88 wherein the insert is a tibial insert having (i) a lateral side with a minimum thickness and (ii) a medial side with a minimum thickness that is non-identical to the minimum thickness of the lateral side.

91. A method for treating a clinical or subclinical condition associated with an implant in a patient, comprising:
   a. identifying an implant in a patient, where the implant has a clinical or subclinical condition; and
   b. delivering a pro-osteointegration agent to a location surrounding the implant.

92. The method of embodiment 91 wherein the pro-osteointegration agent is selected from autologous bone graft, xenograph bone graft, synthetic bone graft, bone pastes, bone growth factor, and growth factor.

93. A method for treating a clinical or subclinical condition associated with an implant in a patient, comprising:
   a. identifying an implant in a patient, where the implant has a clinical or subclinical condition; and
   b. delivering an anti-bacterial agent to a location surrounding the implant.

94. The method of embodiment 93 wherein the anti-bacterial agent is compounded in a sustained release form.

95. The method of any of embodiments 72-94 wherein the implant is an intelligent implant.

96. The method of embodiments 72-94 wherein the implant is selected from a knee implant, a hip implant and a shoulder implant.

97. The method of any of embodiments 72-94 wherein the product of the monitoring-session data comprises a motion mode.

98. The method of any of embodiments 72-94 wherein the product of the monitoring-session data comprises a motion mode, and a status of the implant is determined from the motion mode.

99. The method of any of embodiments 72-94 wherein the product of the monitoring-session data comprises a motion mode, and a status of the patient is determined from the motion mode.

100. The method of any of embodiments 72-94 wherein the implant has been located within the patient for at least 10 weeks prior to the first monitoring session.

101. The method of any of embodiments 72-94 wherein the implant has changed alignment over a period of at least 2 weeks.

102. The method of any of embodiments 72-94 wherein the implant has loosened over a period of at least two weeks.

103. The method of any of embodiments 72-94 wherein the implant has deformed over a period of at least two weeks.

104. The method of any of embodiments 72-94 wherein the implant comprises a control circuit configured to cause the sensor to generate a sensor signal at a frequency that is related to a telemedicine code for the clinical or subclinical condition, and the sensor signal is generated at the frequency.

105. The method of any of embodiments 72-94 wherein the implant comprises a control circuit configured to cause the sensor to generate a sensor signal at a frequency that allows a doctor to qualify for payment under a telemedicine insurance code, and the sensor signal is generated at the frequency.

106. The method of any of embodiments 72-94 wherein the implant comprises a control circuit configured to cause the sensor to generate a sensor signal at a frequency that allows a doctor to qualify for full payment under a telemedicine insurance code, and the sensor signal is generated at the frequency.

107. The method of any of embodiments 72-94 further comprising generating a sensor signal that is related to the implant at a frequency that allows (i) a doctor to qualify for full payment available under a telemedicine insurance code, or (ii) a doctor to qualify for payment available under a telemedicine insurance code.

108. A method comprising:
   a. providing an intelligent prosthesis implanted in a bone adjacent to a joint of a patient, where an accelerometer is contained within the intelligent prosthesis, and where the accelerometer is positioned within the bone;
   b. moving the implanted intelligent prosthesis relative to an external environment wherein the patient is located, where the implanted intelligent prosthesis is moved during a first monitoring session;
   c. making first measurements with the accelerometer during the first monitoring session, where the first measurements provide first monitoring-session-data or a product thereof which identifies a status of the implanted intelligent prosthesis at a time of the first measurements.

109. The method of embodiment 108 wherein the accelerometer is a plurality of accelerometers.

110. The method of embodiment 108 wherein the accelerometer is selected from a 1-axis accelerometer, a 2-axis accelerometer and a 3-axis accelerometer.

111. The method of embodiment 108 wherein the accelerometer operates in a broadband mode.

112. The method of embodiment 108 wherein the bone is a tibia.

113. The method of embodiment 108 wherein the accelerometer is located in a tibial extension of the intelligent prosthesis.

114. The method of embodiment 108 wherein the implanted intelligent prosthesis is moved relative to the external environment without an impact force being applied to the patient or the intelligent prosthesis during the first monitoring session.

115. The method of embodiment 108 wherein the external environment comprises a residence of the patient.

116. The method of embodiment 108 wherein the external environment comprises an operating room wherein the intelligent prosthesis has been implanted into the patient.

117. The method of embodiment 108 wherein the status of the implanted intelligent prosthesis is a characterization of the looseness of the implanted intelligent prosthesis within the bone.

118. The method of embodiment 108 wherein the status of the implanted intelligent prosthesis is a characterization of the alignment of the implanted intelligent prosthesis within the bone.

119. The method of embodiment 108 wherein the status of the implanted intelligent prosthesis is a characterization of the wear of the implanted intelligent prosthesis.

120. The method of embodiment 108 wherein the status of the implanted intelligent prosthesis is a characterization of bacterial infection of a region within the bone adjacent to the implanted intelligent prosthesis.

121. The method of embodiment 108 wherein the status of the implanted intelligent prosthesis indicates a subclinical condition.

122. The method of embodiment 108 wherein step b) is repeated after a waiting period, where the repeat of step b) comprises moving the implanted intelligent prosthesis relative to an external environment wherein the patient is located, where the implanted intelligent prosthesis is moved during a second monitoring session, and wherein second measurements are made with the accelerometer during the second monitoring session, where the second measurements provide second monitoring-session-data or a product thereof which identifies a status of the implanted of the implanted intelligent prosthesis at the time of the second measurements.

123. The method of embodiment 108 wherein step b) is repeated a plurality of times, the plurality of times separated from one another by identical or non-identical waiting periods, where the repeating of step b) comprises moving the implanted intelligent prosthesis relative to an external environment wherein the patient is located, where the implanted intelligent prosthesis is moved during a plurality of monitoring sessions, and wherein measurements are made with the accelerometer during each of the plurality of monitoring sessions, where the measurements provide a plurality of monitoring-session-data or products thereof, each of which identifies a status of the implanted of the implanted intelligent prosthesis at the time of the measurements.

124. The method of embodiment 108 wherein step b) is repeated a plurality of times, the plurality of times separated from one another by identical or non-identical waiting periods, where the repeating of step b) comprises moving the implanted intelligent prosthesis relative to an external environment wherein the patient is located, where the implanted intelligent prosthesis is moved during a plurality of monitoring sessions, and wherein measurements are made with the accelerometer during each of the plurality of monitoring sessions, where the measurements provide a plurality of monitoring-session-data or products thereof, each of which identifies a status of the implanted of the implanted intelligent prosthesis at the time of the measurements; wherein the plurality is optionally selected from 2 to 20 monitoring sessions, and where the plurality of monitoring-session data taken together indicate a change in the status of the implanted intelligent prosthesis during the time when the plurality of monitoring sessions occurred.

125. The method of embodiment 124 wherein the change in the status is indicative of a healing of the tissue surrounding the implanted intelligent prosthesis.

126. The method of embodiment 124 wherein the change in the status is indicative of an infection of the tissue surrounding the implanted prosthesis.

127. The method of embodiment 124 wherein the change in the status is indicative of a loosening of the implanted intelligent prothesis within the bone.

128. The method of embodiment 124 wherein the change in status is indicative of wear of the implanted intelligent prosthesis.

129. The method of embodiment 124 wherein the change in status is indicative of malalignment of the implanted intelligent prosthesis.

130. The method of embodiment 124 wherein the change in status is indicative of a change in alignment of the implanted intelligent prosthesis.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

FIG. 11 is a plot, versus time, of a time-scale-expanded portion of the plot of FIG. 9, according to an embodiment.

FIG. 12 is a plot, versus time, of a time-scale-expanded portion of the plot of FIG. 10, according to an embodiment.

FIG. 34A, FIG. 34B, FIG. 34C and FIG. 34D each illustrate forward and inverse Fourier transforms.

DETAILED DESCRIPTION OF THE INVENTION

Figure 1:
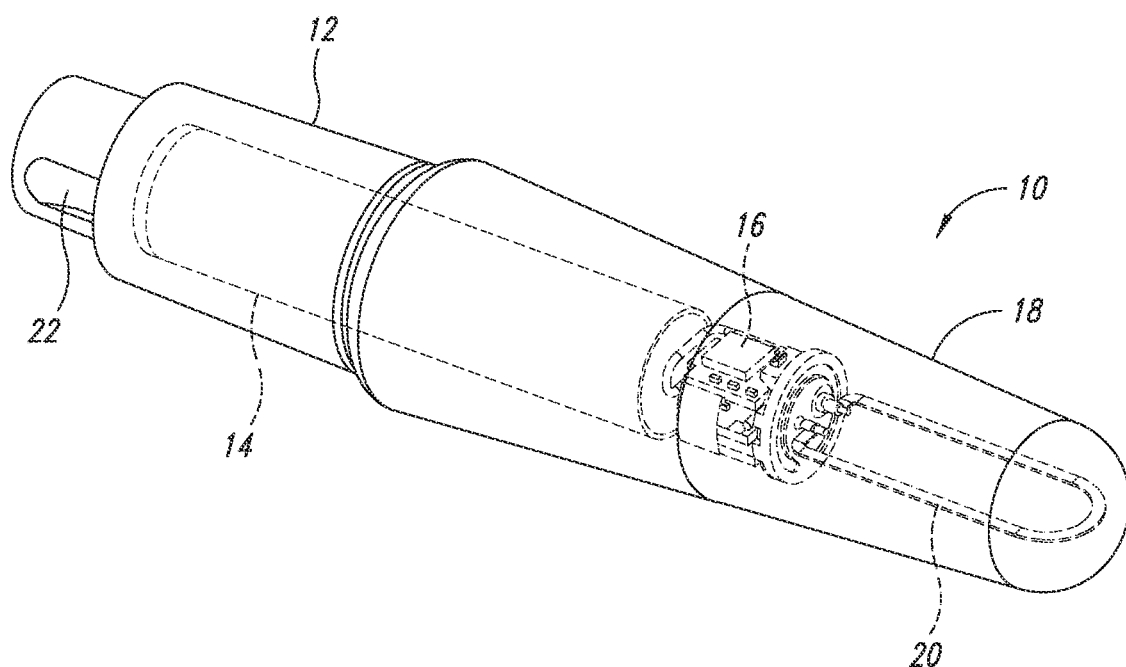
FIG. 1 illustrates an exemplary intelligent implant.

The present disclosure may be understood more readily by reference to the following detailed description of preferred embodiments of the disclosure and the Examples of "intelligent prosthesis" included herein. The following description, along with the accompanying drawings, sets forth certain specific details in order to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components that are associated with the environment of the present disclosure, including but not limited to the communication systems and networks, have not been shown or described in order to avoid unnecessarily obscuring descriptions of the embodiments. Additionally, the various embodiments may be methods, systems, media, or devices. Accordingly, the various embodiments may be entirely hardware embodiments, entirely software embodiments, entirely firmware embodiments, or embodiments combining or subcombining software, firmware, and hardware aspects.

Prior to setting forth this disclosure in more detail, it may be helpful to an understanding thereof to provide definitions of certain terms to be used herein. Additional definitions are set forth throughout this disclosure. The terms "include" and "comprise," as well as derivatives thereof, mean inclusion without limitation. The term "or," is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation, such a device may be implemented in hardware (e.g., electronic circuitry), firmware, or software, or some combination of at least two of the same. The functionality associated with any particular controller may be centralized or distributed, whether locally or remotely. Other definitions of certain words and phrases may be provided within this patent document. Those of ordinary skill in the art will understand that in many, if not most instances, such definitions apply to prior as well as future uses of such defined words and phrases.

An "intelligent prosthesis" or "intelligent medical device" as used in the present disclosure, is an implantable or implanted medical device that desirably replaces or functionally supplements a subject's natural body part. As used herein, the term "intelligent prosthesis" is interchangeably referred to as an "intelligent implant," a "smart implant," a "smart medical device," a "joint implant" an "implanted medical device", or by another like term. When the intelligent prosthesis makes kinematic measurements, it may be referred to as a "kinematic medical device," or a "kinematic implantable device". In describing embodiments of the present disclosure, reference may be made to a kinematic implantable device, however it should be understood that this is exemplary only of the intelligent medical devices which may be employed in the devices, methods, systems etc. of the present disclosure. Whether or not the intelligent prosthesis makes kinematic, or makes other or additional measurements, the prosthesis will comprise or be associated with an implantable reporting processor (IRP). In one embodiment, the intelligent prosthesis is an implanted or implantable medical device having an implantable reporting processor arranged to perform the functions as described herein. The intelligent prosthesis may perform one or more of the following exemplary actions in order to characterize the post-implantation status of the intelligent prosthesis: identifying the intelligent prosthesis or a portion of the intelligent prosthesis, e.g., by recognizing one or more unique identification codes for the intelligent prosthesis or a portion of the intelligent prosthesis; detecting, sensing and/or measuring parameters, which may collectively be referred to as monitoring parameters, in order to collect operational, kinematic, or other data about the intelligent prosthesis or a portion of the intelligent prosthesis and wherein such data may optionally be collected as a function of time; storing the collected data within the intelligent prosthesis or a portion of the intelligent prosthesis; and communicating the collected data and/or the stored data by a wireless means from the intelligent prosthesis or a portion of the intelligent prosthesis to an external computing device. The external computing device may have or otherwise have access to at least one data storage location such as found on a personal computer, a base station, a computer network, a cloud-based storage system, or another computing device that has access to such storage. Non-limiting and non-exhaustive list of embodiments of intelligent prostheses include total joint arthroplasty such as total knee arthroplasty (TKA), a TKA tibial plate, a TKA femoral component, a TKA patellar component, a tibial extension, a total hip arthroplasty (THA), a femoral component for a THA, the acetabular component for a THA, a shoulder arthroplasty, a breast implant, an intramedullary rod for arm or leg breakage repair, a scoliosis rod, a dynamic hip screw, a spinal interbody spacer, a spinal artificial disc, an annuloplasty ring, a heart valve, an intravascular stent, a vascular graft and a vascular stent graft.

"Kinematic data," as used herein, individually or collectively includes some or all data associated with a particular kinematic implantable device and available for communication outside of the particular kinematic implantable device. For example, kinematic data may include raw data from one or more sensors of a kinematic implantable device, wherein the one or more sensors include such as gyroscopes, accelerometers, pedometers, strain gauges, and the like that produce data associated with motion, force, tension, velocity, or other mechanical forces. Kinematic data may also include processed data from one or more sensors, status data, operational data, control data, fault data, time data, scheduled data, event data, log data, and the like associated with the particular kinematic implantable device. In some cases, high resolution kinematic data includes kinematic data from one, many, or all of the sensors of the kinematic implantable device that is collected in higher quantities, resolution, from more sensors, more frequently, or the like.

In one embodiment, kinematics refers to the measurement of the positions, angles, velocities, and accelerations of body segments and joints during motion. Body segments are considered to be rigid bodies for the purposes of describing the motion of the body. They include the foot, shank (leg), thigh, pelvis, thorax, hand, forearm, upper-arm and head. Joints between adjacent segments include the ankle (talocrural plus subtalar joints), knee, hip, wrist, elbow and shoulder. Position describes the location of a body segment or joint in space, measured in terms of distance, e.g., in meters. A related measurement called displacement refers to the position with respect to a starting position. In two dimensions, the position is given in Cartesian co-ordinates, with horizontal followed by vertical position. In one embodiment, a kinematic implant or intelligent kinematic implants obtains kinematic data, and optionally only obtains only kinematic data.

"Sensor" refers to a device that can be utilized to do one or more of detect, measure and/or monitor one or more different aspects of a body tissue (anatomy, physiology, metabolism, and/or function) and/or one or more aspects of the orthopedic device or implant. Representative examples of sensors suitable for use within the present disclosure include, for example, fluid pressure sensors, fluid volume sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors and temperature sensors. Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor. In certain embodiments, the sensor is a device that can be utilized to measure in a quantitative manner, one or more different aspects of a body tissue (anatomy, physiology, metabolism, and/or function) and/or one or more aspects of the orthopedic device or implant. In certain embodiments, the sensor is an accelerometer that can be utilized to measure in a quantitative manner, one or more different aspects of a body tissue (e.g., function) and/or one or more aspects of the orthopedic device or implant (e.g., alignment in the patient).

A wide variety of sensors (also referred to as Microelectromechanical Systems or "MEMS", or Nanoelectromechanical Systems or "NEMS", and BioMEMS or BioNEMS, see generally https://en.wikipedia.org/wiki/MEMS) can be utilized within the present disclosure. Representative patents and patent applications include U.S. Pat. Nos. 7,383,071, 7,450,332; 7,463,997, 7,924,267 and 8,634,928, and U.S. Publication Nos. 2010/0285082, and 2013/0215979. Representative publications include "Introduction to BioM EMS" by Albert Foch, CRC Press, 2013; "From MEMS to Bio-MEMS and Bio-NEMS: Manufacturing Techniques and Applications" by Marc J. Madou, CRC Press 2011; "Bio-MEMS: Science and Engineering Perspectives", by Simona Badilescu, CRC Press 2011; "Fundamentals of BioMEMS and Medical Microdevices" by Steven S. Saliterman, SPIE—The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," J. Microelectromechanical Sys., 11:5, October 2002, 454-461; Yeh, R., et al., "Single Mask, Large Force, and Large Displacement Electrostatic Linear Inchworm Motors," J. Microelectromechanical Sys., 11:4, August 2002, 330-336; and Loh, N. C., et al., "Sub-10 cm3 Interferometric Accelerometer with Nano-g Resolution," J. Microelectromechanical Sys., 11:3, June 2002, 182-187; all of the above of which are incorporated by reference in their entirety.

In order to further understand the various aspects of the embodiments of the present disclosure provided herein, the following sections are provided below: A. Intelligent Medical Devices and Implants; B. Systems with Intelligent Implants; C. Joint Implant and Systems with Joint Implant; D. Computer Systems for Analysis, Dissemination of Information, Ordering, and Supply: Processing IM U Data Recorded During Patient Monitoring; E. Methods and Devices for Stabilizing an Artificial Joint; F. Methods and Devices for Adjusting Position of an Artificial Joint; G. Joint Inserts and Use Thereof; and H. Clinical Solutions and Products.

A. Intelligent Medical Devices and Implants

In one aspect, the present disclosure provides medical devices, including medical devices which may be implanted into a patient (implants), which may be utilized to monitor and report the status and/or activities of the medical device, including post-surgical activities and progress of the patient involved, as well as features thereof. In one embodiment, the present disclosure provides an intelligent implant that achieves the benefit of a medical implant, e.g., the benefit afforded by a prosthesis which replaces or supplements a natural function of a patient, while also achieving the benefit of monitoring and reporting, which provides insight into the function and/or condition of the device and/or the patient who has received the implanted device. In one embodiment, the medical device is an implantable device that is an in vivo implantable prosthesis that can be implanted into the body of a living host (also referred to as a patient), for example, to improve the function of, or to replace, a biological structure or organ of the patient's body.

In one embodiment of the present disclosure, the medical implant is a stent graft and the intelligent implant is a stent graft coupled to a sensor, e.g., as disclosed in PCT Publication No. WO 2014/100795 and U.S. Pat. No. 9,949,692, as well as PCT Publication No. WO 2016/044651 and U.S. Patent Publ. No. 20160310077.

In one embodiment of the present disclosure, the medical implant is a stent and the intelligent implant is a stent coupled to a sensor, e.g., a stent monitoring assembly as disclosed in PCT Publication No. WO 2014/144070 and U.S. Patent Publ. No. 2016/0038087, as well as PCT Publication No. WO 2016/044651 and U.S. Patent Publ. No. 20160310077.

In one embodiment of the present disclosure, the medical implant is a hip replacement prosthesis including one or more of a femoral stem, femoral head and an acetabular implant, and the intelligent implant is a sensor coupled to the hip replacement prosthesis or a component thereof, e.g., a hip replacement as disclosed in PCT Publication No. WO 2014/144107 and U.S. Patent Publ. No. 2016/0029952, as well as PCT Publication No. WO 2016/044651 and U.S. Patent Publ. No. 20160310077.

In one embodiment of the present disclosure, the medical implant is a medical tube, and the intelligent implant is a medical tube coupled to a sensor. Medical tube refers to a generally cylindrical body which can be used in a medical procedure (e.g., the tubes are generally sterile, non-pyrogenic, and/or suitable for use and/or implantation into humans). For example, tubes can be utilized to: 1) bypass an obstruction (e.g., in the case of Coronary Artery Bypass Grafts, or "CABG" and peripheral bypass grafts) or open up an obstruction (balloon dilation catheters, angioplasty balloons); 2) to relieve pressure (e.g., shunts, drainage tubes and drainage catheters, urinary catheters); 3) to restore or support anatomical structures (e.g., endotracheal tubes, tracheostomy tubes, and feeding tubes); and 4) for access (e.g., CVC catheters, peritoneal and hemodialysis catheters). Representative examples of tubes include catheters, auditory or Eustachian tubes, drainage tubes, tracheotomy tubes (e.g., Durham's tube), endobronchial tubes, endotracheal tubes, esophageal tubes, feeding tubes (e.g., nasogastric or NG tubes), stomach tubes, rectal tubes, colostomy tubes, and a wide variety of grafts (e.g., bypass grafts). See, e.g., PCT Publication No. WO 2015/200718 and U.S. Patent Publ. No. 2017/0196478, as well as PCT Publication No. WO 2016/044651 and U.S. Patent Publ. No. 20160310077, for disclosure of medical tubes and sensors attached thereto. In one embodiment the medical tube is selected from a catheter, an auditory or Eustachian tubes a drainage tube, a tracheotomy tube, an endobronchial tube, an endotracheal tube, an esophageal tube, a feeding tube, a stomach tube, a rectal tube, and a colostomy tube.

In one embodiment of the present disclosure, the medical implant is an aesthetic (cosmetic) implant, and the intelligent implant is an aesthetic implant coupled to a sensor. An aesthetic implant refers to an artificial or synthetic prosthesis that has, or can be, implanted into a body. Implants are typically utilized to augment or replace a structure within the body, and have been utilized in a wide variety of aesthetic applications, including for example, for facial (e.g., lips, chin, nasal, nasal/labial fold and malar implants), penile, and body contouring (e.g., breast, pectoral, calf, buttocks, abdomen and biceps/triceps) implants. See, e.g., PCT Publication No. WO 2015/200704 and U.S. Patent Publ. No. 2017/

0181825, as well as PCT Publication No. WO 2016/044651 and U.S. Patent Publ. No. 20160310077, for disclosure of aesthetic implants and sensors attached thereto. In one embodiment the aesthetic implant is a breast implant.

In one embodiment of the present disclosure, the medical implant is a spinal implant, and the intelligent implant is a spinal implant coupled to a sensor. Examples of spinal devices and implants include pedicle screws, spinal rods, spinal wires, spinal plates, spinal cages, artificial discs, bone cement, as well as combinations of these (e.g., one or more pedicle screws and spinal rods, one or more pedicle screws and a spinal plate). In addition medical delivery devices for the placement of spinal devices and implants, along with one or more sensors, may also be an intelligent medical device according to the present disclosure. Examples of medical delivery devices for spinal implants include kyphoplasty balloons, catheters (including thermal catheters and bone tunnel catheters), bone cement injection devices, microdiscectomy tools and other surgical tools. See, e.g., PCT Publication No. WO 2015/200720 and U.S. Patent Publ. No. 2017/0196508, as well as PCT Publication No. WO 2016/044651 and U.S. Patent Publ. No. 20160310077, for disclosure of spinal implants and sensors attached thereto, and delivery devices with sensors attached thereto for the placement of spinal devices, any of which may be an intelligent medical devices or an intelligent implant of the present disclosure.

In one embodiment of the present disclosure, the medical device is a piece of orthopedic hardware, which may or may not be implantable, and the intelligent medical device is a sensor coupled to a piece of orthopedic hardware, which may or may not be implantable orthopedic hardware. Examples of orthopedic devices and implants include external hardware (e.g., casts, braces, external fixation devices, tensors, slings and supports) and internal hardware (e.g., K-wires, pins, screws, plates, and intramedullary devices (e.g., rods and nails)). In addition medical delivery devices for the placement of orthopedic devices and implants, along with one or more sensors, may also be an intelligent medical device of the present disclosure. Examples of medical delivery devices for orthopedic hardware include drills, drill guides, mallets, guidewires, catheters, bone tunneling catheters, microsurgical tools and general surgical tools. See, e.g., PCT Publication No. WO 2015/200722 and U.S. Patent Publ. No. 2017/0196499, as well as PCT Publication No. WO 2016/044651 and U.S. Patent Publ. No. 20160310077, for disclosure of orthopedic hardware and sensors attached thereto, and delivery devices with sensors for the placement of orthopedic hardware, all of which may be intelligent medical devices and intelligent implants of the present disclosure.

In one embodiment of the present disclosure, the medical device is a medical polymer that is used in a medical procedure. A wide variety of polymers may be used as a medical polymer, where the attached sensor may monitor the integrity and efficaciousness of the polymer (whether utilized alone, or as or with another medical device or implant). Medical polymers of the present disclosure can be formed into a vast array of shapes and sizes which are suitable for medical applications. Representative examples of polymer forms include solid forms such as films, sheets, molded, cast, or cut shapes. Other solid forms include extruded forms which can be made into tubes (e.g., shunts, drainage tubes, and catheters), and fibers which can be knitted into meshes or used to make sutures. Liquid forms of polymers include gels, dispersions, colloidal suspensions and the like. Particularly preferred polymers for use within the present disclosure are medical polymers which are provided in a sterile and/or non-pyrogenic form, and suitable for use in humans. Representative examples of polymers include polyester, polyurethanes, silicones, epoxy resin, melamine formaldehyde resin, acetal, polyethyelene terephthalate, polysulphone, polystyrene, polyvinyl chloride, polyamide, polyolefins, polycarbonate, polyethylene, polyamides, polimides, polypropylene, polytetrafluoroethylene, ethylene propylene diene rubber, styrenes (e.g., styrene butadiene rubber), nitriles (e.g., nitrile rubber), hypalon, polysulphide, butyl rubber, silicone rubber, cellulose, chitosan, fibrinogen, collagen, hyaluronic acid, PEEK, PTFE, PLA, PLGA, PCL and PMMA. See, e.g., PCT Publication No. WO 2015/200723 and U.S. Patent Publ. No. 2017/0189553, as well as PCT Publication No. WO 2016/044651 and U.S. Patent Publ. No. 20160310077, for disclosure of polymers and sensors attached thereto, all of which may be intelligent medical devices and intelligent implants of the present disclosure.

In one embodiment of the present disclosure, the medical device is a heart valve, and the intelligent medical device is a heart valve coupled to a sensor. "Heart valve" refers to a device which can be implanted into the heart of a patient with valvular disease. There are three principle types of heart valves: mechanical, biological, and tissue-engineered (although, for purposes of this disclosure tissue-engineered valves will be considered along with other biological valves). Mechanical valves typically fall into two categories: 1) heart valves for surgical procedures utilizing a sternotomy or "open heart" procedure (e.g., 'caged ball', 'tilting disc', bileaflet and trileaflet designs); and 2) heart valves which are percutaneously implanted (e.g., either a stent framed (self-expanding stent or balloon-expandable stent) or non-stent framed design) that can often contain valve cusps which are fabricated from biological sources (bovine or porcine pericardium). Tissue-based or 'biological' valves are typically made from either porcine or bovine sources, and are typically prepared either from the valve of the animal (e.g., a porcine valve), or from tissue of the pericardial sac (e.g., a bovine pericardial valve or a porcine pericardial valve). Tissue-engineered valves are valves that have been artificially created on a scaffold (e.g., through the growth of suitable cells on a tissue scaffold). Tissue-engineered valves have not yet been commercially adopted. See, e.g., PCT Publication No. WO 2015/200707 and U.S. Patent Publ. No. 2017/0196509, as well as PCT Publication No. WO 2016/044651 and U.S. Patent Publ. No. 20160310077, for disclosure of heart valves and sensors attached to heart valves which may be medical devices and intelligent medical devices, respectively, of the present disclosure. In embodiments, the heart valve is a mechanical heart valve, e.g., a caged ball design, a tilting disc mechanical valve, a bileaflet or trileaflet mechanical valve, a self-expanding percutaneous heart valve, a percutaneous heart valve, or a balloon-expandable percutaneous heart artificial valve. The medical device having a sensor may be a balloon delivery device for a balloon-expandable percutaneous heart valve.

In one embodiment, the medical implant replaces a joint of a patient, e.g., a knee, shoulder, or hip joint, and allows the patient to have the same, or nearly the same, mobility as would have been afforded by a healthy joint. When the medical implant replaces a joint, in one embodiment the sensor coupled to the implant can monitor displacement or movement. In general, there are three types of three-dimensional motion that sensors can detect within and round a joint: core gait (or limb mobility in the case of a shoulder or elbow arthroplasty), macroscopic instability, and microscopic instability. While these motions will be discussed associated with a TKA implant, it is understood they may also apply to total hip, shoulder, elbow, and ankle arthroplasty. See, e.g., PCT Publication Nos. WO 2014/144107, WO 2014/209916, WO 2016/044651, and WO 2017/165717 for disclosure of medical implants that may replace the joint of a patient, and intelligent versions thereof, for use in the present disclosure.

In one embodiment, the medical implant is a knee implant, and in particular a total knee implant for total knee arthroscopy. Sensors attached to the total knee implant of the present disclosure can monitor and characterize movement of the knee implant, where that movement may take the form of, e.g., core gait, macroscopic instability and microscopic instability as discussed below.

Figure 2:
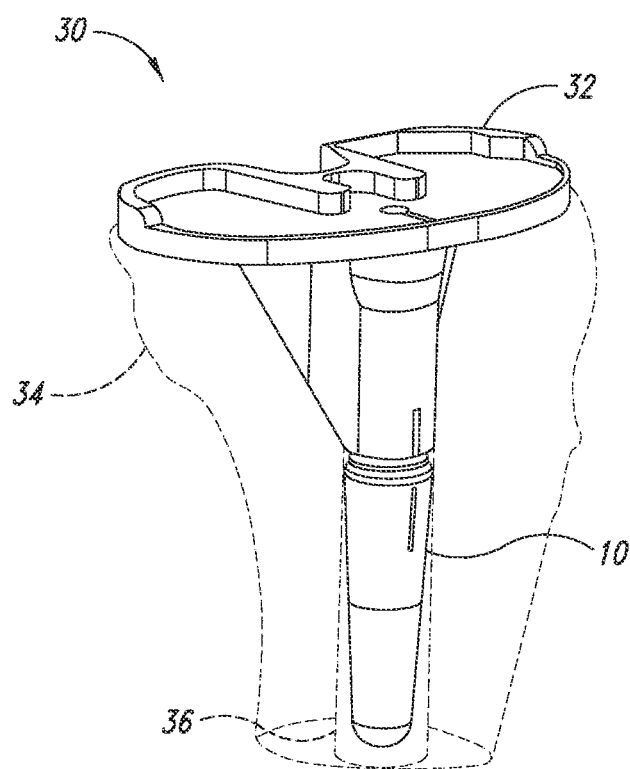
FIG. 2 illustrates including the implant of FIG. 1 as part of a joint prosthesis, and locating that prosthesis in a tibia.

FIG. 1 is a perspective view of an exemplary embodiment of a reporting processor 10 that can be utilized to implement the exemplary intelligent implant depicted in the exemplary embodiment shown in FIG. 2. In the embodiment shown in FIG. 1, the implantable reporting processor 10 includes an outer casing 12 that encloses a power component (battery) 14, an electronics assembly 16, and an antenna 20. One component of the casing is the radome 18, used to cover and protect the antenna which allows the implantable reporting processor to receive and transmit information. The outer casing 12 can include a set-screw engagement hole 22, which can be utilized to physically attach the reporting processor 10 to a tibial plate 32, as depicted in FIG. 2.

FIG. 2 is a perspective view of a tibial component 30 that can be utilized to implement one exemplary embodiment of the present disclosure. For example, the tibial component 30 shown in FIG. 2 can include an implanted medical device for a TKA, such as a tibial extension and the like. Referring to the exemplary embodiment shown in FIG. 2, the tibial component 30 includes a tibial plate 32 physically attached to an upper surface of a tibia 34. For example, the tibial plate 32 can be a base plate section of an artificial knee joint (prosthesis) that can be implanted during a surgical procedure, such as a TKA. Prior to, or during the surgical procedure, the implantable reporting processor 10 from FIG. 1 can be physically attached to the tibial plate 32 and also implanted into the tibia 34. For the exemplary embodiment shown in FIG. 2, the tibial component 30 includes the tibial plate 32 and the reporting processor 10, which are surgically implanted to form a tibial extension 36.

Core gait is described as the motion associated with basic locomotion. It occurs predominantly in the sagittal plane and has a frequency in the range of 0.5 Hz to 5 Hz. Most commonly, this can be thought of as the basic walking motion beginning with toe off, the leg swinging forward bending at the knee in combination with hip motion, the leg extending ending with a heel strike, and rolling on the foot back to a toe off position.

Macroscopic instability is a subset of motion within the core gait and is associated with musculoskeletal instability when loading the joint during the gait process. As an example, simplistically, this can be thought of as uncontrolled medial lateral and/or anterior posterior motion when getting out of a chair or walking up or down stairs and has a frequency in the range of 2 Hz to 20 Hz and would cover a range of motion from 5 mm to 10 cm.

Microscopic instability is a further subset of motion associated with motion within the TKA joint due to misalignment between the femoral component and the tibial plate and its tibial insert. This motion can occur in the anterior posterior plane and/or the medical lateral plane and has a frequency in the range of 5 Hz to 50 Hz covering a range of motion from 0.1 mm to 2 cm in any or a combination of these directions. This motion can be due to improper sizing of the implant at the initial procedure, changes in musculoskeletal structure associated with weight loss and/or further injury, and/or wear in the joint causing changes in the polymer puck geometry and associated fit with the femoral component. In addition, this motion may be caused by loosening of the tibial component itself due to bone subsidence and/or poor bone structure associated with osteoporosis or other metabolic disorders effecting bone density. It is also understood, that the noted microscopic instability may be due to a combination of the aforementioned motion modalities. Both macroscopic and microscopic instability can be associated with pain and decrease in quality of life metrics for a patient and may need intervention to resolve.

A sensor modality implanted in the bone and integrated into the TKA, or even a sensor implanted just in the bone and not necessarily coupled to the implant, resolves the signal fidelity and compliance limits of external devices. However, there is still an unmet need to identify the sensor data signatures indicative of instability, with sufficient fidelity to enable "early warning system" before onset of bone erosion, TKA hardware degradation, and pain that will require more invasive/expensive interventions. The present disclosure addresses this need.

In embodiments, the present disclosure provides method and devices that include: an implanted sensor coupled to TKA hardware and/or coupled to bone, where the sensor has sufficient sensitivity and specificity to detect motion of the tibia (or the tibial component of the TKI) consistent with identifying an instability signature. "Instability signature" is defined as having a characteristic frequency response of greater than about 20 Hz, or greater than about 25 Hz, or greater than about 30 Hz, and less than about 90 Hz, or less than about 100 Hz, or less than about 110 Hz, and indicates that the TKA hardware is not fixedly engaged with the tibia bone. Normal kinematic motions during normal human locomotion are typically less than about 20 Hz, while movement of the device associated with wear, abrasion, and lack of osteointegration (referred to collectively as degradation) is typically associated with movement of greater than 100 Hz. Device instability typically provides motion between about 20 Hz and about 100 Hz. The present disclosure provides a sensor coupled to an intelligent implant of the present disclosure which has sufficient dynamic range that it can detect and distinguish between normal kinematic motion (typically less than about 20 Hz), instability of the implant (typically about 20-100 Hz), and degradation, or lack of osteo-integration of the implant (typically greater than about 100 Hz). The sensor may have sufficient dynamic range that is high enough to not be saturated by normal kinematic motion, but sensitive enough detect small motions/impacts indicative of "instability signature". In addition, the sensor may have sufficient frequency response and sampling rate to differentiate without aliasing; i) normal kinematic motion, ii) instability signatures, and iii) degradation signatures.

In embodiments, the present disclosure provides medical devices coupled to a performing motion sensor (e.g., one or more of a sensor selected from accelerometer that detects acceleration, and a gyroscope), and also provides algorithms that can quantify the extent of instability; i.e., 1 mm movement vs. 2 mm movement or 5 degrees of movement vs. 10 degrees of movement, where the extend of instability is determined from a defined transient signature meeting the temporal and spectral definition. From this information, the extent of instability can be assessed over time and a "threshold for intervention" may be determined based on; i) clinical data, ii) anatomical thresholds, iii) TKA device design limits and analysis, as well as other factors.

In one aspect the present disclosure provides a reporting processor that is intended to be implanted with a medical device, e.g., a prosthesis, where the reporting processor monitors the state of the device after implantation, typically by obtaining kinematic data in the range of about 10-120 Hz. This reporting processor is also referred to as an implantable reporting processor or IRP. As discussed herein, the state of the device may include the integrity of the device, the movement of the device, the forces exerted on the device and other information relevant to the implanted device. The present disclosure also provides medical devices having a structure such that they can be readily fitted with an IRP. An implantable medical device that has been fitted with an IRP is referred to herein as an intelligent implant, in recognition that the implant is monitoring its own state or condition to thereby obtain data, where that data is stored in the implant and then as needed, that data is transmitted to a separate device for review by, e.g., a physician.

For example, an intelligent implantable device of the present disclosure having suitable internal electronic components can be utilized to monitor and measure the movements of a surgical patient's synthetic joint (prosthesis) implanted via a total knee arthroplasty (TKA), store the measurement data and unique identification information of the prosthetic components, and transfer the data to an external recipient (e.g., doctor, clinician, medical assistant, etc.) as required. The IRP will include one or more sensors, such as gyroscopes, accelerometers, and temperature and pressure sensors, and these sensors may be located anywhere within the IRP outer casing, e.g., they may all be located on the PC board. In one embodiment, e.g., when the intelligent implant is a joint prosthesis, the IRP makes kinematic measurements, and in another embodiment the IRP makes only kinematic measurements. Thus, an intelligent joint implant may include sensors for kinematic measurements, to determine the movements experienced by the implanted prosthesis.

The intelligent medical devices of the present disclosure may include a component for a total or partial joint replacement, such as occurs during a total knee arthroplasty (TKA) where the IRP may be a component of, or attached to, a tibial component, a femoral component and/or a tibial extension; or such as occurs during a hip replacement, where the IRP may be a component of, or attached to, the femoral component or the acetabular component for hip replacements; or such as occurs during a shoulder replacement, where the IRP may be a component of, or attached to, the humeral component for shoulder replacements. Other examples of a medical device that may be combined with an IRP to provide an intelligent implant include a breast implant, a lumbar interbody cage, a spinal artificial disc, a dynamic hip screw, and a leg intramedullary rod.

The IRP and the medical device are each intended to be implanted into a living subject, e.g., a mammal, e.g., a human, horse, dog, etc. Accordingly, in one embodiment the IRP is sterile, e.g., is treated with sterilizing radiation or is treated with ethylene oxide. In another embodiment, the intelligent implant comprising the IRP and the medical device is sterile, again optionally by treatment with sterilizing radiation or ethylene oxide, as two examples. In order to be protected from the in vivo environment, in one embodiment the IRP is hermetically sealed, so that fluids cannot enter into the IRP. The subject within whom the medical device has been implanted may alternatively be referred to herein as the patient. In one embodiment, the subject/patient is a human.

The implantable device needs to be sturdy as well as small or space-efficient because of the limited space within the body and/or within the prosthetic implant to place such devices. Challenges to the commercial success of an implantable device with internal electronic components and either internal or external transmitting antennae are that the devices and/or the transmitting antennae should not be unsuitably large, their power consumption should allow them to operate for a suitably long period of time, i.e., not for limited durations, and they should not be adversely affected by their local biologic environment. An IRP of the present disclosure may have suitable internal or external space-efficient and/or power-efficient antennae.

The intelligent implant will optionally have a power source needed to run the electronics inside the IRP that measures, records and transmits data concerning the state of the implant. Some medical implants already have a power supply. An example of an in-vivo implantable prosthesis that can improve the function of an organ and which has a power supply is an implantable atrial defibrillator, which detects when a heart enters into an abnormal rhythm commonly known as "atrial fibrillation," and which generates one or more electrical pulses to restore the heart to a normal sinus rhythm. Typically, this power supply is in the form of a battery.

Because the electrical charge on the battery may last a relatively short period of time, the prosthesis is typically located in a region of the body from which it is practical to remove the prosthesis to replace the battery, or to recharge the battery. For example, an atrial defibrillator is typically implanted just under the skin of a patient's chest. To replace the battery, a surgeon makes an incision, removes the old defibrillator, implants a new defibrillator containing a new battery, and closes the incision. Or, the patient or a physician, such as a cardiologist, recharges the battery, without removing the defibrillator from the subject, by placing, over the implanted defibrillator, a device that recharges the battery via inductive (sometimes called magnetic) coupling.

Unfortunately, removing a prosthesis to replace a battery is often undesirable, at least because it involves an invasive procedure that can be relatively expensive and that can have adverse side effects, such as infection and soreness. Although inductively recharging an implanted battery is non-invasive, it may be impractical or impossible to locate the prosthesis such that the battery may be inductively recharged. Additionally, the size of the coils necessary to transfer power are large relative to the device, and this can pose a problem in the limited space available within the body. The time for re-charging can be excessive, lack of coil alignment can cause excess heat generation, which potentially can damage surrounding tissue, and the inductive battery configuration can render the implant incompatible with MRI use. Additionally, battery chemistries that are compatible with recharging (i.e., secondary cell) generally have a significantly reduced energy-storage capacity in comparison to batteries of similar size constructed using non-rechargeable chemistries (i.e., primary cell).

An alternative that can overcome this latter problem is to implant the battery remotely from the implanted prosthesis in a location in which it is practical to inductively recharge the battery. An advantage of implanting the battery remotely from the implanted prosthesis is that the battery can be made larger, and thus longer lasting, than it would be if it were located inside of the prosthesis. But implanting the battery remotely from the implanted prosthesis can have several disadvantages. For example, even though the battery is suitably located for inductive recharging, the recharging equipment can be too expensive or too complex for home use, the patient may forget to recharge the device, and periodically visiting the doctor to recharge the battery may be inconvenient and expensive for the patient. Furthermore, it can be difficult to implant the wires used to couple the battery to the remote (from the battery) implanted prosthesis or if powering the implant sensors wirelessly from the rechargeable battery, the sensors may be limited in measurement capability. Moreover, because the battery is typically implanted just below the skin to heighten the inductive-coupling coefficient, it can be visible, and thus embarrassing, to the patient, and it can make the patient physically uncomfortable.

Thus, the implantable reporting process (IRP) may contain a power source (e.g., a battery) as well as mechanisms to manage the power output of an implanted power source, so that the power source will provide power for a sufficient period of time regardless of the location of the power source within a body of a patient. The IRP may contain the only power source present in the intelligent implant.

An example of a battery suitable for use with an implantable reporter processor includes a container sized to fit inside of bone of a living patient, and has a lifetime, such as years, that is sufficient to power the electronic circuitry within the implantable reporter processor for a period of time that is suitable for a prosthesis in which the implantable reporter processor is installed. The battery can be configured for disposal directly in the bone, or can be configured for disposal in a portion of the implantable reporting processor that is disposed in the bone. Or, the battery can be configured for disposal in a region of a living body other than a bone where it is impractical to recharge the battery, and where it is impractical to replace the battery before replacing a prosthesis or other device with which the battery is associated.

The IRP will typically comprise an outer casing that encloses a plurality of components. Exemplary suitable IRP components include a signal portal, an electronics assembly, and a power source. In one embodiment, the IRP does include each of a signal portal, an electronics assembly and a power source. The signal portal functions to receive and transmit wireless signals, and may contain, for example, an antenna for transmitting the wireless signals. The electronics assembly includes a circuit assembly which may comprise, e.g., a PC board and electrical components formed on one or more integrated circuits (ICs) or chips, such as a radio transmitter chip, a real-time clock chip, one or more sensor components, e.g., an Inertial Measurement Unit (IMU) chip, temperature sensor, pressure sensor, pedometer, a memory chip, and the like. In addition, the electronics assembly may include a header assembly which provides a communication interface between the circuit assembly and the signal portal (e.g., antenna). The power source provides the energy needed to operate the IRP, and may be, for example, a battery. The IRP will also include one or more sensors, such as gyroscopes, accelerometers, pedometers, and temperature and pressure sensors, and these sensors may be located anywhere within the IRP outer casing, e.g., they may all be located on the PC board. More precisely, an embodiment of the present disclosure is directed to space-efficient, printed-circuit assemblies (PCAs) for an implantable reporting processor (IRP). The implantable reporting processor may also include a plurality of transmitting antennae structured in different configurations. As such, an embodiment of the present disclosure is directed to a plurality of enhanced space-efficient and power-efficient antenna configurations for an implantable reporting processor, such as an IRP.

An example of an implantable reporting processor includes an outer casing, or housing, sized to fit in, or to form a part of, a prosthesis that has at least a portion designed to fit in a bone of a living patient. Electronic circuitry is disposed in the housing and is configured to provide, to a destination outside of a patient's body, information related to the prosthesis. The battery is also disposed in the housing and is coupled to the electronic circuitry.

An example of a prosthesis includes a receptacle for receiving the implantable reporting processor, which can be designed to fit into a cavity formed in a bone of a living patient. For example, the implantable reporting processor can be disposed in, or form part of, a tibial component or tibial extension of a knee prosthesis, where the tibial component or tibial extension is designed to fit into a cavity formed in the tibia of the living patient.

The power profile of the electronic circuitry of the implantable reporting processor can be configured so that the battery has a desired anticipated lifetime suitable for the type of prosthesis (or other device) with which the battery is associated. For example, such a desired anticipated lifetime may range from 1 to 15+ years, e.g., 10 years. An embodiment of such circuitry includes a supply node configured to be coupled to a battery, at least one peripheral circuit, a processing circuit coupled to the supply node and configured to couple the at least one peripheral circuit to the supply node, and a timing circuit coupled to the supply node and configured to activate the processing circuit at a set time or set times.

A base station may be provided to facilitate communications with the implantable reporting processor, and to act as an interface between the reporting processor and another computing system, such as a database or remote server on "the cloud," before and after the implantable reporting processor is implanted in the body of a patient as part of a prosthesis. The base station can have different configurations. For example, the base station can be configured for use by a surgeon or other professional before the prosthesis is implanted. The base station also can be configured for use in the residence of the patient. For example, the base station can be configured to poll the implantable reporting processor, periodically and automatically (for example, while the patient is sleeping), for information that the processor obtains or generates regarding the prosthesis, and to provide this information to the other computing system for storage or analysis via a wireless internet connection. And the base station can be configured for use in a doctor's office while the doctor is checking the operation and function of the prosthesis and the patient's health as it relates to the prosthesis. Furthermore, the network to which the base station belongs can include a voice-command device (e.g., Amazon Echo®, Amazon Dot®, Google Home®) that is configured to interact with the base station.

See, e.g., U.S. Publication No. 2016/0310077, titled Devices, Systems and Methods for Using and Monitoring Medical Devices, which is incorporated herein in its entirety, for disclosure of medical devices with sensors that may be used as an intelligent implant according to the present disclosure, optionally supplemented as described herein. See also, e.g., PCT Publication No. WO 2017/165717, titled Implantable Reporting Processor for an Intelligent Implant, which is incorporated herein in its entirety, for disclosure of medical devices with sensors that may be used as an intelligent implant according to the present disclosure, optionally supplemented as described herein.

B. Systems with Intelligent Implants

An intelligent implant may be a component of a system of the present disclosure that includes one or more of 1) a sensor that detects and/or measures the functioning of the implant and/or the immediate environment around the implant and/or the activity of the patient, 2) memory that stores data from that detection and/or measuring, 3) an antenna that transmits that data; 4) a base station that receives the data generated by the sensor and may transmit the data and/or analyzed data to a cloud-based location; 5) a cloud-based location where data may be stored and analyzed, and analyzed data may be stored and/or further analyzed; 6) a receiving terminal that receives output from the cloud-based location, where that receiving terminal may be accessed, e.g., by a health care professional or an insurance company or the manufacturer of the implant, and the output may identify the status of the implant and/or the functioning of the implant and/or the status of the patient who has received the implant, and may also provide recommendations for addressing any concerns raised by analysis of the original data. Systems of the present disclosure may be illustrated using a kinematic implantable device as the intelligent implant, as provided in the following paragraphs. However, these systems may be employed for any intelligent medical device, including the intelligent medical devices identified herein.

See, e.g., U.S. Publication No. 2016/0310077, titled Devices, Systems and Methods for Using and Monitoring Medical Devices, which is incorporated herein in its entirety, for disclosure of systems according to the present disclosure, optionally supplemented as described herein. See also, e.g., PCT Publication No. WO 2017/165717, titled Implantable Reporting Processor for an Intelligent Implant, which is incorporated herein in its entirety, for disclosure of systems according to the present disclosure, optionally supplemented as described herein.

C. Joint Implant and Systems with Joint Implant

Figure 3:
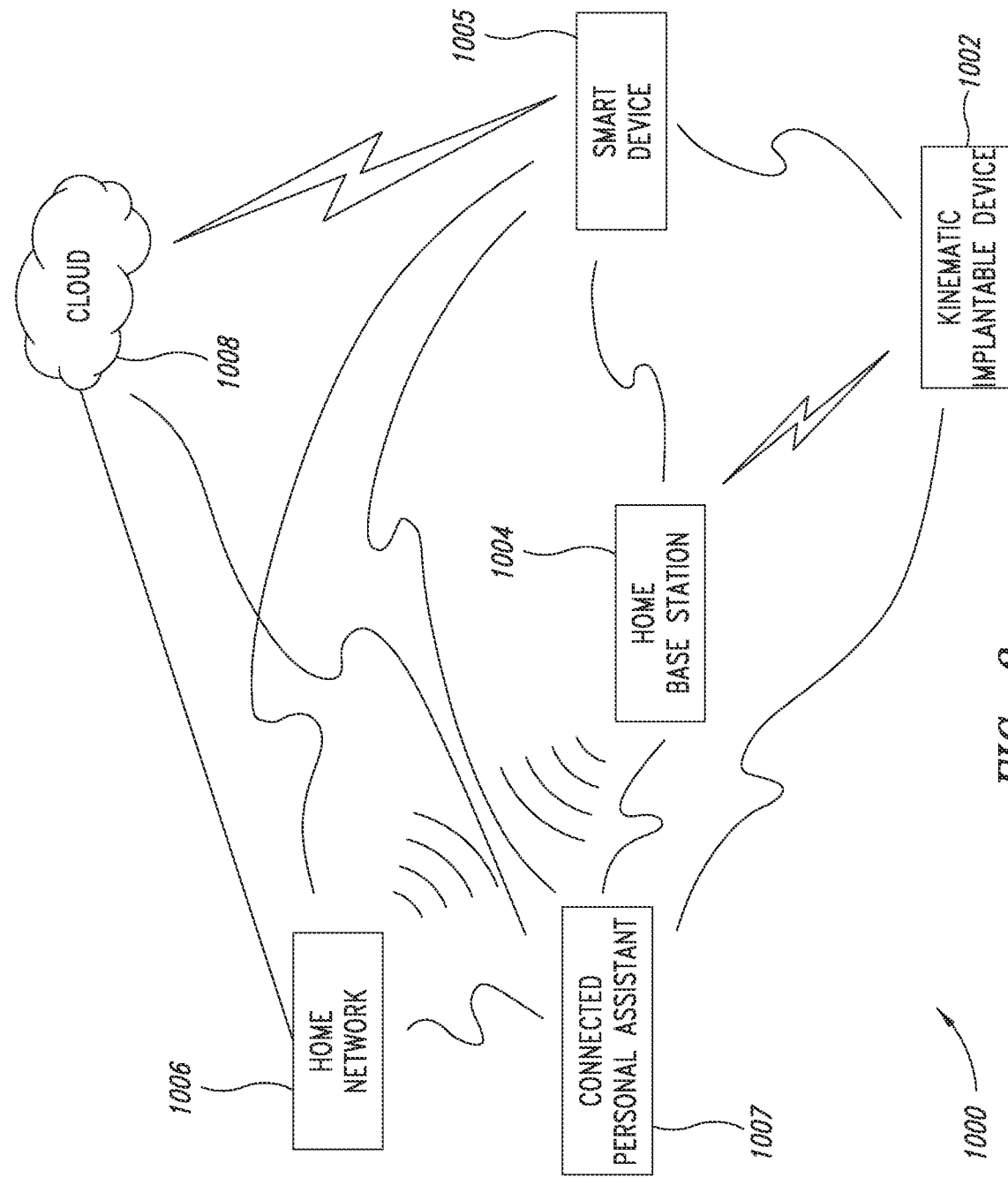
FIG. 3 is a context diagram of a kinematic implantable device environment in a patient's home, according to an embodiment.

FIG. 3 illustrates a context diagram of a kinematic implantable device environment 1000. In the environment, a kinematic implantable device 1002 is implanted by a medical practitioner (not shown in FIG. 3) in the body of a patient (not shown in FIG. 3). The kinematic implantable device 1002 is arranged to collect data including operational data of the device 1002 along with kinematic data associated with particular movement of the patient or particular movement of a portion of the patient's body, for example, one of the patient's knees. The kinematic implantable device 1002 communicates with one or more base stations or one or more smart devices during different stages of monitoring the patient.

For example, in association with a medical procedure, a kinematic implantable device 1002 is implanted in the patient's body. Coetaneous with the medical procedure, the kinematic implantable device 1002 communicates with an operating room base station (not shown in FIG. 3). Subsequently, after sufficient recovery from the medical procedure, the patient returns home wherein the kinematic implantable device 1002 is arranged to communicate with a home base station 1004. At other times, the kinematic implantable device 1002 is arranged to communicate with a doctor office base station (not shown in FIG. 3). The kinematic implantable device 1002 communicates with each base station via a short range network protocol, such as the medical implant communication service (MICS), the medical device radio communications service (MedRadio), or some other wireless communication protocol suitable for use with the kinematic implantable device 1002.

The kinematic implantable device 1002 is implanted into a body of a patient (not shown in FIG. 3). The kinematic implantable device 1002 may be a standalone medical device or it may be a component in a larger medical device, such as an artificial joint (e.g., a knee replacement, a hip replacement, a vertebral device, or the like), a breast implant, a femoral rod, or some other implanted medical device that can desirably collect and provide in situ kinematic data, operational data, or other useful data.

The kinematic implantable device 1002 includes one or more sensors to collect information and kinematic data associated with the use of the body part to which the kinematic implantable device 1002 is associated. For example, the kinematic implantable device 1002 may include an inertial measurement unit that includes gyroscope(s), accelerometer(s), pedometer(s), or other kinematic sensors to collect acceleration data for the medial/lateral, anterior/posterior, and anterior/inferior axes of the associated body part; angular velocity for the sagittal, frontal, and transvers planes of the associated body part; force, stress, tension, pressure, duress, migration, vibration, flexure, rigidity, or some other measurable data.

The kinematic implantable device 1002 collects data at various different times and at various different rates during a monitoring process of the patient. In some embodiments, the kinematic implantable device 1002 may operate in a plurality of different phases over the course of monitoring the patient so that more data is collected soon after the kinematic implantable device 1002 is implanted into the patient, but less data is collected as the patient heals and thereafter.

In one non-limiting example, the monitoring process of the kinematic implantable device 1002 may include three different phases. A first phase may last for four months where kinematic data is collected once a day for one minute, every day of the week. After the first phase, the kinematic implantable device 1002 transitions to a second phase that lasts for eight months and collects kinematic data once a day for one minute, two days a week. And after the second phase, the kinematic implantable device 1002 transitions to a third phase that last for nine years and collects kinematic data one day a week for one minute for the next nine years. Of course, the time periods associated with each phase may be longer, shorter, and otherwise controllable; for example, the time periods can be selected to be compatible with time periods specified by medical-insurance telemedicine codes so that a physician billing under telemedicine codes can collect the maximum reimbursement allowed by a medical insurer. The type and amount of data collected may also be controllable. The added benefit of this passive monitoring process is that after the first phase of monitoring, the patient will be unaware of when data is being collected. Thus, the collected data will be protected from potential bias.

Along with the various different phases, the kinematic implantable device 1002 can operate in various modes to detect different types of movements. In this way, when a predetermined type of movement is detected, the kinematic implantable device 1002 can increase, decrease, or otherwise control the amount and type of kinematic data and other data that is collected.

In one example, the kinematic implantable device 1002 may use a pedometer to determine if the patient is walking. If the kinematic implantable device 1002 measures that a determined number of steps crosses a threshold value within a predetermined time, then the kinematic implantable device 1002 may determine that the patient is walking. In response to the determination, the amount and type of data collected can be started, stopped, increased, decreased, or otherwise suitably controlled. The kinematic implantable device 1002 may further control the data collection based on certain conditions, such as when the patient stops walking, when a selected maximum amount of data is collected for that collection session, when the kinematic implantable device 1002 times out, or based on other conditions. After data is collected in a particular session, the kinematic implantable device 1002 may stop collecting data until the next day, the next time the patient is walking, after previously collected data is offloaded (e.g., by transmitting the collected data to the home base station 1004), or in accordance with one or more other conditions.

The amount and type of data collected by a kinematic implantable device 1002 may be different from patient to patient, and the amount and type of data collected may change for a single patient. For example, a medical practitioner studying data collected by the kinematic implantable device 1002 of a particular patient may adjust or otherwise control how the kinematic implantable device 1002 collects future data.

The amount and type of data collected by a kinematic implantable device 1002 may be different for different body parts, for different types of movement, for different patient demographics, or for other differences. Alternatively, or in addition, the amount and type of data collected may change overtime based on other factors, such as how the patient is healing or feeling, how long the monitoring process is projected to last, how much battery power remains and should be conserved, the type of movement being monitored, the body part being monitored, and the like. In some cases, the collected data is supplemented with personally descriptive information provided by the patient such as subjective pain data, quality of life metric data, co-morbidities, perceptions or expectations that the patient associates with the kinematic implantable device 1002, or the like.

In some embodiments, the kinematic implantable device 1002 is implanted into a patient to monitor movement or other aspects of a particular body part. Implantation of the kinematic implantable device 1002 into the patient may occur in an operating room. As used herein, operating room includes any office, room, building, or facility where the kinematic implantable device 1002 is implanted into the patient. For example, the operating room may be a typical operating room in a hospital, an operating room in a surgical clinic or a doctor's office, or any other operating theater where the kinematic implantable device 1002 is implanted into the patient.

The operating room base station (not shown in FIG. 3) is utilized to configure and initialize the kinematic implantable device 1002 in association with the kinematic implantable device 1002 being implanted into the patient. A communicative relationship is formed between the kinematic implantable device 1002 and the operating room base station, for example, based on a polling signal transmitted by the operating room base station and a response signal transmitted by the kinematic implantable device 1002.

Upon forming a communicative relationship, which will often occur prior to implantation of the kinematic implantable device 1002, the operating room base station (not shown in FIG. 3) transmits initial configuration information to the kinematic implantable device 1002. This initial configuration information may include, but is not limited to, a time stamp, a day stamp, an identification of the type and placement of the kinematic implantable device 1002, information on other implants associated with the kinematic implantable device, surgeon information, patient identification, operating room information, and the like.

In some embodiments, the initial configuration information is passed unidirectionally; in other embodiments, initial configuration is passed bidirectionally. The initial configuration information may define at least one parameter associated with the collection of kinematic data by the kinematic implantable device 1002. For example, the configuration information may identify settings for one or more sensors on the kinematic implantable device 1002 (e.g., accelerometer range, accelerometer output data rate, gyroscope range, gyroscope output data rate, and the like) for each of one or more modes of operation). The configuration information may also include other control information, such as an initial mode of operation of the kinematic implantable device 1002, a particular movement that triggers a change in the mode of operation, radio settings, data collection information (e.g., how often the kinematic implantable device 1002 wakes up to collected data, how long it collects data, how much data to collect), home base station 1004, smart device 1005, and connected personal assistant 1007 identification information, and other control information associated with the implantation or operation of the kinematic implantable device 1002. Examples of the connected personal assistant 1007, which also can be called a smart speaker, include Amazon Echo®, Amazon Dot®, Google Home®, Philips® patient monitor, Comcast's health-tracking speaker, and Apple HomePod®.

In some embodiments, the configuration information may be pre-stored on the operating room base station (not shown in FIG. 3) or an associated computing device. In other embodiments, a surgeon, surgical technician, or some other medical practitioner may input the control information and other parameters to the operating room base station for transmission to the kinematic implantable device 1002. In at least one such embodiment, the operating room base station may communicate with an operating room configuration computing device (not shown in FIG. 3). The operating room configuration computing device includes an application with a graphical user interface that enables the medical practitioner to input configuration information for the kinematic implantable device 1002. In various embodiments, the application executing on the operating room configuration computing device may have some of the configuration information predefined, which may or may not be adjustable by the medical practitioner.

The operating room configuration computing device (not shown in FIG. 100) communicates the configuration information to the operating room base station (not shown in FIG. 3) via a wired or wireless network connection (e.g., via a USB connection, Bluetooth connection, Bluetooth Low Energy (BTLE) connection, or Wi-Fi connection), which in turn communicates it to the kinematic implantable device 1002.

The operating room configuration computing device (not shown in FIG. 3) may also display information regarding the kinematic implantable device 1002 or the operating room base station (not shown in FIG. 3) to the surgeon, surgical technician, or other medical practitioner. For example, the operating room configuration computing device may display error information if the kinematic implantable device 1002 is unable to store or access the configuration information, if the kinematic implantable device 1002 is unresponsive, if the kinematic implantable device 1002 identifies an issue with one of the sensors or radio during an initial self-test, if the operating room base station (not shown in FIG. 3) is unresponsive or malfunctions, or for other reasons.

Although the operating room base station (not shown in FIG. 3) and the operating room configuration computing device (not shown in FIG. 3) are illustrated as separate devices, embodiments are not so limited; rather, the functionality of the operating room configuration computing device and the operating room base station may be included in a single computing device or in separate devices as illustrated. In this way, the medical practitioner may be enabled in one embodiment to input the configuration information directly into the operating room base station.

Once the kinematic implantable device 1002 is implanted into the patient and the patient returns home, the home base station 1004, the smart device 1005 (e.g., the patient's smart phone), the connected personal assistant 1007, or two or more of the home base station, and the smart device, and the connected personal assistant can communicate with the kinematic implantable device 1002. The kinematic implantable device 1002 can collect kinematic data at determined rates and times, variable rates and times, or otherwise controllable rates and times. Data collection can start when the kinematic implantable device 1002 is initialized in the operating room, when directed by a medical practitioner, or at some later point in time. At least some data collected by the kinematic implantable device 1002 may be transmitted to the home base station 1004 directly, to the smart device 1005 directly, to the connected personal assistant 1007 directly, to the base station via one or both of the smart device and the connected personal assistant, to the smart device via one or both of the base station and the connected personal assistant, or to the connected personal assistant via one or both of the smart device and the base station. Here, "one or both" means via an item alone, and via both items serially or in parallel. For example, data collected by the kinematic implantable device 1002 may be transmitted to the home base station 1004 via the smart device 1005 alone, via the connected personal assistant 1007 alone, serially via the smart device and the connected personal assistant, serially via the connected personal assistant and the smart device, and directly, and possibly contemporaneously, via both the smart device and the connected personal assistant. Similarly, data collected by the kinematic implantable device 1002 may be transmitted to the smart device 1005 via the home base station 1004 alone, via the connected personal assistant 1007 alone, serially via the home base station and the connected personal assistant, serially via the connected personal assistant and the home base station, and directly, and possibly contemporaneously, via both the home base station and the connected personal assistant. Further in example, data collected by the kinematic implantable device 1002 may be transmitted to the connected personal assistant 1007 via the smart device 1005 alone, via the home base station 1004 alone, serially via the smart device and the home base station, serially via the home base station and the smart device, and directly, and possibly contemporaneously, via both the smart device and the home base station.

In various embodiments, one or more of the home base station 1004, the smart device 1005, and the connected personal assistant 1007 pings the kinematic implantable device 1002 at periodic, predetermined, or other times to determine if the kinematic implantable device 1002 is within communication range of one or more of the home base station, the smart device, and the connected personal assistant. Based on a response from the kinematic implantable device 1002, one or more of the home base station 1004, the smart device 1005, and the connected personal assistant 1007 determines that the kinematic implantable device 1002 is within communication range, and the kinematic implantable device 1002 can be requested, commanded, or otherwise directed to transmit the data it has collected to one or more of the home base station 1004, the smart device 1005, and the connected personal assistant 1007.

Each of one or more of the home base station 1004, the smart device 1005, and the connected personal assistant 1007 may, in some cases, be arranged with a respective optional user interface. The user interface may be formed as a multimedia interface that unidirectionally or bidirectionally passes one or more types of multimedia information (e.g., video, audio, tactile, etc.). Via the respective user interface of one or more of the home base station 1004, the smart device 1005, and the connected personal assistant 1007, the patient (not shown in FIG. 3) or an associate (not shown in FIG. 3) of the patient may enter other data to supplement the kinematic data collected by the kinematic implantable device 1002. A user, for example, may enter personally descriptive information (e.g., age change, weight change), changes in medical condition, co-morbidities, pain levels, quality of life, an indication of how the implanted prosthesis 1002 "feels," or other subjective metric data, personal messages for a medical practitioner, and the like. In these embodiments, the personally descriptive information may be entered with a keyboard, mouse, touch-screen, microphone, wired or wireless computing interface, or some other input means. In cases where the personally descriptive information is collected, the personally descriptive information may include, or otherwise be associated with, one or more identifiers that associate the information with unique identifier of the kinematic implantable device 1002, the patient, an associated medical practitioner, an associated medical facility, or the like.

In some of these cases, a respective optional user interface of each of one or more of the home base station 1004, the smart device 1005, and the connected personal device 1007 may also be arranged to deliver information associated with the kinematic implantable device 1002 to the user from, for example, a medical practitioner. In these cases, the information delivered to the user may be delivered via a video screen, an audio output device, a tactile transducer, a wired or wireless computing interface, or some other like means.

In embodiments where one or more of the home base station 1004, the smart device 1005, and the connected personal assistant 1007 are arranged with a user interface, which may be formed with an internal user interface arranged for communicative coupling to a patient portal device. The patent portal device may be smartphone, a tablet, a body-worn device, a weight or other health measurement device (e.g., thermometer, bathroom scale, etc.), or some other computing device capable of wired or wireless communication. In these cases, the user is able to enter the personally descriptive information, and the user also may be able to receive information associated with the implantable device 1002.

The home base station 1004 utilizes a home network 1006 of the patient to transmit the collected data (i.e., kinematic data and in some cases, personally descriptive information) to cloud 1008. The home network 1006, which may be a local area network, provides access from the home of the patient to a wide area network, such as the internet. In some embodiments, the home base station 1004 may utilize a Wi-Fi connection to connect to the home network 1006 and access the internet. In other embodiments, the home base station 1004 may be connected to a home computer (not shown in FIG. 3) of the patient, such as via a USB connection, which itself is connected to the home network 1006.

The smart device 1005 can communicate with the kinematic implantable device 1002 directly via, for example, Blue Tooth® compatible signals, and can utilize the home network 1006 of the patient to transmit the collected data (i.e., kinematic data and in some cases, personally descriptive information) to cloud 1008, or can communicate directly with the cloud, for example, via a cellular network. Alternatively, the smart device 1005 is configured to communicate directly with one or both of the base station 1004 and the connected personal assistant 1007 via, for example, Blue Tooth® compatible signals, and is not configured to communicate directly with the kinematic implantable device 1002.

Furthermore, the connected personal assistant 1007 can communicate with the kinematic implantable device 1002 directly via, for example, Blue Tooth® compatible signals, and can utilize the home network 1006 of the patient to transmit the collected data (i.e., kinematic data and in some cases, personally descriptive information) to cloud 1008, or can communicate directly with the cloud, for example, via a modem/internet connection or a cellular network. Alternatively, the connected personal assistant 1007 is configured to communicate directly with one or both of the base station 1004 and the smart device 1005 via, for example, Blue Tooth® compatible signals, and is not configured to communicate directly with the kinematic implantable device 1002.

Along with transmitting collected data to the cloud 1008, one or more of the home base station 1004, the smart device 1005, and the connected personal assistant 1007 may also obtain data, commands, or other information from the cloud 1008 directly or via the home network 1006. One or more of the home base station 1004, the smart device 1005, and the connected personal assistant 1007 may provide some or all of the received data, commands, or other information to the kinematic implantable device 1002. Examples of such information include, but are not limited to, updated configuration information, diagnostic requests to determine if the kinematic implantable device 1002 is functioning properly, data collection requests, and other information.

The cloud 1008 may include one or more server computers or databases to aggregate data collected from the kinematic implantable device 1002, and in some cases personally descriptive information collected from a patient (not shown in FIG. 3), with data collected from other kinematic implantable devices (not illustrated), and in some cases personally descriptive information collected from other patients. In this way, the cloud 1008 can create a variety of different metrics regarding collected data from each of a plurality of kinematic implantable devices that are implanted into separate patients. This information can be helpful in determining if the kinematic implantable devices are functioning properly. The collected information may also be helpful for other purposes, such as determining which specific devices may not be functioning properly, determining if a procedure or condition associated with the kinematic implantable device is helping the patient (e.g., if the knee replacement is operating properly and reducing the patient's pain), and determining other medical information.

At various times throughout the monitoring process, the patient may be requested to visit a medical practitioner for follow up appointments. This medical practitioner may be the surgeon who implanted the kinematic implantable device 1002 in the patient or a different medical practitioner that supervises the monitoring process, physical therapy, and recovery of the patient. For a variety of different reasons, the medical practitioner may want to collect real-time data from the kinematic implantable device 1002 in a controlled environment. In some cases, the request to visit the medical practitioner may be delivered through a respective optional bidirectional user interface of each of one or more of the home base station 1004, the smart device 1005, and the connected personal assistant 1007.

A medical practitioner utilizes the doctor office base station (not shown in FIG. 3), which communicates with the kinematic implantable device 1002, to pass additional data between the doctor office base station and the kinematic implantable device 1002. Alternatively, or in addition, the medical practitioner utilizes the doctor office base station (not shown in FIG. 3) to pass commands to the kinematic implantable device 1002. In some embodiments, the doctor office base station instructs the kinematic implantable device 1002 to enter a high-resolution mode to temporarily increase the rate or type of data that is collected for a short time. The high-resolution mode directs the kinematic implantable device 1002 to collect different (e.g., large) amounts of data during an activity where the medical practitioner is also monitoring the patient.

In some embodiments, the doctor office base station (not shown in FIG. 3) enables the medical practitioner to input event or pain markers, which can be synchronized with the high-resolution data collected by the kinematic implantable device 1002. For example, assume the kinematic implantable device 1002 is a component in a knee replacement. The medical practitioner can have the patient walk on a treadmill while the kinematic implantable device 1002 is in the high-resolution mode. As the patient walks, the patient may complain about pain in his/her knee. The medical practitioner can click a pain marker button on the doctor office base station to indicate the patient's discomfort. The doctor office base station records the marker and the time at which the marker was input. When the timing of this marker is synchronized with the timing of the collected high-resolution data, the medical practitioner can analyze the data to try and determine the cause of the pain.

In other embodiments, the doctor office base station (not shown in FIG. 3) may provide updated configuration information to the kinematic implantable device 1002. The kinematic implantable device 1002 can store this updated configuration information, which can be used to adjust the parameters associated with the collection of the kinematic data. For example, if the patient is doing well, the medical practitioner can direct a reduction in the frequency at which the kinematic implantable device 1002 collects data. On the contrary, if the patient is experiencing an unexpected amount of pain, the medical practitioner may direct the kinematic implantable device 1002 to collect additional data for a determined period of time (e.g., a few days). The medical practitioner may use the additional data to diagnose and treat a particular problem. In some cases, the additional data may include personally descriptive information provided by the patient (not shown in FIG. 3) after the patient has left presence of the medical practitioner and is no longer in range of the doctor office base station. In these cases, the personally descriptive information may be collected and delivered from via one or more of the home base station 1004, the smart device 1005, and the connected personal assistant 1007. Firmware within the kinematic implantable device and/or the base station will provide safeguards limiting the duration of such enhanced monitoring to insure the battery retains sufficient power to last for the implant's lifecycle.

In various embodiments, the doctor office base station (not shown in FIG. 3) may communicate with a doctor office configuration computing device (not shown in FIG. 3). The doctor office configuration computing device includes an application with a graphical user interface that enables the medical practitioner to input commands and data. Some or all of the commands, data, and other information may be later transmitted to the kinematic implantable device 1002 via the doctor office base station. For example, in some embodiments, the medical practitioner can use the graphical user interface to instruct the kinematic implantable device 1002 to enter its high-resolution mode. In other embodiments, the medical practitioner can use graphical user interface to input or modify the configuration information for the kinematic implantable device 1002. The doctor office configuration computing device transmits the information (e.g., commands, data, or other information) to the doctor office base station via a wired or wireless network connection (e.g., via a USB connection, Bluetooth connection, or Wi-Fi connection), which in turn transmits some or all of the information to the kinematic implantable device 1002.

The doctor office configuration computing device (not shown in FIG. 3) may also display, to the medical practitioner, other information regarding the kinematic implantable device 1002, regarding the patient (e.g., personally descriptive information), or the doctor office base station. For example, the doctor office configuration computing device may display the high-resolution data that is collected by the kinematic implantable device 1002 and transmitted to the doctor office base station (not shown in FIG. 3). The doctor office configuration computing device may also display error information if the kinematic implantable device 1002 is unable to store or access the configuration information, if the kinematic implantable device 1002 is unresponsive, if the kinematic implantable device 1002 identifies an issue with one of the sensors or radio, if the doctor office base station is unresponsive or malfunctions, or for other reasons.

In some embodiments, doctor office configuration computing device (not shown in FIG. 3) may have access to the cloud 1008. In at least one embodiment, the medical practitioner can utilize the doctor office configuration computing device to access data stored in the cloud 1008, which was previously collected by the kinematic implantable device 1002 and transmitted to the cloud 1008 via one or both of the home base station 1004 and smart device 1005. Similarly, the doctor office configuration computing device can transmit the high-resolution data obtain from the kinematic implantable device 1002 via the doctor office base station to the cloud 1008. In some embodiments, the doctor office base station may have internet access and may be enabled to transmit the high-resolution data directly to the cloud 1008 without the use of the doctor office configuration computing device.

In various embodiments, the medical practitioner may update the configuration information of the kinematic implantable device 1002 when the patient is not in the medical practitioner's office. In these cases, the medical practitioner can utilize the doctor office configuration computing device (not shown in FIG. 3) to transmit updated configuration information to the kinematic implantable device 1002 via the cloud 1008. One or more of the home base station 1004, the smart device 1005, and the connected personal assistant 1007 can obtain updated configuration information from the cloud 1008 and pass updated configuration information to the cloud. This can allow the medical practitioner to remotely adjust the operation of the kinematic implantable device 1002 without needing the patient to come to the medical practitioner's office. This may also permit the medical practitioner to send messages to the patient (not shown in FIG. 3) in response, for example, to personally descriptive information that was provided by the patient and passed through one or more of the home base station 1004, the smart device 1005, and the connected personal assistant 1007 to the doctor office base station (not shown in FIG. 3). For example, if a patient with a knee prosthesis speaks "my leg hurts when I walk" into the connected personal assistant 1007, then the medical practitioner may issue a prescription for a pain reliever and cause the connected personal assistant to notify the patient by "speaking" "the doctor has called in a prescription for Vicodin® to your preferred pharmacy; the prescription will be ready for pick up at 4 pm."

Although the doctor office base station (not shown in FIG. 3) and the doctor office configuration computing device (not shown in FIG. 3) are described as separate devices, embodiments are not so limited; rather, the functionality of the doctor office configuration computing device and the doctor office base station may be included in a single computing device or in separate devices (as illustrated). In this way, the medical practitioner may be enabled in one embodiment to input the configuration information or markers directly into the doctor office base station and view the high-resolution data (and synchronized marker information) from a display on the doctor office base station.

Still referring to FIG. 3, alternate embodiments are contemplated. For example, one or two of the home base station 1004, the smart device 1005, and the connected personal assistant 1007 may be omitted from the kinematic implantable device environment 1000. Furthermore, each of the base station 1004, the smart device 1005, and the connected personal assistant 1007 may be configured to communicate with one or both of the implantable device 1002 and the cloud 1008 via another one or two of the base station, the smart device, and the connected personal assistant. Moreover, the smart device 1005 can be temporarily contracted as an interface to the implantable prosthesis 1002, and can be any suitable device other than a smart phone, such as a smart watch, a smart patch, and any IoT device, such as a coffee pot, capable of acting as an interface to the implantable device 1002. In addition, one or more of the base station 1004, smart device 1005, and connected personal assistant 1007 can act as a communication hub for multiple prostheses implanted in one or more patients. Furthermore, one or more of the base station 1004, smart device 1005, and connected personal assistant 1007 can automatically order or reorder prescriptions or medical supplies (e.g., a knee brace) in response to patient input or implantable-prosthesis input (e.g., pain level, instability level) if a medical professional and insurance company have preauthorized such an order or reorder; alternatively, one or more of the base station, smart device, and connected personal assistant can be configured to request, from a medical professional or an insurance company, authorization to place the order or reorder. Moreover, one or more of the base station 1004, smart device 1005, and connected personal assistant 1007 can be configured with a personal assistant such as Alexa® or Siri®. In addition, one or more alternate embodiments described below in conjunction with FIGS. 4-27 may be applicable to the kinematic implantable device environment 1000.

Figure 4:
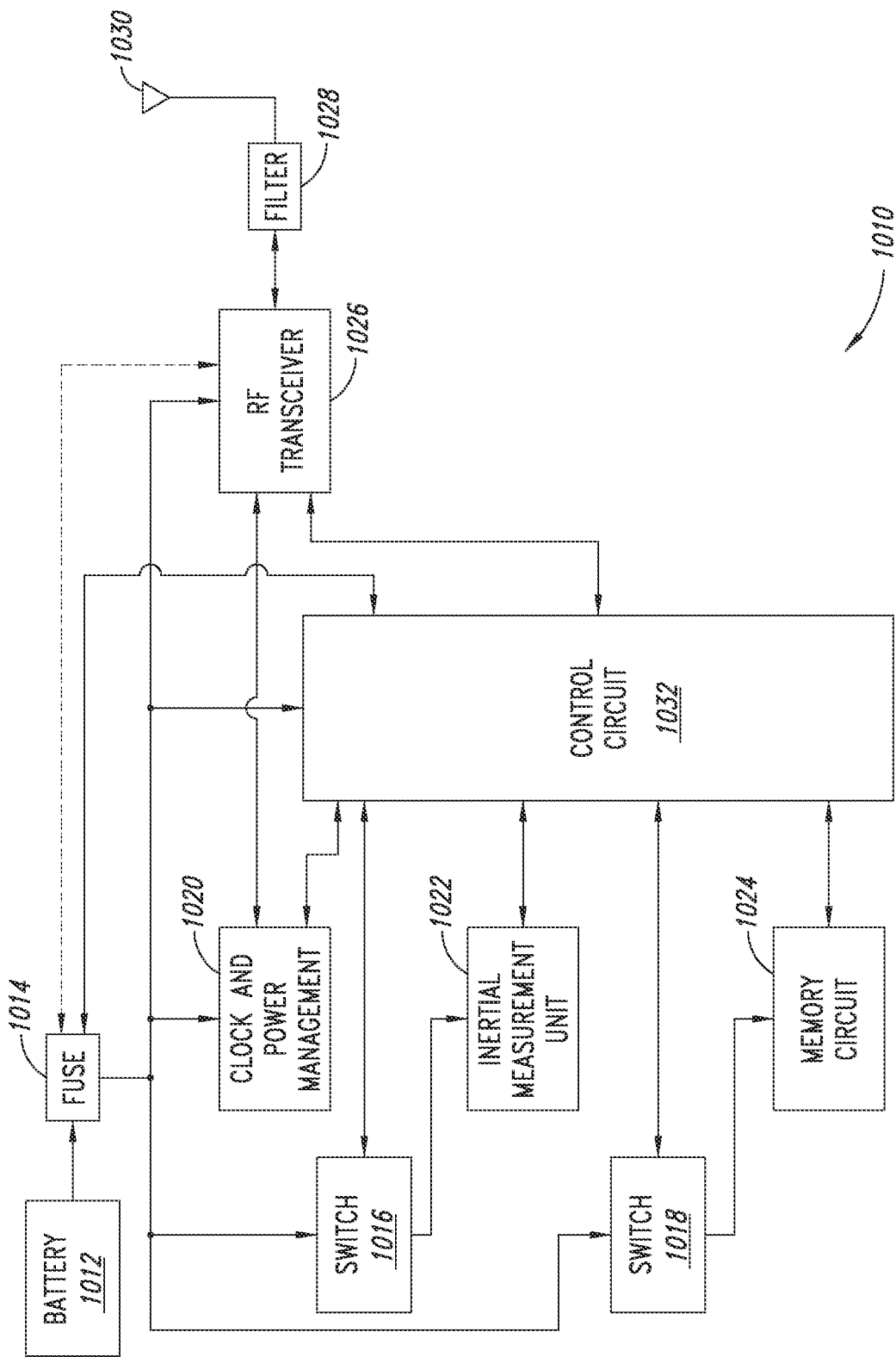
FIG. 4 is a block diagram of an implantable circuit for an implantable prosthesis, such as an implantable knee prosthesis, where the circuit includes an implantable reporting processor (IRP), according to an embodiment.

FIG. 4 is a diagram of an implantable circuit 1010, which is configured for inclusion within, or otherwise for use with, an alert kinematic implant such as a knee prosthesis implantable as part of a total knee arthroplasty (TKA).

The circuit 1010 is powered by a battery, or other suitable implantable power source, 1012, and includes a fuse 1014, switches 1016 and 1018, a clock generator and power-management unit 1020, an inertial measurement unit (IMU) 1022, a memory circuit 1024, a radio-frequency (RF) transceiver 1026, an RF filter 1028, an RF-compatible antenna 1030, and a control circuit 1032. Examples of some or all of these components are described elsewhere in this application or in U.S. Ser. No. 16/084,544, which is incorporated by reference in all jurisdictions which allow incorporation by reference.

The battery 1012 can be any suitable battery, such as a Lithium Carbon Monofluoride (LiCFx) battery, or other storage cell configured to store energy for powering the circuit 1000 for an expected lifetime (e.g., 5-25+ years) of the kinematic implant.

The fuse 1014 can be any suitable fuse (e.g., permanent) or circuit breaker (e.g., resettable) configured to prevent the battery 1012, or a current flowing from the battery, from injuring the patient and damaging the battery and one or more components of the circuit 1000. For example, the fuse 1014 can be configured to prevent the battery 1012 from generating enough heat to burn the patient, to damage the circuit 1000, to damage the battery, or to damage structural components of the kinematic implant.

The switch 1016 is configured to couple the battery 1012 to, or to uncouple the battery from, the IMU 1022 in response to a control signal from the control circuit 1032. For example, the control circuit 1032 may be configured to generate the control signal having an open state that causes the switch 1016 to open, and, therefore, to uncouple power from the IMU 1022, during a sleep mode or other low-power mode to save power, and, therefore, to extend the life of the battery 1012. Likewise, the control circuit 1032 also may be configured to generate the control signal having a closed state that causes the switch 1016 to close, and therefore, to couple power to the IMU 1022, upon "awakening" from a sleep mode or otherwise exiting another low-power mode. Such a low-power mode may be for only the IMU 1022 or for the IMU and one or more other components of the implantable circuit 1010.

The switch 1018 is configured to couple the battery 1012 to, or to uncouple the battery from, the memory circuit 1024 in response to a control signal from the control circuit 1032. For example, the control circuit 1032 may be configured to generate the control signal having an open state that causes the switch 1018 to open, and, therefore, to uncouple power from the memory 1024, during a sleep mode or other low-power mode to save power, and, therefore, to extend the life of the battery 1012. Likewise, the control circuit 1032 also may be configured to generate the control signal having a closed state that causes the switch 1018 to close, and therefore, to couple power to the memory 1024, upon "awakening" from a sleep mode or otherwise exiting another low-power mode. Such a low-power mode may be for only the memory circuit 1024 or for the memory circuit and one or more other components of the implantable circuit 1010.

The clock and power management circuit 1020 can be configured to generate a clock signal for one or more of the other components of the implantable circuit 1010, and can be configured to generate periodic commands or other signals (e.g., interrupt requests) in response to which the control circuit 1032 causes one or more components of the implantable circuit to enter or to exit a sleep, or other low-power, mode. The clock and power management circuit 1020 also can be configured to regulate the voltage from the battery 1012, and to provide a regulate power-supply voltage to some or all of the other components of the implantable circuit 1010.

The IMU 1022 has a frame of reference with coordinate x, y, and z axes, and can be configured to measure, or to otherwise quantify, acceleration that the IMU experiences along each of the x, y, and z axes, and angular velocity that the IMU experiences about each of the x, y, and z axes. Such a configuration of the IMU 1022 is at least a six-axis configuration, because the IMU 1022 measures six unique quantities, $acc_x(t)$, $acc_y(t)$, $acc_z(t)$, $\Omega_x(t)$, $\Omega_y(t)$, and $\Omega_z(t)$. Alternatively, the IMU 1022 can be configured in a nine-axis configuration, in which the IMU can use gravity to compensate for, or to otherwise correct for, accumulated errors in $acc_x(t)$, $acc_y(t)$, $acc_z(t)$, $\Omega_x(t)$, $\Omega_y(t)$, and $\Omega_z(t)$. But in an embodiment in which the IMU measures acceleration and angular velocity over only short bursts (e.g., 0.10-100 seconds(s)), for many applications accumulated error typically can be ignored without exceeding respective error tolerances. The IMU 1022 can include a respective analog-to-digital converter (ADC) for each of the x, y, and z accelerometers and gyroscopes. Alternatively, the IMU 1022 can include a respective sample-and-hold circuit for each of the x, y, and z accelerometers and gyroscopes, and as few as one ADC that is shared by the accelerometers and gyroscopes. Including fewer than one ADC per accelerometer and gyroscope can decrease one or both of the size and circuit density of the IMU 1022, and can reduce the power consumption of the IMU. But because the IMU 1022 includes a respective sample-and-hold circuit for each accelerometer and each gyroscope, samples of the analog signals generated by the accelerometers and the gyroscopes can be taken at the same or different sample times, at the same or different sample rates, and with the same or different output data rates (ODR).

The memory circuit 1024 can be any suitable nonvolatile memory circuit, such as EEPROM or FLASH memory, and can be configured to store data written by the control circuit 1032, and to provide data in response to a read command from the control circuit.

The RF transceiver 1026 can be a conventional transceiver that is configured to allow the control circuit 1032 (and optionally the fuse 1014) to communicate with a base station (not shown in FIG. 4) configured for use with the kinematic implantable device. For example, the RF transceiver 1026 can be any suitable type of transceiver (e.g., Bluetooth, Bluetooth Low Energy (BTLE), and WiFi®), can be configured for operation according to any suitable protocol (e.g., MICS, ISM, Bluetooth, Bluetooth Low Energy (BTLE), and WiFi®), and can be configured for operation in a frequency band that is within a range of 1 MHz-5.4 GHz, or that is within any other suitable range.

The filter 1028 can be any suitable bandpass filter, such as a surface acoustic wave (SAW) filter or a bulk acoustic wave (BAW) filter.

The antenna 1030 can be any antenna suitable for the frequency band in which the RF transceiver 1026 generates signals for transmission by the antenna, and for the frequency band in which a base station (not shown in FIG. 4) generates signals for reception by the antenna.

The control circuit 1032, which can be any suitable implantable reporting processor (IRP) such as a microcontroller or microprocessor, is configured to control the configuration and operation of one or more of the other components of the implantable circuit 1010. For example, the control circuit 1032 is configured to control the IMU 1022 to take measurements of movement of the implantable prosthesis with which the implantable circuit 1010 is associated, to quantify the quality of such measurements (e.g., is the measurement "good" or "bad"), to store, in the memory 1024, measurement data generated by the IMU, to generate messages include the stored data as a payload, to packetize the messages, to provide the message packets to the RF transceiver 1026 for transmission to the base station (not shown in FIG. 4). The control circuit 1032 also can be configured to execute commands received from a base station (not shown in FIG. 4) via the antenna 1030, filter 1028, and RF transceiver 1026. For example, the control circuit 1032 can be configured to receive configuration data from the base station, and to provide the configuration data to the component of the implantable circuit 1010 to which the base station directed the configuration data. If the base station directed the configuration data to the control circuit 1032, then the control circuit is configured to configure itself in response to the configuration data.

Still referring to FIG. 4, operation of the circuit 1010 is described, according to an embodiment in which an implantable prosthesis in which the circuit is disposed, or with which the circuit is otherwise associated, is implanted in a patient (not shown in FIG. 4).

The fuse 1014, which is normally electrical closed, is configured to open electrically in response to an event that can injure the patient in which the implantable circuit 1010 resides, or damage the battery 1012 of the implantable circuit, if the event persists for more than a safe length of time. An event in response to which the fuse 1014 can open electrically includes an overcurrent condition, an overvoltage condition, an overtemperature condition, an over-current-time condition, and over-voltage-time condition, and an over-temperature-time condition. An overcurrent condition occurs in response to a current through the fuse 1014 exceeding an overcurrent threshold. Likewise, an overvoltage condition occurs in response to a voltage across the fuse 1014 exceeding an overvoltage threshold, and an overtemperature condition occurs in response to a temperature of the fuse exceeding a temperature threshold. An over-current-time condition occurs in response to an integration of a current through the fuse 1014 over a measurement time window (e.g., ten seconds) exceeding a current-time threshold, where the window can "slide" forward in time such that the window always extends from the present time back the length, in units of time, of the window. Alternatively, an over-current-time condition occurs if the current through the fuse 1014 exceeds an overcurrent threshold for more than a threshold time. Similarly, an over-voltage-time condition occurs in response to an integration of a voltage across the fuse 1014 over a measurement time window, and an over-temperature-time condition occurs in response to an integration of a temperature of the fuse over a measurement time window. Alternatively, an over-voltage-time condition occurs if the voltage across the fuse 1014 exceeds an overvoltage threshold for more than a threshold time, and an over-temperature-time condition occurs if a temperature associated with the fuse 1014, battery 1012, or implantable circuit 1010 exceeds an overtemperature threshold for more than a threshold time. But even if the fuse 1014 opens, thus uncoupling power from the implantable circuit 1010, the mechanical and structural components of the kinematic prosthesis (not shown in FIG. 4) with which the implantable circuit is associated are still fully operational. For example, if the kinematic prosthesis is a knee prosthesis, then the knee prosthesis still can function fully as a patient's knee; abilities lost, however, are the abilities to detect and to measure kinematic motion of the prosthesis, to generate and to store data representative of the measured kinematic motion, and to provide the stored data to a base station or other destination external to the kinematic prosthesis. Operation of the fuse is further described below in conjunction with FIG. 27.

The control circuit 1032 is configured to cause the IMU 1022 to measure, in response to a movement of the kinematic prosthesis with which the implantable circuit 1010 is associated, the movement over a window of time (e.g., ten seconds, twenty seconds, one minute), to determine if the measured movement is a qualified movement, to store the data representative of a measured qualified movement, and to cause the RF transceiver 1026 to transmit the stored data to a base station or other source external to the prosthesis.

For example, the IMU 1022 can be configured to begin sampling the sense signals output from its one or more accelerometers and one or more gyroscopes in response to a detected movement within a respective time period (day), and the control circuit 1032 can analyze the samples to determine if the detected movement is a qualified movement. Further in example, the IMU 1022 can detect movement in any conventional manner, such as by movement of one or more of its one or more accelerometers. In response to the IMU 1022 notifying the control circuit 1032 of the detected movement, the control circuit can correlate the samples from the IMU to stored accelerator and gyroscope samples generated with a computer simulation or while the patient, or another patient, is walking normally, and can measure the time over which the movement persists (the time equals the number of samples times the inverse of the sampling rate). If the samples of the accelerator and gyroscope output signals correlate with the respective stored samples, and the time over which the movement persists is greater than a threshold time, then the control circuit 1032 effectively labels the movement as a qualified movement.

In response to determining that the movement is a qualified movement, the control circuit 1032 stores the samples, along with other data, in the memory circuit 1024, and may disable the IMU 1022 until the next time period (e.g., the next day or the next week) by opening the switch 1016 to extend the life of the battery 1012. The clock and power management circuit 1020 can be configured to generate periodic timing signals, such as interrupts, to commence each time period. For example, the control circuit 1032 can close the switch 1016 in response to such a timing signal from the clock and power management circuit 1020. Furthermore, the other data can include, e.g., the respective sample rate for each set of accelerometer and gyroscope samples, a respective time stamps indicating the time at which the IMU 1022 acquired the corresponding sets of samples, the respective sample times for each set of samples, an identifier (e.g., serial number) of the implantable prosthesis, and a patient identifier (e.g., a number or name). The volume of the other data can be significantly reduced if the sample rate, time stamp, and sample time are the same for each set of samples (i.e., samples of signals from all accelerometers and gyroscopes taken at the same times at the same rate) because the header includes only one sample rate, one time stamp, and one set of sample times for all sets of samples. Furthermore, the control circuit 1032 can encrypt some or all of the data in a conventional manner before storing the data in the memory 1024. For example, the control circuit 1032 can encrypt some or all of the data dynamically such that at any given time, same data has a different encrypted form than if encrypted at another time.

As further described below in conjunction with FIGS. 9-24 and elsewhere in this application, the stored data samples of the signals that the IM U 1022 one or more accelerometers and one or more gyroscopes generate can provide clues to the condition of the implantable prosthesis. For example, one can analyze the data samples (e.g., with a remote server such as a cloud server) to determine whether a surgeon implanted the prosthesis correctly, to determine the level(s) of instability and degradation that the implanted prosthesis exhibits at present, to determine the instability and degradation profiles over time, and to compare the instability and degradation profiles to benchmark instability and degradation profiles developed with stochastic simulation or data from a statistically significant group of patients.

Furthermore, the sampling rate, output data rate (ODR), and sampling frequency of the IMU 1022 can be configured to any suitable values. For example, the sampling rate may be fixed to any suitable value such as at 3200 Hz, the ODR, which can be no greater than the sampling rate and which is generated by "dropping" samples periodically, can be any suitable value such as 800 Hz, and the sampling frequency (the inverse of the interval between sampling periods) for qualified events can be any suitable value, such as twice per day, once per day, once per every 2 days, once per week, once per month, or more or less frequently. And sampling rate or ODR can be varied depending on the type of event being sampled. For example, to detect that the patient is walking without analyzing the patient's gait or the implant for instability or wear, the sampling rate or ODR can be 200 Hz, 25 Hz, or less. Therefore, such a low-resolution mode can be used to detect a precursor (a patient taking steps with a knee prosthesis) to a qualified event (a patient taking at least ten consecutive steps) because a "search" for a qualified event may include multiple false detections before the qualified even is detected. By using a lower sampling rate or ODR, the IMU 1032 saves power while conducting the search, and increases the sampling rate or the ODR (e.g., to 800 Hz, 1600, or 3200 Hz) only for sampling a detected qualified event so that the accelerator and gyroscope signals have sufficient sampling resolution for analysis of the samples for, e.g., instability and wear of the prosthesis.

Still referring to FIG. 4, in response to being polled by a base station (not shown in FIG. 4) or by another device external to the implanted prosthesis, the control circuit 1032 generates conventional messages having payloads and headers. The payloads include the stored samples of the signals that the IMU 1022 accelerators and gyroscopes generated, and the headers include the sample partitions in the payload (i.e., in what bit locations the samples of the x-axis accelerometer are located, in what bit locations the samples of the x-axis gyroscope are located, etc.), the respective sample rate for each set of accelerometer and gyroscope samples, a time stamp indicating the time at which the IMU 1022 acquired the samples, an identifier (e.g., serial number) of the implantable prosthesis, and a patient identifier (e.g., a number or name).

The control circuit 1032 generates data packets that include the messages according to a conventional data-packetizing protocol. Each packet can also include a packet header that includes, for example, a sequence number of the packet so that the receiving device can order the packets properly even if the packets are transmitted or received out of order.

The control circuit 1032 encrypts some or all parts of each of the data packets, for example, according to a conventional encryption algorithm, and error encodes the encrypted data packets. For example, the control circuit 1032 encrypts at least the prosthesis and patient identifiers to render the data packets compliant with the Health Insurance Portability and Accountability Act (HIPAA).

The control circuit 1032 provides the encrypted and error-encoded data packets to the RF transceiver 1026, which, via the filter 1028 and antenna 1030, transmits the data packets to a destination, such as the base station 1004 (FIG. 3), external to the implantable prothesis. The RF transceiver 1026 can transmit the data packets according to any suitable data-packet-transmission protocol.

Still referring to FIG. 4, alternate embodiments of the implantable circuit 1010 are contemplated. For example, the RF transceiver can perform encryption or error encoding instead of, or complementary to, the control circuit 1032. Furthermore, one or both of the switches 1016 and 1018 can be omitted from the implantable circuit 1010. Moreover, the implantable circuit 1010 can include components other than those described herein and can omit one or more of the components described herein. In addition, one or more embodiments described in conjunction with FIG. 3 and FIGS. 5-27 may be applicable to the implantable circuit 1010.

Figure 5:
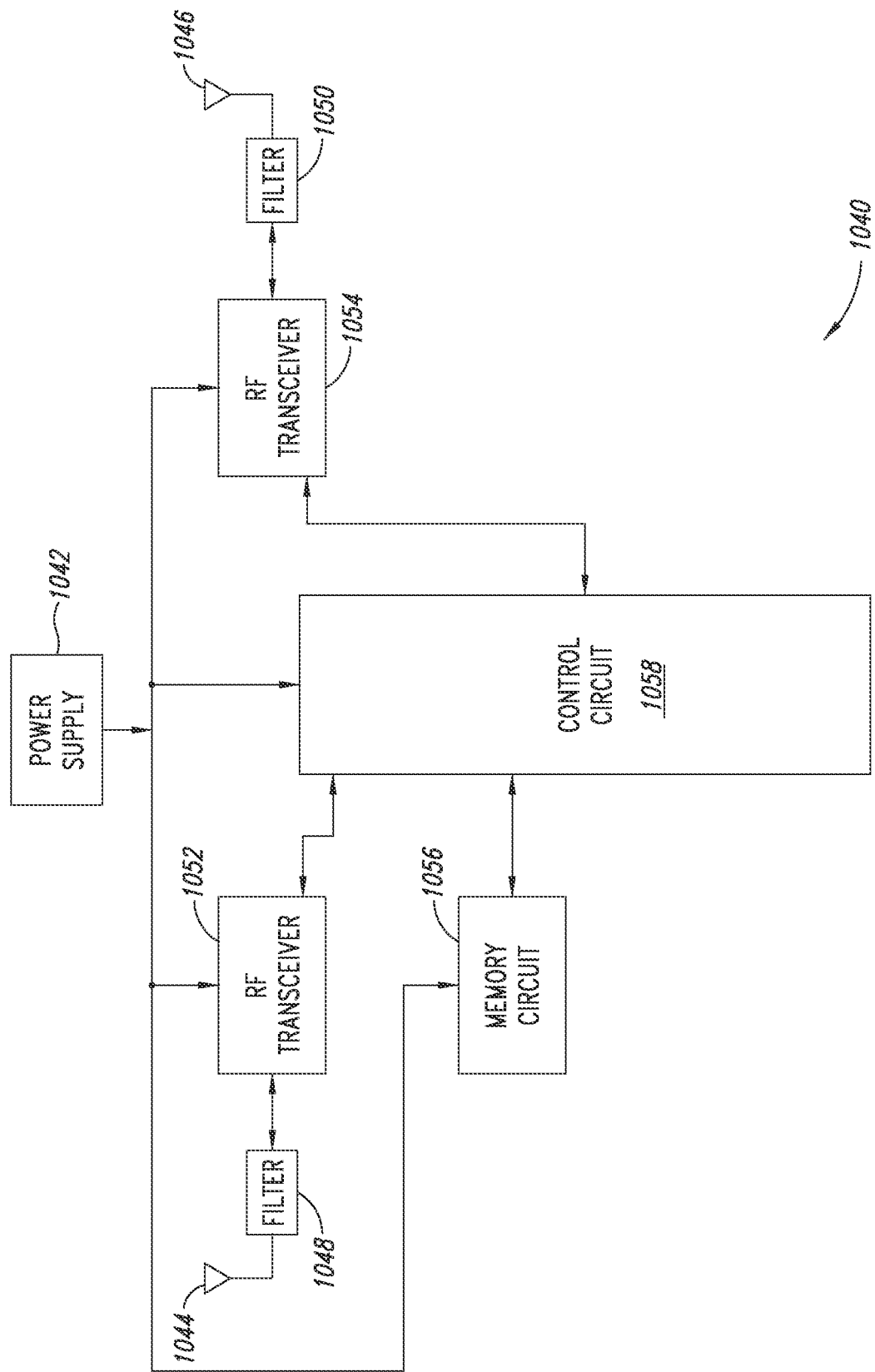
FIG. 5 is a block diagram of a base-station circuit for a base station configured to communicate with the implantable circuit of FIG. 101, and to forward data from the implantable circuit to a remote processing server such as a cloud-based server.

FIG. 5 is a diagram of a base-station circuit 1040, which is configured for inclusion within, or otherwise for use with, a base station, such as the home base station 1004 of FIG. 3, configured for communication with the implantable circuit 100 of FIG. 4, according to an embodiment.

The base-station circuit 1040 is powered by a power supply 1042, and includes first and second antennas 1044 and 1046, first and second RF filters 1048 and 1050, first and second RF transceivers 1052 and 1054, a memory circuit 1056, and a base-station control circuit 1058. Examples of some or all of these components are described elsewhere in this application or in U.S. patent application Ser. No. 16/084,544, which is incorporated by reference in all jurisdictions which allow incorporation by reference.

The power supply 1042 can be any suitable power supply, such as a battery or a supply that receives power from an electrical outlet; if the power supply is of the latter type, then the power supply also can include a battery backup for power outages or for while the base-station circuit 1040 is "unplugged."

The antenna 1044 can be any antenna suitable for the frequency band in which the RF transceiver 1052 communicates with the implant circuit 1010 of FIG. 4.

Likewise, the antenna 1046 can be any antenna suitable for the frequency band in which the RF transceiver 1054 communicates with a component, e.g., a WiFi® router, access point, or repeater, of the home network 1006 of FIG. 3.

Each of the filters 1048 and 1050 can be any suitable bandpass filter, such as a surface acoustic wave (SAW) filter or a bulk acoustic wave (BAW) filter.

The RF transceiver 1052 can be a conventional transceiver that is configured to allow the control circuit 1058 to communicate with the implant circuit 1010 of FIG. 4 while the implant circuit is disposed within, or is otherwise associated with, an implantable prosthesis such as the kinematic implantable device 1002 of FIG. 3. For example, the RF transceiver 1052 can be any suitable type of transceiver (e.g., Bluetooth, Bluetooth Low Energy (BTLE), and WiFi®), can be configured for operation according to any suitable protocol (e.g., M ICS, ISM, Bluetooth, Bluetooth Low Energy (BTLE), and WiFi®), and can be configured for operation in a frequency band that is within a range of 1 MHz-5.4 GHz, or that is within any other suitable range.

Likewise, the RF transceiver 1054 can be any conventional transceiver that is configured to allow the control circuit 1058 to communicate with a component, e.g., a WiFi® router, access point, or repeater, of the home network 1006 of FIG. 3, or with one or more of the home base station 1004, the smart device 1005, and the connected personal assistant 1000 of FIG. 3. For example, the RF transceiver 1026 can be any suitable type of transceiver (e.g., Bluetooth, Bluetooth Low Energy (BTLE), and WiFi®), can be configured for operation according to any suitable protocol (e.g., MICS, ISM, Bluetooth, Bluetooth Low Energy (BTLE), and WiFi®), and can be configured for operation in a frequency band that is within a range of 1 MHz-5.4 GHz, or that is within any other suitable range.

The memory circuit 1056 can be any suitable nonvolatile memory circuit, such as EEPROM or FLASH memory, and can be configured to store data written by the control circuit 1058, and to provide data in response to a read command from the control circuit. For example, the control circuit 1058 can store, in the memory 1056, data packets received from the implantable circuitry 1010 of FIG. 5, and can store data packets received from a cloud server via the RF transceiver 1054, where the data packets include, for example, commands, instructions, or configuration data for the implantable circuit 1010 of FIG. 4. Alternatively, the memory 1056 can include volatile memory.

The base-station control circuit 1058, which can be any suitable processor such as a microcontroller or microprocessor, is configured to control the configuration and operation itself and of one or more of the other components of the base-station circuit 1040. For example, the base-station control circuit 1058 can be configured to receive data packets from the implantable circuit 1010 of FIG. 4 via the RF transceiver 1052, to convert the received data packets into data packets suitable for transmission to the home network 1006 of FIG. 3, and to transmit the converted data packets to the home network via the RF transceiver 1054. And the base-station control circuit 1058 also can be configured to receive data packets from the home network 1006 via the RF transceiver 1054, to convert the received data packets into data packets suitable for transmission to the implantable circuit 1010, and to transmit the converted data packets to the implantable circuit via the RF transceiver 1052.

Still referring to FIG. 5, operation of the base-station circuit 1040 is described, according to an embodiment in which an implantable prosthesis (not shown in FIG. 5) with which the base-station circuit communicates is implanted in a patient (not shown in FIG. 5).

The control circuit 1058 polls the implantable circuit 1010 (FIG. 4) of the implanted prosthesis (not shown in FIG. 5) at regular intervals, such as once per day, once every other day, once per week, or once per month. If the control circuit 1058 receives no response to a poll, then the control circuit may poll the implantable circuit 1010 more frequently (e.g., every 5 minutes, every 30 minutes, every hour) until it receives a response or determines that the implanted prosthesis is out of range of the base station.

The implantable circuit 1010 (FIG. 4) responds to a poll by transmitting all the data packets of IMU samples that the implantable circuit generated since the last transmission of data packets.

The antenna RF transceiver 1052 receives the data packets from the implantable circuit 1010 (FIG. 4) via the antenna 1044 and filter 1048, and provides the received data packets to the base-station control circuit 1058, which decodes and decrypts the data packets, parses the messages from the data packets, and stores the parsed messages in the memory circuit 1056. Before storing the parsed messages, the base-station control circuit 1058 may encrypt part of all of each of the parsed messages for compliance with HIPAA.

Then, the base-station control circuit 1058 reformats the stored messages, or generates new messages in response to the headers and payloads of the stored messages. For example, the base-station control circuit 1058 may generate new messages that each include a respective payload and header from a received message, but that each include additional header information such as an identifier of the base station 1004 (FIG. 4), a time of reception of the original message from the implantable circuit 1010 (FIG. 4), and time of generation of the new message.

Before generating the new messages, the base-station control circuit 1058 may decrypt the parsed messages stored in the memory 1056.

The base-station control circuit 1058 then generates data packets that include the new messages, encrypts part or all of each of the data packets, and error encodes the data packets, and provides the encrypted and encoded data packets to the RF transceiver 1054, which transmits the encrypted and encoded data packets to the home network 1006 via the filter 1050 and the antenna 1046. The base-station control circuit 1058 may store the encrypted and encoded data packets in the memory 1056 temporarily (e.g., in a buffer) before providing the data packets to the RF transceiver 1054.

In an alternative embodiment, the base-station control circuit 1058 "passes through" the data packets received from the implantable circuit 1010 (FIG. 4) to the home network 1006 (FIG. 3). That is, the base-station control circuit 1058 receives one or more data packets from the implantable circuit 1010 via the RF transceiver 1052, temporarily stores the one or more data packets in the memory 1056, and causes the RF transceiver 1054 to transmit the one or more data packets to the home network 1006.

In yet another alternative, the control circuit 1058 modifies the one or more data packets received from the implantable circuit 1010 (FIG. 4) without first parsing the one or more data packets, or with parsing some, but not all, of each data packet.

The home network 1006 (FIG. 3) may "pass through" the one or more data packets received from the base station 1004 to a destination such as a server on the cloud 1008 (FIG. 3), or may modify the one or more data packets according to a suitable communication protocol before sending the one or more data packets to the destination.

Figure 26:
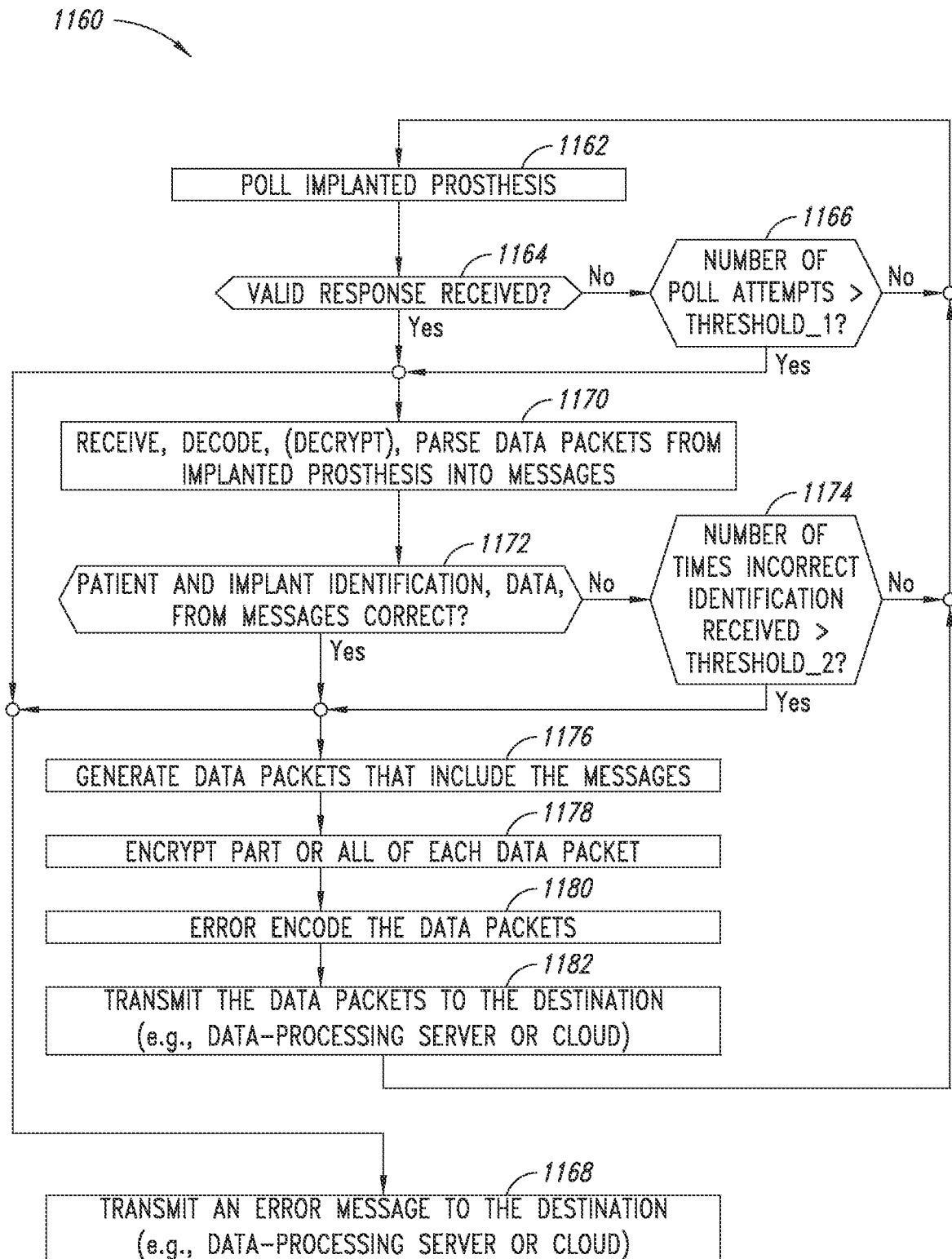
FIG. 26 is a flow diagram of operation of the base-station circuitry of FIG. 5, according to an embodiment.

Operation of the base-station circuit 1040 is described further in conjunction with FIG. 26.

Still referring to FIG. 5, alternate embodiments of the base-station circuit 1040 are contemplated. For example, embodiments described in conjunction with FIGS. 3-4 and 6-27 may be applicable to the base-station circuit 1040.

Figure 6:
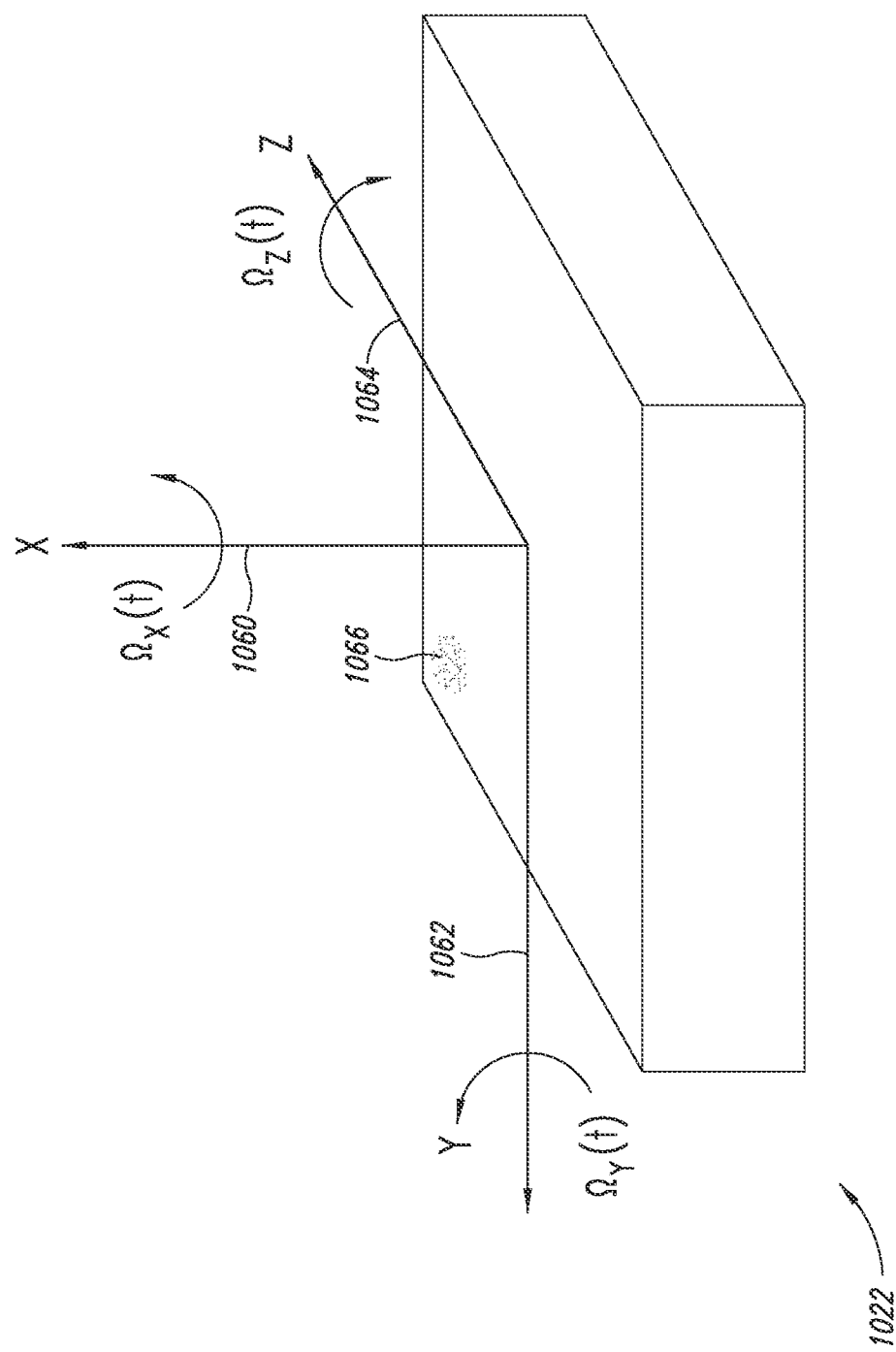
FIG. 6 is a perspective view of an inertial measurement unit (IMU) of the implantable circuit of FIG. 4 and of a set of coordinate axes within the frame of reference of the IMU, according to an embodiment.

FIG. 6 is a perspective view of the IMU 1022 of FIG. 4, according to an embodiment. For example, the IMU 1022 can be a Bosch BMI 160 small, low-power, IMU.

As described above in conjunction with FIG. 4, the IMU 1022 includes three measurement axes 1060, 1062, and 1064, which, for purposes of description, are arbitrarily labeled x, y, z. That is, in a Cartesian coordinate system, the labels "x," "y," and "z" can be applied arbitrarily to the axes 1060, 1062, and 1064 in any order or arrangement. A mark 1066 is a reference that indicates the locations and orientations of the axes 1060, 1062, and 1064 relative to the IMU 1022 package.

The IMU 1022 includes three accelerometers (not shown in FIG. 6), each of which senses and measures an acceleration a(t) along a respective one of the axes 1060 (x), 1062 (y), and 1064 (z), where $a_x(t)$ is the acceleration along the x axis, $a_y(t)$ is the acceleration along the y axis, and $a_z(t)$ is the acceleration along the z axis. Each accelerometer generates a respective analog sense or output signal having an instantaneous magnitude that represents the instantaneous magnitude of the sensed acceleration along the corresponding axis. For example, the magnitude of the magnitude of the accelerometer output signal at a given time is proportional the magnitude of the acceleration along the accelerometer's sense axis at the same time.

The IMU 1022 also includes three gyroscopes (not shown in FIG. 6), each of which senses and measures angular velocity $\Omega(t)$ about a respective one of the axes 1060 ($x$), 1062 ($y$), and 1064 ($z$), where $\Omega_x(t)$ is the angular velocity along the x axis, $\Omega_y(t)$ is the angular velocity along the y axis, and $\Omega_z(t)$ is the angular velocity along the z axis. Each gyroscope generates a respective analog sense or output signal having an instantaneous magnitude that represents the instantaneous magnitude of the sensed angular velocity about the corresponding axis. For example, the magnitude of the gyroscope output signal at a given time is proportional the magnitude of the angular velocity about the gyroscope's sense axis at the same time.

The IMU 1022 includes at least two analog-to-digital converters (ADCs) (not shown in FIG. 6) for each axis 1060, 1062, and 1064, one ADC for converting the output signal of the corresponding accelerometer into a corresponding digital acceleration signal, and the other ADC for converting the output signal of the corresponding gyroscope into a corresponding digital angular-velocity signal. For example, each of the ADCs may be an 8-bit, 16-bit, or 24-bit ADC.

A circuit designer can configure each ADC (not shown in FIG. 6) to have respective parameter values that are the same as, or that are different from, the parameter values of the other ADCs. Examples of such parameters having settable values include sampling rate, dynamic range at the ADC input node(s), and output data rate (ODR). One or more of these parameters may be set to a constant value, while one or more others of these parameters may be settable dynamically (e.g., during run time). For example, the respective sampling rate of each ADC may be settable dynamically so that during one sampling period the sampling rate has one value and during another sampling period the sampling rate has another value.

For each digital acceleration signal and for each digital angular-velocity signal, the IMU 1022 can be configured to provide the parameter values associated with the signal. For example, the IMU 1022 can provide, for each digital acceleration signal and for each digital angular-velocity signal, the sampling rate, the dynamic range, and a time stamp indicating the time at which the first sample or the last sample was taken. The IMU 1022 can be configured to provide these parameter values in the form of a message header (the corresponding samples form the message payload) or in any other suitable form.

Still referring to FIG. 6, alternate embodiments of the IMU 1022 are contemplated. For example, the IMU 1022 can have a shape other than square or rectangular. Furthermore, embodiments described in conjunction with FIGS. 3-5 and 7-27 may be applicable to the IMU 1022.

Figure 7:
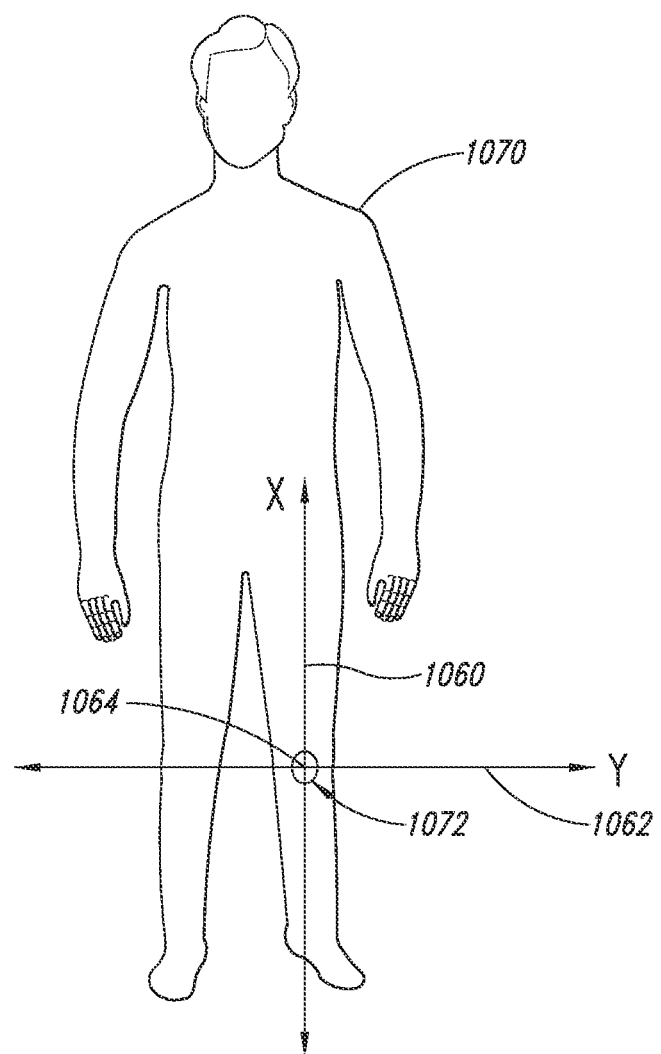
FIG. 7 is a front view of a standing patient in which a knee prosthesis is implanted and of two of the axes of the IMU of FIG. 6, according to an embodiment.

FIG. 7 is a front view of a standing male patient 1070 with a knee prosthesis 1072 implanted to replace his left knee joint, and of the axes 1060, 1062, and 1064 (arbitrarily labeled x, y, and z) of the IMU 1022 (FIG. 6), according to an embodiment.

Figure 8:
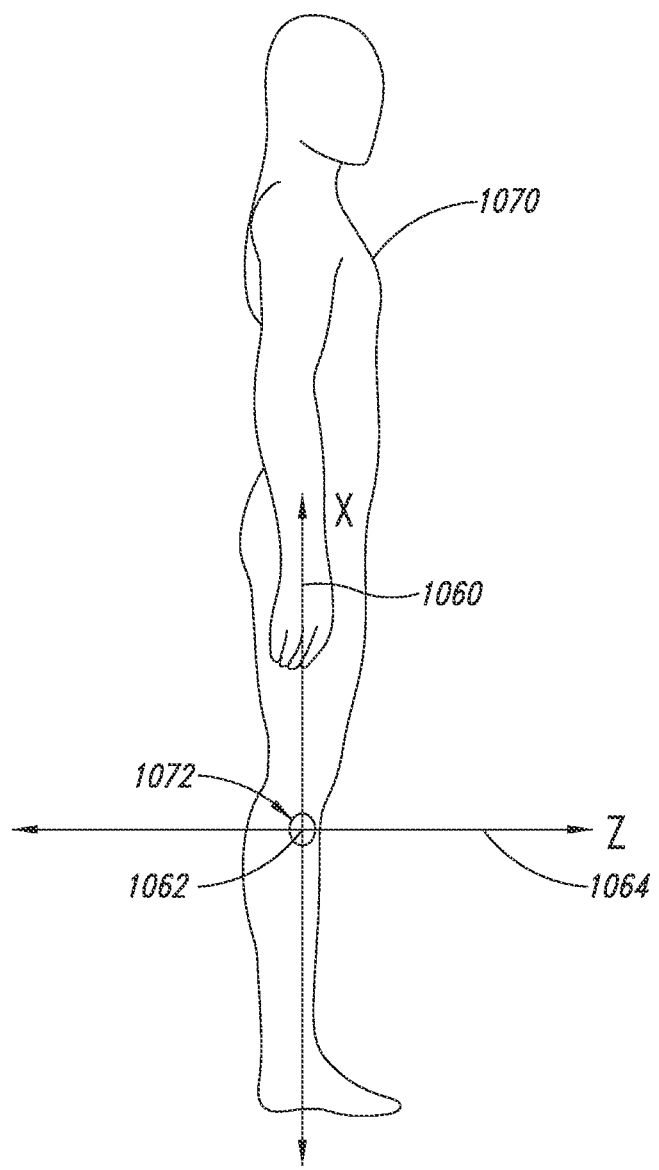
FIG. 8 is a side view of the patient of FIG. 7 in a supine position and of two of the axes of the IMU of FIG. 6, according to an embodiment.

FIG. 8 is a side view of the patient 1070 of FIG. 7 in a supine position, and of the axes 1060, 1062, and 1064 (arbitrarily labeled x, y, and z) of the IMU 1022 (FIG. 6), according to an embodiment (the knee prosthesis 1072 is shown through the patient's right leg).

Referring to FIGS. 7-8, in an embodiment, ideally one IMU axis (the x axis 1060 in FIGS. 7-8) is vertical while the patient 1070 is standing straight, one IMU axis (the y axis 1062 in FIGS. 7-8) that is, or that is parallel to, the axis about which the knee prosthesis rotates or bends, and the remaining IMU axis (the z axis 1064 in FIGS. 7-8) perpendicular to the other two axes, where all three axes intersect at the origin of the coordinate system.

There are a number of techniques that aid the surgeon who implants the knee prosthesis 1072 to align the IMU axes 1060, 1062, and 1064 with the ideal axis orientational. First, the orientation of the IMU 1022 (FIG. 6) within the tibial extension (described elsewhere in this document) is fixed within a relatively tight tolerance from extension to extension during the process of assembling the tibial extension by the physical design of the components. Second, both the tibial extension and the tibial baseplate (described elsewhere in this document) include alignment markers that the surgeon uses to align the tibial extension with the tibial baseplate component during the procedure for implanting the knee prosthesis such that the extension-plate alignment is within a relatively tight tolerance from implant to implant. Third, the uniformity of the tibial head from patient to patient, and the uniformity of how the surgeon modifies the tibial head for accepting the tibial baseplate, fixes the orientation of the tibial baseplate component within a relatively tight tolerance from patient to patient.

Despite these axis-alignment techniques, the IMU axes 1060, 1062, and 1064 may be misaligned relative to the ideal axis alignments described above. For example, such misalignment can have one or both of a translational component and a rotational component, although the rotational component is typically more prominent than the translational component. Further in example, the rotational misalignment can range from approximately a fraction of degree to approximately 90°.

Techniques for compensating for, or correcting, such axis misalignment are described elsewhere in this patent application.

Still referring to FIGS. 7-8, alternate embodiments of the described axis orientation and axis-orientation techniques are contemplated. For example, the described axis orientation can be modified for other types of implanted prostheses, such as shoulder prosthesis and hip prostheses. Furthermore, embodiments described in conjunction with FIGS. 3-6 and FIGS. 9-27 may be applicable to the described axis orientation and axis-orientation techniques.

Figure 9:
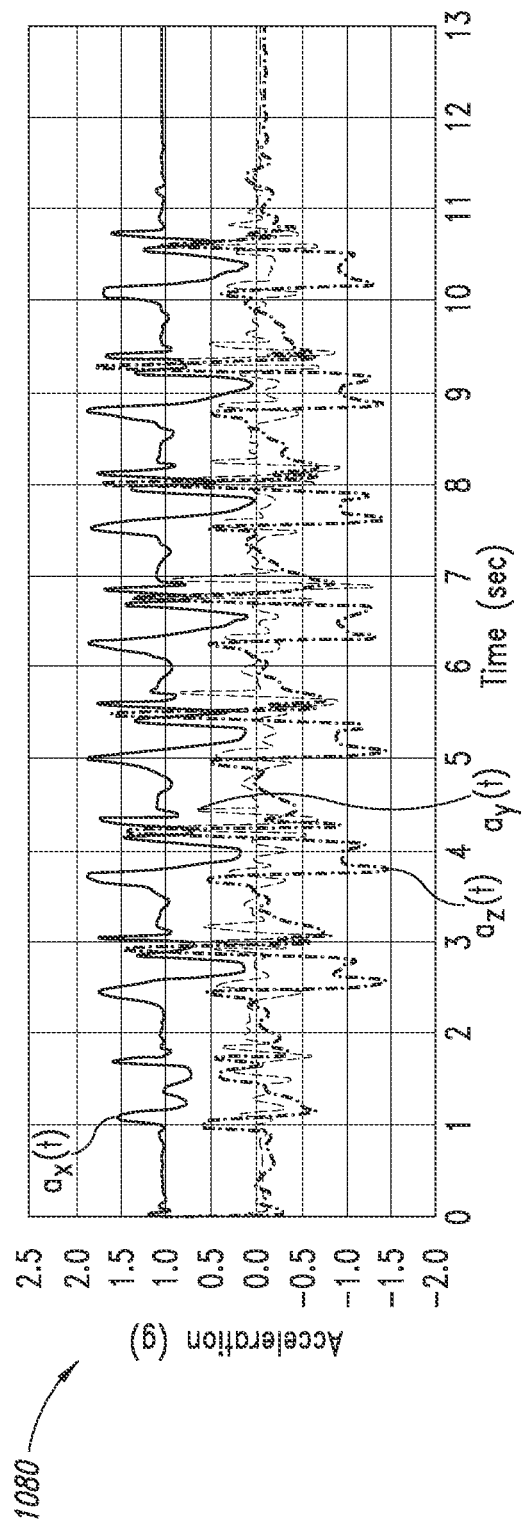
FIG. 9 is a plot, versus time, of the accelerations measured along the x, y, and z axes of the IMU of FIG. 6 while the patient of FIGS. 7 and 8 is walking with a normal gait, according to an embodiment.

FIG. 9 is a plot 1080, versus time, of the digitized versions of the analog acceleration signals $a_x(t)$, $a_y(t)$, and $a_z(t)$ (in units of m/s$^2$) that the accelerometers of the IMU 1022 (FIG. 4) respectively generate in response to accelerations along the x axis 1060, they axis 1062, and the z axis 1064 (FIG. 6) while the patient 1070 (FIGS. 7-8) is walking forward with a normal gait for a period of about ten seconds, according to an embodiment. In the described example, the x, y, and z axes have the ideal alignment described in conjunction with FIGS. 7-8, the knee prosthesis 1072 (FIGS. 7-8) exhibits little or no instability or wear-induced degradation, and the IMU 1022 samples each of the analog acceleration signals $a_x(t)$, $a_y(t)$, and $a_z(t)$ at the same sample times, the sampling rate is 3200 Hz, and the output data rate (ODR) is 800 Hz. The ODR is the rate of the samples output by the IMU 1022 and is generated by down sampling the samples taken at 3200 Hz. That is, because 3200 Hz/800

Hz=4, the IMU 1022 generates an 800 Hz ODR by outputting only every fourth sample taken at 3200 Hz.

Figure 10:
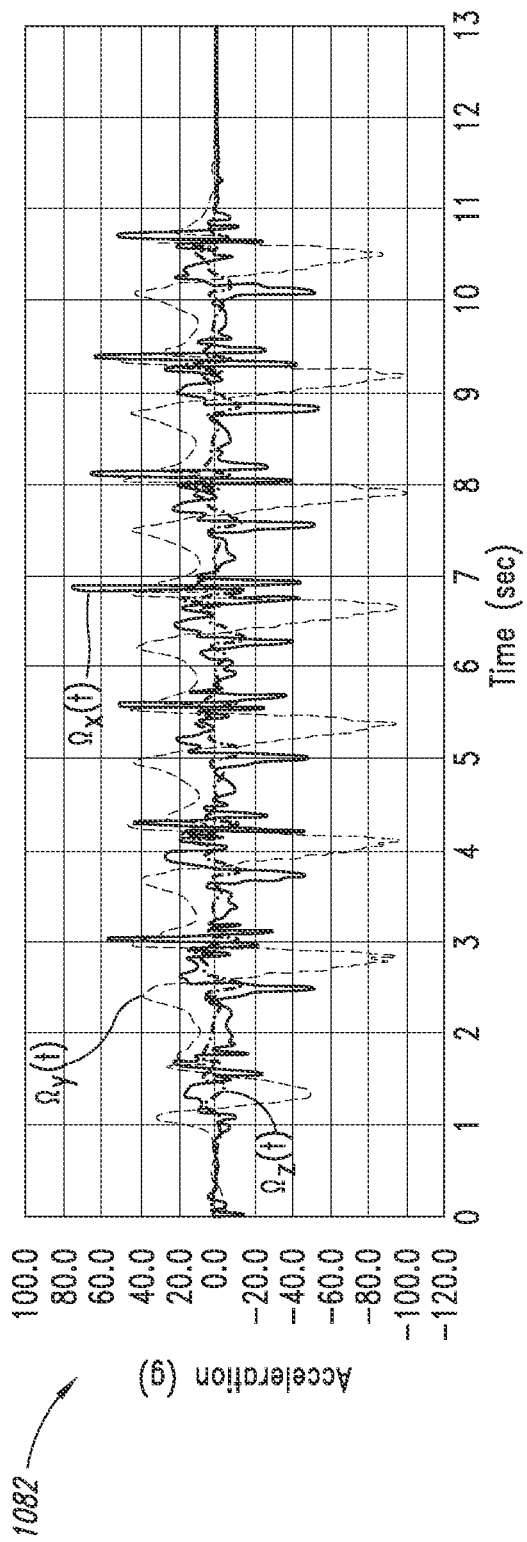
FIG. 10 is a plot, versus time, of the angular velocities measured about the x, y, and z axes of the IMU of FIG. 6 while the patient of FIGS. 7 and 8 is walking with a normal gait, according to an embodiment.

FIG. 10 is a plot 1082, versus time, of the digitized versions of the analog angular-velocity signals $\Omega_x(t)$, $\Omega_y(t)$, and $\Omega_z(t)$ (in units of degrees/s) that the gyroscopes of the IMU 1022 (FIG. 4) respectively generate in response to angular velocities about the x axis 1060, the y axis 1062, and the z axis 1064 (FIG. 6) while the patient 1070 (FIGS. 7-8) is walking forward with a normal gait for a period of about ten seconds, according to an embodiment. In the described example, the x, y, and z axes have the ideal alignment described in conjunction with FIGS. 7-8, the knee prosthesis 1072 (FIGS. 7-8) exhibits little or no instability or wear-induced degradation, and the IMU 1022 samples each of the analog angular-velocity signals $\Omega_x(t)$, $\Omega_y(t)$, and $\Omega_z(t)$ and each of the analog acceleration signals $a_x(t)$, $a_y(t)$, and $a_z(t)$ at the same sample times and at the same sampling rate of 3200 Hz and ODR of 800 Hz. That is, the plot 1082 is aligned, in time, with the plot 1080 of FIG. 9.

FIG. 11 is a middle portion 1084 of the plot 1080 of FIG. 9 with an expanded (i.e., higher-resolution) time scale and with walk-related events marked, according to an embodiment. For example, the times at which the heel of the patient 1070 (FIGS. 7-8) strikes the surface on which he is walking, and the times at which the patients lifts his toe off from the surface, are marked. Furthermore, the middle portion 1084 excludes the beginning portion of the plot 1080, which beginning portion represents the period during which the patient 1070 is accelerating to his normal walking speed, excludes the ending portion of the plot 1080, which ending portion represents the period during which the patient is decelerating to a stop, and, therefore, represents the period during which the patient is walking at an approximately constant velocity.

FIG. 12 is a middle portion 1086 of the plot 1082 of FIG. 10 with the same expanded (i.e., higher-resolution) time scale as the plot 1084 of FIG. 11, according to an embodiment. For example, the times at which the heel of the patient 1070 (FIGS. 7-8) strikes the surface on which he is walking, the times at which the patients lifts his toe off from the surface, and the times of peak angular velocity $\Omega_y(t)$ of the knee prosthesis as it bends about the y axis (or about an axis that is approximately parallel to the y axis), are marked. Furthermore, the middle portion 1086 excludes the beginning portion of the plot 1082, which beginning portion represents the period during which the patient 1070 is accelerating to his normal walking speed, excludes the ending portion of the plot 1082, which ending portion represents the period during which the patient is decelerating to a stop, and, therefore, represents the period during which the patient is walking at an approximately constant velocity.

Referring to FIGS. 4 and 9-12, the implantable control circuit 1032 can be configured to determine whether the patient 1070 is walking by comparing the acceleration and angular-velocity signals generated by the accelerometers and gyroscopes of the IMU 1020 to benchmark normal-gait signals such as those shown in the plots 1080, 1082, 1084, and 1086. For example, the implantable control circuit 1032 can be configured to correlate the digitized acceleration signals $a_x(t)$, $a_y(t)$, and $a_z(t)$ and the digitized angular-velocity signals $\Omega_x(t)$, $\Omega_y(t)$, and $\Omega_z(t)$ generated by the accelerometers, gyroscopes, and ADCs of the IMU 1020 with the respective benchmark normal-gait signals, and can determine that the patient 1070 is walking if the correlation yields a correlation value greater than a correlation threshold, which can have a value, for example, in an approximate range of 0.60-0.95 (1.0 is the maximum value that the correlation can yield). Alternatively, to save processing power and time, the implantable control circuit 1032 can be configured to correlate regions of the acceleration and angular-velocity signals generated by the accelerometers and gyroscopes of the IMU 1020 to regions, such as the heel-strike regions, of the benchmark normal-gait signals. And determining that the patient 1070 is walking is one of one or more determinations that the implantable control circuit 1032 can be configured to make to determine whether the acceleration and angular-velocity signals from the IMU 1020 are qualified signals that that implantable control circuit 1032 is configured to store. The respective benchmark normal-gait signals can be generated by the patient 1070 himself, for example in a doctor's office (the doctor can control the implantable control circuit 1032 to store the benchmark normal-gait signals in the memory circuit 1024). Or, the respective benchmark normal-gait signals can be generated by simulation of the normal gait of the patient 1070, or in response to a statistical analysis of the normal gaits of a group of other patients with the same or similar knee prosthesis. If the respective benchmark normal-gait signals are generated in response to other than the actual gait of the patient 1070 himself, then, during the correlation, the implantable control circuit 1032 can expand or contract the benchmark normal-gait signals in the time or magnitude dimensions to account for the stride of the patient 1070. For example, the taller the patient 1070, the longer his stride; conversely, the shorter the patient 1070 the shorter his stride.

Still referring to FIGS. 9-12, alternate embodiments of the described benchmark-signal generation techniques and signal-comparison techniques are contemplated. For example, embodiments described in conjunction with FIGS. 3-8 and 13-27 may be applicable to the signals and techniques described in conjunction with FIGS. 9-12.

Figure 13:
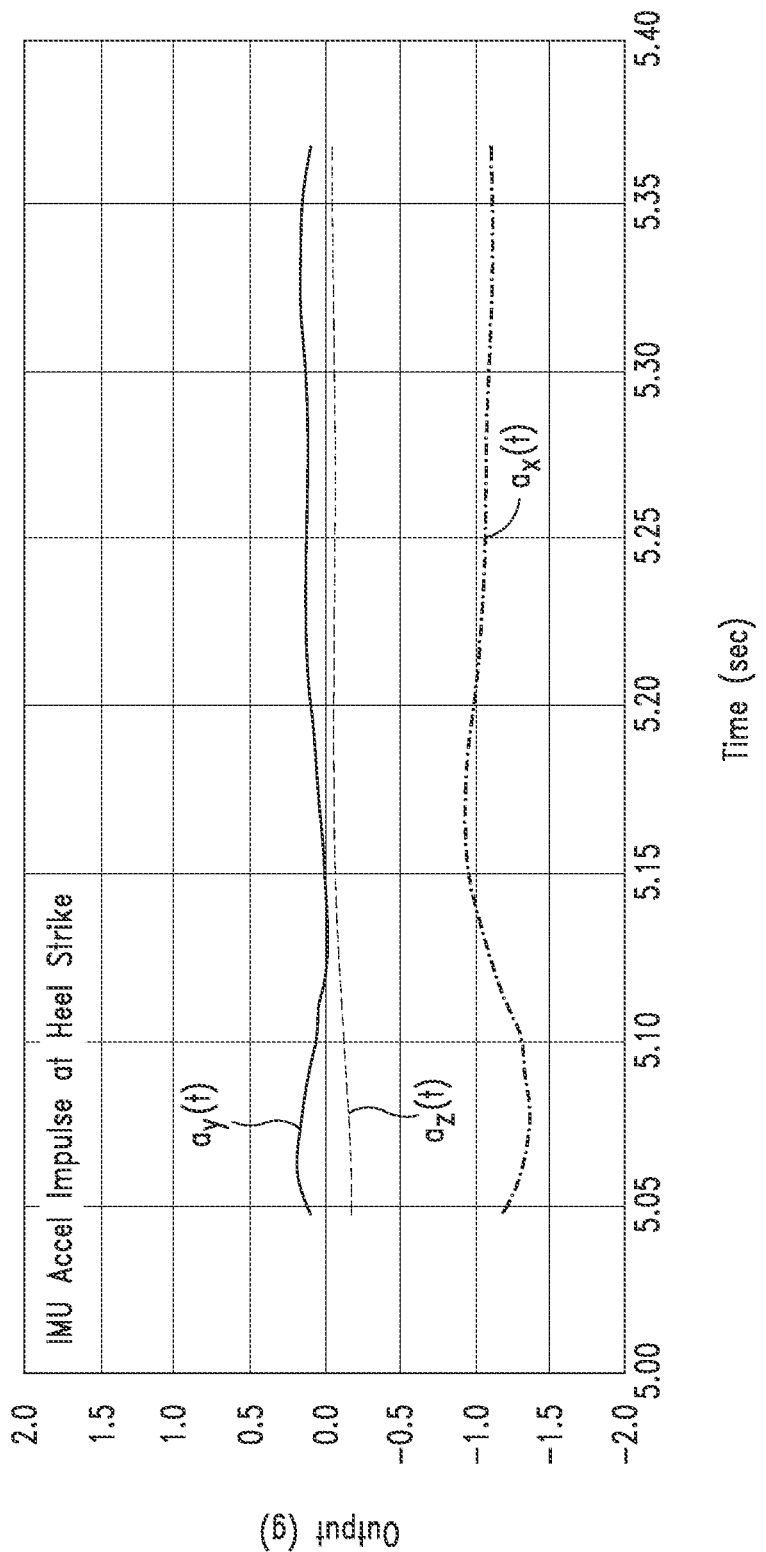
FIG. 13 is a plot, versus time, of the accelerations measured along the x, y, and z axes of the IMU of FIG. 6 during impact of the heel of the patient of FIGS. 7 and 8 while the patient is walking with a normal gait, according to an embodiment.

FIG. 13 is a plot 1090, versus time, of the digitized versions of the analog acceleration signals $a_x(t)$, $a_y(t)$, and $a_z(t)$ that the accelerometers of the IMU 1022 (FIG. 4) respectively generate in response to accelerations along the x axis 1060, the y axis 1062, and the z axis 1064 (FIG. 6) during one of the heel strikes described above in conjunction with FIGS. 9-12 while the patient 1070 is walking forward with a normal gait, according to an embodiment. In the described example, the x, y, and z axes have the ideal alignment described in conjunction with FIGS. 7-8, the knee prosthesis 1072 (FIGS. 7-8) exhibits little or no instability or wear-induced degradation, and the IMU 1022 samples each of the analog acceleration signals $a_x(t)$, $a_y(t)$, and $a_z(t)$ at the same sample times, and the effective sampling rate is 800 Hz. For example, because, for a knee prosthesis, weight is transferred to the prosthetic joint during a heel strike, heel-strike regions can be good regions of a gait signal to analyze for instability and wear of the prosthesis.

Figure 14:
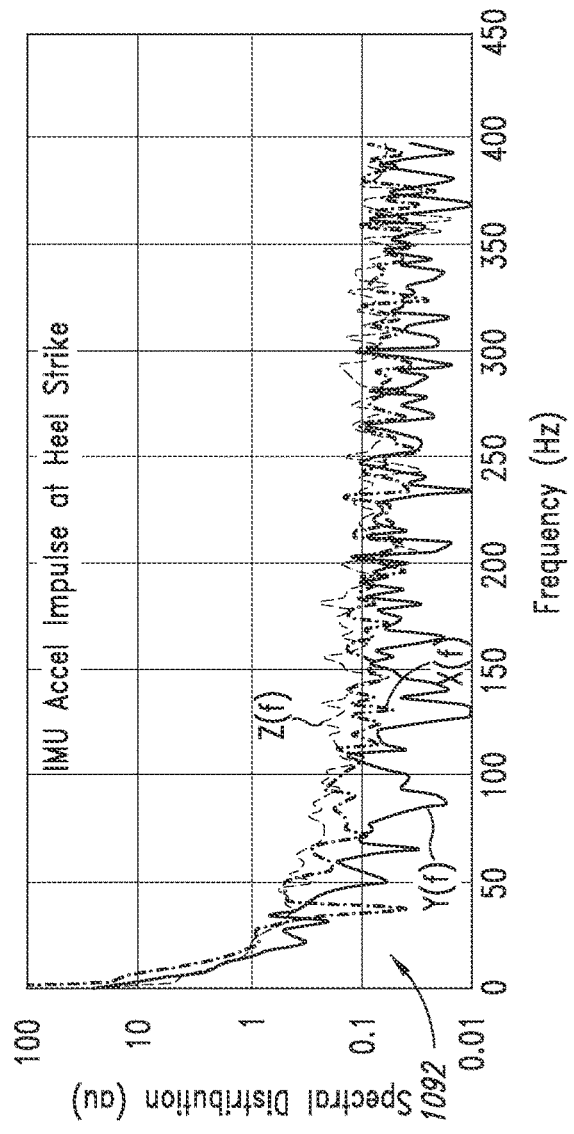
FIG. 14 is a plot, versus frequency, of the respective spectral distribution of each of the x, y, and z accelerations of FIG. 13, according to an embodiment.

FIG. 14 is a plot 1092, versus frequency, of the respective spectral distributions X(f), Y(f), and Z(f) of the x, y, and z accelerations represented by the digitized versions of the analog acceleration signals $a_x(t)$, $a_y(t)$, and $a_z(t)$ of FIG. 13, according to an embodiment. For example, a server (e.g., a cloud server) remote from the knee prosthesis can generate the spectral distributions X(f), Y(f), and Z(f) by taking the Discrete Fourier Transform (DFT), or (Fast Fourier Transform (FFT)), of each of the digitized versions of the analog acceleration signals $a_x(t)$, $a_y(t)$, and $a_z(t)$. Although described as having arbitrary units, the spectral distributions X(f), Y(f), and Z(f) can be mathematically manipulated to have any suitable units such as units of, e.g., energy (Joules, Joules Root Mean Square).

Figure 15:
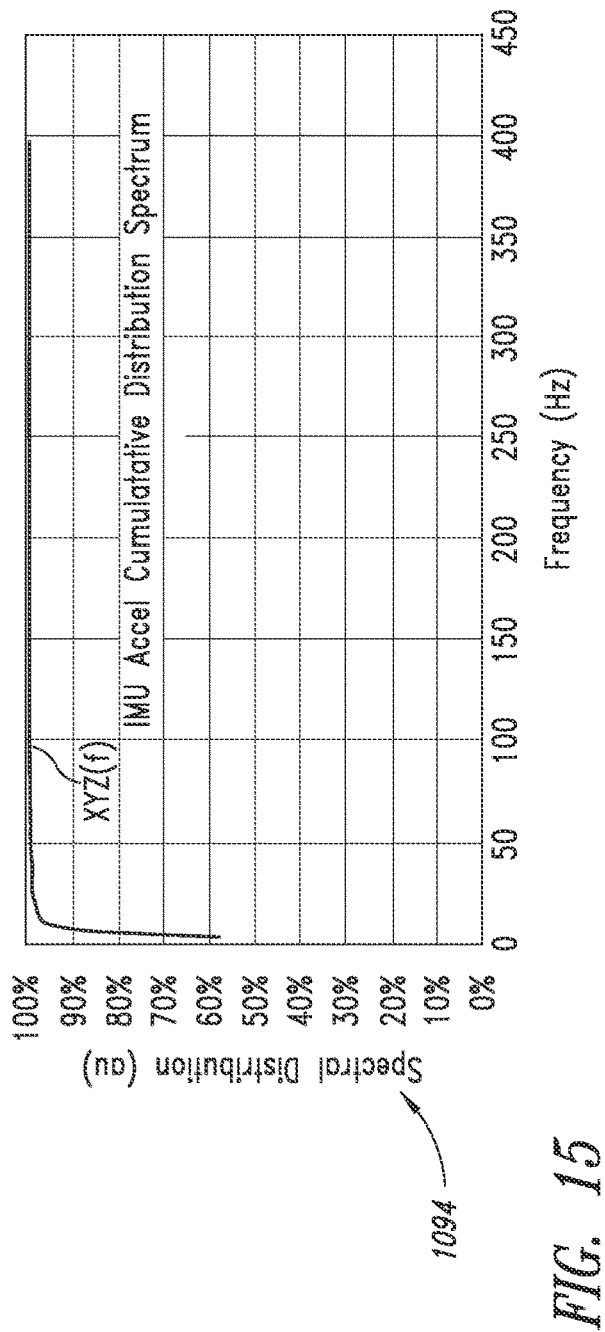
FIG. 15 is a plot, versus frequency, of the cumulative spectral distribution of the x, y, and z accelerations of FIG. 13, according to an embodiment.

FIG. 15 is a plot 1094, versus frequency, of the cumulative spectral distributions XYZ(f) (e.g., in units of Joules Root Mean Square, logarithmic scale, or otherwise in arbitrary units) of the x, y, and z accelerations represented by the digitized versions of the analog acceleration signals $a_x(t)$, $a_y(t)$, and $a_z(t)$ of FIG. 13, according to an embodiment. For example, a server (e.g., a cloud server) remote from the knee prosthesis can generate the cumulative spectral distribution by integrating each of the contents X(f), Y(f), and Z(f) (FIG. 14) over time and by summing together the respective integration results.

Referring to FIGS. 13-15, one can use the spectral distributions X(f), Y(f), and Z(f), and the cumulative spectral distribution XYZ(f), as benchmarks for determining whether the knee prosthesis 1072 exhibits instability or wear-induced degradation. For example, analysis of the cumulative spectral distribution XYZ(f) shows that for a knee prosthesis 1072 that exhibits no instability or degradation, approximately 90% of the RMS motion is at frequencies of less than 10 Hz, and approximately 98% of the RMS motion is at frequencies less than 20 Hz. Therefore, if the cumulative spectral distribution XYZ(f) were to yield significant RMS motion above 20 Hz, then this would be an indication that the knee prosthesis 1072 may be exhibiting instability or degradation.

The respective benchmark analog acceleration signals $a_x(t)$, $a_y(t)$, and $a_z(t)$, in response to which the benchmark spectral distributions X(f), Y(f), and Z(f) and the benchmark cumulative spectral distribution XYZ(f) are generated, can be generated by the patient 1070 himself, for example in a doctor's office (the doctor can control the implantable control circuit 1032 to store the benchmark normal-gait-no-instability-and-no-degradation signals in the memory circuit 1024). Or, the respective benchmark normal-gait-no-instability-and-no-degradation signals can be generated by simulation of the normal gait of the patient 1070, or in response to a statistical analysis of the normal gaits of a group of other patients with the same or similar knee prosthesis.

Still referring to FIGS. 13-15, alternate embodiments of the described benchmark-signal, spectral-distribution, and cumulative-spectral-distribution generation techniques and analysis techniques are contemplated. For example, the sampling rate and the ODR that the IMU 1022 implements to generate the described benchmark signal may be other than 3200 Hz and 800 Hz, respectively. Moreover, embodiments described in conjunction with FIGS. 3-12 and 16-27 may be applicable to the signals, spectral distributions, cumulative spectral distributions, and techniques described in conjunction with FIGS. 13-15.

Figure 16:
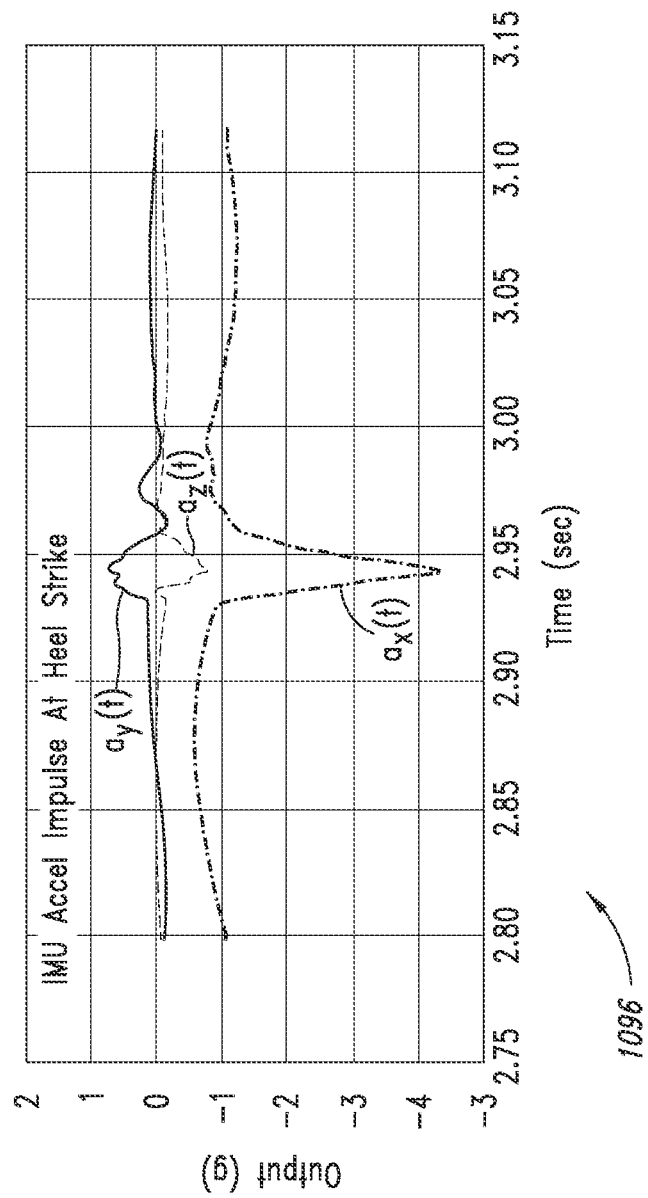
FIG. 16 is a plot, versus time, of the accelerations measured along the x, y, and z axes of the IMU of FIG. 6 during impact of a heel of the patient of FIGS. 7 and 8 while the patient is walking with a normal gait and while a knee prosthesis implanted in the patient exhibits an instability, according to an embodiment.

FIG. 16 is a plot 1096, versus time, of the digitized versions of the analog acceleration signals $a_x(t)$, $a_y(t)$, and $a_z(t)$ (in units of m/s$^2$) that the accelerometers of the IMU 1022 (FIG. 4) respectively generate in response to accelerations along the x axis 1060, they axis 1062, and the z axis 1064 (FIG. 6) during one of the heel strikes described above in conjunction with FIGS. 9-12 while the patient 1070 (FIGS. 7-8) is walking forward with a normal gait, according to an embodiment. In the described example, the x, y, and z axes have the ideal alignment described in conjunction with FIGS. 7-8, the knee prosthesis 1072 (FIGS. 7-8) exhibits instability but exhibits little or no wear-induced degradation, and the IMU 1022 samples each of the analog acceleration signals $a_x(t)$, $a_y(t)$, and $a_z(t)$ at the same sample times, the sampling rate (sometimes called the "raw sampling rate") is 3200 Hz, the ODR (effective sampling rate) is 800 Hz. Here, "instability" means that the bending of the knee prosthesis 1072 (FIGS. 7-8) is not smooth while the patient 1070 is walking. That is, the knee prosthesis 1072 exhibits instability if the femoral component of the knee prosthesis vibrates along, or about, one or more of the x, y, and z axes 1060, 1062, and 1064 in an unintended, or in an otherwise undesirable, manner.

Figure 17:
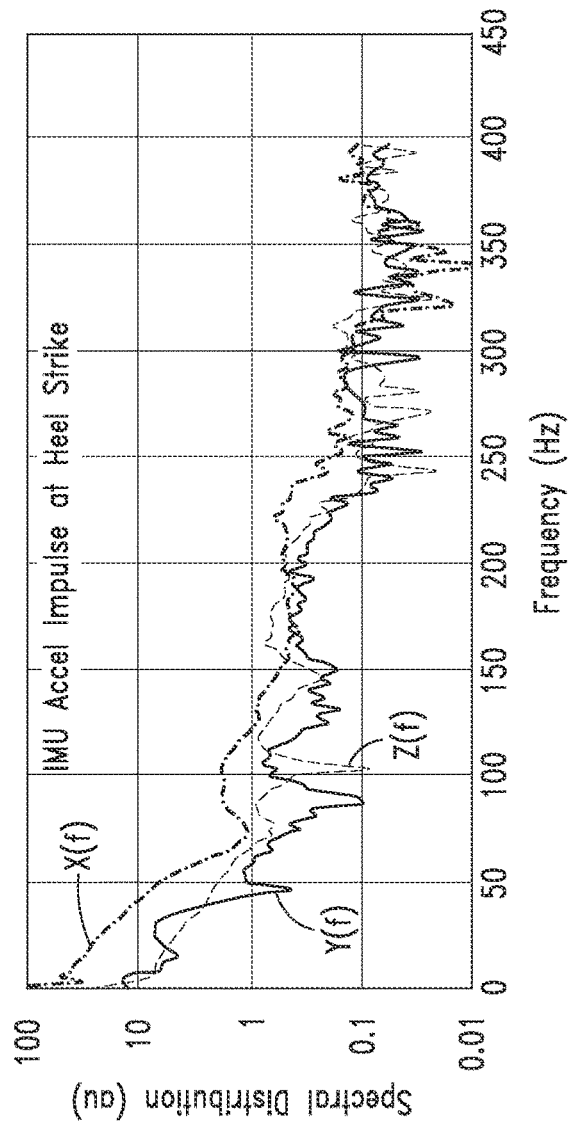
FIG. 17 is a plot, versus frequency, of the respective spectral distribution of each of the x, y, and z accelerations of FIG. 16, according to an embodiment.

FIG. 17 is a plot 1098, versus frequency, of the respective spectral distributions X(f), Y(f), and Z(f) (in arbitrary units such as Joules, logarithmic scale) of the x, y, and z accelerations represented by the digitized versions of the analog acceleration signals $a_x(t)$, $a_y(t)$, and $a_z(t)$ of FIG. 16, according to an embodiment. For example, a server (e.g., a cloud server) remote from the knee prosthesis can generate the spectral distributions X(f), Y(f), and Z(f) by taking the Discrete Fourier Transform (DFT), or (Fast Fourier Transform (FFT)), of each of the digitized versions of the analog acceleration signals $a_x(t)$, $a_y(t)$, and $a_z(t)$.

Figure 18:
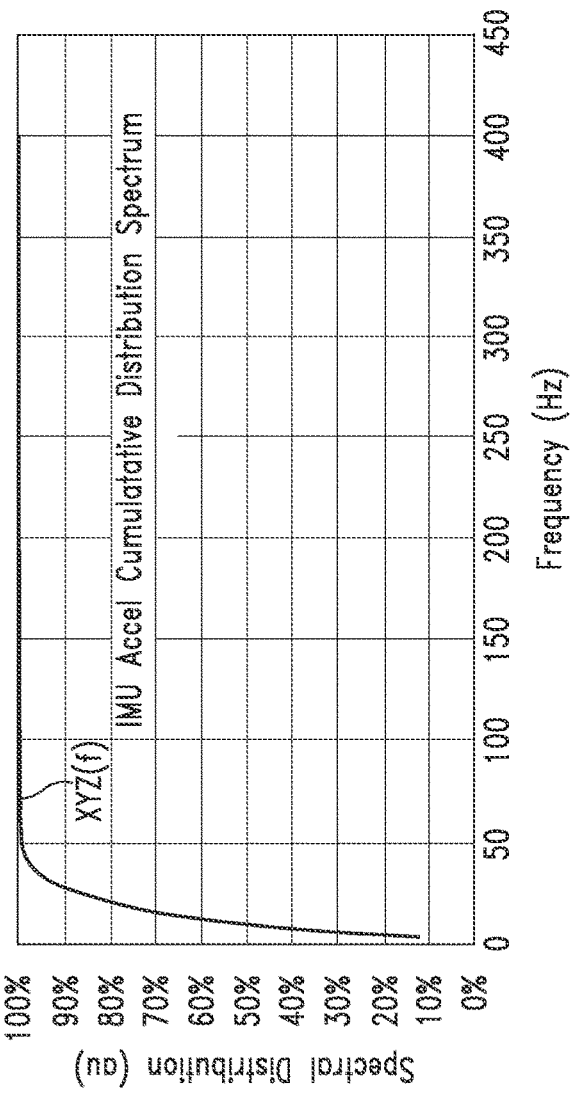
FIG. 18 is a plot, versus frequency, of the cumulative spectral distribution of the x, y, and z accelerations of FIG. 16, according to an embodiment.

FIG. 18 is a plot 1100, versus frequency, of the cumulative spectral distribution XYZ(f) (in arbitrary units such as Joules Root Mean Square, logarithmic scale) of the x, y, and z accelerations represented by the digitized versions of the analog acceleration signals $a_x(t)$, $a_y(t)$, and $a_z(t)$ of FIG. 16, according to an embodiment. For example, a server (e.g., a cloud server) remote from the knee prosthesis 1072 (FIGS. 7-8) can generate the cumulative spectral distribution by integrating each of the distributions X(f), Y(f), and Z(f) (FIG. 14) over time and by summing together the respective integration results.

Referring to FIGS. 16-18, an analysis of the cumulative spectral distribution XYZ(f) shows that for a knee prosthesis 1072 that exhibits instability but no degradation, approximately 90% of the RMS motion is at frequencies of less than 28 Hz (compared to 10 Hz (FIGS. 13-15) for the knee prosthesis 1072 exhibiting no instability), and approximately 98% of the RMS motion is at frequencies less than 44 Hz (compared to 20 Hz (FIGS. 13-15) for the knee prosthesis 1072 exhibiting no instability). The frequency ranges at 90% and 98% for the RMS motion of the knee prosthesis 1072 being significantly wider than the corresponding benchmark frequency ranges for the RMS motion of the knee prosthesis exhibiting no instability and no degradation can be indicative of the knee prosthesis 1072 exhibiting at least one of instability or degradation (early experimental results tend toward the RMS motion frequency ranges yielded by the spectral distribution XYZ(f) plotted in FIG. 18 being indicative of knee-prosthesis instability, and not being indicative of degradation).

To determine the magnitude, type, and other characteristics of the instability that the knee prosthesis 1072 (FIGS. 7-8) exhibits, one can analyze (e.g., automatically on a server, such as a cloud server, remote from the knee prosthesis), for example, one or more of the following parameters:

(1) the magnitudes, numbers, and relative phases of the peaks of one or more of the digitized versions of the analog acceleration signals $a_x(t)$, $a_y(t)$, and $a_z(t)$ of FIG. 16;

(2) the respective magnitude of each of one or more of the spectral distributions X(f), Y(f), and Z(f) at each of one or more frequencies; and (3) the respective magnitude of the cumulative spectral distribution XYZ(f) at each of one or more frequencies.

As described elsewhere in this patent application, one can use one or more deterministic algorithms, or one or more machine-learning algorithms (e.g., neural networks), to characterize the instability and to suggest one or more procedures for remediating the instability. For example, an algorithm can process one or more of the digitized versions of the analog acceleration signals $a_x(t)$, $a_y(t)$, and $a_z(t)$ (FIG. 16), the spectral distributions $X(f)$, $Y(f)$, and $Z(f)$, and the cumulative spectral distribution $XYZ(f)$ to determine a peak-to-peak magnitude (e.g., less than 2 millimeters (mm) translation or rotation, 2-3 millimeters (mm) translation or rotation, and 3+ mm translation or rotation) of the instability, a likely cause (e.g., too much "slop" between the femoral component and the spacer ("puck")) of the instability, and a procedure (e.g., resize and replace the puck, send the patient 1070 (FIGS. 7-8) to physical therapy to tighten the muscles, ligaments, and tendons associated with the knee prosthesis) likely to remediate the instability.

Still referring to FIGS. 16-18, alternate embodiments of the described analyses and algorithms for detecting, quantifying, and proposing remediation of instability in the knee prosthesis 1072 (FIGS. 7-8) are contemplated. For example, the described analyses and algorithms can be used, or can be modified for use, with an implantable prosthesis other than a knee prosthesis. Furthermore, embodiments described in conjunction with FIGS. 3-15 and 19-27 may be applicable to the analyses and algorithms described in conjunction with FIGS. 16-18.

Figure 19:
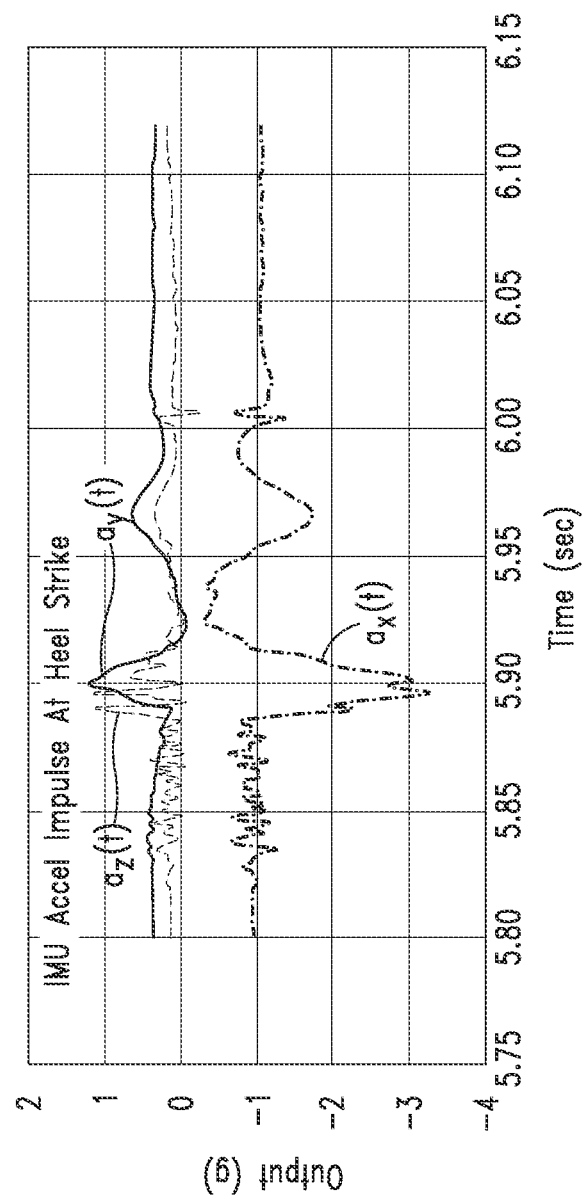
FIG. 19 is a plot, versus time, of the accelerations measured along the x, y, and z axes of the IMU of FIG. 6 during impact of a heel of the patient of FIGS. 7 and 8 while the patient is walking with a normal gait and while a knee prosthesis implanted in the patient exhibits an instability and early-onset degradation, according to an embodiment.

FIG. 19 is a plot 1102, versus time, of the digitized versions of the analog acceleration signals $a_x(t)$, $a_y(t)$, and $a_z(t)$ (in units of m/s$^2$) that the accelerometers of the IMU 1022 (FIG. 4) respectively generate in response to accelerations along the x axis 1060, the y axis 1062, and the z axis 1064 (FIG. 6) during one of the heel strikes described above in conjunction with FIGS. 9-12 while the patient 1070 (FIGS. 7-8) is walking forward with a normal gait, according to an embodiment. In the described example, the x, y, and z axes have the ideal alignment described in conjunction with FIGS. 7-8, the knee prosthesis 1072 (FIGS. 7-8) exhibits instability and early-onset wear-induced degradation, and the IMU 1022 samples each of the analog acceleration signals $a_x(t)$, $a_y(t)$, and $a_z(t)$ at the same sample times, the sampling rate is 3200 Hz, and the ODR is 800 Hz. Here, "early-onset degradation" means that the knee prosthesis 1072 (FIGS. 7-8) has just begun to exhibit symptoms (e.g., rough engagement (grinding) of the femoral component with the plastic spacer of the knee prosthesis) of wear induced by repeated flexing of the knee prosthesis. That is, the knee prosthesis 1072 exhibits wear if the femoral component roughly engages, e.g., grinds against, the plastic spacer while the patient 1070 (FIGS. 7-8) flexes the knee prosthesis, e.g., while walking.

Figure 20:
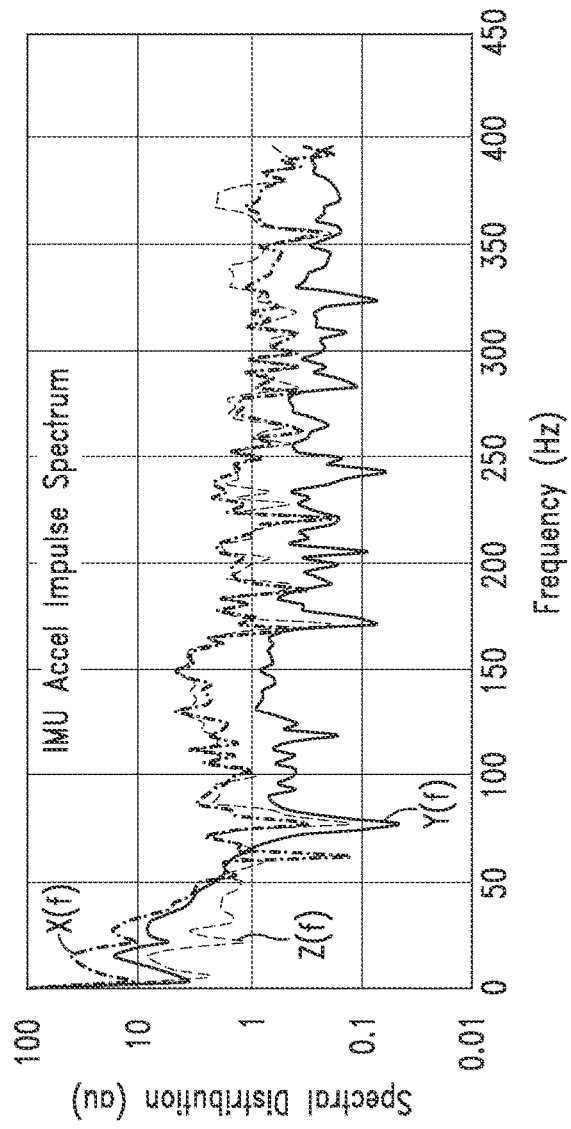
FIG. 20 is a plot, versus frequency, of the respective spectral distribution of each of the x, y, and z accelerations of FIG. 19, according to an embodiment.

FIG. 20 is a plot 1104, versus frequency, of the respective spectral distributions $X(f)$, $Y(f)$, and $Z(f)$ (in arbitrary units such as Joules, logarithmic scale) of the x, y, and z accelerations represented by the digitized versions of the analog acceleration signals $a_x(t)$, $a_y(t)$, and $a_z(t)$ of FIG. 19, according to an embodiment. For example, a server (e.g., a cloud server) remote from the knee prosthesis can generate the spectral distributions $X(f)$, $Y(f)$, and $Z(f)$ by taking the Discrete Fourier Transform (DFT), or (Fast Fourier Transform (FFT)), of each of the digitized versions of the analog acceleration signals $a_x(t)$, $a_y(t)$, and $a_z(t)$.

Figure 21:
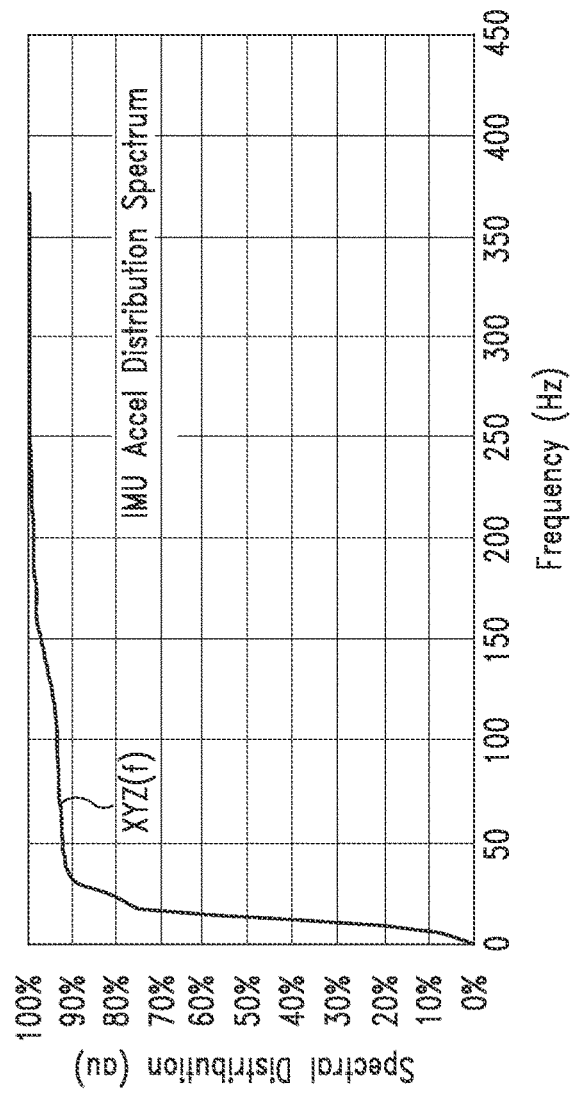
FIG. 21 is a plot, versus frequency, of the cumulative spectral distribution of the x, y, and z accelerations of FIG. 19, according to an embodiment.

FIG. 21 is a plot 1106, versus frequency, of the cumulative spectral density $XYZ(f)$ (in arbitrary units such as Joules Root Mean Square, logarithmic scale) of the x, y, and z accelerations represented by the digitized versions of the analog acceleration signals $a_x(t)$, $a_y(t)$, and $a_z(t)$ of FIG. 19, according to an embodiment. For example, a server (e.g., a cloud server) remote from the knee prosthesis 1072 (FIGS. 7-8) can generate the cumulative spectral density by integrating each of the spectral distributions $X(f)$, $Y(f)$, and $Z(f)$ (FIG. 14) over time and by summing together the respective integration results.

Referring to FIGS. 19-21, an analysis of the cumulative spectral distribution $XYZ(f)$ shows that for a knee prosthesis 1072 that exhibits instability and early-onset degradation, approximately 90% of the RMS motion is at frequencies of less than 34 Hz (compared to 10 Hz (FIGS. 13-15) for the knee prosthesis exhibiting no instability and no degradation, and 28 HZ (FIGS. 16-18) for the knee prosthesis exhibiting instability but no degradation), and approximately 98% of the RMS motion is at frequencies less than 175 Hz (compared to 20 Hz (FIGS. 13-15) for the knee prosthesis 1072 exhibiting no instability and no degradation, and 44 HZ (FIGS. 16-18) for the knee prosthesis exhibiting instability but no degradation). The frequency ranges at 90% and 98% for the RMS motion of the knee prosthesis 1072 being significantly wider than the corresponding benchmark frequency ranges for the RMS motion of the knee prosthesis exhibiting no instability and no degradation and the corresponding frequency ranges for the RMS motion of the knee prosthesis exhibiting instability but no degradation, can be indicative of the knee prosthesis 1072 exhibiting both instability and early-onset degradation.

To determine the magnitude, type, and other characteristics of the instability and the degradation that the knee prosthesis 1072 (FIGS. 7-8) exhibits, one can analyze (e.g., automatically on a server, such as a cloud server, remote from the knee prosthesis), for example, one or more of the following parameters:

(1) the magnitudes, numbers, and relative phases of the peaks of one or more of the digitized versions of the analog acceleration signals $a_x(t)$, $a_y(t)$, and $a_z(t)$ of FIG. 19;

(2) the respective magnitude of each of one or more of the spectral distributions $X(f)$, $Y(f)$, and $Z(f)$ of FIG. 20 at each of one or more frequencies; and (3) the respective magnitude of the cumulative spectral distribution $XYZ(f)$ of FIG. 21 at each of one or more frequencies.

As described elsewhere in this patent application, one can use one or more deterministic algorithms, or one or more machine-learning algorithms (e.g., neural networks), to characterize one or both of the instability and the degradation and to suggest one or more procedures for remediating one or both of the instability and the degradation. For example, an algorithm can process one or more of the digitized versions of the analog acceleration signals $a_x(t)$, $a_y(t)$, and $a_z(t)$ (FIG. 16), the spectral distributions $X(f)$, $Y(f)$, and $Z(f)$, and the cumulative spectral distribution $XYZ(f)$ to determine a peak-to-peak magnitudes (e.g., less than 2 millimeters (mm) translation or rotation, 2-3 millimeters (mm) translation or rotation, and 3+ mm translation or rotation) of one or both of the instability and the degradation, likely causes (e.g., too much "slop" between the femoral component and the spacer ("puck") for instability, wear of the puck or femoral component for degradation) of one or both of the instability and the degradation, and procedure (e.g., resize and replace the puck, send the patient 1070 (FIGS. 7-8) to physical therapy to tighten the muscles, ligaments, and tendons associated with the knee prosthesis) likely to remediate one or both of the instability and the degradation.

Still referring to FIGS. 19-21, alternate embodiments of the described analyses and algorithms for detecting, quantifying, and proposing remediation of instability in the knee prosthesis 1072 (FIGS. 7-8) are contemplated. For example, the described analyses and algorithms can be used, or can be modified for use, with an implantable prosthesis other than a knee prosthesis. Furthermore, embodiments described in conjunction with FIGS. 3-18 and 22-27 may be applicable to the analyses and algorithms described in conjunction with FIGS. 19-21.

Figure 22:
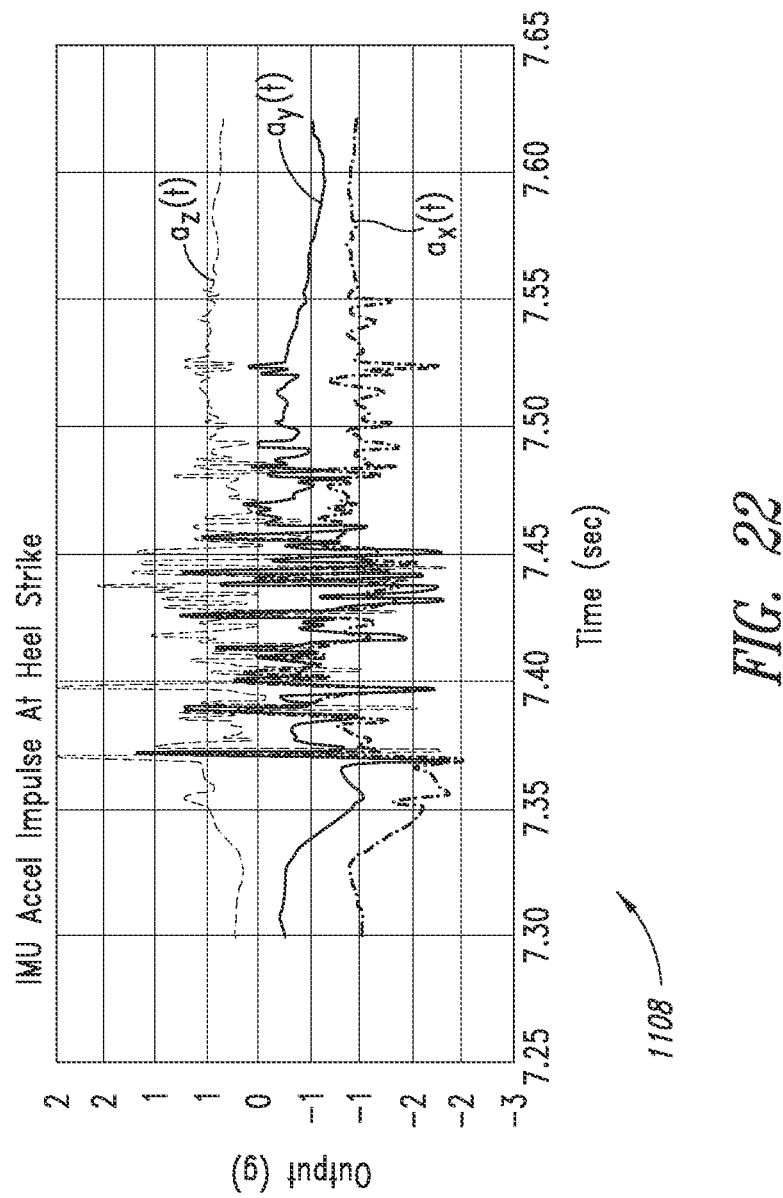
FIG. 22 is a plot, versus time, of the accelerations measured along the x, y, and z axes of the IMU of FIG. 6 during impact of a heel of the patient of FIGS. 7 and 8 while the patient is walking with a normal gait and while a knee prosthesis implanted in the patient exhibits an instability and advanced degradation, according to an embodiment.

FIG. 22 is a plot 1108, versus time, of the digitized versions of the analog acceleration signals $a_x(t)$, $a_y(t)$, and $a_z(t)$ (in units of m/s$^2$) that the accelerometers of the IMU 1022 (FIG. 4) respectively generate in response to accelerations along the x axis 1060, the y axis 1062, and the z axis 1064 (FIG. 6) during one of the heel strikes described above in conjunction with FIGS. 9-12 while the patient 1070 (FIGS. 7-8) is walking forward with a normal gait, according to an embodiment. In the described example, the x, y, and z axes have the ideal alignment described in conjunction with FIGS. 7-8, the knee prosthesis 1072 (FIGS. 7-8) exhibits instability and advanced wear-induced degradation, the IMU 1022 samples each of the analog acceleration signals $a_x(t)$, $a_y(t)$, and $a_z(t)$ at the same sample times, the sampling rate is 3200 Hz, and the ODR is 800 Hz. Here, "advanced degradation" means that the knee prosthesis 1072 (FIGS. 7-8) apparently has been exhibiting symptoms (e.g., rough engagement (grinding) of the femoral component with the plastic spacer of the knee prosthesis) of wear induced by repeated flexing of the knee prosthesis. That is, the knee prosthesis 1072 exhibits wear if the femoral component roughly engages, e.g., grinds against, the plastic spacer while the patient 1070 (FIGS. 7-8) flexes the knee prosthesis, e.g., while walking.

Figure 23:
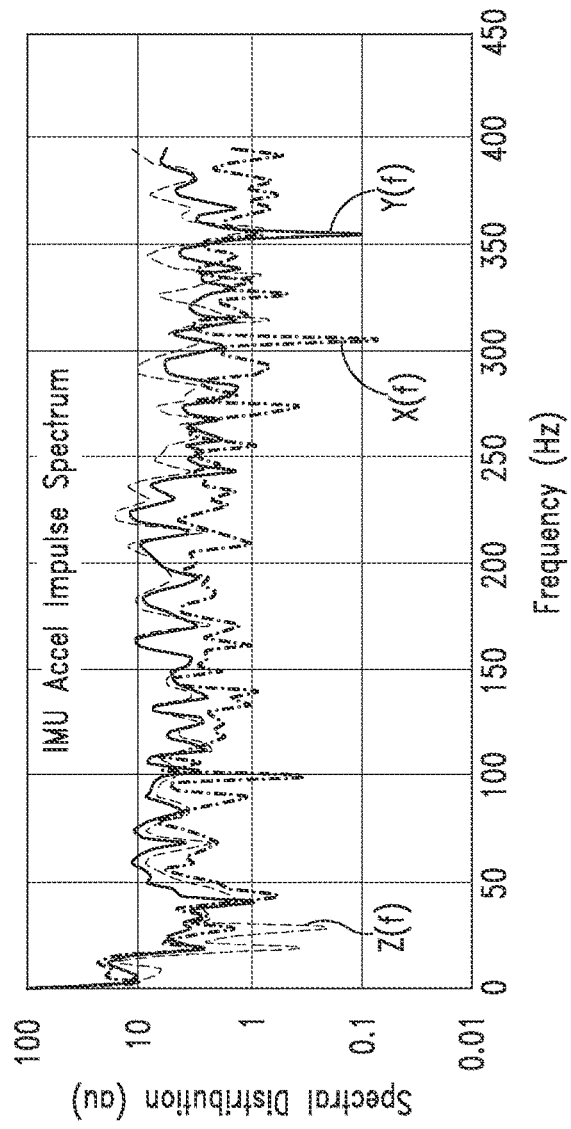
FIG. 23 is a plot, versus frequency, of the respective spectral distribution of each of the x, y, and z accelerations of FIG. 22, according to an embodiment.

FIG. 23 is a plot 1110, versus frequency, of the respective spectral distributions X(f), Y(f), and Z(f) (in arbitrary units such as Joules, logarithmic scale) of the x, y, and z accelerations represented by the digitized versions of the analog acceleration signals $a_x(t)$, $a_y(t)$, and $a_z(t)$ of FIG. 22, according to an embodiment. For example, a server (e.g., a cloud server) remote from the knee prosthesis can generate the spectral distributions X(f), Y(f), and Z(f) by taking the Discrete Fourier Transform (DFT), or (Fast Fourier Transform (FFT)), of each of the digitized versions of the analog acceleration signals $a_x(t)$, $a_y(t)$, and $a_z(t)$.

Figure 24:
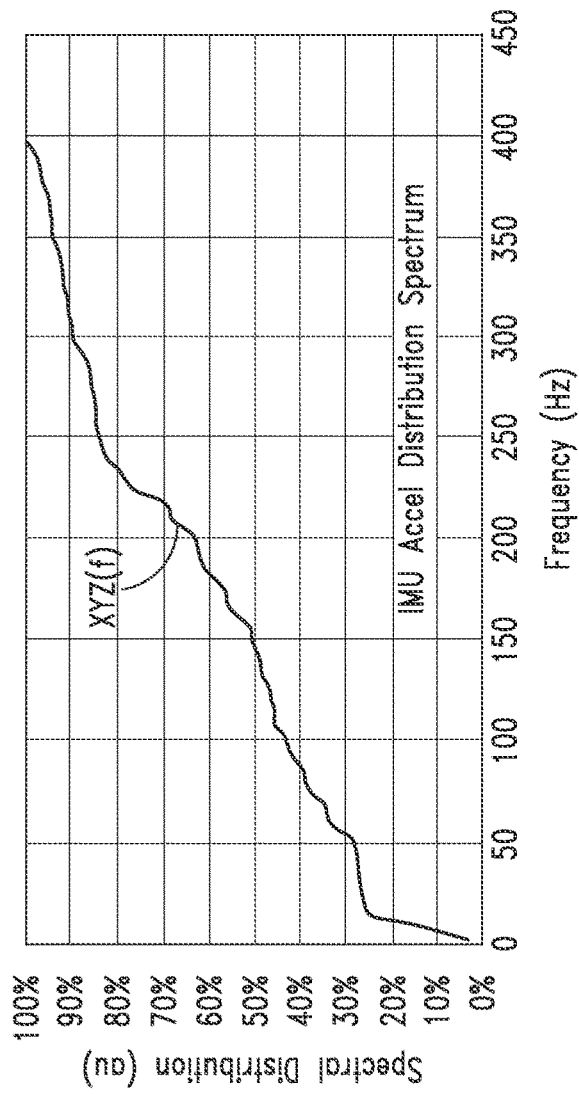
FIG. 24 is a plot, versus frequency, of the cumulative spectral distribution of the x, y, and z accelerations of FIG. 22, according to an embodiment.

FIG. 24 is a plot 1112, versus frequency, of the cumulative spectral distribution XYZ(f) (in arbitrary units such as Joules Root Mean Square, logarithmic scale) of the x, y, and z accelerations represented by the digitized versions of the analog acceleration signals $a_x(t)$, $a_y(t)$, and $a_z(t)$ of FIG. 22, according to an embodiment. For example, a server (e.g., a cloud server) remote from the knee prosthesis 1072 (FIGS. 7-8) can generate the cumulative spectral distribution by integrating each of the contents X(f), Y(f), and Z(f) (FIG. 14) over time and by summing together the respective integration results.

Referring to FIGS. 22-24, an analysis of the cumulative spectral distribution XYZ(f) shows that for a knee prosthesis 1072 that exhibits instability and early-onset degradation, approximately 90% of the RMS motion is at frequencies less than 306 Hz (compared to 10 Hz (FIGS. 13-15) for the knee prosthesis exhibiting no instability and no degradation, 28 Hz (FIGS. 16-18) for the knee prosthesis exhibiting instability but no degradation, and 34 Hz for the knee prosthesis exhibiting instability and early-onset degradation), and approximately 98% of the RMS motion is at frequencies less than 394 Hz (compared to 20 Hz (FIGS. 13-15) for the knee prosthesis 1072 exhibiting no instability and no degradation, 44 HZ (FIGS. 16-18) for the knee prosthesis exhibiting instability but no degradation, and 175 Hz for the knee prosthesis exhibiting instability and early-onset degradation). The frequency ranges at 90% and 98% for the RMS motion of the knee prosthesis 1072 being significantly wider than the corresponding benchmark frequency ranges for the RMS motion of the knee prosthesis exhibiting no instability and no degradation, and the corresponding frequency ranges for the RMS motion of the knee prosthesis exhibiting instability but no degradation and instability and early-onset degradation, can be indicative of the knee prosthesis 1072 exhibiting both instability and advanced degradation.

To determine the magnitude, type, and other characteristics of the instability and the degradation that the knee prosthesis 1072 (FIGS. 7-8) exhibits, one can analyze (e.g., automatically on a server, such as a cloud server, remote from the knee prosthesis), for example, one or more of the following parameters:

(1) the magnitudes, numbers, and relative phases of the peaks of one or more of the digitized versions of the analog acceleration signals $a_x(t)$, $a_y(t)$, and $a_z(t)$ of FIG. 22;

(2) the respective magnitude of each of one or more of the spectral distributions X(f), Y(f), and Z(f) of FIG. 23 at each of one or more frequencies; and (3) the respective magnitude of the cumulative spectral distribution XYZ(f) of FIG. 24 at each of one or more frequencies.

As described elsewhere in this patent application, one can use one or more deterministic algorithms, or one or more machine-learning algorithms (e.g., neural networks), to characterize one or both of the instability and the degradation and to suggest one or more procedures for remediating one or both of the instability and the degradation. For example, an algorithm can process one or more of the digitized versions of the analog acceleration signals $a_x(t)$, $a_y(t)$, and $a_z(t)$ (FIG. 22), the spectral distributions X(f), Y(f), and Z(f), and the cumulative spectral distribution XYZ(f) to determine a peak-to-peak magnitudes (e.g., less than 2 millimeters (mm) translation or rotation, 2-3 millimeters (mm) translation or rotation, and 3+ mm translation or rotation) of one or both of the instability and the degradation, likely causes (e.g., too much "slop" between the femoral component and the spacer ("puck") for instability, wear of the puck or femoral component for degradation) of one or both of the instability and the degradation, and procedure(s) (e.g., resize and replace the puck, send the patient 1070 (FIGS. 7-8) to physical therapy to tighten the muscles, ligaments, and tendons associated with the knee prosthesis) likely to remediate one or both of the instability and the degradation.

Still referring to FIGS. 22-24, alternate embodiments of the described analyses and algorithms for detecting, quantifying, and proposing remediation of instability in the knee prosthesis 1072 (FIGS. 7-8) are contemplated. For example, the described analyses and algorithms can be used, or can be modified for use, with an implantable prosthesis other than a knee prosthesis. Furthermore, an algorithm can generate results in response to the digitized versions of one of more of the angular velocities $\Omega_x(t)$, $\Omega_y(t)$, and $\Omega_z(t)$ (in units of degrees/s) that the gyroscopes of the IMU 1022 (FIG. 4) respectively generate in response to angular velocities about the x axis 1060, the y axis 1062, and the z axis 1064 (FIG. 6). Moreover, an algorithm can generate results in response to one or more portions (e.g., toe off) of the gait of the patient 1070 (FIGS. 7-8) other than, or in addition too, a heel strike. In addition, embodiments described in conjunction with FIGS. 3-21 and 25-27 may be applicable to the analyses and algorithms described in conjunction with FIGS. 22-24.

Figure 25:
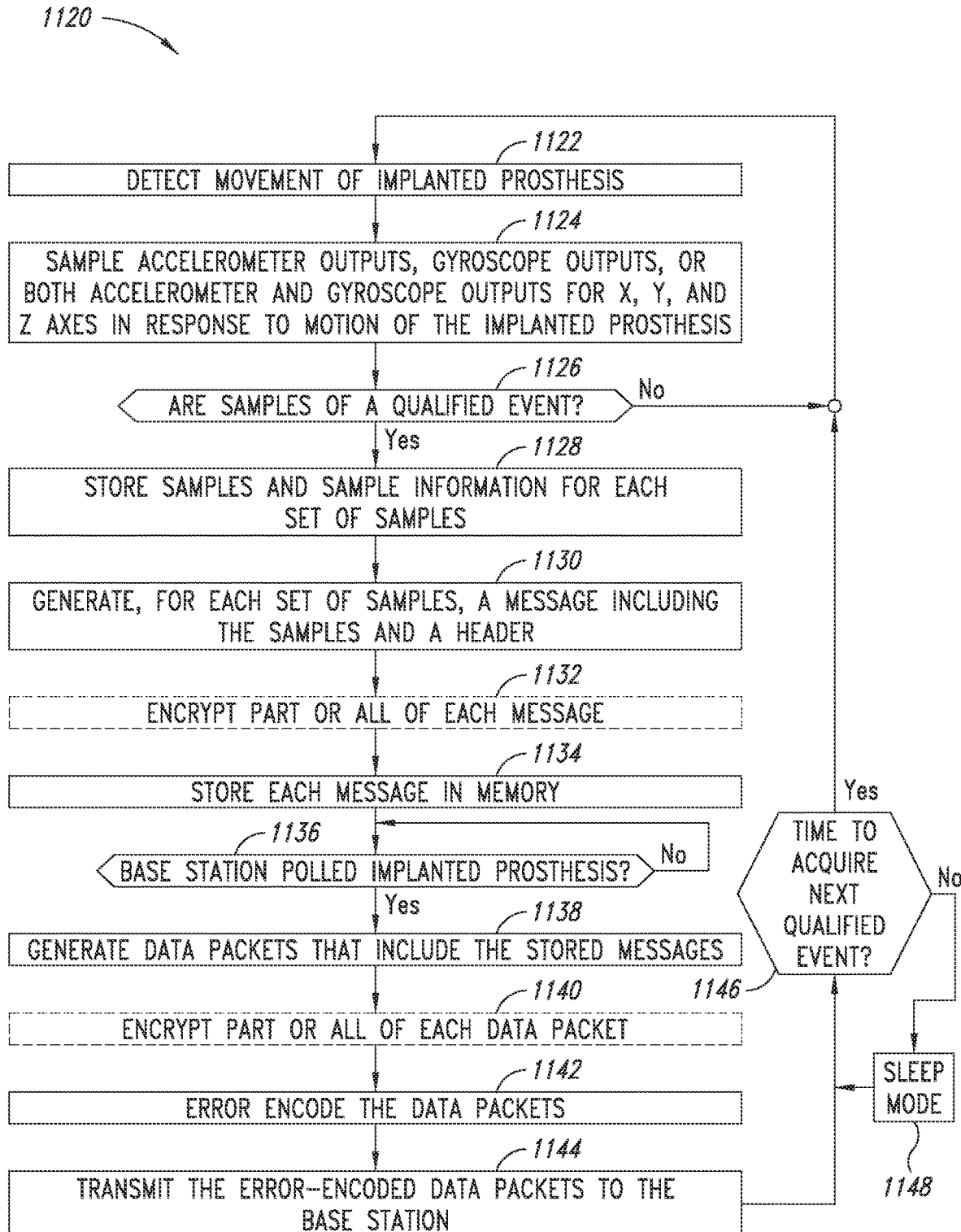
FIG. 25 is a flow diagram of operation of the implantable circuitry of FIG. 4, according to an embodiment.

FIG. 25 is a flow diagram 1120 of the operation of the implantable circuit 1010 of FIG. 4, according to an embodiment.

Referring to FIGS. 4 and 25, at a step 1122, the implantable circuit 1010 detects movement of the implanted prosthesis, such as the knee prosthesis 1072 of FIGS. 7-8. For example, the control circuit 1032 monitors the respective digitized output signal from each of one or more of the accelerometers and gyroscopes of the IMU 1022 and detects movement of the implanted prosthesis in response to a respective magnitude of each of one or more of the digitized output signals exceeding a movement-detection threshold.

Next, at a step 1124, in response to detecting movement of the implanted prosthesis at step 1122, the control circuit 1032 causes the IMU 1022 to sample the analog signals output from one or both of the IMU accelerometers and gyroscopes (it is assumed hereinafter that the IMU 1022 samples the analog signals output from both of IMU accelerometers and gyroscopes). The IMU 1022 samples the analog signals at the same sampling rate, or at respective sampling rates. For example, the IMU 1022 samples the analog signals output from all of the x, y, and z accelerometers and gyroscopes at 1600 Hz (raw sampling rate), and scales down the raw sampling rate to achieve, for each of the accelerometer and gyroscope signals, an effective sampling rate (also called the output data rate (ODR)) of 800 Hz. Furthermore, the control circuit 1032 causes the IMU 1022 to sample the analog signals output from the accelerometers and gyroscope for a finite time, such as, for example, during a time window of ten seconds.

Then, at a step 1126, the control circuit 1032 determines whether the samples that the IMU 1022 took at step 1124 are samples of a qualified event, such as the patient 1070 (FIGS. 7-8) walking with the implanted knee prosthesis 1072 (FIGS. 7-8). For example, the control circuit 1032 correlates the respective samples from each of one or more of the accelerometers and gyroscopes with corresponding benchmark samples (e.g., stored in memory circuit 1024 of FIG. 4) of the qualified event, compares the correlation result to a threshold, and determines that the samples are of a qualified event if the correlation result equals or exceeds the threshold or determines that the samples are not of a qualified event if the correlation result is less than the threshold. Alternatively, the control circuit 1032 may perform a less-complex, and less energy-consuming determination by determining that the samples are of a qualified event if, for example, the samples have a peak-to-peak amplitude and a duration that could indicate that the patient is walking for a threshold length of time. A determination as to whether the samples actually were taken while the patient was walking can be made by the remote destination (e.g., a cloud server). For example, if the control circuit 1032 is configured to cause the IMU 1022 to sample, at a relatively high sample rate (e.g., 3200 Hz) and ODR (e.g., 800 Hz), the analog signals output by one or both of the accelerometers and gyroscopes in response to three detected patient movements per day, and, statistically, at least one of the detected movements is the patient walking for at least a threshold length of time, then this technique can provide suitable prosthesis information while consuming less energy from the battery 1012 than the IMU would consume sampling fewer events but determining that the movement corresponding to the sampled events is the patient walking.

If the control circuit 1032 determines that the samples that the IMU 1022 took at step 1124 are not of a qualified event, then the control circuit returns to step 1122.

But if the control circuit 1032 determines that the samples that the IMU 1022 took at step 1124 are of a qualified event, then the control circuit proceeds to a step 1128, during which the control circuit stores, for each set of samples, in the memory circuit 1024, the samples themselves and respective sample information. A set of samples includes the samples from a respective one of the accelerometers and gyroscopes, and the sample information includes, for example, the identity of the accelerometer or gyroscope that generated the analog signal of which the samples of the set were taken, the raw sample rate and the ODR, the start time of the sample set (the time at which the first sample of the set was taken), the end time of the sample set (the time at which the last sample of the set was taken), the length of the sample window, and the dynamic amplitude input range and the amplitude output range of the ADC that took the samples. The dynamic amplitude input range is the maximum peak, or peak-to-peak, signal amplitude that the ADC can accept without "cutting off" the input signal. And the amplitude output range is the maximum peak, or peak-to-peak, range that the samples cover, and is an indication of the analog amplitude represented by each digital sample. If the sample information (e.g., raw sample rate, ODR, sample window) is the same for the respective samples from each accelerometer and gyroscope, then the control circuit 1032 can group all of the accelerometer and gyroscope samples taken during a same time window into a single set of samples with common sample information.

Next, at a step 1130, the control circuit 1032 generates, for each stored set of samples and corresponding sample information, a respective message including a header and a payload. The header includes the sample information, and the payload includes the samples that form the set. The header may also include additional information, such as a unique identifier (e.g., a serial number) of the implanted prosthesis, a unique identifier of the patient 1070 (FIGS. 7-8), and the length of the payload.

Then, at step 1132, which is optional, the control circuit 1032 encrypts part or all of each message, for example, as may be specified by HIPAA. As part of this step or step 1130, the control circuit 1032 may include, in the message header, a public encryption key that allows an authorized recipient of the message to decrypt the encrypted portion of the message. Alternatively, the control circuit 1032 may not encrypt the sample messages or may not perform any encryption until transmitting the sample messages to a remote destination.

Next, at a step 1134, the control circuit 1032 stores each message, encrypted or not, in the memory 1024.

Then, at a step 1136, the control circuit 1032 determines whether the base station 1004 (FIG. 3) has polled the implantable circuit 1010 for all messages generated since the last time that the implantable circuit sent messages to the base station.

If the control circuit 1032 determines that the base station 1004 (FIG. 3) has not polled the implantable circuit 1010, then the control circuit takes no further action regarding the messages, and effectively waits for the base station to poll the implantable circuit.

But if the control circuit 1032 determines that the base station 1004 (FIG. 3) has polled the implantable circuit 1010, then the control circuit proceeds to a step 1138.

At the step 1138, the control circuit 1032 generates one or more data packets that collectively include the messages stored in the memory 1024 as described above in conjunction with the step 1134. The control circuit 1032 generates the one or more data packets according to any suitable communication protocol, and each of the data packets includes a header and a payload. The header includes information such as an identifier (e.g., serial number) unique to the implanted prosthesis, an identifier unique to the patient 1070 (FIGS. 7-8), and a sequence number that represents a relative position within the sequence of data packets that the control circuit 1032 will send to the base station 1004 (FIG. 4) (information in the data-packet header may be redundant relative to some or all of the information in the message header). And the payload includes one or more of the messages (in whole or in part) stored in the memory circuit 1024. For example, if a stored message is too long for a single data packet, then the control circuit 1032 can split the message into two or more data packets (hence the sequence number allows a destination of the message to reconstruct the message). In contrast, if a stored message is not long enough to fill the payload of the data packet, then the data packet may include the message plus one or more other messages in whole or in part. Furthermore, instead of including the message header, the data-packet payload can include only the message payload (the samples), and the contents of the message header can be merged with, or otherwise included in, the data-packet header.

Next, at a step 1140, which is optional, the control circuit 1032 encrypts part or all of each data packet, for example, at least the prosthesis and patient identifiers as may be specified by HIPAA. As part of this step or step 1140, the control circuit 1032 may include, in the data-packet header, a public encryption key that allows an authorized recipient of the message to decrypt the encrypted portion of the data-packet header. If some or all of the message is encrypted per step 1132, then the control circuit 1032 may decrypt the message before forming the data packet. Alternatively, the control circuit 1032 may maintain the message in encrypted form such that at least a portion of the encrypted portion of the message is double encrypted (message-level encryption and data-packet-level encryption). In another alternative, the control circuit 1032 may not encrypt the prosthesis identifier so that the base station 1004 or smart device 1005 (FIG. 3) can use the prosthesis identifier to determine whether the base station or smart device should ignore the data packet or receive and process the data packet.

Then, at a step 1142, the control circuit 1032 error encodes the one or more data packets, whether encrypted or unencrypted, according to any suitable error-encoding technique (the communication protocol with which the one or more data packets are compatible may specify the error-encoding technique). Error encoding the one or more data packets allows the destination to recover a data packet having an error acquired during propagation of the data packet from the control circuit 1032 to the destination.

Next, at a step 1144, the control circuit 1032 transmits the error-encoded one or more data packets to the base station 1004 (FIG. 3) via the RF transceiver 1025, filter 1028, and antenna 1030. Alternatively, the control circuit 1032 transmits the error-encoded one or data packets to the base station 1004 via the smart device 1005, to the smart device 1005 directly, or to the smart device via the base station.

Then, at a step 1146, the control circuit 1032 determines whether it is time to acquire samples of another qualified event.

If the control circuit 1032 determines that it is not yet time to acquire samples of another qualified event, then the control circuit causes the implantable circuit 1010 to enter a sleep, or other low-power, mode, at a step 1148 to save power and extend the life of the battery 1012. For example, the control circuit 1032 may open the switches 1016 and 1018 to cut power to the IMU 2022 and the memory circuit 1024, respectively. Furthermore, the clock-and-power-management circuit 1020 includes a timer that notifies the control circuit 1032 to "wake up" the implantable circuit 1010 at a programmed absolute time or after a programmed amount of time (e.g., one day, two days, one week, one month) has elapsed. In addition, the time between qualified events can be related e.g., to how long it has been since the prosthesis was implanted in the patient 1070 (FIGS. 7-8) post-implantation or to health-insurance billing codes such as telemedicine codes or CPT codes. Regarding the former, for example, for the first three months (0-3 months) post implant, the control circuit 1032 is configured to measure at least one qualified event (e.g., a walking of at least ten steps) each day so that the patient's physician can monitor the functioning of the implant. Then, 3-6 months post implant, the control circuit 1032 may be configured to measure at least one qualified event every other day, e.g., after a waiting period of at least 24 hours, or every third day, e.g., after a waiting period of at least 48 hours. From 6-12 months the control circuit 1032 may be configured to measure at least one qualified event per week, and thereafter one or two qualified events per month. Regarding the latter (health-insurance billing codes), a telemedicine code or CPT code is an insurance code under which a physician can bill an insurance company for reviewing patient information remotely, such as over the internet, by email, or by phone. An example of such information is the result of an analysis performed on the samples of one or more qualified events detected and sampled by the IMU 1022 (FIG. 4). The insurance plan typically specifies the maximum payment that the physician can receive (e.g., $3000/year) under telemedicine codes or CPT codes for a medical issue (e.g., knee prosthesis), and how frequently the physician must the review patient information to qualify for the maximum payment. Consequently, the control circuit 1032 or other portions (e.g., the Clock and Power Management circuit 1020) of the implantable circuit 1010 can be configured to detect and measure a qualified prosthesis event at a frequency that allows a patient's physician to qualify for the payment that he/she can receive from an insurance company under one or more telemedicine, CPT or other reimbursement codes. For example, if an insurance plan requires a physician to review the results yielded by analyzing samples generated by the IMU 1022 daily for 0-6 months post implant, weekly for 6-12 months post implant, and monthly thereafter, then one can configure the control circuit 1032, or other portions of the implantable circuit 1010, to detect, to sample, and to store samples of at least one qualified event per day for months 0-6, of at least one qualified event per week for months 6-12, and at least one qualified event per month thereafter. Alternatively, one can configure the control circuit 1032, or other portions of the implantable circuit 1010, to detect, to sample, and to store samples of at least one qualified event per day for at least sixteen days per month.

If, however, the control circuit 1032 determines, at the step 1146, that it is time to acquire samples of another qualified event, then the control circuit returns to step 1122.

Still referring to FIG. 25, alternate embodiments of the operation of the implantable circuit 1010 are contemplated. For example, one or more of the steps of the flow diagram 1120 may be omitted, and one or more additional steps may be added. In addition, embodiments described in conjunction with FIGS. 3-24 and 26-27 may be applicable to the operation of the implantable circuit 1010.

FIG. 26 is a flow diagram 1160 of the operation of the base-station circuit 1040 of FIG. 5, according to an embodiment.

Referring to FIGS. 5 and 26, at a step 1162, the base-station circuit 1040 polls the implantable circuit 1010 (FIG. 4) for data packets that include kinematic-movement messages (if any) that the implantable circuit has generated since the last time that the implantable circuit sent data packets to the base station 1004 (FIG. 3).

Next, at a step 1164, the base-station circuit 1040 determines whether it has received, from the implantable circuit 1010 (FIG. 4) of the implanted prosthesis (e.g., the knee prosthesis 1072 of FIGS. 7-8), a valid response to the poll. For example, the base-station circuit 1040 determines whether it has received a valid response from the implanted prosthesis by comparing the implant identifier in the response to a version of the implant identifier stored in the base station's memory circuit 1056 to determine whether the implant is registered to the base station 1004. If the implant identifier in the response is encrypted, then the base-station circuit 1040 decrypts the response before determining whether the implant identifier is valid registered to the base station 1004.

If the base-station circuit 1040 determines that it has not yet received a valid polling response from the implantable circuit 1010 (FIG. 4), then, at a step 1166, the control circuit 1058 determines whether a number of unsuccessful polling attempts during the present polling period exceeds a first threshold, Threshold_1.

If, at the step 1166, the control circuit 1058 determines that the number of unsuccessful polling attempts does not exceed Threshold_1, then the control circuit returns to the step 1162 and again polls the implantable circuit 1010 of the implanted prosthesis; the control circuit may wait a programmed delay time before re-polling the implantable circuit. For example, Threshold_1 may have a value in an approximate range of 1-100.

But if, at the step 1166, the control circuit 1058 determines that the number of unsuccessful polling attempts exceeds Threshold_1, then the control circuit proceeds to a step 1168.

At the step 1168, the control circuit 1058 transmits, via the RF transceiver 1054, filter 1050, and antenna 1046, an error message to a destination, such as cloud or other server, where the error message indicates that the implanted prosthesis is not responding to base-station polling. As described elsewhere in this application, the destination may take appropriate action, such as notifying the patient 1070 (FIGS. 7-8) via email or text to check that the base station 1004 (FIG. 3) is powered "on" and is properly linked to the patient's home network 1006 (FIG. 3).

Referring again to the step 1164, if the control circuit 1058 determines that it has received a valid response to its poll of the implantable circuit 1010 of FIG. 4, then the control circuit proceeds to a step 1170.

At the step 1170, the control circuit 1058 receives, from the implantable circuit 1010 (FIG. 4) of the implantable prosthesis via the antenna 1044, filter 1048, and RF transceiver 1052, data packets that include the samples taken by the IMU 1022 (FIG. 4) and related information. The control circuit 1058 also decodes and decrypts (if needed) the data packets and parses the IMU samples and related information (e.g., unique prosthesis identifier, unique patient identifier).

At a step 1172, the control circuit 1058 determines whether the patient and prosthesis identifiers, and the data, parsed from the received data packets per the step 1170 are correct (if the control circuit 1058 already determined that the prosthesis identifier is correct per step 1164, then the control circuit may forgo again determining whether the prosthesis identifier is correct). For example, the control circuit 1058 error decodes a data packet using a suitable error-decoding algorithm (e.g., cyclic-redundancy check (CRC), Reed-Solomon) that corresponds to the error-encoding algorithm used by the control circuit 1032 (FIG. 4) and determines whether the data packet includes an unrecoverable error in response to the decoding result. Ad if the control circuit 1058 determines that the data packet includes no unrecoverable error, then the control circuit 1058 compares the received patient and prosthesis identifiers with respective identifiers stored in the memory circuit 1056 or downloaded from remote location. If the control circuit 1058 determines that the data packet includes an unrecoverable error or that at least one of the received patient and prosthesis identifiers is incorrect, then the control circuit proceeds to a step 1174; otherwise, the control circuit 1058 acknowledges (e.g., according to a suitable handshake protocol), to the implant circuit 1010, receipt of a valid data packet, and proceeds to a step 1176.

At the step 1174, the base-station control circuit 1058 determines whether the number of times that it has received an erroneous data packet (e.g., a data packet with an unrecoverable error or an incorrect patient identifier or an incorrect prosthesis identifier) during the current polling cycle exceeds a second threshold Threshold_2. If the control circuit 1058 determines that the number of times an erroneous data packet has been received during the current polling cycle does not exceed Threshold_2, then the control circuit returns to the step 1162 and repolls the implanted circuit 1010 (FIG. 4) of the prosthesis to resend the data packet that the control circuit 1058 determined to be erroneous upon receipt at the base station 1004 (FIG. 3). But if the control circuit 1058 determines that the number of times an erroneous data packet has been received during the current polling cycle does exceed Threshold_2, then the control circuit proceeds to the step 1168 and sends an error message as described above.

If, at the step 1172, the base-station control circuit 1058 determines that the patient and prosthesis identifiers are correct, then, at the step 176, the control circuit generates base-station data packets that include the parsed messages from the implantable circuit 1010 (FIG. 4) of the implanted prosthesis and that conform to any suitable communication protocol. That is, the control circuit 1058 effectively re-packetizes the messages into one or more base-station data packets. The respective header of each base-station data packet may include some or all of the information in the message headers and prosthesis data packets received from the prosthesis, plus additional information such as base-station-data-packet-routing information, e.g., internet, or other, addresses of the packet source (e.g., home network 1006 (FIG. 3)) and packet destination (e.g., cloud server). And the respective payload of each data packet includes accelerometer or gyroscope samples taken by the IMU 1022 (FIG. 4). Furthermore, if a message is too long for a single base-station data packet, then the control circuit 1058 can split the message into two or more data packets (hence the sequence number allows a destination of the message to reconstruct the message). In contrast, if a message is not long enough to fill the payload of the data packet, then the data packet may include the message plus one or more other messages in whole or in part. Moreover, instead of including the message header, the data-packet payload can include only the message payload (the samples), and the contents of the message header can be merged with, or otherwise included in, the data-packet header.

Then, at step 1178, the base-station control circuit 1058 encrypts part or all of each base-station data packet, for example, as may be specified by one or both of HIPAA and the communication protocol via which the control circuit sends base-station data packets. As part of this step or step 1176, the control circuit 1058 may include, in the data-packet header, a public encryption key that allows an authorized recipient of the data packet to decrypt the encrypted portion of the data packet. If some or all of the message or prosthesis data packet is encrypted, then the control circuit 1058 may decrypt the message before forming the base-station data packet. Alternatively, the control circuit 1058 may maintain the message and prosthesis data packet in encrypted form such that at least a portion of the encrypted portion of the base-station data packet is double or triple encrypted (two or more of message-level encryption, prosthesis-data-packet-level encryption, and base-station-data-packet-level encryption).

Then, at a step 1180, the control circuit 1032 error encodes the one or more encrypted base-station data packets according to any suitable error-encoding technique (the communication protocol with which the one or more base-station data packets are compatible may specify the error-encoding technique). Error encoding the one or more base-station data packets allows the destination to recover a data packet having an error acquired during propagation of the data packet from the base-station control circuit 1058 (FIG. 5) to the destination.

Next, at a step 1182, the base-station control circuit 1058 transmits the error-encoded one or more base-station data packets to the destination (e.g., a cloud server) via the RF transceiver 1054, filter 1050, antenna 1046, home network 1006 (FIG. 3), and the internet or other communications network.

Then, the base-station control circuit 1058 returns to the step 1162, waits a programmed time (e.g., one day, between two and six days, one week, one month), and then polls the implanted prosthesis again after the elapse of the programmed time.

Still referring to FIG. 26, alternate embodiments of the operation of the base-station circuit 1040 are contemplated. For example, the smart device 1005 (FIG. 3) may operate in a manner similar to that described above in conjunction with the flow diagram 1160. Furthermore, the smart base-station circuit 1040 may perform one or more of the steps in the flow diagram 1160, and the smart device 1005 may perform the one or more remaining steps in the flow diagram 1160. Moreover, as described above, the base-station circuit 1040 may communicate with the implantable circuit 1010 (FIG. 4) via the smart device 1005, or the smart device may communicate with the implantable circuit via the base-station circuit. In addition, one or more of the steps of the flow diagram 1160 may be omitted, and one or more additional steps may be added. Furthermore, embodiments described in conjunction with FIGS. 3-25 and 27 may be applicable to the operation of the base-station circuit 1040.

Figure 27:
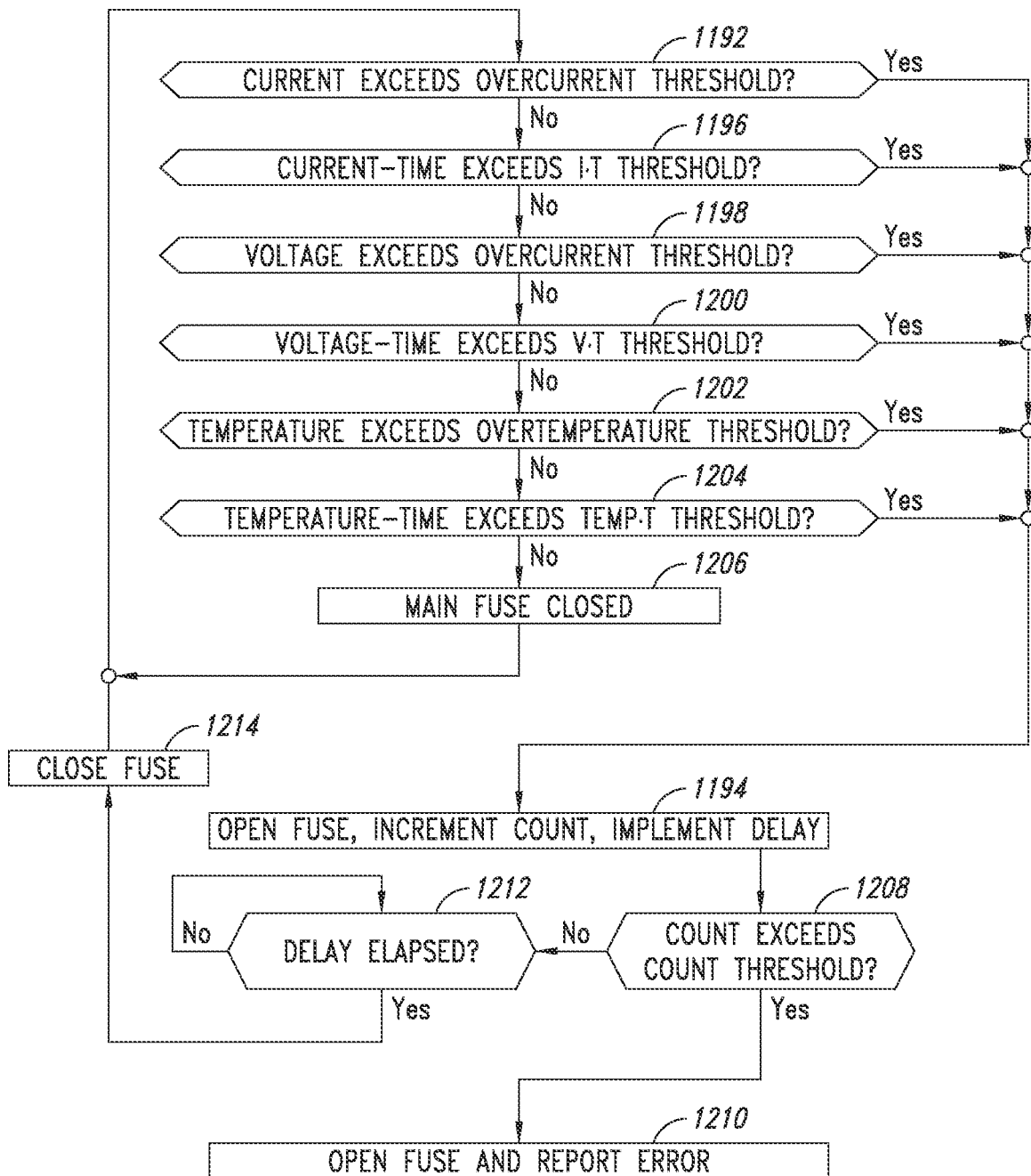
FIG. 27 is a flow diagram of operation of the fuse of FIG. 4, according to an embodiment.

FIG. 27 is a flow diagram 1190 of the operation of the fuse 1014 and the control circuit 1032 of FIG. 4, according to an embodiment.

Referring to FIGS. 4 and 27, at a step 1192, the fuse 1014 is electrically closed and the control circuit 1032 determines whether a current from the battery 1012 through the fuse exceeds a first overcurrent threshold. For example, the control circuit 1032, or another portion of the implantable circuit 1010, makes this determination by comparing the current through the fuse 1014 with a reference that represents the overcurrent threshold.

If the control circuit 1032 determines that the current through the fuse 1014 exceeds the overcurrent threshold, then the control circuit proceeds to a step 1194; otherwise, the control circuit proceeds to a step 1196.

At the step 1194, the control circuit 1032 electrically opens the fuse 1014, increments a count value, and implements a delay before determining whether to re-close the fuse. To have the ability to open and re-close the fuse 1014, a connection between the battery 1012 and the control circuit 1032 bypasses the fuse such that opening the fuse does not cut power to the control circuit, or the control circuit has, or is coupled to, another power source (e.g., battery) that powers the control circuit even while the fuse 1014 is open.

At the step 1196, the control circuit 1032 determines whether a current from the battery 1012 through the fuse 1014 exceeds a second overcurrent threshold for a first threshold length of time, where the second overcurrent threshold is less than the first overcurrent threshold. For example, the control circuit 1032, or another portion of the implantable circuit 1010, makes this determination by comparing the current through the fuse 1014 with a reference that represents the second overcurrent threshold and by determining a length of time that the current is greater than the second overcurrent threshold.

If the control circuit 1032 determines that the current through the fuse 1014 exceeds the second overcurrent threshold for the first threshold length of time, then the control circuit proceeds to the step 1194 and opens the fuse, at least temporarily, as described above; otherwise, the control circuit proceeds to a step 1198.

At a step 1198, the fuse 1014 the control circuit 1032 determines whether a voltage across the closed fuse exceeds a first overvoltage threshold. For example, the control circuit 1032, or another portion of the implantable circuit 1010, makes this determination by comparing the voltage across the fuse 1014 with a reference that represents the overvoltage threshold.

If the control circuit 1032 determines that the voltage across the fuse 1014 exceeds the overvoltage threshold, then the control circuit proceeds to the step 1194; otherwise, the control circuit proceeds to a step 1200.

At the step 1194, the control circuit 1032 electrically opens the fuse 1014, at least temporarily, as described above.

At the step 1200, the control circuit 1032 determines whether the voltage across the fuse 1014 exceeds a second overvoltage threshold for a second threshold length of time, where the second overvoltage threshold is less than the first overvoltage threshold. For example, the control circuit 1032, or another portion of the implantable circuit 1010, makes this determination by comparing the voltage across the fuse 1014 with a reference that represents the second overvoltage threshold and by determining a length of time that the voltage is greater than the second overvoltage threshold.

If the control circuit 1032 determines that the voltage across the fuse 1014 exceeds the second overvoltage threshold for the second threshold length of time, then the control circuit proceeds to the step 1194 and opens the fuse, at least temporarily, as described above; otherwise, the control circuit proceeds to a step 1202.

At the step 1202, the control circuit 1032 determines whether a temperature of the closed fuse 1014 (or the temperature of another part of the prosthesis) exceeds a first overtemperature threshold. For example, the control circuit 1032, or another portion of the implantable circuit 1010, makes this determination by comparing the temperature with a reference that represents the overtemperature threshold.

If the control circuit 1032 determines that the temperature exceeds the overtemperature threshold, then the control circuit proceeds to the step 1194; otherwise, the control circuit proceeds to a step 1204.

At the step 1194, the control circuit 1032 electrically opens the fuse 1014, at least temporarily, as described above.

At the step 1204, the control circuit 1032 determines whether the temperature of the fuse 1014 (or the temperature of another part of the prosthesis) exceeds a second overtemperature threshold for a third threshold length of time, where the second overtemperature threshold is less than the first overtemperature threshold. For example, the control circuit 1032, or another portion of the implantable circuit 1010, makes this determination by comparing the temperature with a reference signal that represents the second overtemperature threshold and by determining a length of time that the temperature is greater than the second overtemperature threshold.

If the control circuit 1032 determines that the temperature exceeds the second overtemperature threshold for the third threshold length of time, then the control circuit proceeds to the step 1194 and opens the fuse, at least temporarily, as described above; otherwise, the control circuit proceeds to a step 1206.

At the step 1206, the control circuit 1032 maintains the fuse 1014 electrically closed and returns to the step 1192.

If, however, the control circuity 1032 proceeded to the step 1194 from any of the steps 1192-1204, then the control circuit proceeds to a step 1208.

At the step 1208, the control circuit 1032 determines whether the count exceeds a count threshold (the count represents the number of times that the control circuit has opened the fuse 1014 since the battery 1012 has been powering the implantable circuit 1010. If the control circuit 1032 determines that the count exceeds the count threshold, then the control circuit proceeds to a step 1210; otherwise, the control circuit proceeds to a step 1212.

At the step 1210, the control circuit 1032 opens the fuse 1014 permanently. And if the prosthesis has a power source other than the battery 1012 for powering the implantable circuit 1010 even while the fuse 1014 is open, then the control circuit 1032 generates an error message and one or more data packets that include the error message, stores the one or more data packets in the memory circuit 1024, and transmits, via the RF transceiver 1026, the filter 1028, and the antenna 1030, the one or more data packets to the base station 1004 (FIG. 3) in response to the next polling request from the base station.

At the step 1212, the control circuit 1032 determines if the delay has elapsed. If the delay has not elapsed, then the control circuit 1032 effectively waits until the delay has elapsed. If, however, the delay has elapsed, the control circuit 1032 proceeds to a step 1214.

At the step 1214, the control circuit 1032 closes the fuses 1014, and returns to the step 1192. The steps 1212 and 1214 allow the control circuit 1032 to reset the fuse 1014 on the chance that the event that caused the control circuit 1032 to open the fuse at the step 1194 was temporary such that the fuse need not be permanently opened.

Still referring to FIGS. 4 and 27, alternate embodiments of the fuse 1014 and the related operation of the implantable circuit 1010 are contemplated. For example, the fuse 1014 can be a one-time openable fuse that is not controllable by the control circuit 1032 such that once the fuse opens, it remains open. Furthermore, the fuse 1014 may open in response to fewer than all, or to only one, of the conditions described in conjunction with steps 1192-1204. For example, the fuse 1014 may open only in response to a current through the fuse exceeding an overcurrent threshold per step 1192. Moreover, one or more of the steps of the flow diagram 1190 may be omitted, and one or more additional steps may be added. In addition, embodiments described in conjunction with FIGS. 3-26 may be applicable to the fuse 1014 and the related operation of the implantable circuit 1010.

The following are exemplary embodiments of the present disclosure:

1) An implantable medical device, comprising:
   a. a circuit configured to be fixedly attached to an implantable prosthetic device;
   b. a power component; and
   c. a device configured to uncouple the circuit from the power component.

2) The implantable medical device of embodiment 1, wherein the circuit includes an implantable reporting processor.

3) The implantable medical device of embodiment 1, wherein the power component includes a battery.

4) The implantable medical device of embodiment 1, wherein the device includes a fuse.

5) The implantable medical device of embodiment 1, wherein the device includes a resettable fuse.

6) The implantable medical device of embodiment 1, wherein the device includes a switch.

7) The implantable medical device of embodiment 1, wherein the device includes a one-time openable fuse.

8) The implantable medical device of embodiment 1, wherein the device is configured to uncouple the circuit from the power component in response to a current through the device exceeding a threshold current.

9) The implantable medical device of embodiment 1, wherein the device is configured to uncouple the circuit from the power component in response to a voltage across the device exceeding a threshold voltage.

10) The implantable medical device of embodiment 1, wherein the device is configured to uncouple the circuit from the power component in response to a temperature exceeding a threshold temperature.

11) The implantable medical device of embodiment 1, wherein the device is configured to uncouple the circuit from the power component in response to a temperature of the circuit exceeding a threshold temperature.

12) The implantable medical device of embodiment 1, wherein the device is configured to uncouple the circuit from the power component in response to a temperature of the power component exceeding a threshold temperature.

13) The implantable medical device of embodiment 1, wherein the device is configured to uncouple the circuit from the power component in response to a temperature of the device exceeding a threshold temperature.

14) The implantable medical device of embodiment 1, wherein the device is configured to uncouple the circuit from the power component in response to a current through the device exceeding a threshold current for at least a threshold time.

15) The implantable medical device of embodiment 1, wherein the device is configured to uncouple the circuit from the power component in response to a voltage across the device exceeding a threshold voltage for at least a threshold time.

16) The implantable medical device of embodiment 1, wherein the device is configured to uncouple the circuit from the power component in response to a temperature exceeding a threshold temperature for at least a threshold time.

17) The implantable medical device of embodiment 1, wherein the device is configured to uncouple the circuit from the power component in response to a temperature of the circuit exceeding a threshold temperature for at least a threshold time.

18) The implantable medical device of embodiment 1, wherein the device is configured to uncouple the circuit from the power component in response to a temperature of the power component exceeding a threshold temperature for at least a threshold time.

19) The implantable medical device of embodiment 1, wherein the device is configured to uncouple the circuit from the power component in response to a temperature of the device exceeding a threshold temperature.

20) The implantable medical device of embodiment 1, further comprising at least one mechanical component that is configured to function while the device uncouples the circuit from the power component.

21) An implantable medical device, comprising:
 a. a circuit configured to be fixedly attached to an implantable prosthetic device;
 b. a battery; and
 c. a fuse coupled between the circuit and the battery.

22) A method, comprising electrically opening a fuse that is disposed between a circuit and a battery, at least the fuse and the circuit being disposed on an implanted prosthetic device.

23) The method of embodiment 22, further comprising operating at least one mechanical component of the implanted prosthetic device while the fuse is electrically open.

24) The method of embodiment 22 wherein the battery is disposed on the implanted prosthetic device.

25) An implantable medical device, comprising:
 a. at least one sensor configured to generate a sensor signal; and
 b. a control circuit configured to cause the at least one sensor to generate the sensor signal at a frequency that is related to a telemedicine code.

26) An implantable medical device, comprising:
 a. at least one sensor configured to generate a sensor signal; and
 b. a control circuit configured to cause the at least one sensor to generate the sensor signal at a frequency that allows a doctor to qualify for payment under a telemedicine insurance code.

27) An implantable medical device, comprising:
 a. at least one sensor configured to generate a sensor signal; and
 b. a control circuit configured to cause the at least one sensor to generate the sensor signal at a frequency that allows a doctor to qualify for full payment under a telemedicine insurance code.

28) A method, comprising, generating a sensor signal that is related to an implanted medical device at a frequency that allows a doctor to qualify for payment available under a telemedicine insurance code.

29) A method, comprising, generating a sensor signal that is related to an implanted medical device at a frequency that allows a doctor to qualify for full payment available under a telemedicine insurance code.

30) An implantable prosthesis, comprising:
 a. a housing; and
 b. an implantable circuit disposed in the housing and configured
  i. to generate at least one first signal representative of a movement;
  ii. to determine whether the signal meets at least one first criterion; and
  iii. to send the signal to a remote location in response to determining that the signal meets the at least one first criterion.

31) The implantable prosthesis of embodiment 30 wherein the housing includes a tibial extension.

32) The implantable prosthesis of embodiment 30 wherein the movement includes a movement of a patient.

33) The implantable prosthesis of embodiment 30 wherein the movement includes a patient walking.

34) The implantable prosthesis of embodiment 30 wherein the at least one first criterion includes that the signal represents the movement for at least a threshold duration.

35) The implantable prosthesis of embodiment 30 wherein the at least one first criterion includes that the signal represents the movement for at least a threshold number of events.

36) The implantable prosthesis of embodiment 30 wherein:
 a. the movement includes a patient walking; and
 b. the at least one first criterion includes that the signal represents the movement for at least a threshold number of steps taken by the patient.

37) The implantable prosthesis of embodiment 30 wherein the implantable circuit is further configured:
 a. to determine whether the movement meets at least one second criterion before determining whether the signal meets the at least one first criterion; and
 b. to determine whether the signal meets the at least one first criterion in response to determining that the movement meets the second criterion.

38) The implantable prosthesis of embodiment 37 wherein the at least one second criterion includes that the movement is a patient walking.

39) The implantable prosthesis of embodiment 30 wherein the implantable circuit is further configured:
 a. to determine, in response to the signal, whether the movement meets at least one second criterion before determining whether the signal meets the at least one first criterion; and
 b. to determine whether the signal meets the at least one first criterion in response to determining that the movement meets the second criterion.

40) The implantable prosthesis of embodiment 30 wherein the implantable circuit is further configured:
 a. to determine, in response to the signal, whether the movement meets at least one second criterion; and
 b. to cease generating the signal in response to determining that the movement does not meet the at least one second criterion.

41) The implantable prosthesis of embodiment 30 wherein the implantable circuit is further configured:
 a. to determine, in response to the signal, whether the movement meets at least one second criterion; and
 b. to cease generating the signal before determining whether the signal meets the at least one first criterion in response to determining that the movement does not meet the at least one second criterion.

42) The implantable prosthesis of embodiment 30 wherein the implantable circuit is further configured:
 a. to store the signal in response to determining that the signal meets the at least one first criterion; and
 b. to send the stored signal to the remote location.

43) The implantable prosthesis of embodiment 30 wherein the implantable circuit is further configured to encrypt the signal before sending the signal to the remote location.

44) The implantable prosthesis of embodiment 30 wherein the implantable circuit is further configured to encode the signal before sending the signal to the remote location.

45) The implantable prosthesis of embodiment 30 wherein the implantable circuit is further configured:
 a. to generate a message that includes the signal; and
 b. wherein sending the signal includes sending the message.

46) The implantable prosthesis of embodiment 30 wherein the implantable circuit is further configured:
 a. to generate a data packet that includes the signal; and
 b. wherein sending the message includes sending the data packet to the remote location.

47) A base station, comprising:
 a. a housing; and
 b. a base-station circuit disposed in the housing and configured
  i. to receive, from an implantable prosthesis, at least first signal representative of a movement;
  ii. to send the at least one first signal to a destination;
  iii. to receive at least one second signal from a source; and
  iv. to send the at least one second signal to the implantable prosthesis.

48) The base station of embodiment 47 wherein the base-station circuit is configured to poll the implantable prosthesis for the first signal.

49) The base station of embodiment 47 wherein the base-station circuit is configured to decrypt the at least one first signal before sending the at least one first signal to the destination.

50) The base station of embodiment 47 wherein the base-station circuit is configured to encrypt the at least one first signal before sending the at least one first signal to the destination.

51) The base station of embodiment 47 wherein the base-station circuit is configured to decode the at least one first signal before sending the at least one first signal to the destination.

52) The base station of embodiment 47 wherein the base-station circuit is configured to encode the at least one first signal before sending the at least one first signal to the destination.

53) A method, comprising opening a fuse disposed on an implantable prosthesis between a power source and an implantable circuit in response to a current through the fuse exceeding an overcurrent threshold.

54) A method, comprising opening a fuse disposed on an implantable prosthesis between a power source and an implantable circuit in response to a current through the fuse exceeding an overcurrent threshold for at least a threshold time.

55) A method, comprising opening a fuse disposed on an implantable prosthesis between a power source and an implantable circuit in response to a voltage across the fuse exceeding an overvoltage threshold.

56) A method, comprising opening a fuse disposed on an implantable prosthesis between a power source and an implantable circuit in response to a voltage across the fuse exceeding an overvoltage threshold for at least a threshold time.

57) A method, comprising opening a fuse disposed on an implantable prosthesis between a power source and an implantable circuit in response to a temperature exceeds an overtemperature threshold.

58) A method, comprising opening a fuse disposed on an implantable prosthesis between a power source and an implantable circuit in response to a temperature exceeding an overtemperature threshold for at least a threshold length of time.

59) A method, comprising:
 a. generating a sensor signal in response to a movement of a subject in which a prosthesis is implanted; and
 b. transmitting the sensor signal to a remote location.

60) A method, comprising:
 a. generating a sensor signal in response to a movement of a subject in which a prosthesis is implanted;
 b. sampling the sensor signal; and
 c. transmitting the samples to a remote location.

61) A method, comprising:
 a. generating a sensor signal in response to a movement of a subject in which a prosthesis is implanted;
 b. determining whether the sensor signal represents a qualified event; and
 c. transmitting the signal to a remote location in response to determining that the sensor signal represents a qualified event.

62) A method, comprising:
 a. generating a sensor signal in response to a movement of a subject in which a prosthesis is implanted;
 b. receiving a polling signal from a remote location; and
 c. transmitting the sensor signal to the remote location in response to the polling signal.

63) A method, comprising:
 a. generating a sensor signal in response to a movement of a subject in which a prosthesis is implanted;
 b. generating a message that includes the sensor signal or data representative of the sensor signal; and
 c. transmitting the message to a remote location.

64) A method, comprising:
 a. generating a sensor signal in response to a movement of a subject in which a prosthesis is implanted;
 b. generating a data packet that includes the sensor signal or data representative of the sensor signal; and
 c. transmitting the data packet to a remote location.

65) A method, comprising:
 a. generating a sensor signal in response to a movement of a subject in which a prosthesis is implanted;
 b. encrypting at least a portion of the sensor signal or data representative of the sensor signal; and
 c. transmitting the encrypted sensor signal to a remote location.

66) A method, comprising:
 a. generating a sensor signal in response to a movement of a subject in which a prosthesis is implanted;
 b. encoding at least a portion of the sensor signal or data representative of the sensor signal; and
 c. transmitting the encoded sensor signal to a remote location.

67) A method, comprising:
 a. generating a sensor signal in response to a movement of a subject in which a prosthesis is implanted;
 b. transmitting the sensor signal to a remote location; and
 c. entering an implantable circuit associated with the prosthesis into a lower-power mode after transmitting the sensor signal.

68) A method, comprising:
a. generating a first sensor signal in response to a movement of a subject in which a prosthesis is implanted;
b. transmitting the first sensor signal to a remote location;
c. entering at least one component of an implantable circuit associated with the prosthesis into a lower-power mode after transmitting the sensor signal; and
d. generating a second sensor signal in response to a movement of the subject after an elapse of a low-power-mode time for which the implantable circuit is configured.

69) A method, comprising:
a. receiving a sensor signal from a prosthesis implanted in a subject; and
b. transmitting the received sensor signal to a destination.

70) A method, comprising:
a. sending an inquiry to a prosthesis implanted in a subject
b. receiving a sensor signal from a prosthesis after sending the inquiry; and
c. transmitting the received sensor signal to a destination.

71) A method, comprising:
a. receiving a sensor signal and at least one identifier from a prosthesis implanted in a subject;
b. determining whether the identifier is correct; and
c. transmitting the received sensor signal to a destination in response to determining that the identifier is correct.

72) A method, comprising:
a. receiving a message including a sensor signal from a prosthesis implanted in a subject;
b. decrypting at least a portion of the message; and
c. transmitting the decrypted message to a destination.

73) A method, comprising:
a. receiving a message including a sensor signal from a prosthesis implanted in a subject;
b. decoding at least a portion of the message; and
c. transmitting the decoded message to a destination.

74) A method, comprising:
a. receiving a message including a sensor signal from a prosthesis implanted in a subject;
b. encoding at least a portion of the message; and
c. transmitting the encoded message to a destination.

75) A method, comprising:
a. receiving a message including a sensor signal from a prosthesis implanted in a subject;
b. encrypting at least a portion of the message; and
c. transmitting the encrypted message to a destination.

76) A method, comprising:
a. receiving a data packet including a sensor signal from a prosthesis implanted in a subject;
b. decrypting at least a portion of the data packet; and
c. transmitting the decrypted data packet to a destination.

77) A method, comprising:
a. receiving a data packet including a sensor signal from a prosthesis implanted in a subject;
b. decoding at least a portion of the data packet; and
c. transmitting the decoded data packet to a destination.

78) A method, comprising:
a. receiving a data packet including a sensor signal from a prosthesis implanted in a subject;
b. encoding at least a portion of the data packet; and
c. transmitting the encoded data packet to a destination.

79) A method, comprising:
a. receiving a data packet including a sensor signal from a prosthesis implanted in a subject;
b. encrypting at least a portion of the data packet; and
c. transmitting the encrypted data packet to a destination.

80) A method, comprising:
a. receiving a sensor signal from a prosthesis implanted in a subject;
b. decrypting at least a portion of the sensor signal; and
c. transmitting the decrypted sensor signal to a destination.

81) A method, comprising:
a. receiving a sensor signal from a prosthesis implanted in a subject;
b. decoding at least a portion of the sensor signal; and
c. transmitting the decoded sensor signal to a destination.

82) A method, comprising:
a. receiving a sensor signal from a prosthesis implanted in a subject;
b. encoding at least a portion of the sensor signal; and
c. transmitting the encoded sensor signal to a destination.

83) A method, comprising:
a. receiving a sensor signal from a prosthesis implanted in a subject;
b. encrypting at least a portion of the sensor signal; and
c. transmitting the encrypted sensor signal to a destination.

84) An implantable circuit for an implantable prosthesis.

85) An implanted or an implantable prosthesis, including an implantable circuit.

86) An implanted, or an implantable prosthesis, including a fuse.

87) A base station for communication with an implanted, or an implantable, prosthesis.

D. Computer Systems for Analysis, Dissemination of Information, Ordering, and Supply: Processing IMU Data Recorded During Patient Monitoring As discussed in previous sections of this document, a patient is intermittently monitored, at home, in a work environment, at a doctor's office, or in another environment frequently inhabited by the patient, by the sensors incorporated in an implant in combination with a base station or another communications device. The sensor data is uploaded to a base station from the implant, temporarily stored within the base station during accumulation of data during a patient-monitoring session, and subsequently transmitted from the base station to a data-processing application running within one or more standalone servers, data centers, or cloud-computing facilities. As also discussed in previous sections of this document, the data may be transferred by various different types of communications media, associated communications devices and subsystems, and operating-system communications services and functionalities using many different types of data-transfer protocols. The data is encoded according to predetermined formats and digital-encoding conventions and encrypted. In the current section of this document, the monitoring data is assumed to be transmitted from the base station to the data-processing application in a series of sequenced messages. It is assumed that the data includes a time sequence of encoded IMU data vectors, discussed in more detail below, a patient identifier, a device identifier, configuration parameters for the IMU, and other information needed by the data-processing application to interpret the encoded IMU data vectors, identify the patient and sensor-equipped implant, authorize receiving and processing of monitoring data from the patient, generate output results and output reports, and distribute the output results and output reports to various predetermined recipients, such as clinicians, insurance providers, and other such recipients. In alternative implementations, the monitoring data may be transferred as one or more files by various file-transfer protocols and facilities, although, of course, file-transfer protocols are implemented above message protocols. In certain implementations, patient-monitoring-session data may be received on various types of optical or electromagnetic data-storage devices physically transported to a computer or computing facility in which the data-processing application runs.

The primary task of the data-ingress and monitoring-data-processing components of the data-processing application is to convert raw sensor data output, during a monitoring session, by the sensors incorporated in an implant into a digitally-encoded, human-readable report and/or digitally-encoded output results that may be forwarded to clinicians, insurance providers, and/or additional automated systems for further automated processing tasks. In addition, the monitoring-data-processing components of the data-processing application may raise various different types of events and alarms, based on the output results for a monitoring session, that may be handled by other components of the data-processing application or by other applications concurrently running within the one or more computers or distributed computer systems.

There are a very large number of different approaches that can be undertaken, in different implementations, to analyze the raw sensor data in order to generate output results. One approach is next described below with reference to FIGS. 28-37H. In alternative implementations, different and/or additional types of sensor data may be included in the monitoring data received by the data-processing application from multiple different sensors and incorporated into the analysis. For example, an implant may include a temperature sensor, various types of chemical sensors, acoustic sensors, and other types of sensors, the data output from which may be useful for diagnosing many types of problems and anomalies that occur in various different types of implants. The current discussion focuses on IMU data produced by an implant proximately located to a knee joint. An initial portion of the following discussion is devoted to a discussion of the processing of IMU output data to generate a number of metrics that can be subsequently used to infer the operational condition and characteristics of a prosthetic knee joint as well as to infer characteristics of a patient's ambulation.

Figure 28:
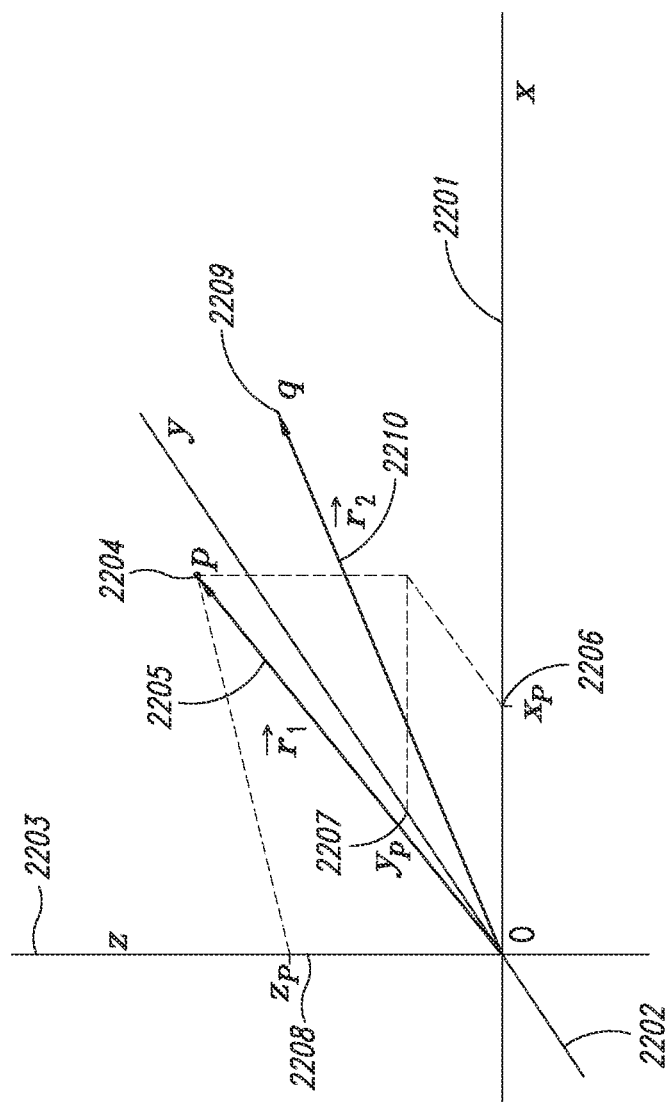
FIG. 28 illustrates a three-dimensional Cartesian coordinate space and the representation of a point in the space by a vector.

FIG. 28 illustrates a three-dimensional Cartesian coordinate space and the representation of a point in the space by a vector. The three-dimensional coordinate space is defined by familiar x, y, and z coordinate axes, 2201-2203, respectively. The location of a point p 2204 in this space can be represented by a vector r 2205, with vector components $r_x$, $r_y$, and $r_z$ corresponding to the lengths of the projections of the vector onto the coordinate axes 2206-2208. A different point q 2209 is associated with a different position vector 2210. A vector-valued function of time, $f(t)$, may return a position vector for each point in time within the time domain of the function. One type of vector-valued function may return position vectors for different points of time that describe a space curve, or trajectory, such as an object moving in space. Another type of discrete vector-valued function may be a function that represents the output of an IMU over time.

Figure 29A:
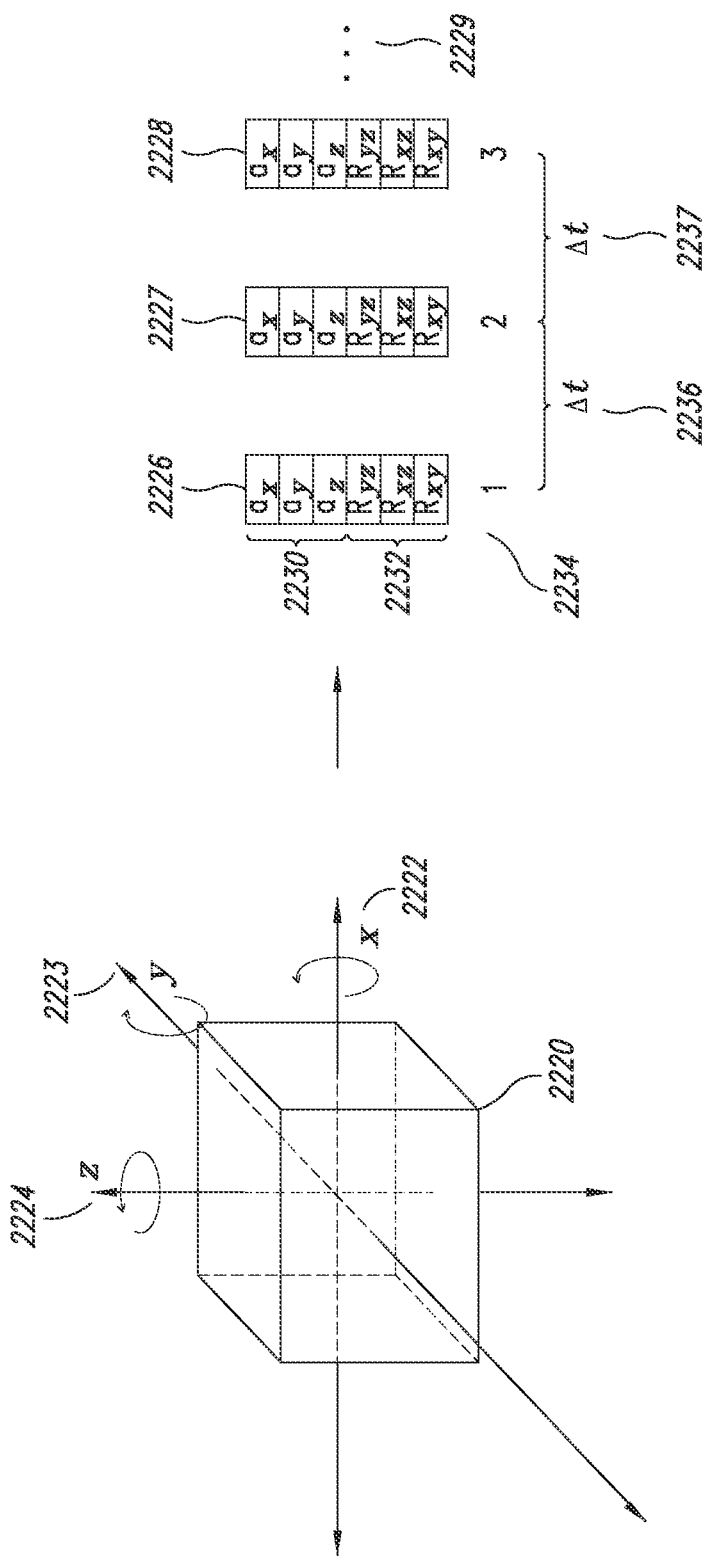
FIG. 29A and FIG. 29B each illustrate the data output by an IMU.
Figure 29B:
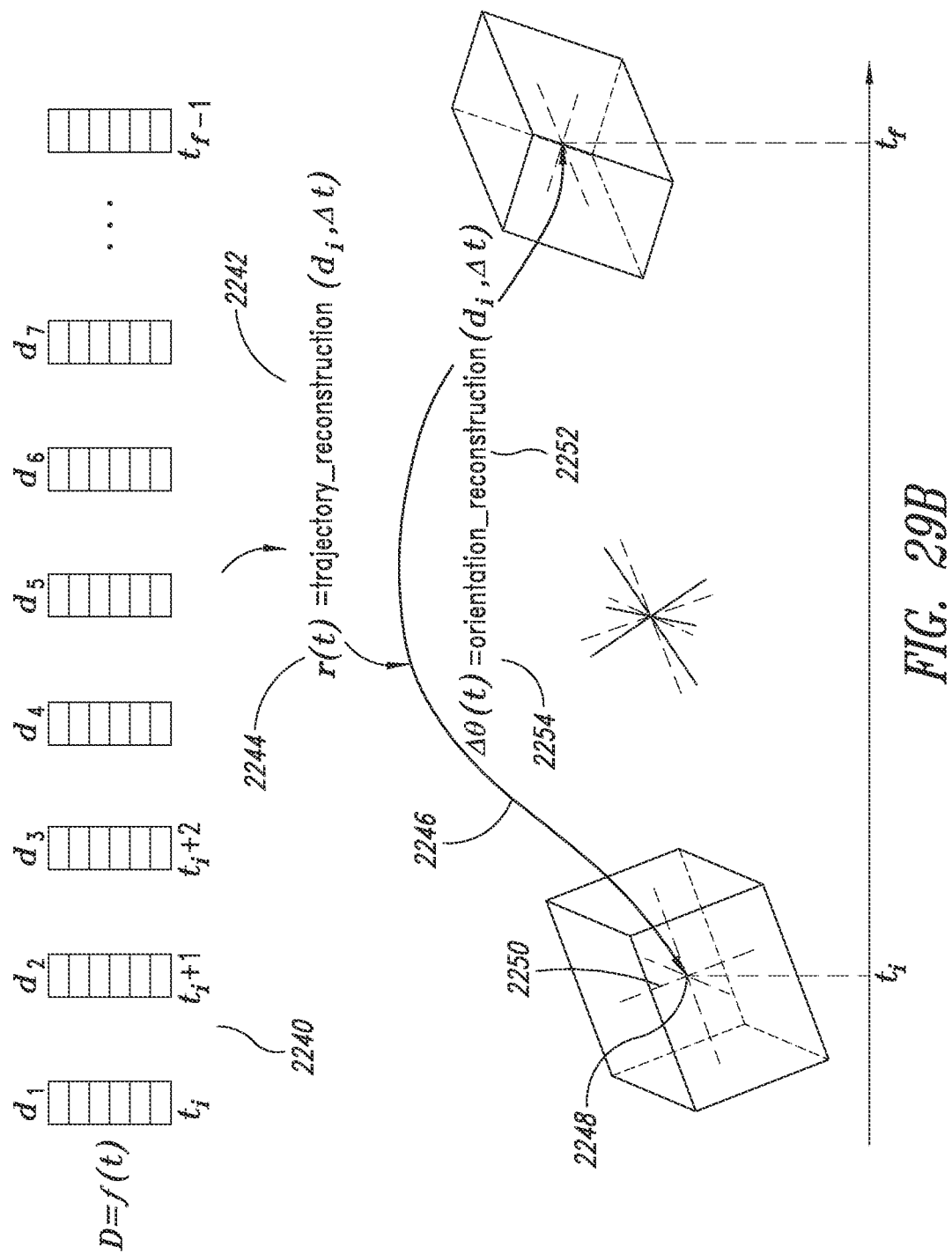

FIGS. 29A-B illustrate the data output by an IMU. The IMU can be thought of as a black-box device 2220 with a fixed internal coordinate system 2222-2224 which outputs a time-ordered sequence of 6-dimensional vectors 2226-2228, where ellipsis 2229 indicates continuation of the sequence. Ellipses are used to indicate additional elements of a sequence or series throughout FIGS. 28-37H. Each 6-dimensional vector, such as a vector 2226, includes three numerical indications 2230 of the linear accelerations of the IMU in the directions of the three coordinate axes and three numerical indications 2232 of the rotational or angular velocity about each of the three IMU coordinate axes. The vectors output by the IMU are associated with sequence numbers, such as sequence number "1" 2234 associated with vector 2226. In general, the accelerations and angular velocities are sampled at regular intervals in time 2236-2237, so that the relative sampling time for each vector is a linear function of the sequence number associated with the vector. The sampling rate as well as the meaning of the numerical values is specified by IMU parameters, including fixed parameters and configuration, or operational, parameters. As mentioned above, the data received by the data-processing application includes sufficient information with respect to these parameters to decode the numerical values into accelerations and angular velocities expressed in a particular set of units and to determine the sampling interval. In the following discussion, it is assumed that the vector data has been processed, if needed, so that the angular-velocity and acceleration data refer to the same internal coordinate system. It is also assumed that the sampling rate is uniform over the data. When the sampling rate is not uniform, then the sampling-rate-dependent portions of the analyses, discussed below, may need to be carried out piecewise over subsequences of the data-vector IMU output with uniform sampling rates.

FIG. 29B illustrates one type of information that can be derived from the data-vector output of an IMU. As discussed above, the vectors output by the IMU can be thought of as a vector-valued function of time 2240. This function can be converted, by a trajectory-reconstruction process 2242, to produce a corresponding vector-valued function 2244 that returns a position vector for each point in the time domain of the function, thus describing a space-curve trajectory 2246 of the origin 2248 of the IMU internal coordinate system that represents the motion of the origin of the IMU in space and time relative to the initial position of the origin of the IMU internal coordinate system. The IMU-output vector-valued function can also be converted by an orientation-reconstruction process 2252 to produce a corresponding vector-valued function 2254 that outputs orientation vectors that describe the orientation, at any point in time, of the IMU internal coordinate system with respect to the initial orientation of the internal coordinate system 2250. When the real-world initial position and orientation of the IMU are known, the space curve can be oriented with respect to the real-world coordinate system and the relative orientations produced by vector-valued function 2254 can be transformed into orientations defined by the real-world coordinate system. Of course, there are a variety of different real-world coordinate systems. As discussed below, the current analyses considers a coordinate system in which the x axis is parallel to the ground and has a direction parallel to the direction in which a patient is walking, during the monitoring session, the z axis is perpendicular to the ground and parallel to the bilateral axis of symmetry of the patient, and the y axis is normal to both the x and z axes. This coordinate system is referred to as the "natural coordinate system" in the following discussion. Many other coordinate systems can be used in alternative implementations, including coordinate systems fixed to a particular rigid part of a patient's body, and cylindrical or spherical coordinate systems fixed to the patient or to a position and orientation with respect to the Earth's surface.

The above-mentioned trajectory-reconstruction and orientation-reconstruction processes are not further discussed.

These processes are well-known and are based on Newtonian mechanics, including integration of accelerations to produce velocities and integration of linear and angular velocities to produce linear and angular distances. However, additional, sophisticated mathematical processes are employed in trajectory and orientation reconstruction. As with all interpretation of instrumental data, there are many sources of error, and the errors can propagate and accumulate to produce significant variations between the computed trajectories and orientations and those actually experienced by the IMU during position and orientation monitoring by the IMU. When possible, additional data and information is used to detect and account for instrumental errors during the processing of IMU data. In the approach to IMU-data processing described below, the numerical values of the IMU output vectors are converted into numerical values that express the accelerations and angular velocities with respect to the natural coordinate system. One approach to carrying out this conversion is discussed below.

Figure 30A:
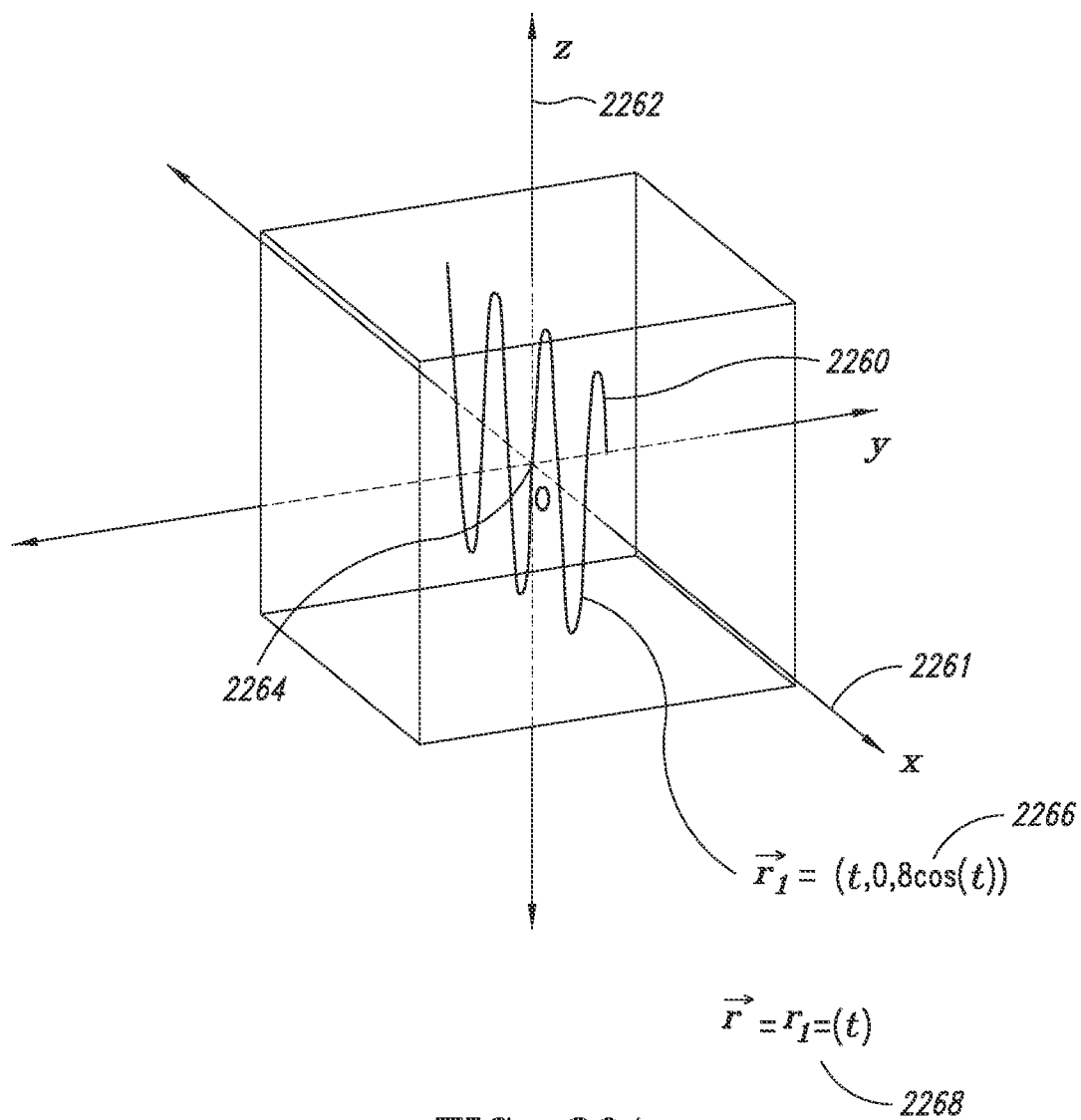
FIG. 30A, FIG. 30B, FIG. 30C, FIG. 30D, FIG. 30E, FIG. 30F and FIG. 30G each illustrate complex space curves that represent motions and resolution of the complex space curves into component motions.
Figure 30B:
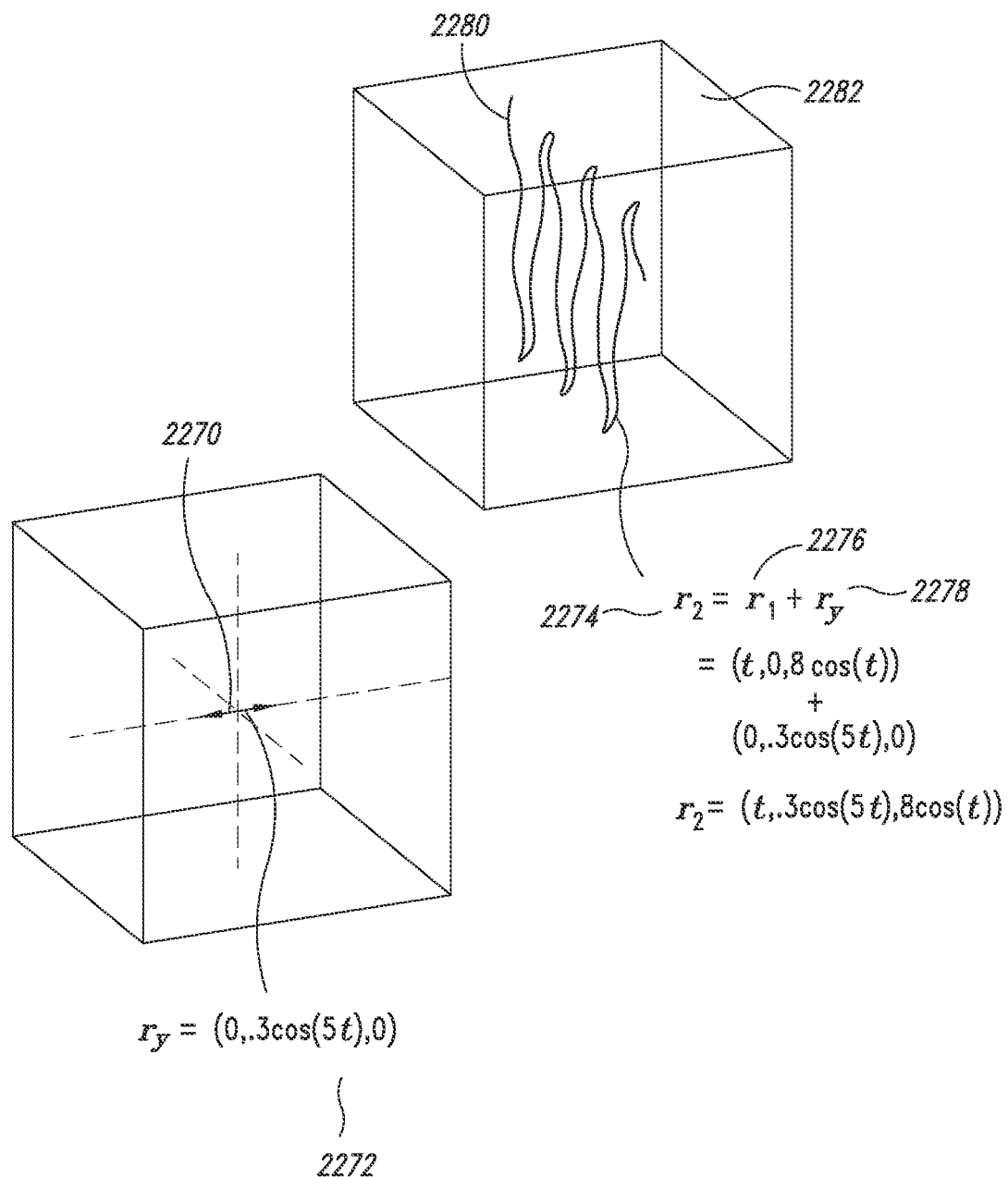
Figure 30C:
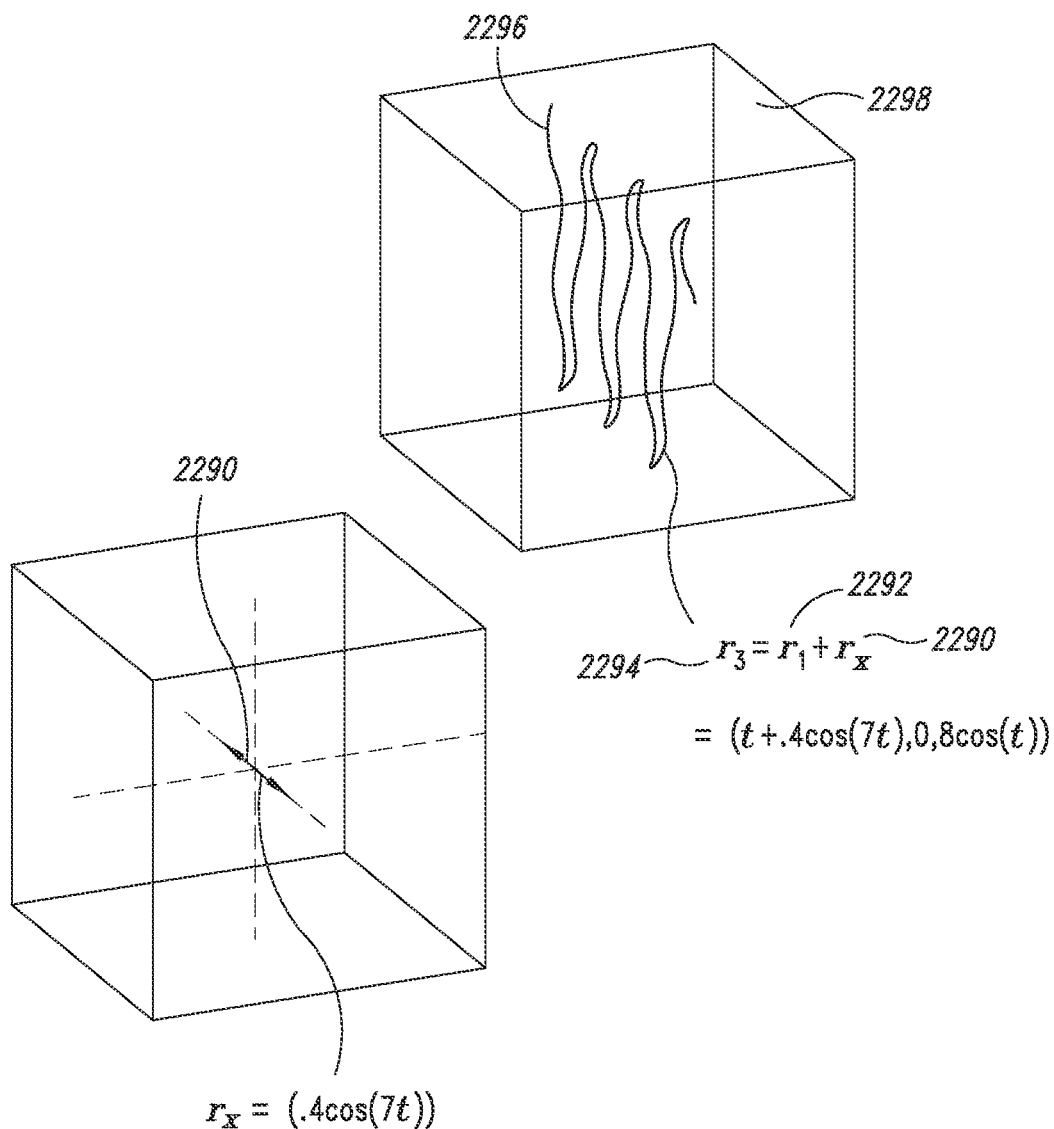
Figure 30D:
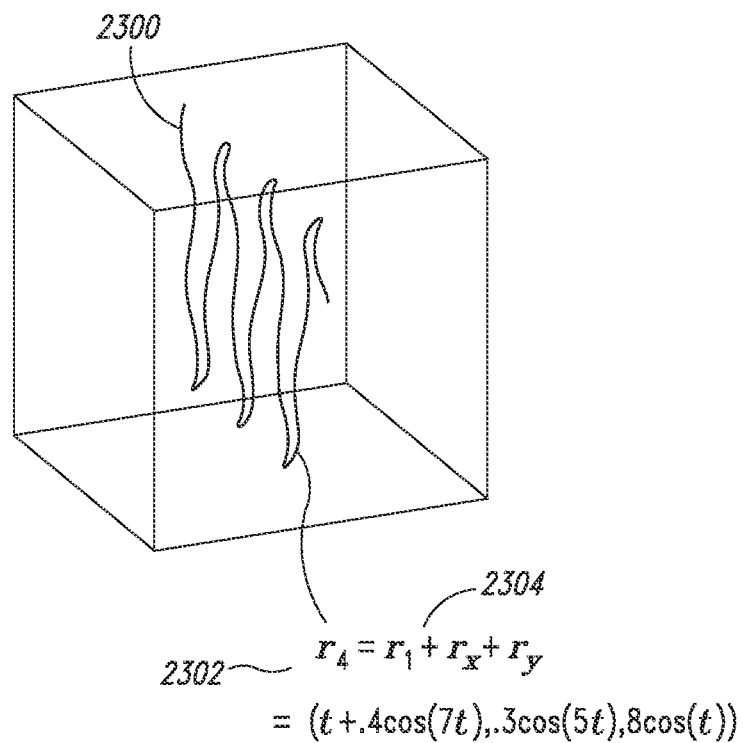

FIGS. 30A-G illustrate complex space curves that represent motions and resolution of the complex space curves into component motions. FIG. 30A shows a short section of a harmonic spatial trajectory within a volume of three-dimensional Cartesian space. The harmonic trajectory 2260 is contained within the xz plane that is coincident with the x and z axes 2261-2262 and the origin 2264. This harmonic trajectory is expressed by the vector-valued function 2266, which is a vector-valued function of time 2268. This type of harmonic trajectory may be similar to, at a high level, the trajectory of an IMU within an implant proximal to a knee joint during ambulation by a patient. FIG. 30B introduces an additional motion component to the motion, or trajectory, shown in FIG. 30A. The new motion component 2270 is a linear harmonic motion in the y direction centered about the origin of the internal IMU coordinate system, and is expressed by the vector-valued function 2272. A composite vector-valued function 2274 that includes both the original trajectory 2276 shown in FIG. 30A and the new motion component 2278 is shown as curve 2280 within spatial volume 2282. The new trajectory remains periodic with respect to the x axis, but has a rather complex shape that features periodic deviations, in the y direction, of a higher frequency and smaller amplitude than the periodic frequency and amplitude of the original harmonic trajectory. FIG. 30C illustrates addition of a new linear, harmonic motion in the x direction 2292 the original trajectory 2292 to produce a composite vector-valued function 2294 that represents the complex space curve 2296 shown within volume 2298. In this case, the complex space curve 2296 is planar, but includes periodic deviations in the x direction of a higher frequency and smaller amplitude than the than the periodic frequency and amplitude of original harmonic motion shown in FIG. 30A. FIG. 30D illustrates, using the same illustration conventions as used in FIGS. 30A-C, a space curve 2300 that represents a composite vector-valued function 2302 that includes the original harmonic trajectory 2304 shown in FIG. 30A, the y-direction motion component discussed above with reference to FIG. 30B, and the x-direction motion component discussed above with reference to FIG. 30C. Space curve 2300 is quite complex, even though representing a relatively simple vector-valued function that combines only three component motions.

The trajectory of an IMU within a knee-joint implant during ambulation may be an extremely complex space curve featuring many different component motions that oscillate at many different frequencies. One motion component may be the rotation of the implant about the knee joint as the lower leg rotates with respect to the upper leg during walking. Another component motion is the motion of the patient in the direction of walking. Combination of these two motions may produce a periodic trajectory in the xz plane of the natural coordinate system. However, there may be many other component motions, including lateral motions of the knee joint, component motions due to rocking of the patient's bilateral axis during ambulation, and higher-frequency motions related to frictional forces within the knee joint and other components of the patient's body as well as to the complex geometries of the patient's body components, and may additionally include high-frequency motions due to vibration or jostling of the implants with respect to the patient's body due to loose fittings and other causes. As a result, the spatial trajectory of the IMU may be far too complex to decompose into component motions by spatial-domain analytical techniques.

Figure 30E:
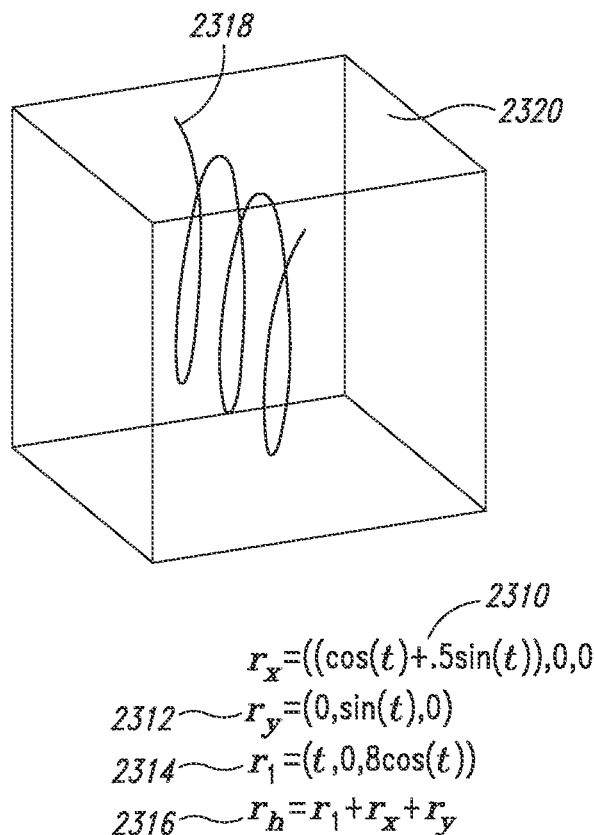

As shown in FIG. 30D, component motions that have higher frequencies and lower amplitudes than the base trajectory shown in FIG. 30A, when added to the component motion responsible for the base trajectory, produce relatively fine-grained and complex deviations from the base trajectory. By contrast, additional component motions with the same frequency as the motion that produces the base trajectory tend to generate geometric alterations in the base trajectory. FIG. 30E illustrates the addition of two low-amplitude component motions 2310 and 2312 to the component motion 2314 that generates the base trajectory to produce a composite vector-valued function 2316 represented by space curve 2318 shown in volume 2320. This new trajectory is clearly periodic and has the same frequency as the base trajectory (2260 in FIG. 30A), but now has a slightly helical form rather than the planar form of the base trajectory. The normal trajectory from ambulation may include numerous different component motions, in addition to the primary rotational and translation walking motions, but with frequencies similar to the ambulation frequency, and may thus have a somewhat complex form but without the finer-granularity complexities that arise from higher-frequency component motions.

Figure 30F:
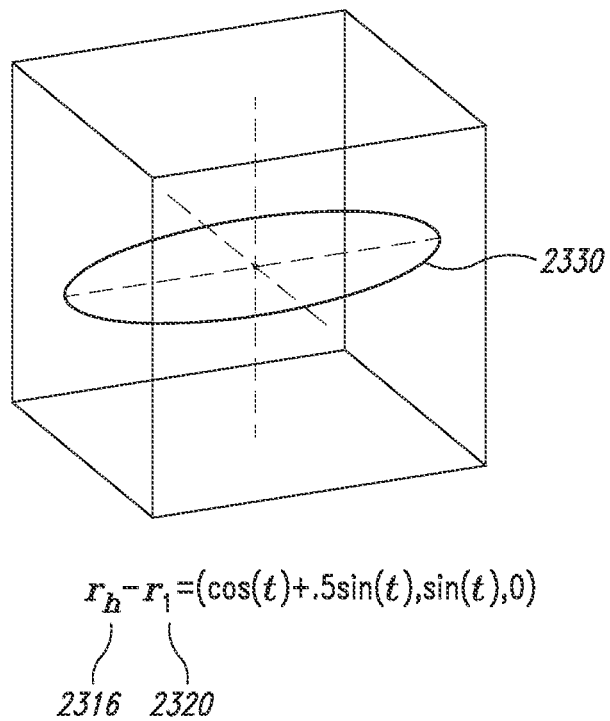
Figure 30G:
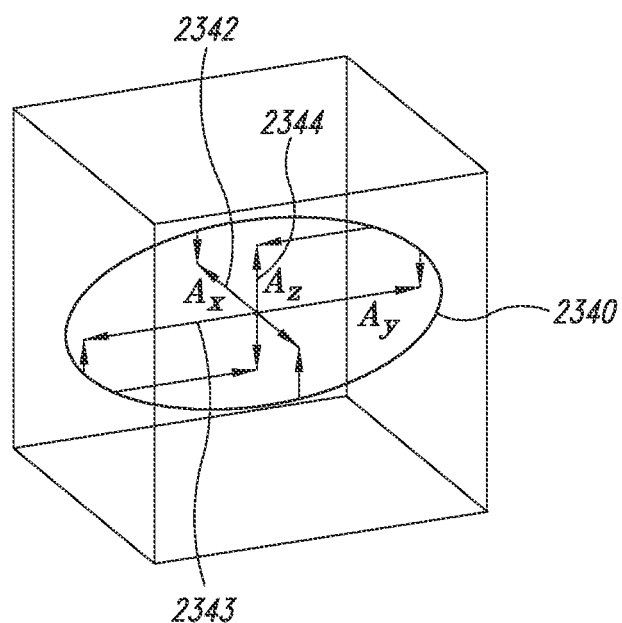

FIG. 30F illustrates a trajectory corresponding to the vector-valued function obtained by subtracting the base-trajectory function 2320 from the complex function 2316 discussed above with reference to FIG. 30E. The trajectory 2330 produced by the vector-valued function representing the difference between the vector-valued function 2316 and the base vector-valued function 2320 is an ellipse. This is not surprising, since, by subtracting away the base trajectory, there is no longer a translational motion component corresponding to movement of the patient along a path in space as the patient walks. The elliptical trajectory may have different orientations and eccentricities, depending on the particular harmonic component motions that remain in the vector-valued function representing the difference between the complex vector-valued function and the base trajectory. When only one linear harmonic motion component in the direction of a coordinate axis remains, the elliptical trajectory collapses into a line segment representing linear harmonic motion. As shown in FIG. 30G, an elliptical trajectory 2340 can be projected onto each of the natural coordinate axes to generate the amplitudes 2342-2344 of the sum of the component motions in the x, y, and x directions. Thus, a patient's ambulatory trajectory can be described as a composite motion obtained by adding, to a base trajectory, the x, y, and x amplitudes of an elliptical trajectory representing additional motion components of the same frequency as the frequency of the ambulatory trajectory as well as x, y, and x amplitudes of elliptical trajectories representing additional motion components an additional non-gait-frequency frequencies. As discussed below, Fourier analysis is one technique that can be used to decompose a complex multi-frequency-component-motion trajectory into component motions of different frequencies. When a range of frequencies, or a frequency band, is considered rather than a single frequency, the above-described elliptical trajectories may become somewhat distorted, but can still be analyzed, as discussed above with reference to FIG. 30G, to obtain x, y, and x amplitudes for the frequency band. A particular elliptical trajectory obtained for a particular frequency band may represent a single rotational-motion component or multiple linear harmonic motion components, so it is not possible to decompose a complex spatial curve into exactly the set of motion components that correspond to the individual motions of individual body parts and implant parts, but it is possible to decompose a complex spatial curve into a set of x, y, and x amplitudes for each of multiple different frequency bands that, when recombined, produce a motion associated with a trajectory very similar to the original measured trajectory. The x, y, and x amplitudes for each of multiple different frequency band can serve as a very detailed and reliable numerical fingerprint for many different types of trajectories resulting from particular problems, pathologies, and other causes superimposed on a basis gait profile, or trajectory.

Other types of techniques, including wavelets, may be used instead of, or in addition to, Fourier techniques and, in certain cases, may have significant advantages over Fourier techniques. As one example, the many different higher-frequency motion components may be periodic, but their amplitudes may decrease and increase periodically at lower frequencies. A loose implant screw, for example, may result in relatively high-frequency vibrations, but only during relatively short periods of time following each heel strike or knee rotation. Thus, additional analytical methods, including wavelets, may be useful in correlating higher-frequency motion components with lower-frequency gait-related events. These techniques may be used to, for example, provide indications that a higher-frequency motion component is strongly correlated with heel strikes, maximum knee rotations, and other gait-related events. These types of correlations, in turn, may be useful in resolving higher-frequency motion components into underlying, physiology based linear harmonics.

Figure 31:
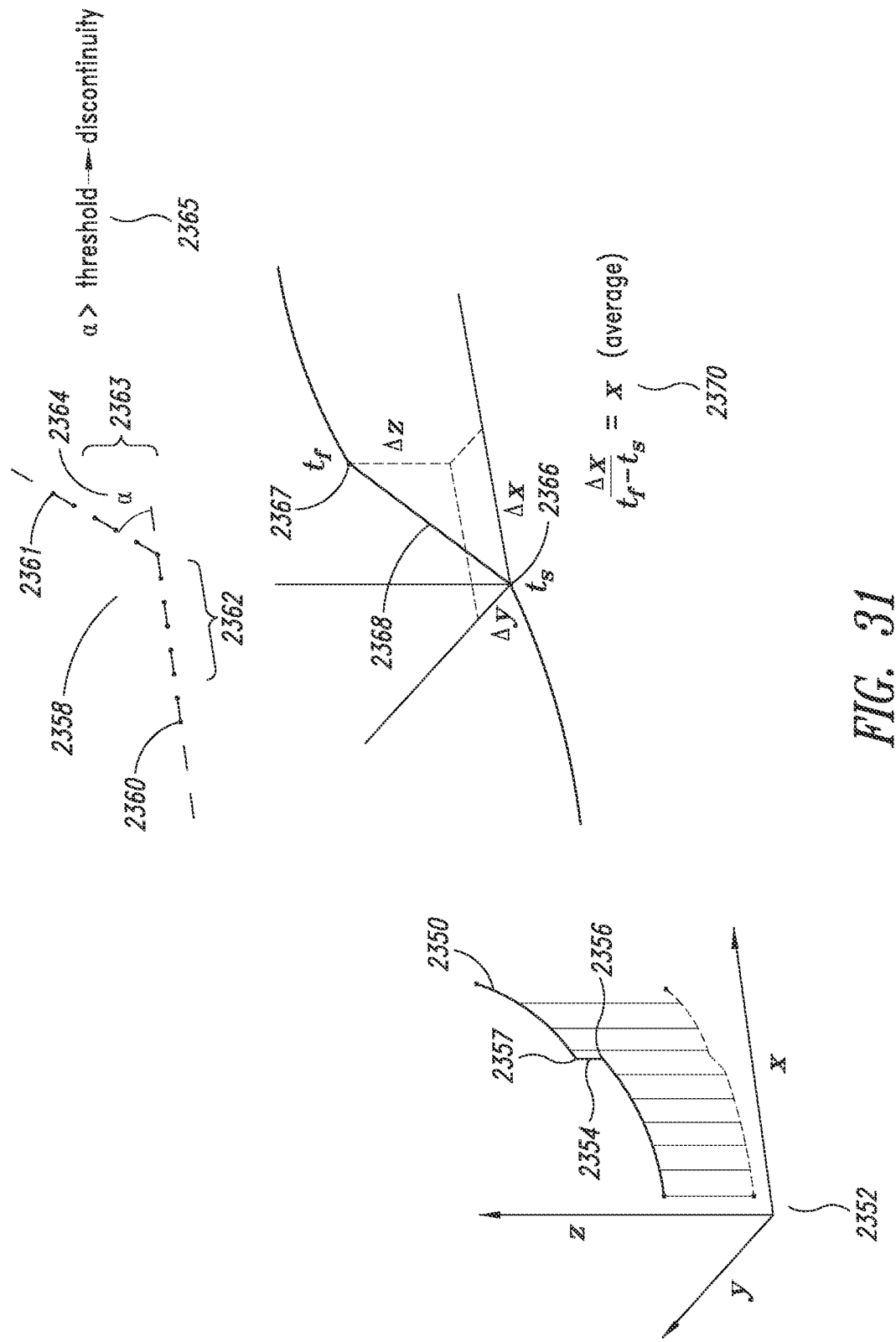
FIG. 31 illustrates one method for dealing with types of non-periodic motions.

The resolution of a periodic space curve into component harmonic motions, discussed above with reference to FIGS. 30A-G, provides a type of numerical fingerprint for the component harmonic motions of the periodic space curve. However, there may be non-periodic motions, such as occasional slippages of an implant or non-periodic muscle contractions. FIG. 31 illustrates one method for dealing with various types of non-periodic motions. Consider the space curve 2350 plotted in three dimensions 2352 in FIG. 31. This curve is generally continuous but includes a short linear section 2354 that may represent a sudden slippage of the implant containing the IMU. This type of non-periodic motion can be recognized by a pair of discontinuities 2356 and 2357 in the space curve. Because an IMU discretely samples accelerations and rotational velocities, the space curves obtained from IMU data are generally discrete, rather than continuous, although continuous curves can be obtained by various types of interpolation. A small portion 2358 of space curve 2350 near discontinuity 2356 is shown at the top of FIG. 31 at much higher resolution. Individual points of the discrete curve are represented by dots, such as dots 2360-2361. The resolution is sufficiently high that the portions of the curve 2362 and 2363 appear nearly linear. The intersection of these two linear portions produces an intersection angle 2364 with an apex at the discontinuity. A point in a trajectory can be identified as a discontinuity when the interaction angle for best-fit line segments for two series of points preceding and following the point is greater than a threshold value 2365. A discontinuity operator can be mathematically moved along a trajectory to identify pairs of discontinuities 2366-2367 that define a non-periodic motion, such as a shift or slip 2368. The average velocity in each of the component directions can be computed 2370, along with the distance of the non-periodic motion, for such non-periodic motions bracketed by discontinuities in order to characterize the severity of the slip or shift.

Figure 32A:
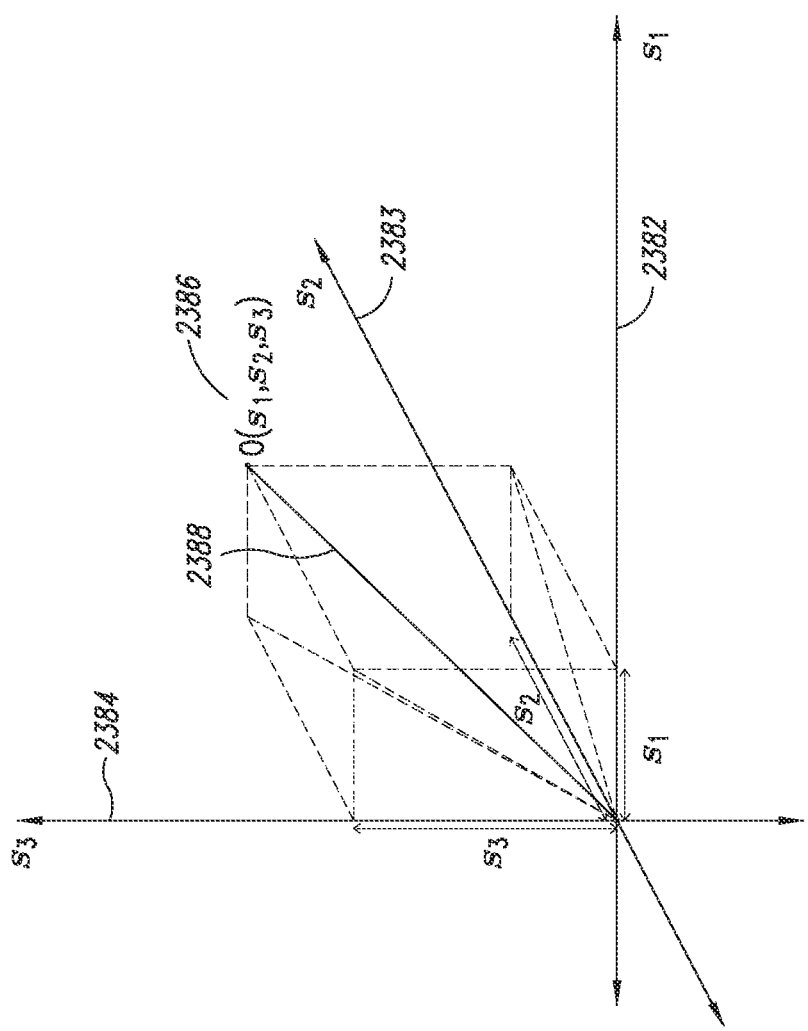
FIG. 32A, FIG. 32B, FIG. 32C, FIG. 32D, FIG. 32E and FIG. 32F each illustrate the principle-component-analysis method that is used to rotate an initial coordinate system to a coordinate system in which the axes are aligned with the distributions of points representing experimental observations.

FIGS. 32A-F illustrates the principle-component-analysis method that is used to rotate an initial coordinate system to a coordinate system in which the axes are aligned with the distributions of points representing experimental observations. The principle component analysis method is frequently used in data analysis. Each observation is a vector of metric data values. FIG. 32A illustrates the equivalence between an observation made at a particular time point and a P-dimensional vector in a P-dimensional space. In the example shown in FIG. 32A, there are only three metrics S1, S2, and S3, and thus P=3. Each metric is considered to be a dimension, and so the three Cartesian axes 2382, 2383, and 2384 are each assigned to one of the metrics. Each observation is a tuple of three metric data values 2386 which, when used as components of a vector, describes a vector 2388 in the P-dimensional metric space.

Figure 32B:
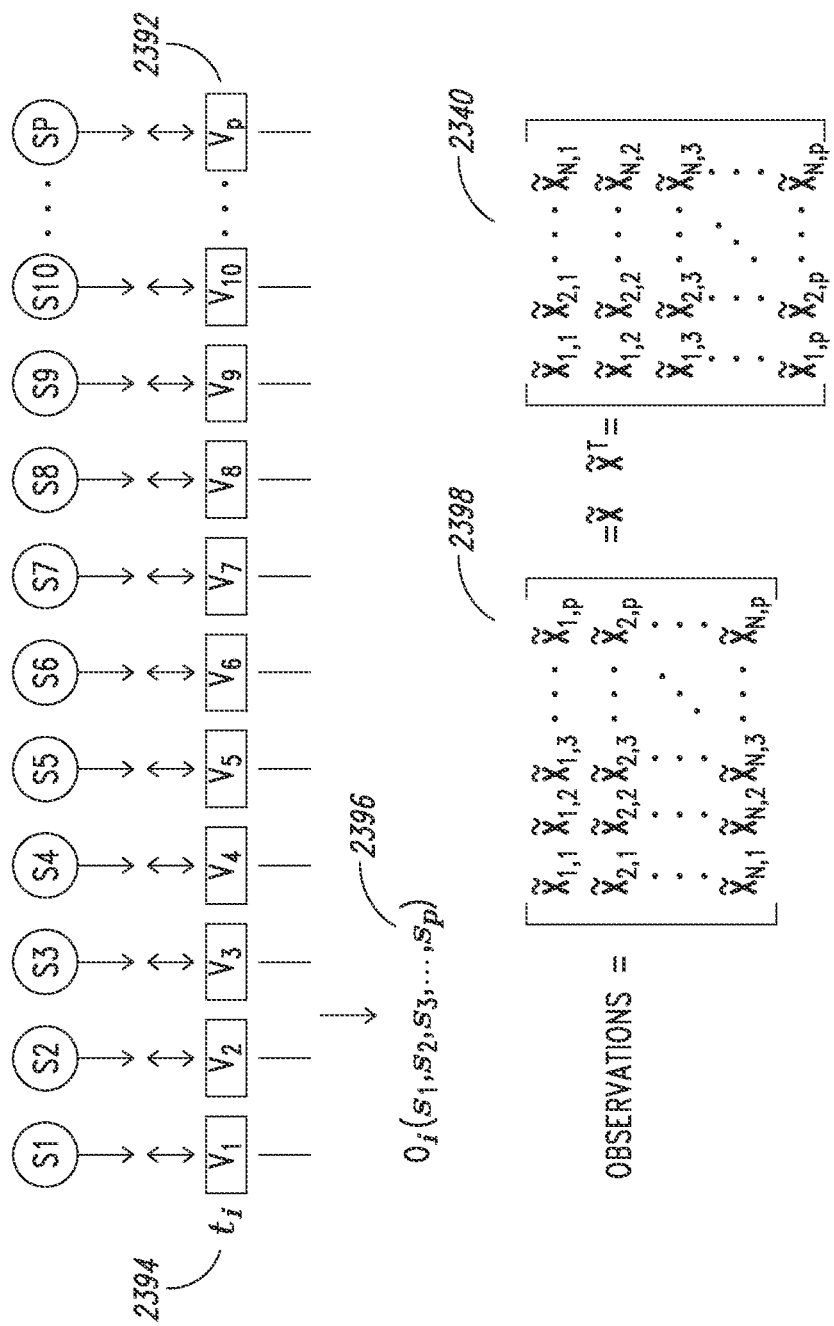
Figure 32H:
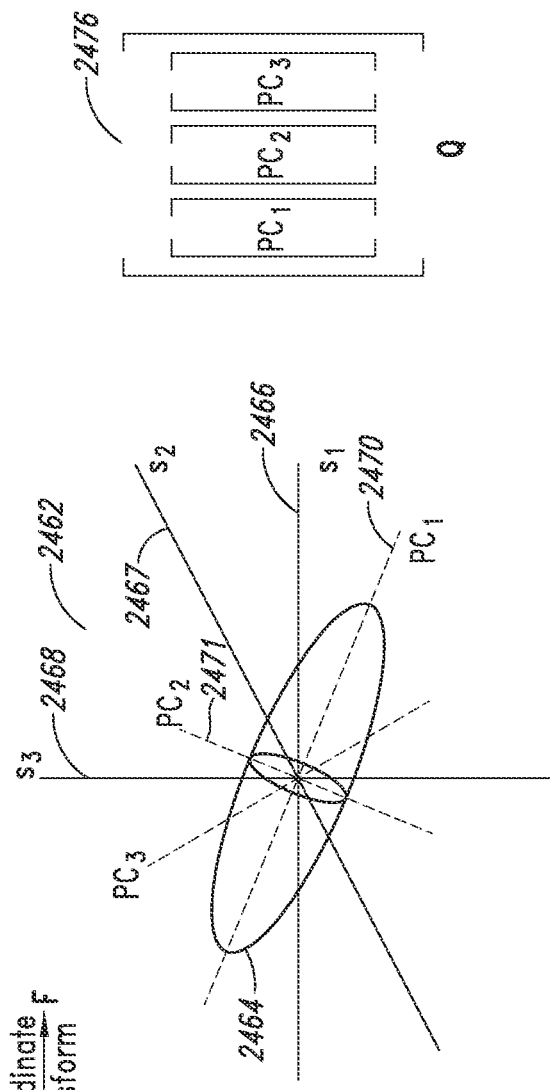

FIG. 32B representation of observations, each consisting of a set of metric data values for each data source obtained at, or calculated for, a particular time point, as a matrix. Each row of metric data values, such as row 2392, for a particular time point, such as time point $t_i$ 2394, may be considered to be a P-dimensional vector 2396, referred to as an "observation." A sequence of N observations can be organized as an N×P matrix $\tilde{X}^T$ 2398 in which each row represents an observation and in which each column represents a time sequence of data values for a particular metric. Again, the time point corresponding to an observation is inferred from the row index of the observation since the observations represent a time sequence with a uniform time interval between successive observations. Alternatively, the transpose of matrix $\tilde{X}$, $\tilde{X}^T$ 400, can be considered to include column vectors representing observations.

FIG. 32C illustrates scaling and normalization of the set of observations represented by the matrix $\tilde{X}$. Several statistical parameters are computed for each time sequence of metric data values for particular metrics, such as the metric data values for the second metric contained in the second column 2402 of the matrix $\tilde{X}$ 2404, including the average $\mu_j$ 406, the variance $\sigma_j^2$ 408, and the standard deviation 410. Then, for each column j, each metric data value in the column can be scaled and normalized by subtracting the average metric data value from the metric data value and dividing by the standard deviation 2412. When this is done for every element in the matrix, a scaled and normalized matrix X 2414 is produced.

FIGS. 32D and 32E illustrate eigenvectors and eigenvalues. A 3×3 matrix A 2422 and a column vector u 2424 are shown at the top of FIG. 32D. When u is an eigenvector of the matrix A, then equation 2426 expresses the relationship of the eigenvector u and its corresponding eigenvalue $\lambda$, which is a constant or scaler. This equation is expanded in matrix form as matrix equation 2428. Using a set of simple matrix-algebra manipulations 2430 and 2432 of equation 2426, it can be shown that either the eigenvector u can be generated by multiplying the inverse of the matrix A-λI, where I is the identity matrix, by the column vector 0 2434 or that the inverse of the matrix A-λI does not exist, as expressed by the fact that the determinant of this matrix is 0 2436. Only the latter proposition is reasonable, which indicates that, by solving the polynomial equation 2444 shown in FIG. 32E, obtained from the expression 2436 via expansion 2442 of expression 2436, the eigenvalues for the matrix A can be found. Because the polynomial equation 2444 is of order 3, the dimension of u, there are generally 3 eigenvalues, although one or more of the roots of equation 2444 may be degenerate. The matrix equation 2446 expresses the relationship between the matrix A, a matrix U in which each column is one of the eigenvectors of the matrix A, and the matrix Λ, which is a diagonal matrix in which the elements along the diagonal are the eigenvalues of the matrix A in the order of the corresponding eigenvectors in the matrix U. Multiplying each side of equation 2446 from the right by the inverse of matrix U, $U^{-1}$, produces equation 2448. When the matrix A is the product of a matrix X and its transpose $X^T$, as shown in expression 2450, the eigenvalues of matrix are positive real numbers 2451, the eigenvectors of matrix are orthogonal 2452 when their corresponding eigenvalues are not equal, and the inverse of matrix U, $U^{-1}$, is equal to the transpose of matrix U, $U^T$ 453. Thus, when matrix A is the product of a matrix X and its transpose $X^T$, matrix A is equal to the matrix Λ multiplied from the left by the matrix U and multiplied from the right by the transpose of matrix U, $U^T$. While a 3×3 matrix example is used in FIGS. 32D and 32E, the above-described characteristics of eigenvectors and eigenvalues apply to matrices of arbitrary dimension.

The principal-component-analysis ("PCA") method, next discussed with reference to FIGS. 32F, represents a change of basis vectors for the scaled and normalized observations organized into the matrix X 2414, discussed above with reference to FIG. 32C. As shown in the three-dimensional plot 2462 in FIG. 20A, the distribution of observations, or observation data points, corresponding to the rows of the matrix X or columns of the matrix $X^T$, in the case of a three-dimensional metric space, such as that shown in FIG. 32A, may fall within an ellipsoidal volume 2464 within the three-dimensional metric space. As shown in plot 2462 of FIG. 32F, the ellipsoidal volume has major and minor axes that are not coincident with the axes corresponding to metrics S1 2466, S2 2467, and S3 2468. A basis-vector change, equivalent to a set of coordinate changes, may be desired so that a set of new coordinate axes, corresponding to what is referred to as "principal components," ("PCs"), can be found. The new coordinate axes are aligned with the major and minor axes of the ellipsoidal volume representing the distribution of observations in three-dimensional space. Moreover, principal component PC1 2470 is aligned with the major axis of the ellipsoidal volume, principal component PC2 is aligned with the longer of the two minor axes 2471 of the ellipsoidal volume, and principal component PC3 2472 is aligned with the shorter of the two minor axes of the ellipsoidal volume. The basis vectors corresponding to the principal components of the new coordinate axes are contained as columns in a matrix Q 2476. The principal components correspond to the directions of greatest variability within the ellipsoidal volume in decreasing order of variability and the basis vectors corresponding to the principal components are orthogonal. In general, the bulk of the variability within a distribution of observations can be largely explained in terms of, or expressed as a function of, an initial subset of the principal components. For example, in the distribution shown in FIG. 32F, were the ellipsoidal volume projected onto a plane normal to the third principal component 2472, the majority of the variability in the distribution of observations would be apparent in the resulting two-dimensional ellipsoid with major axis corresponding to the first principal component 2470 and minor axis corresponding to the second principal component 2471. In essence, the principal components can be viewed as a new set of metrics each derived from the original metrics as a linear combination of the original metrics. The data values corresponding to the new set of metrics, contained in a factor score matrix F, which is defined to be generated from the original metric data values stored in the matrix X by multiplying the matrix X from the right by the matrix Q, which contains the principal components as column vectors 2478, under the constraints that the matrix $F^T F = Q^T X^T X Q$ is a diagonal matrix 2480 and that the matrix Q is orthogonal 2482. By using the technique of Lagrangian multipliers, it can be shown that $X^T X = Q \Lambda Q^T$ 484, where Λ is a diagonal matrix of Lagrangian multipliers, which leads to expression 2486. Thus, determining the principal components, which is equivalent to determining the matrix Q, reduces to a problem of determining the eigenvectors and eigenvalues of the matrix $X^T X$. With the matrix Q in hand, the coordinate transformation that takes the original scaled and normalized metric data values in the matrix X to the data values for a new set of metrics referred to as principal components, stored in the matrix F, is carried out by multiplying the matrix X from the right by the matrix Q, as expressed in expression 2478.

Figure 33:
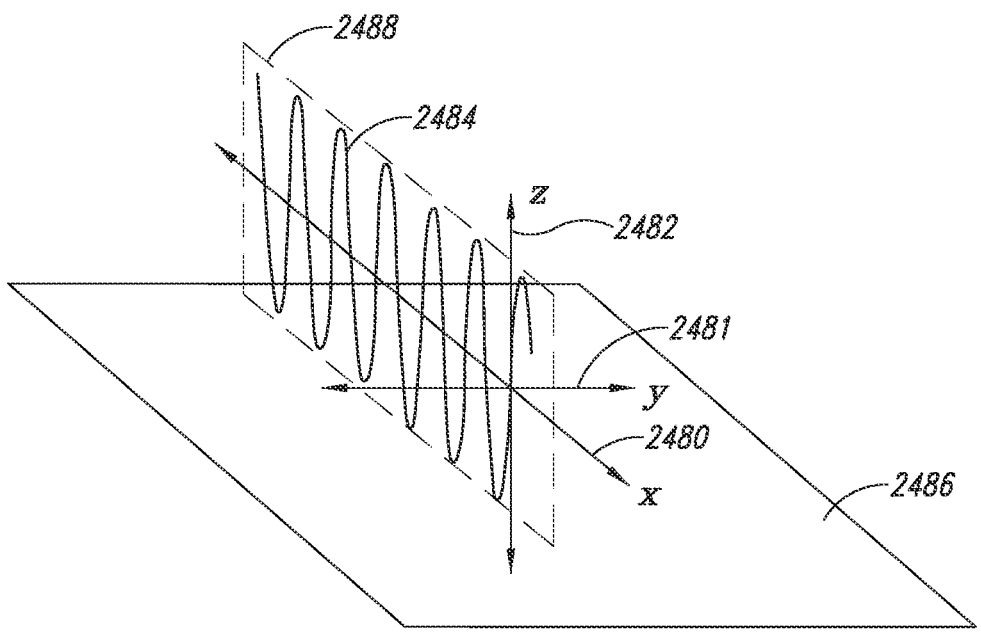
FIG. 33 illustrates use of principal component analysis to determine the natural coordinate system based on raw or filtered IMU output data.

FIG. 33 illustrates use of principal component analysis to determine the natural coordinate system based on raw or filtered IMU output data. The natural coordinate system 2480-482 is shown in FIG. 33 aligned with a base trajectory 2484 and the ground 2486. Generally, a patient is vertical while walking, and the patient's legs move primarily in a vertical plane 2488. Therefore, most of the linear accelerations are parallel or nearly parallel to this plane. Because the patient is moving along a path, in the x direction, principal component analysis, when applied to the linear-acceleration components of the IMU output data, determines the x axis of the natural coordinate system as the principal axis. The z axis of the natural coordinate system is determined to be the secondary principal axis, and the y axis of the natural coordinate system is the tertiary principal axis, since few linear accelerations should have y components. Similarly, most of the angular velocities should be in the xz plane perpendicular to the y axis during walking, and principal component analysis, when applied to the angular-velocity components of the IMU output data, determines the y axis of the natural coordinate system to be the principal axis. Filtering the IMU output data to retain only the walking-cycle-frequency data components may provide greater reliability to the principal axes determinations by principal component analysis. A rotation matrix can be then determined that, when applied, by matrix multiplication, to the IMU output data vectors convert the numerical values within the data vectors to numerical values corresponding to the natural coordinate system. In alternative implementations, the spatial trajectory produced by processing IMU output data can be rotated in three-dimensional space to align the base-trajectory plane to the vertical plane, and a rotation matrix can then be derived from the rotations needed to make this alignment. Other types of implementations are possible.

Figure 34C:
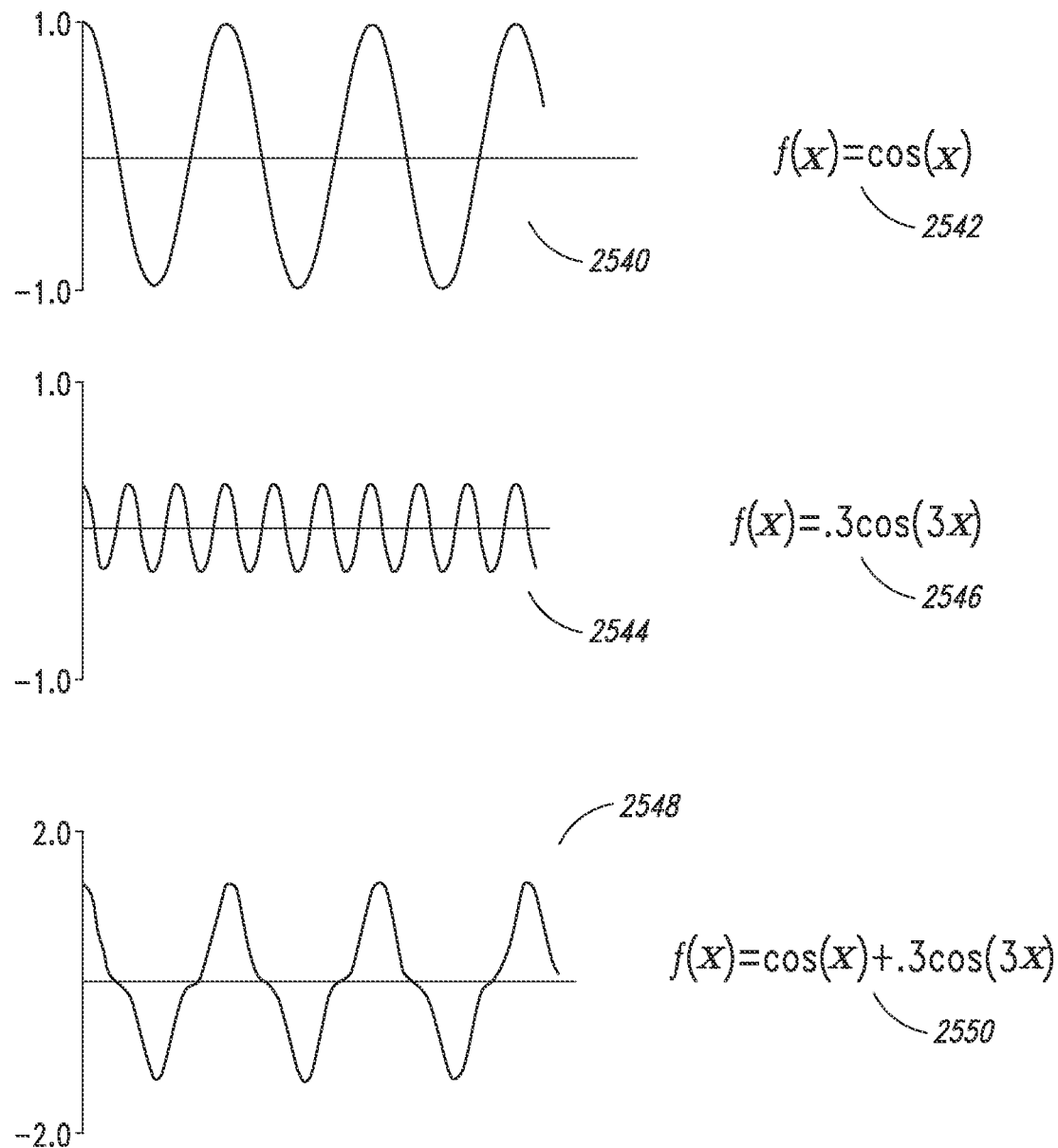

FIGS. 34A-D illustrate forward and inverse Fourier transforms. As shown in FIG. 34A, a continuous function of a real variable 2490 can be transformed by a forward Fourier transform 2492 to a function of a frequency variable 2494. The inverse Fourier transform 2496 transforms the function of the frequency variable back to the original function 2498. The function of the frequency variable generally produces complex values, having both real and imaginary components 2499. The values produced by the function of the frequency variable can each be alternately represented by the product of a magnitude, or modulus, and a phase angle 2500. Often, the square of the absolute values of the complex values produced by a Fourier transform of a function of a real variable are plotted to visualize the Fourier transform, the visualization referred to as a "power spectrum" 2502. The complex exponential term in the Fourier transform, viewed as a sum of n discrete real-variable values 2504, is equivalent to n harmonics 2506, which illustrates the fact that a Fourier transform can be thought of as the limit of the sum of an infinite number of harmonics.

In the lower portion of FIG. 34A, an expression for an example function of a real value 2508 and a corresponding plot of the function 2509 are shown. Computation of the Fourier transform of the function is illustrated by expressions 2510 and plot 2511 shows a plot of the absolute value of the Fourier-transform, a function of the frequency variable u. Expressions 2512 at the top of FIG. 34B illustrate a Fourier transform and inverse Fourier transform for a function of two real variables 2514. An example two-variable function 2516 and its corresponding Fourier transform 2518 are shown in the middle of FIG. 34B. Often, as illustrated by plot 2520 in FIG. 34B, a function is discrete, representing samples of the y values produced by the function for discrete values of the domain 2522-2526. The forward and inverse Fourier transforms for a discrete function of a single real variable are shown by expressions 2530 in FIG. 34B. Forward and inverse Fourier transforms for a discrete function of two real variables are shown in expressions 2532.

Figure 34D:
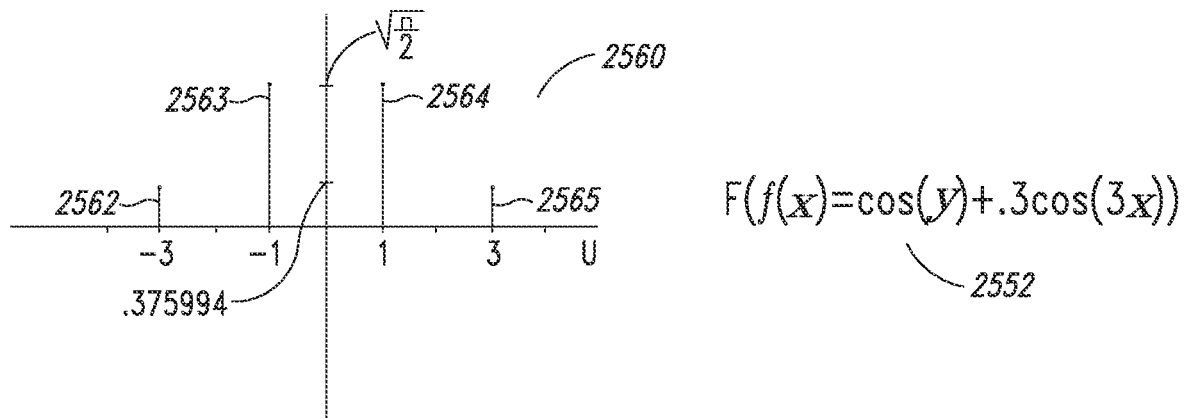
Figure 34D:
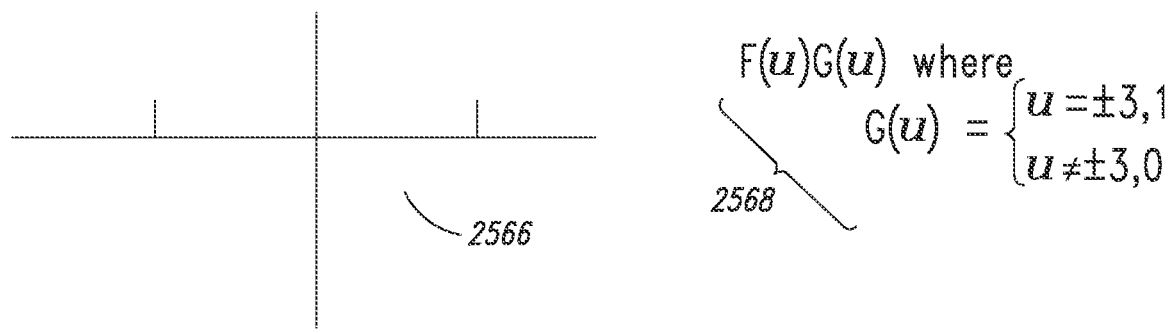
Figure 34D:
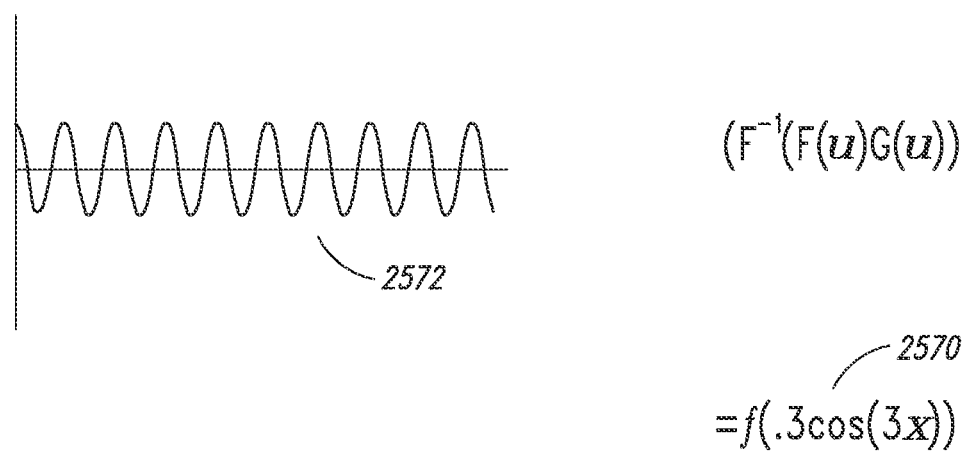

Fourier transforms are used widely in mathematics and all branches of quantitative science for many different purposes. FIGS. 34C-D illustrate how Fourier transforms can be used to filter frequency components from a periodic function. Plot 2540 is a graphical representation of the cosine function 2542. Plot 2544 is a graphical representation of a harmonic function 2546 with a frequency 3 times greater than that of function 2542. Plot 2548 is a graphical representation of the composite function 2550 obtained by adding functions 2542 and 2546. Just as in the examples of adding space curves representing different types of harmonic motion, discussed above with reference to FIGS. 30A-30G, the graph of the composite function 2550 has a somewhat complicated form. When many different types of harmonic functions are added together, the form can be extremely complicated. In order to decompose such complicated functions, Fourier transforms are employed. Plot 2560 in FIG. 34D is a graphical representation of the absolute value of the Fourier transform of function 2550 represented by plot 2548 in FIG. 34C. The Fourier transform plot contains four points, or vertical line segments 2562-565. Vertical line segments 2562 and 2565 occur at the frequencies −3 and 3, while vertical line segments 2563 and 2564 occur at frequencies −1 and 1. Thus, the plot indicates that there are two harmonic components of function 2550, one with the frequency of the base harmonic of the composite function and one with a frequency three times greater than the base frequency. In order to recover the latter component, the base-frequency values of the Fourier transform can be removed, as shown in plot 2566 and represented by expressions 2568, to generate a new function of a frequency variable. When inverse Fourier transform is applied to this new function of a frequency variable, the resulting real-valued function 2570, graphically represented by plot 2572, is the harmonic component of function 2550 with a frequency equal to three times the base frequency. Thus, to select a desired harmonic component of a composite function with many different harmonic components, the composite function can be Fourier transformed to the frequency domain, all of the values for frequencies other than the frequency of the desired harmonic component are set to 0, and the altered frequency-domain function can then be inverse Fourier transformed to produce the desired harmonic component of the original complex function. This process is referred to as "bandpass filtering."

Figure 35:
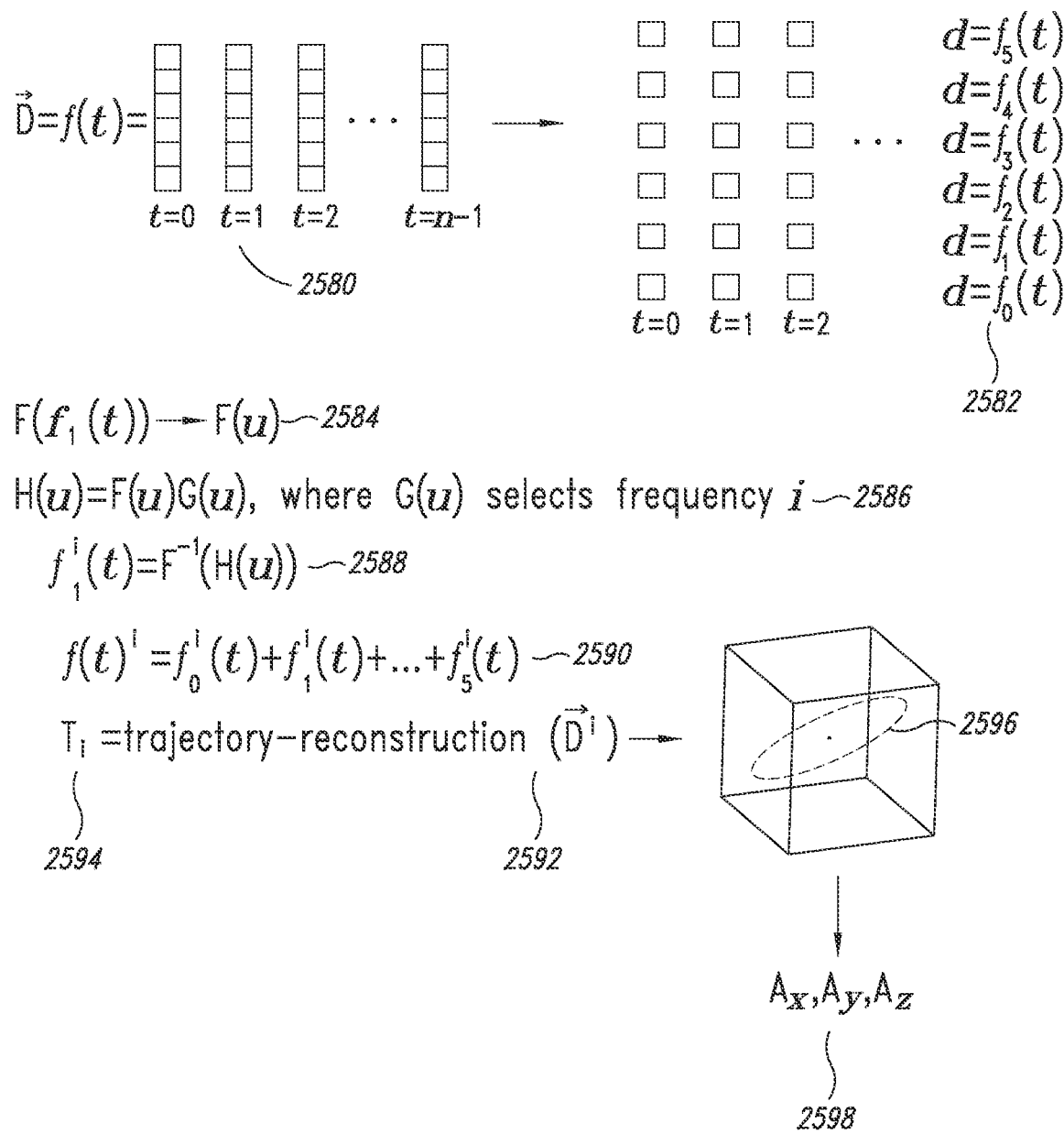
FIG. 35 illustrates the use of Fourier transforms on the data-vector output of the IMU.

FIG. 35 illustrates the use of Fourier transforms on the data-vector output of the IMU. The vector-valued function representing the IMU data output 2580 can be decomposed into six functions 2582 that return single floating-point values. Each of the six functions returns the numerical value of one of the components of the 6-dimensional vectors output by the IMU. These discrete functions can be Fourier transformed to the frequency domain 2584, the frequency-domain functions can be filtered for a particular frequency 2586, and the inverse Fourier transform then applied to return the harmonic component of the desired frequency of the original function 2588. A filtered vector-valued function 2590 for the IMU data can then be obtained by adding together all of the filtered floating-point-valued functions. The above-discussed trajectory-reconstruction process can then be carried out on the filtered vector-valued function 2592 to produce a trajectory 2594 for the component harmonics of the output data at the specified frequency. In general, as discussed above, the trajectory will be an ellipse 2596 from which the x, y, and z amplitudes for the sum of the harmonic components at the specified frequency can be determined by projection 2598. There may be additional complexities associated with the angular-velocity-angle data, but, in general, it is possible using bandpass filtering to isolate the component motion trajectories of the overall trajectory represented by data vectors output by an IMU.

Figure 36A:
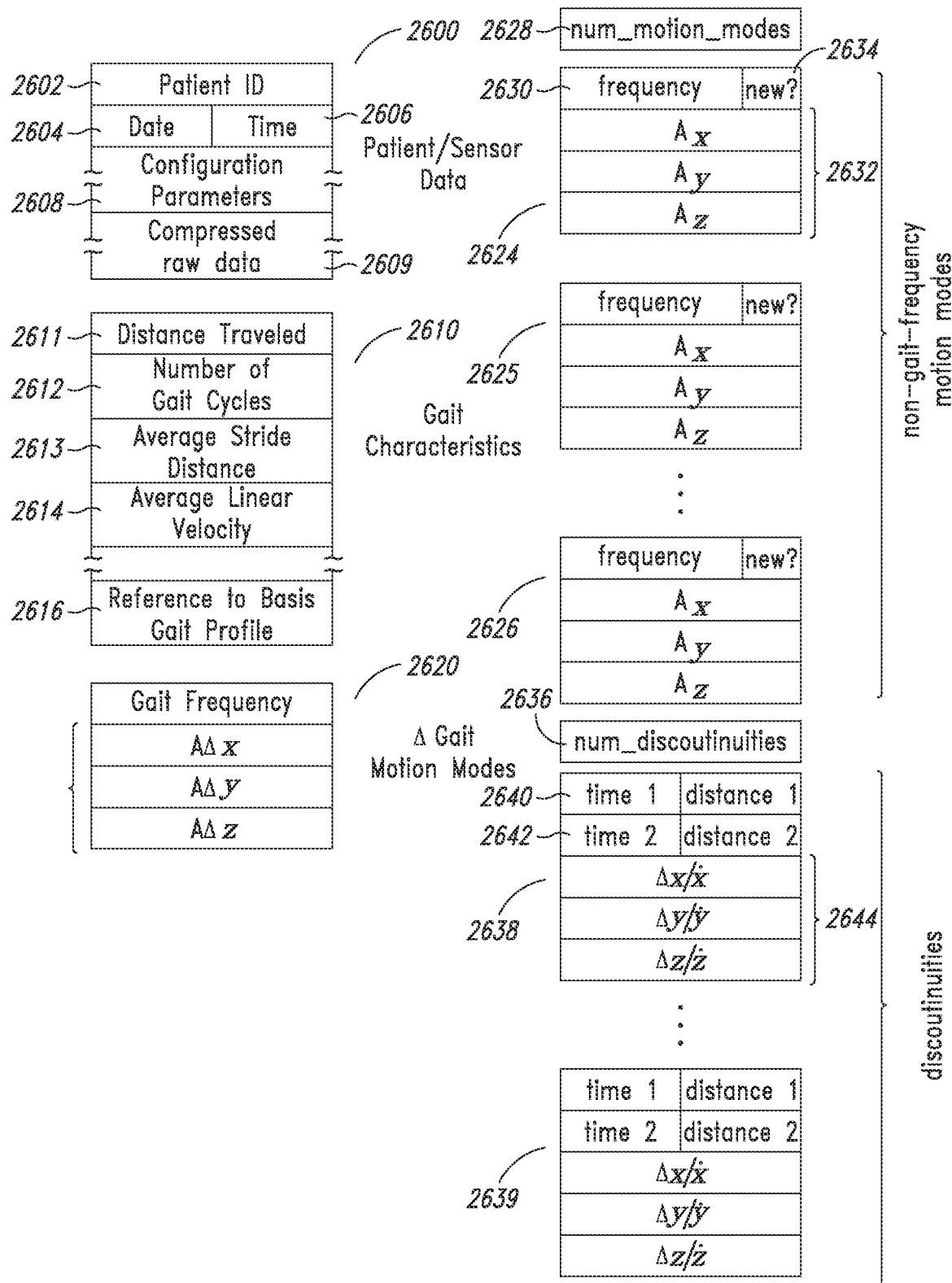
FIG. 36A and FIG. 36B each illustrate the data output by the data-processing application as a result of processing and analyzing the raw data, obtained during a monitoring session that is received from a base station.
Figure 36B:
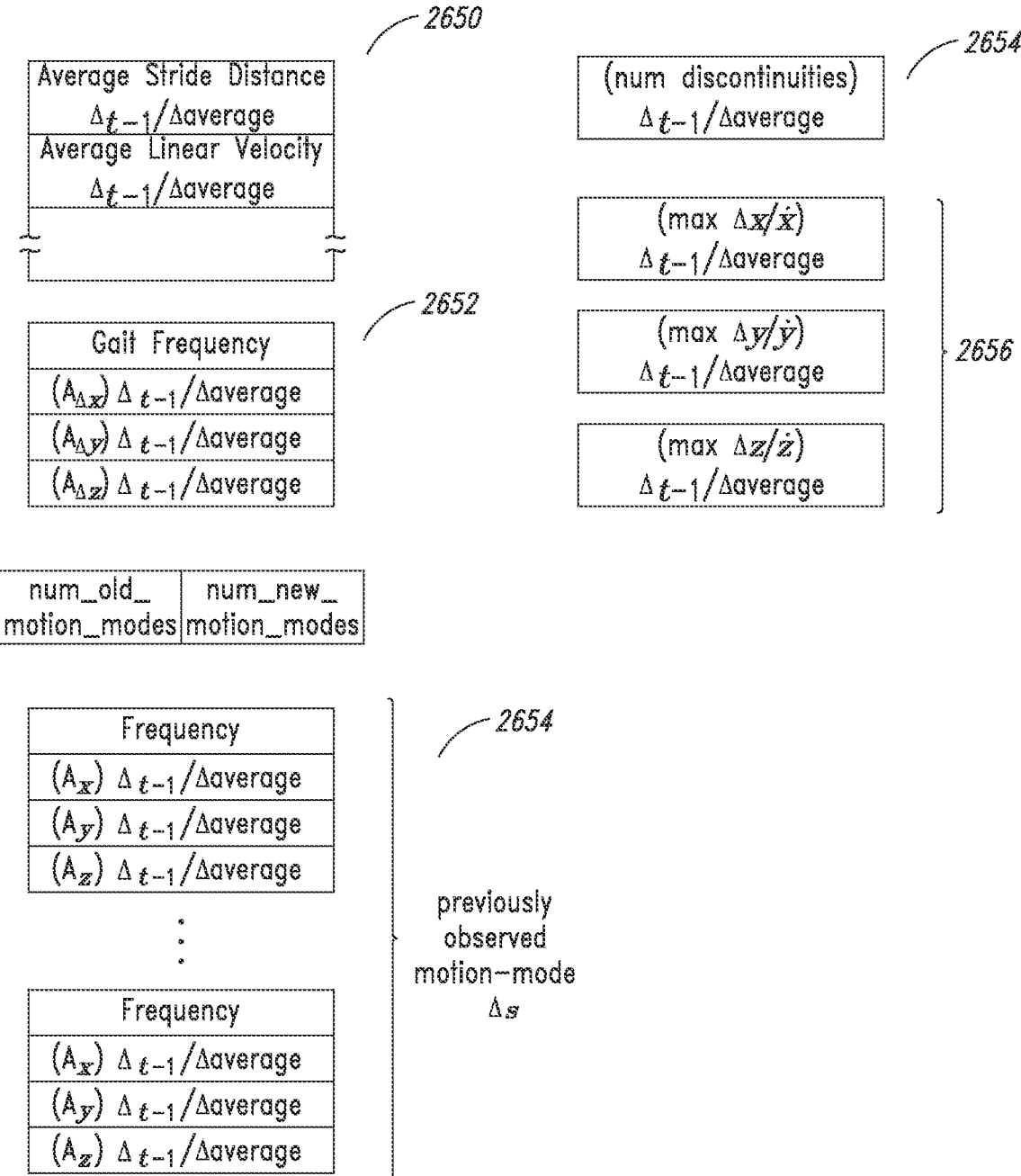

FIGS. 36A-B illustrate the data output by the data-processing application as a result of processing and analyzing the raw data, obtained during a monitoring session, that is received from a base station. The output data includes patient and sensor data 2600, such as a patient ID 2602, a date 2604 and time 2606, sensor-configuration parameters 2608, and a reference to the compressed raw data archived within the computing facility 2609. There may be a great deal of additional patient and sensor data included, depending on the implementation. A next block of data 2610 output by the data-processing application contains various parameters and metrics that represent characteristics of the patient's gait. These may include the distance traveled during the recorded monitoring session 2611, the number of gait cycle 2612 observed, the average stride distance 2613, the average linear velocity of the patient while walking 2614, additional results 2615 that can be obtained by analyzing the gait-frequency spatial trajectory, and a reference to the basis gait profile 2616 for the patient. The basis gait profile may be a gait trajectory previously recorded for the patient or may be selected, based on the patient's physical characteristics, from a set of standard basis gait profiles. The patient's gait is next represented 2620 by the x, y, z amplitudes computed from the elliptical trajectory obtained by subtracting the basis gait profile or trajectory from the gait-frequency trajectory observed in the monitoring session, obtained by bandpass filtering, along with the basis gait profile, as discussed above with reference to FIGS. 30E-G. Next, all the various non-gait-frequency motion modes detected by bandpass filtering of the IMU data and trajectory reconstruction are represented by the x, y, z amplitudes computed from the elliptical trajectories generated from the bandpass-filtered IMU data 2624-2626. This data includes an indication of the number of detected non-gait-frequency motion modes 2628 followed by representations of the motion modes, each of which includes the frequency of the motion mode, such as frequency 2634 in motion-mode data block 2624, along with the x, y, z amplitudes, such as amplitude 2632 for motion mode 2624. The representation of each motion mode also may include a field, such as field 2634 for motion mode 2624, indicating whether or not the motion mode was first detected in the data output from the currently considered monitoring session. Next, the output data includes an indication of the number of detected discontinuities in the reconstructed gait cycle 2636 and a representation of each of these discontinuities 2638-2639. The representations, such as representation 2638, may include indications of the times and distance traveled by the patient during the slip or shift bracketed by the two discontinuities 2640 and 2642 as well as indications of the velocities of the non-periodic motion in the x, y, z directions 2644. Then, as shown in FIG. 36B, the current results obtained by data analysis for the monitoring session are compared against the results from a previous monitoring session as well as to the running average of the results for all of the monitoring sessions up to the current point in time. This results in pairs of Δ values for many of the metrics shown in FIG. 36A, each pair including the difference between the current result for each metric and the result for the metric obtained in the previous monitoring session, referred to as a $\Delta_{t-1}$ value for the metric, and the difference between the current result for the metric and the running average for the metric over all or a most recent subset of the previous monitoring sessions, referred to as $\Delta_{average}$. Pairs of Δ values are produced for the gait-characteristics data 2650, the gait-frequency additional motion modes 2652, the non-gait-frequency motion modes 2654, the number of discontinuities 2654, and the maximum observed discontinuity velocities 2656. As mentioned above, the results may also include metrics that indicate correlations between different motion components, such as correlations between higher-frequency motion modes with gait-cycle events, such as heel strikes, maximum extensions of the lower leg, change in rotational direction of the knee, and other such events.

In many cases, data may be acquired, during monitoring sessions, from multiple sensors. There may be, for example, multiple IMU sensors in multiple implants within a patient's body, such as implants in the bones above and below and artificial knee joint. In other cases, there may be multiple sensors of different types. In these cases, there may be a set of output results, discussed above with reference to FIGS. 36A-B, that include output results for each of the different sensors. In addition, time correlations between the output results for multiple sensors may be included as an additional output result. As one example, a lower-leg IMU based sensor may detect a high-frequency motion component that always follows, in time, a motion component detected by an upper-leg IMU based sensor of a different frequency. This might be indicative of an instability in the upper leg that propagates through the knee to the lower leg, or may, instead, represent two events correlated with a motion within the knee joint.

Figure 36C:
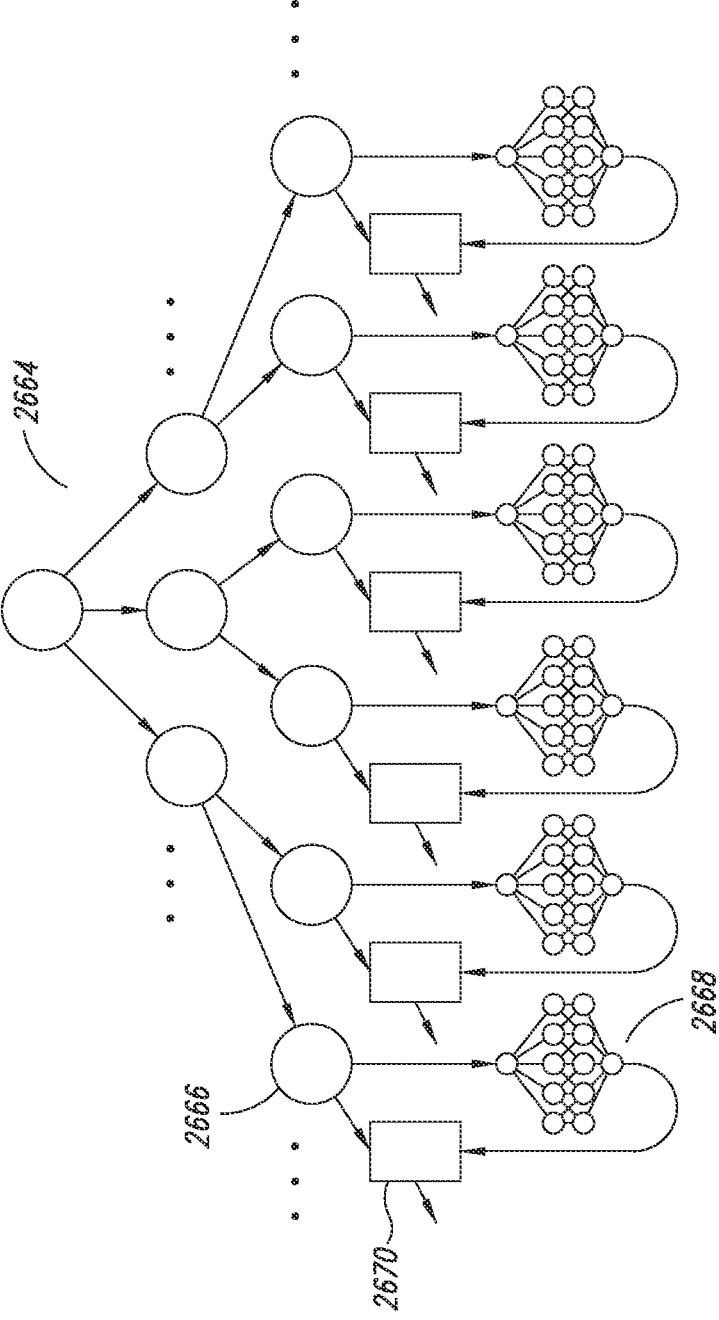
FIG. 36C illustrates a final portion of the results generated by the data processing application as a result of processing and analyzing the raw data, obtained during a monitoring session that is received from a base station.

FIG. 36C illustrates a final portion of the results generated by the data-processing application. All of the various results obtained from the analysis of the monitoring-session data 2660 can be considered to be a set of parameters 2662. These parameters can be input to a decision tree 2664 that analyzes the parameters in order to determine what the data appear to indicate about the state of the implant in the state of the patient. The decision tree may contain many levels of nodes, for more than those shown in FIG. 36C, each of which represents a decision as to what subcategories of implant state and patient state may be indicated by the data results. In the leaf nodes of the decision tree, such as leaf node 2666, a portion of the parameters may be input to a neural network 2668 or some other type of machine-learning or pattern-recognition entity to derive more detailed inferences and suggestions with regard to any problems or anomalies detected in the monitoring session and how these problems or anomalies might be addressed by therapy, additional equipment, or other interventions. The results of this analysis are output as additional report components, such as additional report component 2670, containing higher-level analytical result and inferences. For example, based on the particular harmonic motion modes observed in the monitoring session, along with the various $\Delta_{t-1}$ and $\Delta_{average}$ data, the additional report may include an inference that a particular implant screw has loosened, as a result of which the lower leg exhibits a rotational vibration during walking, and may suggest that this problem may be addressed either by an additional external prosthesis, by surgery, or by other interventions. This additional report component containing higher-level analysis and inferences is packaged, along with the output data discussed above with reference to FIGS. 36A-B, as the output report and output data generated by the data-processing application for the received monitoring-session data.

Figure 37A:
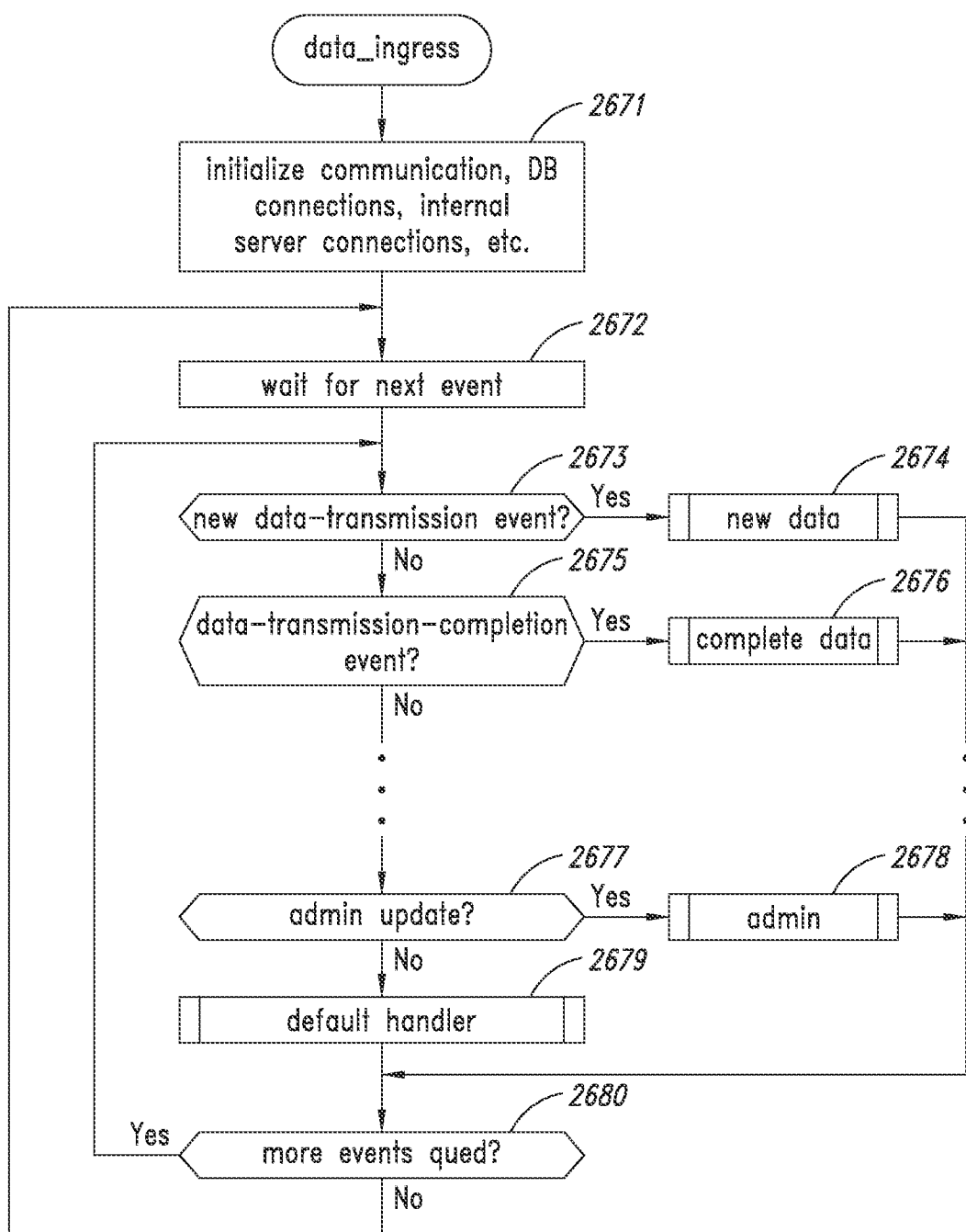
FIG. 37A, FIG. 37B, FIG. 37C, FIG. 37D, FIG. 37E, FIG. 37F, FIG. 37G, and FIG. 37H each provide control-flow diagrams that illustrate the currently discussed implementation of the data-processing application that processes patient-monitoring-session data.

FIGS. 37A-H provide control-flow diagrams that illustrate the currently discussed implementation of the data-processing application that processes patient-monitoring-session data. FIG. 37A shows a control-flow diagram for the data-ingress component of the data-processing application. This component may run on one or more frontend servers within a cloud-computing facility that receive communications from external computer systems. In step 2671, on power up, the data-ingress component initializes communications support, database connections, and internal server connections, and carries out other types of initializations to prepare for receiving data messages from external computers. In step 2672, the data-ingress component waits for a next event to occur. When the next event is a new data-transmission event, as determined in step 2673, a new-data handler is called, in step 2674, to handle the new data transmission. When the next event is a data-transmission-completion event, as determined in step 2675, a complete-data handler is called, in step 2676, to complete reception of a data transmission. Many other different types of events may be handled, such as a handler for all but the last of the additional messages in a data transmission and a handler for an administration-update event which, as determined in step 2677, is handled by calling and administration handler 2678. A default handler 2679 handles any rare or unexpected events. When there are more events queued for handling, as determined in step 2680, control returns to step 2673 to process a next event. Otherwise, control returns to step 2672, where the data-ingress component waits for a next event to occur.

Figure 37B:
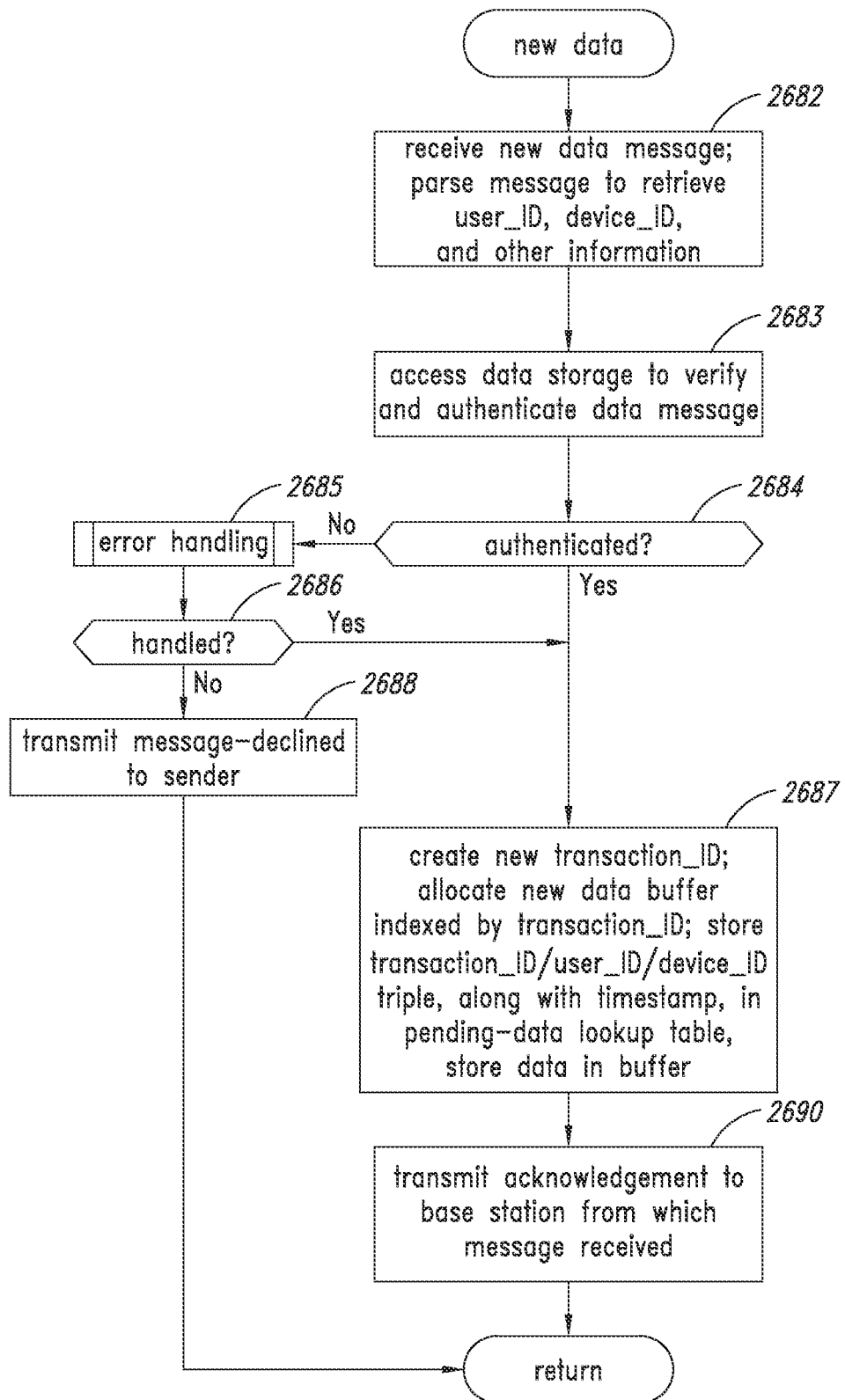

FIG. 37B provides a control-flow diagram for the handler "new data," called in step 2674 in FIG. 37A. In step 2682, the new-data handler receives the new-data message and parses the message to receive the user ID, device ID, and other such information. In step 2683, the new-data handler accesses data storage to verify and authenticate the data message. For example, the user ID and device ID should correspond to a patient and the patient's implant recorded in a database table or file. Authentication may also involve passwords, encryption keys, and other types of security data and corresponding security measures to ensure that only legitimate data messages are processed. If the new-data message fails authentication, as determined in step 2684, the new-data handler invokes various error-handling procedures 2685. In the case that the error-handling procedures manage to authenticate the data message, as determined in step 2686, or when the message was initially authenticated, control flows to step 2687. Otherwise, in step 2688, the new-data handler transmits a message-declined response to the sender. In step 2687, the new-data handler creates a new transaction ID for the data transmission, allocates a new data buffer indexed by the transaction ID, stores a transaction-ID/user-ID/device-ID triple in a pending-data lookup table, along with a timestamp, and stores the initial portion of the data transmission contained in the data message in the data buffer allocated for the data transmission. In step 2690, the new-data handler transmits an acknowledgment message to the base station from which the message was received.

Figure 37C:
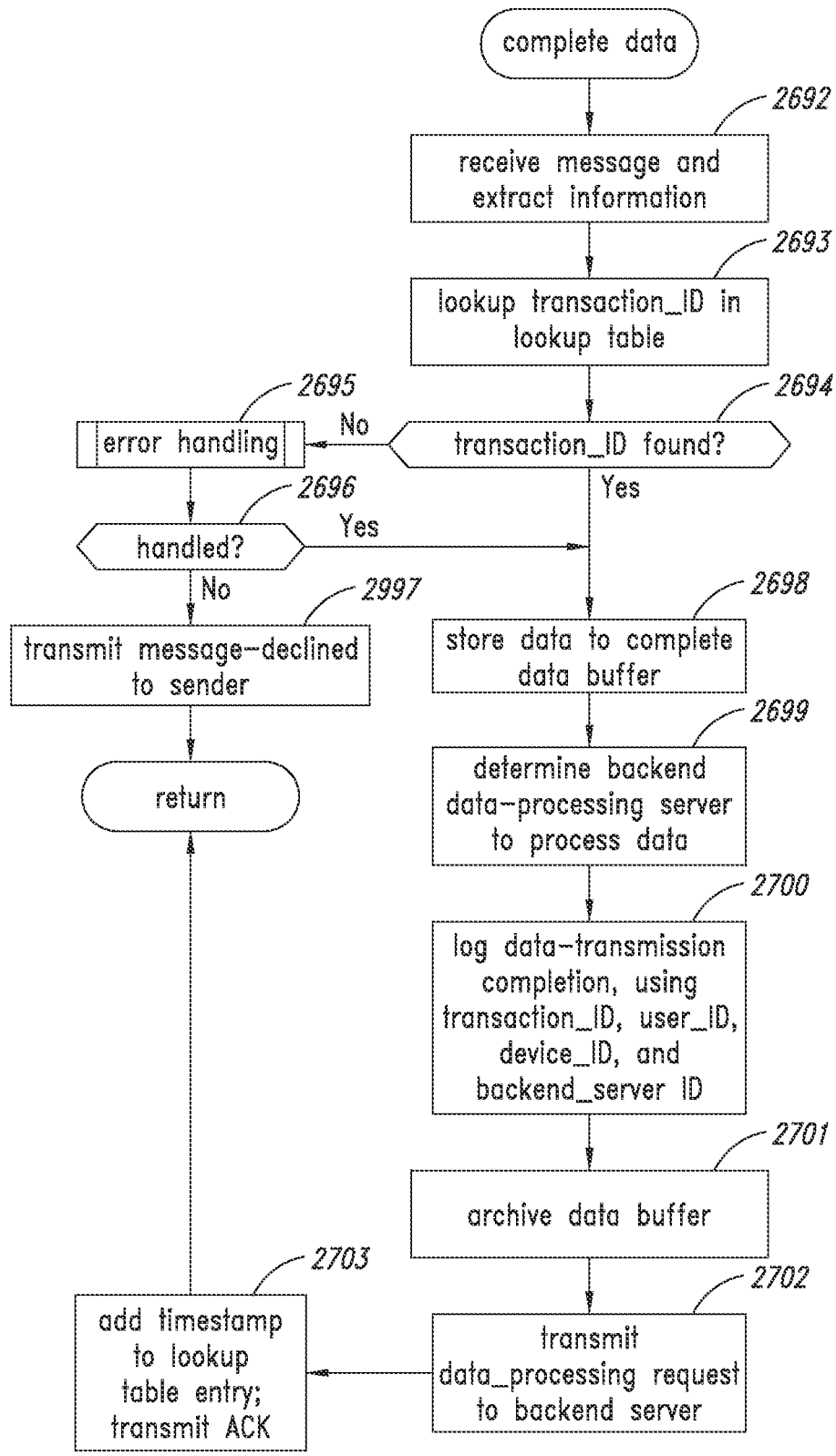

FIG. 37C provides a control-flow diagram for the complete-data handler called in step 2676 of FIG. 37A. In step 2692, the complete-data handler receives a final message in a data transmission and extracts identifying information from the message. In step 2693, the complete-data handler checks the lookup table for the user ID and device ID and retrieves the transaction ID associated with the user ID and device ID. If the transaction ID cannot be found, as determined in step 2694, the complete-data handler undertakes error handling, in step 2695. If a transaction ID is found, as determined in step 2696, control flows to step 2698, as it does when the transaction ID is initially found. Otherwise, in step 2697, a message-declined message is transmitted back to the base station. The complete-data handler stores the data contained in the data message into the data buffer to complete the data transmission, in step 2698, determines a backend data-processing server for processing the data, in step 2699, logs a data-transition-completion event in a log file, in step 2700, archives the transmitted data in step 2701, transmits a data-processing request to the selected backend server in step 2702, and, finally, adds a timestamp to the lookup table entry for the data transmission and returns an acknowledgment to the base station in step 2703.

Figure 37D:
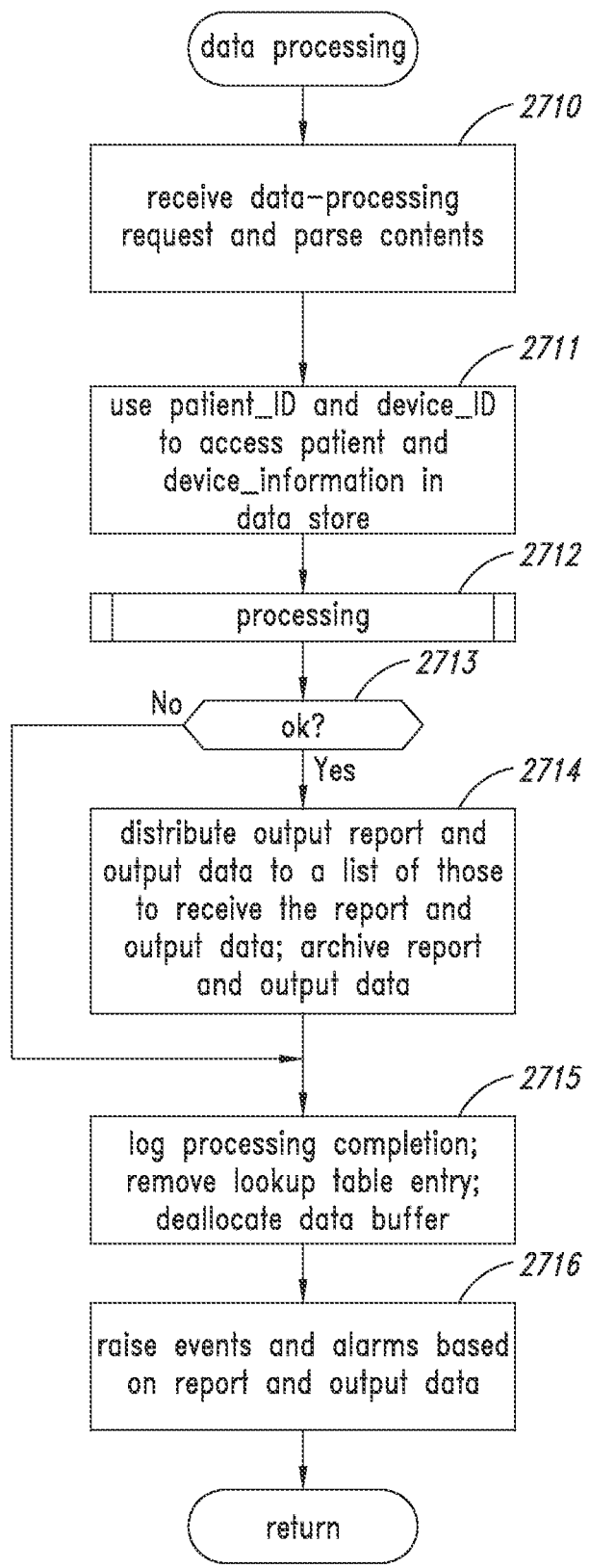
Figure 37E:
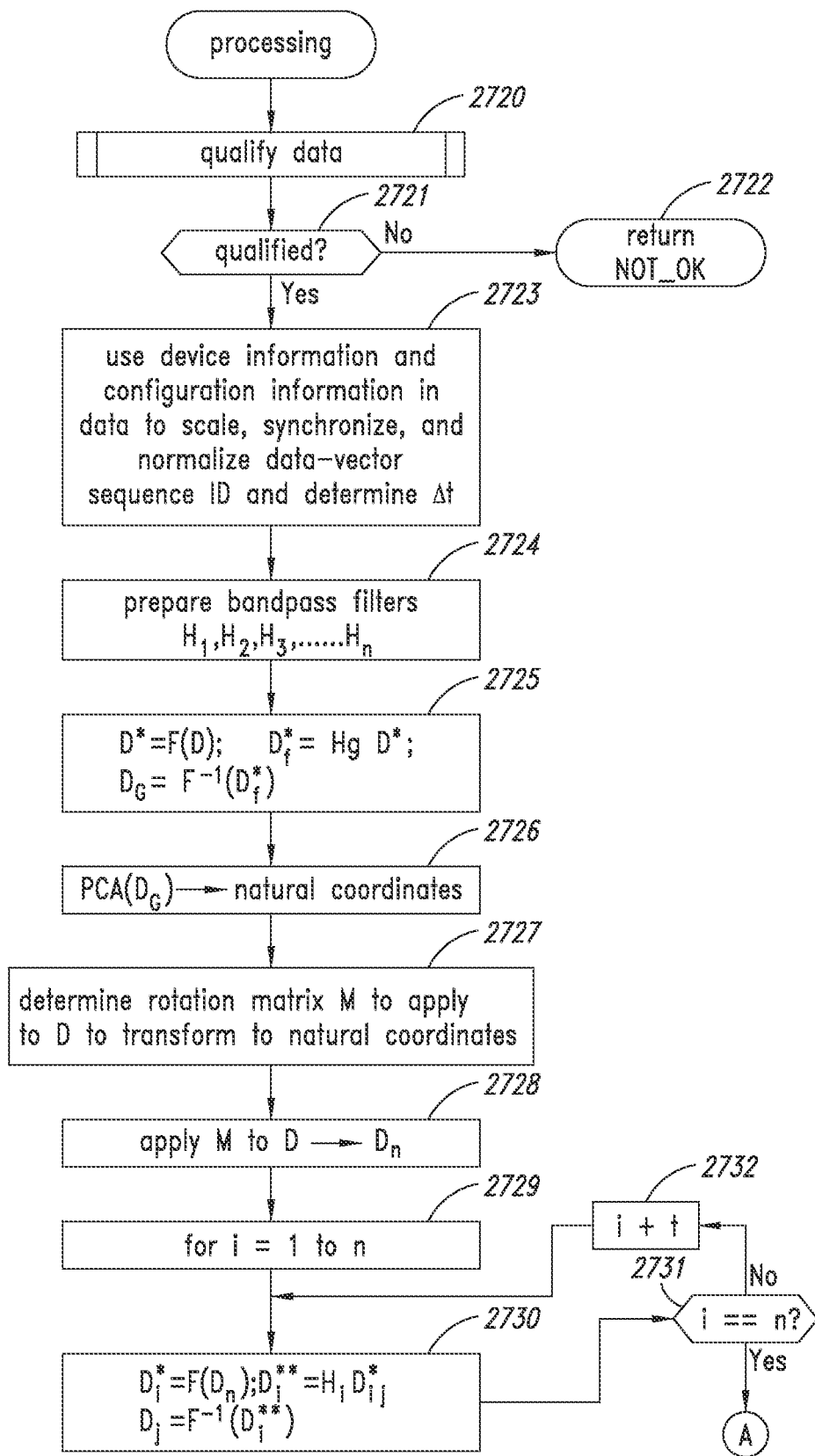
Figure 37F:
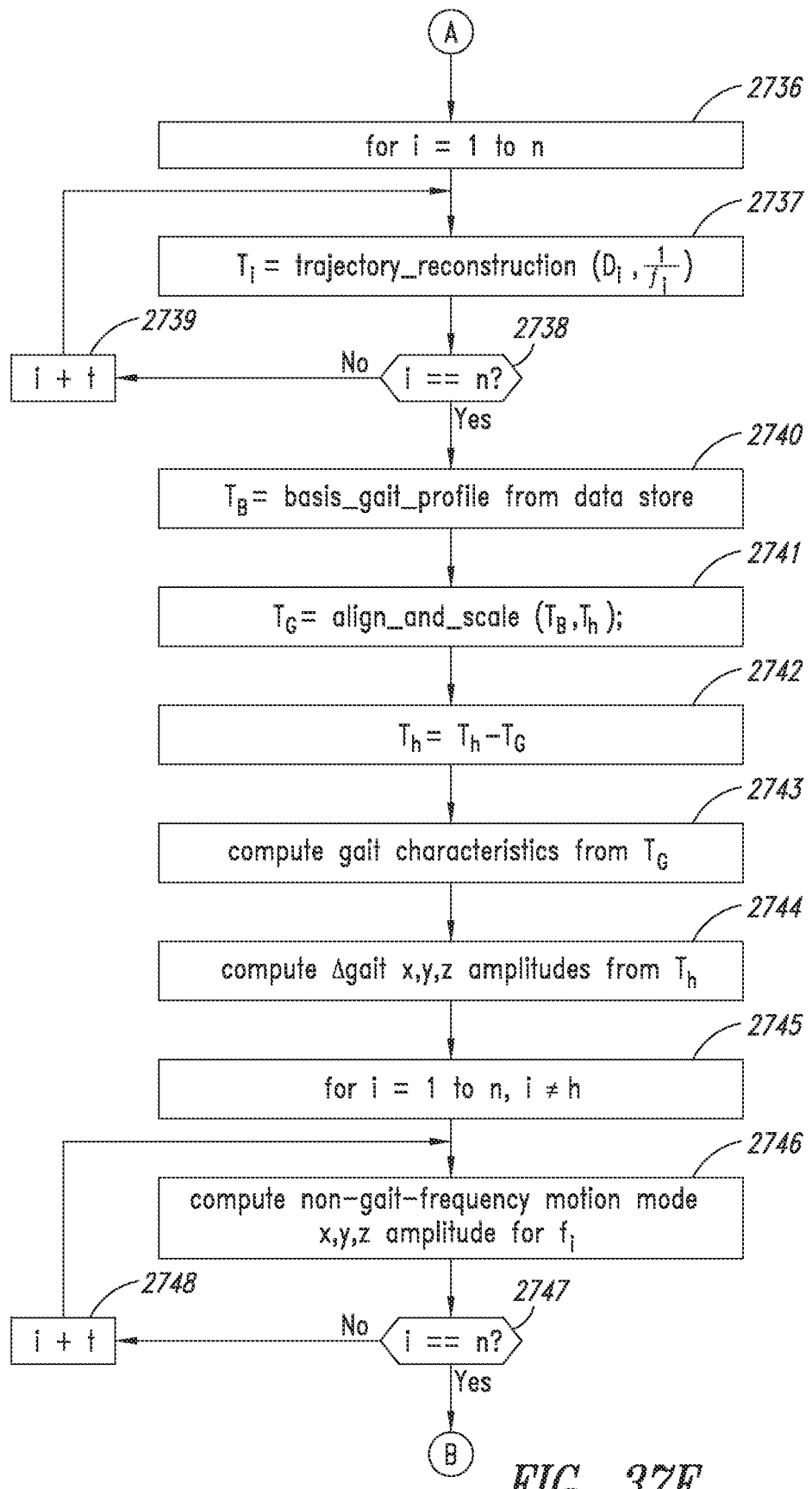

FIG. 37D provides a control-flow diagram for a data-processing routine executed by a backend server to process a data-processing request sent to the backend server by the data-ingress server, or frontend server, discussed above with reference to FIGS. 37A-C. Like the front-end server, the backend server can be viewed as implemented above an underlying event loop, similar to the event loop discussed above with reference to FIG. 37A. The data-processing routine is called from the underlying event loop to handle a newly received data-processing-request. In step 2710, the data-processing routine receives the data-processing request from the front-end server and parses the contents of the request. In step 2711, the data-processing routine uses the patient ID and device ID included in the data-processing request to access patient and device information in the data store as well as to obtain the transaction ID for the data transmission, in the case that the transaction ID is not included in the data-processing request, in order to access the data buffer containing the patient-monitoring-session data received by the front-end server. In step 2712, the data-processing routine calls the routine "processing" to process the patient-monitoring-session data indexed by the transaction ID. When the processing routine returns an indication of successful processing, as determined in step 2713, the data-processing routine, in step 2714, distributes the output report and output data to a list of recipients for the output report and output data, and additionally stores the reporting output data in the data store. As discussed above, the analysis-output data generated for a previous patient-monitoring session is employed during generation of the analysis-output data for the subsequent patient monitoring session. Ultimately, the stored output reports and output data are archived after some threshold period of time. In step 2715, the data-processing routine enters a processing-completion entry into a log file, removes the lookup-table entry associated with the data transmission, deallocates the transaction-ID-index data buffer in which the data was stored by the front-end server, and updates running averages of metrics for the patient and implant.

Finally, in step 2716, the data-processing routine may raise various events and alarms based on the content of the report and output data from data processing and analysis of the patient-monitoring-session data. A variety of different types of events and alarms may be raised. As one example, the report may indicate that a serious problem has developed that needs immediate attention, in which case an alert may be raised for handling by other components of the data-processing application or other applications executing within the computer system. These components may transmit messages to the base station, which may include output devices that alert the patient of the need to contact a medical practitioner or that may directly alert one or more medical practitioners or emergency services. As another example, when the report indicates the need for additional prosthetic equipment, or other types of additional equipment or services, an event may be raised that can be handled by other components of the data-processing application or other applications executing within the computer system to arrange for the additional equipment to be purchased by or on behalf of the patient and the additional services provided to the patient. Thus, the reports and data output from the data processing may be the basis not only of informing medical practitioners of the current patient and device states, but may also be the basis for provision of many additional types of services related to the states of the patient and device in order to assist the patient.

Figure 37G:
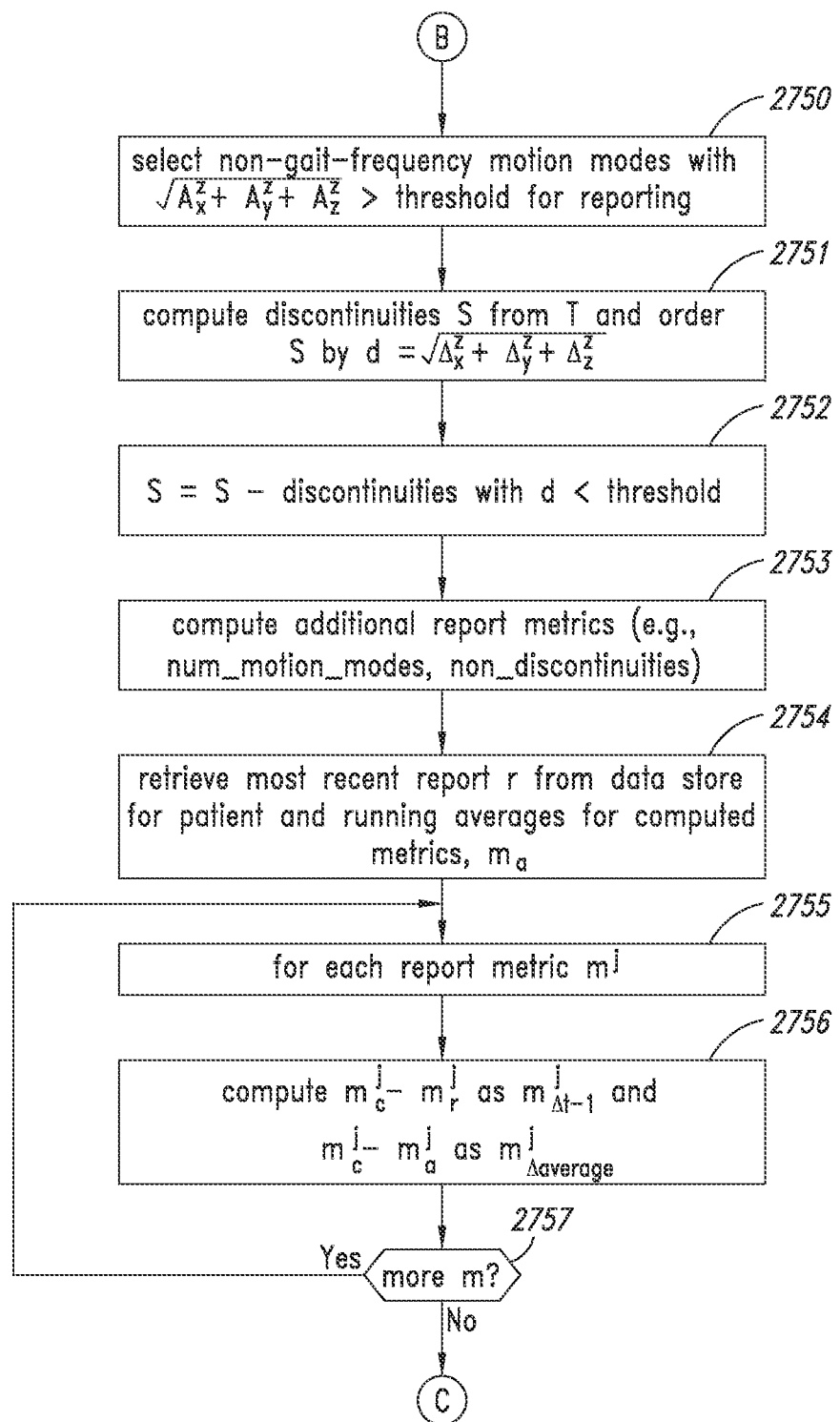
Figure 37H:
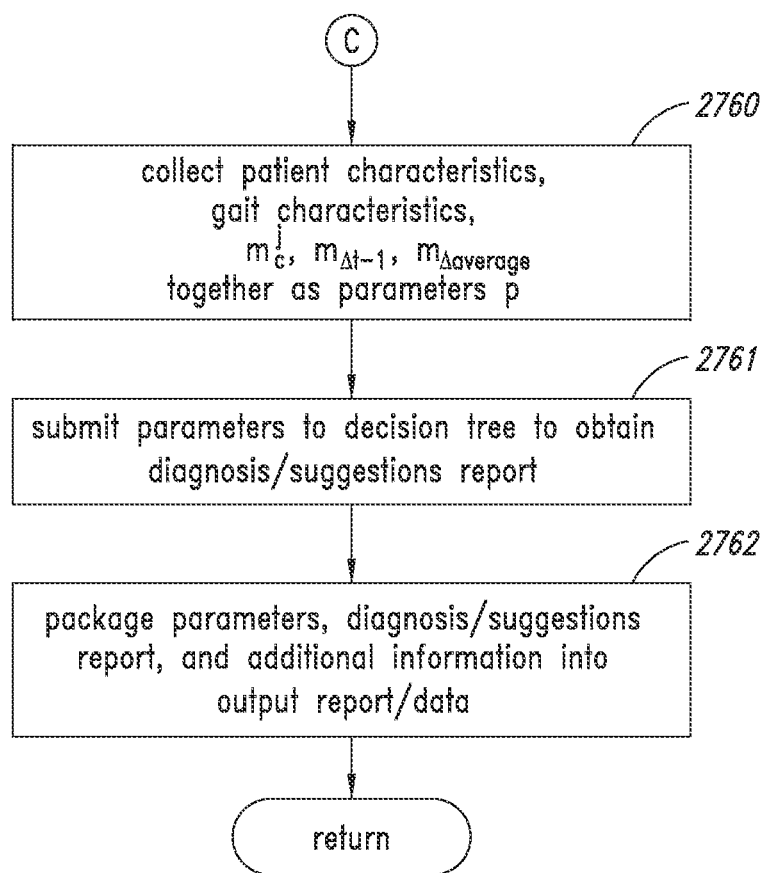

FIGS. 37E-H provide control-flow diagrams for the processing routine called in step 2712 of FIG. 37D. The processing routine employs the various different types of analytic tools discussed above with reference to FIGS. 28-35. It is assumed, for compactness of illustration and description, that only data for a single sensor is included in the data transmission. In the case that data for multiple sensors is included in a data transmission, the data-processing routine includes a higher-level looping control structure to control processing data for each of the multiple sensors, and the data processing routine may additionally include logic for correlating component motions with gait-cycle events and correlating component motions detected by different sensors, as discussed above. In step 2728, the processing routine calls a routine "qualify data" to generate various different metrics from the raw IMU data and/or from an initial trajectory computed from that data to determine whether or not the transmitted data corresponds to the period of time of sufficient length, during which the patient is walking, for application of the above-discussed analysis methods. These initial metrics generally are sufficient to recognize the gait cycle and determine the gait-cycle frequency, and may provide even finer-granularity information with regard to the patient's ambulation, in the case that the data corresponds to a period of patient ambulation. When, as determined in step 2721, the data appears to be sufficient for analysis, as determined from the return value output by the qualify-data routine in step 2720, control flows to step 2723, where the data analysis begins. Otherwise, the processing routine returns a failure indication, in step 2722. When the data is qualified, the device information and sensor-configuration information included in the transmitted data is used to scale, synchronize, and normalize the data-vector sequence output by the IMU and determine the sampling interval, in step 2723. In certain implementations, the raw data may be filtered to detect erroneous data values resulting from transmission errors. In step 2724, a series of n bandpass filters, discussed above with reference to FIG. 34D, are generated or retrieved from the data store. Each of the bandpass filters is used to recover data corresponding to a particular relatively narrow frequency range. In step 2725, the IMU data is filtered to recover the gait-frequency data, including both limb rotation as well as movement of the patient along a walking path, and principal component analysis is applied to the gait-frequency data to determine the natural coordinate system, as discussed above with reference to FIG. 33. In step 2727, a rotation matrix is generated for transformation of the numerical values in the numerical values that would be produced by an IMU aligned with the natural coordinate system. In the for-loop of steps 2728-2730, the various bandpass filters generated or retrieved in step 2724 are successively applied to the raw IMU data in order to recover IMU data for each of the frequency ranges selected by the bandpass filters. Of course, one of those filters likely corresponds to the gait-cycle frequency, in which case the filtering and data recovery for that frequency has already been carried out, in step 2725. Next, turning to FIG. 37F, spatial trajectories are reconstructed for each of the frequency ranges in the for-loop of steps 2736-2739. Additionally, an initial full-data trajectory reconstruction T is also performed. In step 2740-2742, the trajectory representing the difference between the observed patient gait and a basis gait profile is generated, as discussed above with reference to FIGS. 30E-F. In step 2743, the gait-characteristics output data is obtained from the trajectory computed from the gait-frequency-data and aligned and scaled with respect to the basis gait profile, in step 2741, included as the gait-characteristics data 2610 in the output report. In step 2744, the x, y, z amplitudes for the trajectory representing the difference between the observed patient gait and the basis gait profile are computed to produce the harmonic motion modes that represent the departures of the observed patient gait from the basis gait profile, included as the Δgait motion modes 2620 in the output report. In the for-loop of steps 2745-2748, the harmonic non-gait-frequency motion modes are computed from the non-gait-frequency trajectories computed in the for-loop of steps 2736-2739. Turning to FIG. 37G, only the non-gait-frequency modes with an overall amplitude greater than a threshold value are selected for reporting. These are reported in the non-gait-frequency motion modes (624-626 in FIG. 36A). In steps 2751-2752, the discontinuities in the gait trajectory, discussed above with reference to FIG. 31, are determined and those with overall velocities or displacements greater than a threshold value are selected for reporting (638-639 in FIG. 36A). Additional output values, such as the number of non-gait-frequency motion modes reported and the number of discontinuities reported are computed in step 2753. In step 2754, the most recent output report is retrieved from the data store for the patient, as well as running averages for the various computed metrics discussed above. Then, in the for-loop of steps 2755-2757, the above-discussed $\Delta_{t-1}/\Delta_{average}$ pairs for each metric are computed for the portion of the output report illustrated in FIG. 36B. Turning to FIG. 37H, all of the computed metrics obtained by analysis of the patient-monitoring-session data are collected as a set of parameters that are submitted to the decision tree, in step 2761, to obtain the diagnoses/suggestions report discussed above with reference to FIG. 36C. The computed metrics, the diagnoses/suggestions report, and other information, including device and patient information, are then packaged together, in step 2762, as the output report and output data generated by the data-processing system in response to receiving the patient-monitoring-session data.

Using the methodology described above, in one aspect, the present disclosure provides algorithm features for discriminating instability signature from kinematic motion and degradation anomalies (including incomplete osteo-integration). These algorithms will make use of data obtained over a defined spectral specification of about 10 Hz to about 120 Hz, and a temporal specificity of about 0.05-0.5 seconds. In addition, the data generated by the sensor will provide some directional specificity. For example, medial-lateral instability may be observed from data obtained by a y-axis accelerometer and a z-axis gyroscope, where these two data sets may optionally be correlated or multiplied to increase specificity (referred to as sensor fusion). As another example, anterior-posterior instability may be observed from data obtained by a z-axis accelerometer and a y-axis gyroscope, where again these two data sets may optionally be correlated or multiplied to increase specificity.

In one embodiment, the methods of the present disclosure make use of sensor fusion, which refers to the combination or correlation of different sensor inputs that qualify or increase algorithm confidence/performance, and help to reject external noise. Possible noise sources that could introduce anomalies overlapping or interfering with "instability signature" might be riding in a car. Example of sensor fusion to reject car vibrations: correlate and qualify "instability signature" as occurring repeatedly at specific points of normal kinematic motion; car noise/vibration will be random or occurring in the absence of normal kinematic motion; instability will correlate to inflection points of normal kinematic motion—for instance a lateral (medial-lateral) instability will be detected by y-axis accelerometer for instability signature and will correlate in time with either heel strike (detected most likely by x-axis accelerometer), toe-off (detected most likely by y-axis gyro), or mid-stride during peak tibial angular velocity. Sensor fusion is enabled and possible necessitated by "free range" humans with autonomous data collection; not a clinical or controlled experimental environment.

A further example of using data generated by the sensor to provide some directional specificity is identifying inferior-superior instability, which will be apparent from data obtained by a x-axis accelerometer. Yet another example is detecting rotational instability of the implant, which will be apparent from data generated by the x-axis gyroscope.

Figure 38A:
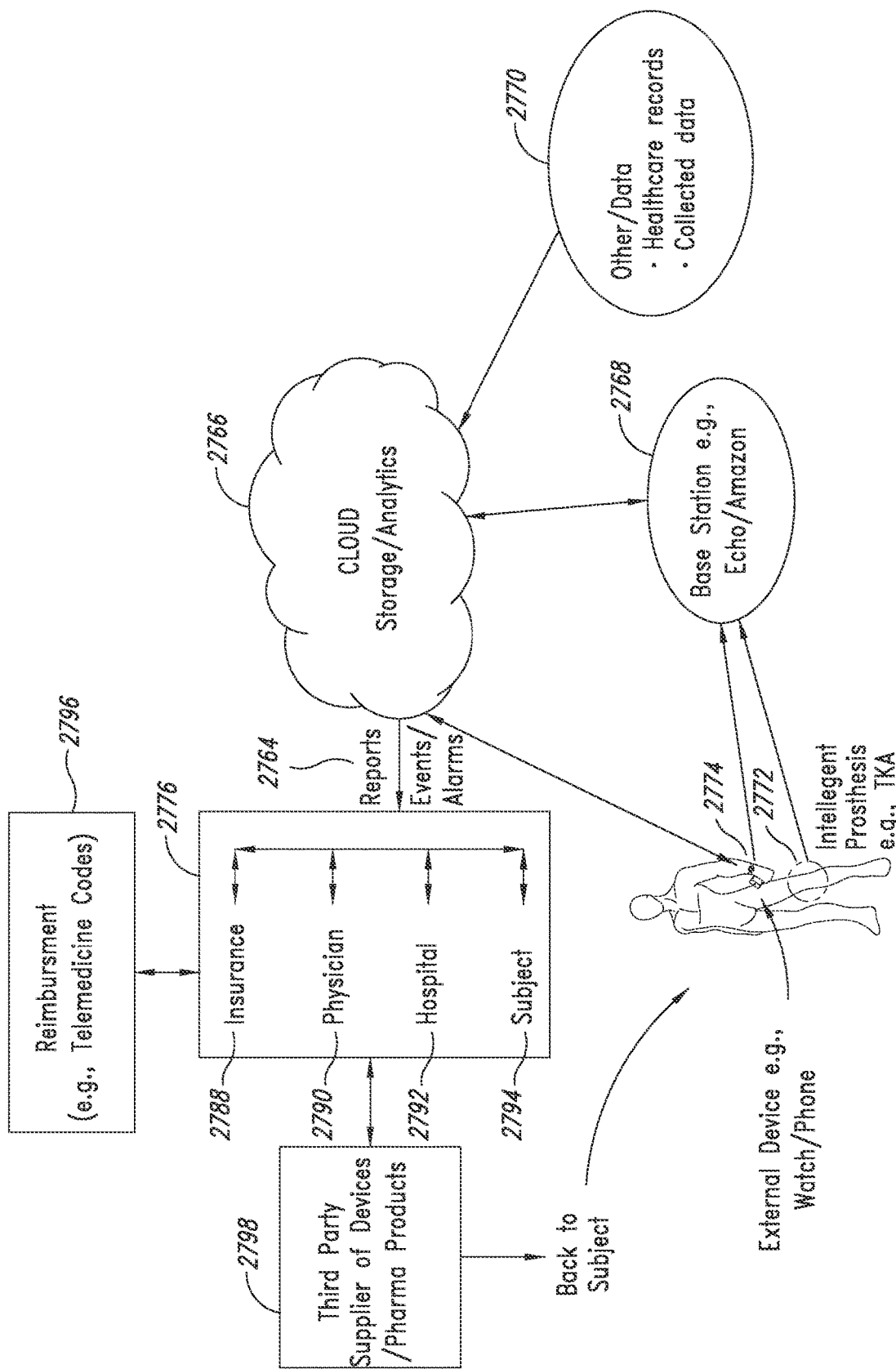
FIG. 38A illustrates representative cloud-based systems and methods for generating and processing data, communication pathways, report generation and revenue generation.
Figure 38B:
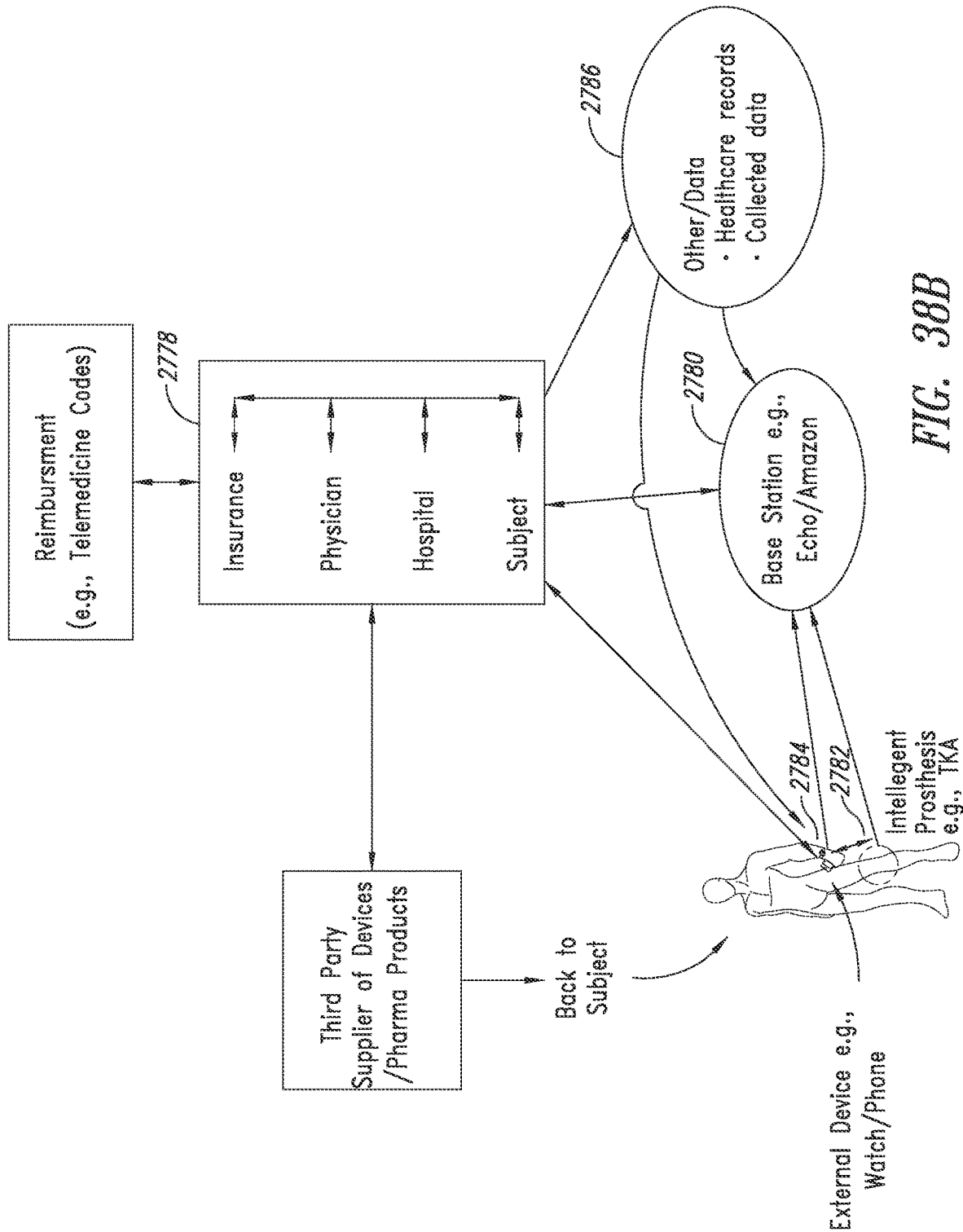
FIG. 38B illustrates representative local based systems and methods for generating and processing data, communication pathways, report generation and revenue generation.

FIG. 38A illustrates representative cloud based systems and methods for generating and processing data, communication pathways, report generation and revenue generation. FIG. 38B illustrates representative local based systems and methods for generating and processing data, communication pathways, report generation and revenue generation.

FIGS. 38A-B illustrate and summarize the roles of the intelligent prosthesis, base station, analytics, stored information, and various external entities in providing automated and semi-automated services to the patient. FIG. 38A illustrates a services-provisioning environment that includes cloud-resident data storage and analytics and FIG. 38B illustrates an alternative services-provisioning environment without cloud-resident data storage and analytics. In FIG. 38A, the reports, events, and alarms generated and distributed by the cloud-resident data storage and analytics 2764, as discussed above with reference to FIG. 37D, are output from cloud-resident data storage and analytics 2766 in response to receiving, and following processing, of monitoring-session data and other data from the base station 2768 and additional data collected from additional sources 2770. As also discussed above, the monitoring-session data is provided by the intelligent prosthesis 2772 and/or additional patient-resident devices 2774 to the base station 2768. The additional data 2770 may be cloud resident or may be alternatively requested from various types of on-line sources, including institutional sources of healthcare records. The reports, events, and alarms 2764 are consumed by various different entities and individuals represented by block 2776. By contrast, in the services-provisioning environment shown in FIG. 38B, the reports, events, and alarms are generated by one or more of the various different entities and individuals represented by block 2778 in cooperation with the base station 2780, the intelligent prosthesis 2782, additional patient-resident devices 2784, and various additional types of data 2786. In short, FIG. 38A illustrates a services-provisioning environment in which cloud-resident storage and analytics plays a centralized role in collecting information and generating reports, events, and alarms for consumption by the various different entities and individuals represented by block 2776 while FIG. 38B illustrates an alternative services-provisioning environment in which reports, events, and alarms are generated in a more distributed fashion by the various different entities and individuals represented by block 2778.

Either in the first services-provisioning environment shown in FIG. 38A or the second services-provisioning environment shown in FIG. 38B, the reports, events, and/or alarms generated from analysis of monitoring-session data and other information, as shown in FIG. 38A, are consumed by insurance companies 2788, medical practitioners 2790, medical facilities, including clinics and hospitals 2792, and, in certain cases, the patient 2794. Different types of reports, events, and/or alarms are generated for the different consuming entities and individuals, depending on their information needs as well as on confidentiality constraints, regulatory constraints, and other constraints. Each of the different types of reports may be generated at different time intervals over different reporting time spans. As one example, monitoring-session data may be analyzed and aggregated to generate progress reports furnished to a medical practitioner and/or clinical staff at a regular time interval over weeks to months following installation of the prosthesis, allowing the medical practitioner to carefully monitor a patient's progress during the critical, initial period of prosthesis use. Within certain embodiments the reports may also include recorded video or audio from a patient, as well as subjective data which may be collected from any of a number of sources. Subsequently, progress reports may be furnished less frequently.

As another example, a cumulative report of the distribution of progress reports to one or more medical practitioners may be furnished to one or more insurance companies to allow automated generation of telemedicine codes 2796 or other means for medical-practitioner reimbursement. Within various embodiments, the services-provisioning environment can record physician and/or clinical staff review of the reports, and provide evidence of the same for reimbursement. Within preferred embodiments at least 10, 15, 20, 30, 45, or 60 minutes of physician and/or clinical staff review would be recorded over the course of a month, and be prepared and submitted in a form suitable for reimbursement.

The various entities and individuals may cooperate to generate secondary reports or requests that are automatically furnished to various third-party suppliers and service providers 2798. For example, the responsible medical practitioner and/or clinical staff may determine, from a review of the aggregated monitoring-session reports, that the patient needs additional equipment, pharmaceuticals, or other services and products, and may enter indications of these needs into the system for automated procurement of the additional equipment, pharmaceuticals, or other services and products on behalf of the patient. Within certain embodiments, the physician and/or clinical staff may require additional equipment such as a knee brace, cane, walker, blood pressure monitoring, and/or a pharmaceutical product.

In further embodiments, automated procurement may involve patient interaction with the equipment, pharmaceutical, and service providers notified by these secondary requests and/or reports. Reports may be distributed by a variety of different means, including email, audio recordings, and textual and graphical information provided through various types of electronic interfaces, including physician dashboards and automated information services.

In addition to the reports, the system may generate various different types of alarms and events, as discussed above with reference to FIG. 37D. For example, the cloud-resident automated analytics module may detect certain types of anomalies or problems that require immediate attention, and may generate alarms via the patient-resident devices 2774, the base station 2768, or by telephone or electronic alerts to a patient's tablet or laptop, and may generate similar alarms for consumption by medical practitioners, medical facilities and even emergency medical-services providers. By contrast, events generated by the cloud-resident automated analytics module may be used for concise reporting and notification to external automated systems used by insurance companies, medical practitioners, and medical facilities. As one example, the cloud-resident automated analytics module may, in certain implementations, generate events corresponding to monitoring sessions that are transmitted to a medical practitioner's dashboard so that the medical practitioner is made aware of the fact that the patient is being successfully automatically monitored by the system. In many implementations, medical practitioners, medical facilities, and insurance companies are provided tools for configuring the types of alarms and events that they wish to receive and configuring the various methods for alarm and event transmission and notification of received alarms and events.

The services-provisioning environments shown in FIGS. 38A-B can be viewed, perhaps most generally, as a highly capable communications system that supports data transmission and other communications between a patient, an intelligent prosthesis within or on the patient, a variety of different individuals and institutions, and many different electronic devices and systems. As with all communication systems, the services-provisioning environments shown in FIGS. 38A-B can be used for many different purposes, all of which may significantly contribute to high quality, timely, and objective-data-driven care for the patient. By automating communications and interactions, as well as prosthesis and patient monitoring, the high-quality medical services are provided in a far more time-efficient and cost-effective manner than these services can be provided by individuals and institutions lacking the highly capable automated communications system.

The following are exemplary embodiments of the present disclosure:

1. A monitoring-session-data collection, analysis, and status-reporting system implemented as a component of one or more computer systems, each computer system having one or more processors, one or more memories, one or more network connections, and access to one or more mass-storage devices, the one or more the monitoring-session-data collection, data-analysis, and status-reporting system comprising:
 a monitoring-session-data-receiving component that receives monitoring-session-data, including acceleration data generated by sensors within or proximal to a prosthesis attached or implanted within a patient, from an external monitoring-session-data source and that stores the received monitoring-session-data in one or more of the one or more memories and one or more mass-storage devices;
 a monitoring-session-data-processing component that prepares the monitoring-session-data for processing, determines component trajectories representing motion modes and additional metric values from the monitoring-session-data; and
 a monitoring-session-data-analysis component that determines a prosthesis status and a patient status from the motion modes and additional metric values, distributes the determined prosthesis status and patient status to target computer systems through the network connections, and when indicated by the determined prosthesis status and patient status, distributes one or more alarms and events to target computer systems through the network connections.

2. The monitoring-session-data collection, analysis, and status-reporting system of embodiment 1 wherein the monitoring-session-data includes: a patient identifier; a device identifier; a timestamp; device-configuration data; and an ordered set of data.

3. The monitoring-session-data collection, analysis, and status-reporting system of embodiment 2 wherein the ordered set of data comprises one of:
 a time sequence of data vectors, each data vector including numerical values related to linear-accelerations with respect to three coordinate axes of an internal device coordinate system; and
 a time sequence of data vectors, each data vector including numerical values related to linear-accelerations with respect to three coordinate axes of a first internal device coordinate system and including numerical values related to angular velocities, numerical values related to angular velocities relative to the first internal device coordinate system or to a second internal device coordinate system.

4. The monitoring-session-data collection, analysis, and status-reporting system of embodiment 1 wherein the monitoring-session-data-processing component prepares the monitoring-session-data for processing by:
 receiving a time sequence of data vectors, each data vector including three numerical values related to linear-accelerations in the directions of three coordinate axes of a first internal device coordinate system and including three numerical values related to angular velocities about each axis of the first or a second internal device coordinate system;
 when rescaling of the data-vector sequence is needed, rescaling the numerical values of the data vectors;
 when normalization of the data-vector sequence is needed, normalizing the numerical values of the data vectors;
 when transformation of one or more of the numerical values related to linear-acceleration and the numerical values related to angular velocities is needed to relate the numerical values related to linear-acceleration and the numerical values related to angular velocities to a common internal coordinate system, transforming one or more of the numerical values related to linear-acceleration and the numerical values related to angular velocities to relate to the common internal coordinate system; and
 when the time sequence of data vectors needs to be synchronized with respect to a fixed-interval time sequence, synchronizing the data vectors with respect to a fixed-interval time sequence.

5. The monitoring-session-data collection, analysis, and status-reporting system of embodiment 1 wherein the monitoring-session-data-processing component determines component trajectories representing motion modes and additional metric values from the monitoring-session-data by:
 orienting the prepared monitoring-session-data, comprising data vectors, each data vector including three numerical values related to linear-accelerations in the directions of three coordinate axes of an internal device coordinate system and including three numerical values related to angular velocities about each axis of the internal device coordinate system, with respect to a natural coordinate system;
 bandpass filtering the oriented data vectors to obtain a set of data vectors for each of multiple frequencies, including a normal-motion frequency;
 determining, from the data vectors for each of the non-normal-motion frequencies, a spatial amplitude in each of the coordinate-axis directions of the natural coordinate system;
 determining, from a basis trajectory for the patient and the data vectors for the normal-motion frequency, a spatial amplitude in each of the coordinate-axis directions of the natural coordinate system; and
 determining, from the basis trajectory for the patient and the data vectors for the normal-motion frequency, current normal-motion characteristics.

6. The monitoring-session-data collection, analysis, and status-reporting system of embodiment 5 wherein determining, from the data vectors for a frequency, a spatial amplitude in each of the coordinate-axis directions of the natural coordinate system further comprises:
 generating a spatial trajectory from the data vectors;
 projecting the spatial frequency onto each of the coordinate axes; and
 determining the lengths of the protections of the spatial frequency onto each of the coordinate axes.

7. The monitoring-session-data collection, analysis, and status-reporting system of embodiment 1 wherein the monitoring-session-data-analysis component determines a prosthesis status and a patient status from the motion modes and additional metric values by:
- submitting the motion modes and additional metric values to a decision tree that generates a diagnosis-and-suggestions report; and
- packaging the diagnosis-and-suggestions report together with amplitudes generated for the motion modes, metrics generated from a normal-motion-frequency trajectory and a base trajectory, and additional metric values to generate one or both of an output report and output data values that characterize the prosthesis status and the patient status.

8. The monitoring-session-data collection, analysis, and status-reporting system of embodiment 1 wherein the monitoring-session-data-analysis component wherein the one or more alarms and events distributed to target computer systems include:
- an alarm that notifies a medical practitioner or medical facility of the need, by the patient, of immediate assistance or intervention; and
- an event that indicates additional services and/or equipment needed by the patient that may be handled by various external computer systems to automatically provide the additional services and/or equipment to the patient or inform the patient of the additional services and/or equipment and provide the patient with information regarding procurement of the additional services and/or equipment.

9. A method, carried out by a monitoring-session-data collection, analysis, and status-reporting system implemented as a component of one or more computer systems, each computer system having one or more processors, one or more memories, one or more network connections, and access to one or more mass-storage devices, the method comprising:
- receiving monitoring-session-data, including acceleration data generated by sensors within or proximal to a prosthesis attached or implanted within a patient, from an external monitoring-session-data source;
- storing the received monitoring-session-data in one or more of the one or more memories and one or more mass-storage devices;
- determining a prosthesis status and a patient status from the motion modes and additional metric values,
- distributing the determined prosthesis status and patient status to target computer systems through the network connections, and
- when indicated by the determined prosthesis status and patient status, distributing one or more alarms and events to target computer systems through the network connections.

10. The method of embodiment 9 wherein determining a prosthesis status and a patient status from the motion modes and additional metric values further comprises:
- preparing the monitoring-session-data for processing,
- determines component trajectories representing motion modes and additional metric values from the monitoring-session-data;
- submitting the motion modes and additional metric values to a decision tree that generates a diagnosis-and-suggestions report; and
- packaging the diagnosis-and-suggestions report together with amplitudes generated for the motion modes, metrics generated from a normal-motion-frequency trajectory and a base trajectory, and additional metric values to generate one or both of an output report and output data values that characterize the prosthesis status and the patient status.

11. The method of embodiment 9 wherein preparing the monitoring-session-data for processing further comprises
- receiving a time sequence of data vectors, each data vector including three numerical values related to linear-accelerations in the directions of three coordinate axes of a first internal device coordinate system and including three numerical values related to angular velocities about each axis of the first or a second internal device coordinate system;
- when rescaling of the data-vector sequence is needed, rescaling the numerical values of the data vectors;
- when normalization of the data-vector sequence is needed, normalizing the numerical values of the data vectors;
- when transformation of one or more of the numerical values related to linear-acceleration and the numerical values related to angular velocities is needed to relate the numerical values related to linear-acceleration and the numerical values related to angular velocities to a common internal coordinate system, transforming one or more of the numerical values related to linear-acceleration and the numerical values related to angular velocities to relate to the common internal coordinate system; and
- when the time sequence of data vectors needs to be synchronized with respect to a fixed-interval time sequence, synchronizing the data vectors with respect to a fixed-interval time sequence.

12. The method of embodiment 9 wherein determining component trajectories representing motion modes and additional metric values from the monitoring-session-data by:
- orienting the prepared monitoring-session-data, comprising data vectors, each data vector including three numerical values related to linear-accelerations in the directions of three coordinate axes of an internal device coordinate system and including three numerical values related to angular velocities about each axis of the internal device coordinate system, with respect to a natural coordinate system;
- bandpass filtering the oriented data vectors to obtain a set of data vectors for each of multiple frequencies, including a normal-motion frequency;
- determining, from the data vectors for each of the non-normal-motion frequencies, a spatial amplitude in each of the coordinate-axis directions of the natural coordinate system;
- determining, from a basis trajectory for the patient and the data vectors for the normal-motion frequency, a spatial amplitude in each of the coordinate-axis directions of the natural coordinate system; and
- determining, from the basis trajectory for the patient and the data vectors for the normal-motion frequency, current normal-motion characteristics.

13. The method of embodiment 9 wherein determining, from the data vectors for a frequency, a spatial amplitude in each of the coordinate-axis directions of the natural coordinate system further comprises:
- generating a spatial trajectory from the data vectors;
- projecting the spatial frequency onto each of the coordinate axes; and
- determining the lengths of the protections of the spatial frequency onto each of the coordinate axes.

14. The method of embodiment 9 wherein determining a prosthesis status and a patient status from the motion modes and additional metric values further comprises:

submitting the motion modes and additional metric values to a decision tree that generates a diagnosis-and-suggestions report; and packaging the diagnosis-and-suggestions report together with amplitudes generated for the motion modes, metrics generated from a normal-motion-frequency trajectory and a base trajectory, and additional metric values to generate one or both of an output report and output data values that characterize the prosthesis status and the patient status.

15. The method of embodiment 9 wherein the one or more alarms and events distributed to target computer systems include:

an alarm that notifies a medical practitioner or medical facility of the need, by the patient, of immediate assistance or intervention; and an event that indicates additional services and/or equipment needed by the patient that may be handled by various external computer systems to automatically provide the additional services and/or equipment to the patient or inform the patient of the additional services and/or equipment and provide the patient with information regarding procurement of the additional services and/or equipment.

16. A physical data-storage device encoded with computer instructions that, when executed by one or more processors within one or more computer systems of a monitoring-session-data collection, analysis, and status-reporting system, each computer system having one or more processors, one or more memories, one or more network connections, and access to one or more mass-storage devices, control the monitoring-session-data collection, analysis, and status-reporting system to:

receive monitoring-session-data, including acceleration data generated by sensors within or proximal to a prosthesis attached or implanted within a patient, from an external monitoring-session-data source.

In each of the foregoing exemplary embodiments of the present disclosure, the present disclosure also provides exemplary embodiments wherein, in the computer system(s), the monitoring session-data-processing component determines component trajectories representing motion modes and not necessarily also representing additional metric values, from the monitoring-session data. In other words, determining component trajectories representing the additional metric values is optionally performed. Likewise, in the methods carried out by a monitoring-session-data collection in embodiments of the present disclosure, the present disclosure also provides exemplary embodiments wherein determining a prosthesis status and/or a patient status is accomplished from the motion mode, and not necessarily also from the additional metric values. In other words, determining a prosthesis status and/or a patient status is optionally done from the additional metric values. Also, in the methods carried out by a monitoring-session-data collection in embodiments of the present disclosure, the present disclosure also provides exemplary embodiments wherein the method may also include determining component trajectories representing motion modes, and optionally additional metric values, from the monitoring-session-data, to thereby provide the motion modes and/or the additional metric values from which may be determined a prosthesis status and/or a patient status as recited in the methods of the exemplary embodiments.

E. Methods and Devices for Stabilizing an Artificial Joint

Total joint arthroplasty (TJA) prosthetic devices are available for replacement of multiple joints in the human body, such as total knee arthroplasty (TKA), total hip arthroplasty (THA), total shoulder arthroplasty (TSA), ankle arthroplasty and elbow arthroplasty. While the design differs by anatomical location and the specific needs of the patient, typically both articular surfaces of the diseased joint are surgically removed (although in some instances only one joint surface is completely, or partially, removed), one articular surface is replaced by a polished metallic prosthesis anchored directly into one adjacent long bone, and the opposing articular surface is replaced by a polymeric "spacer" supported by a metallic prosthesis anchored into the other adjacent long bone marrow cavity. While different metal alloys, polymeric formulations and even ceramic or other materials may be used in various combinations, all TJA devices follow the same basic design principles. The intelligent implant technology described in the present embodiment can be contained in any of the components of a TJA, including the metallic prostheses on one or both sides of the joint and the polymeric spacer located in between them. Particularly preferred locations to incorporate the intelligent implant technology include: the tibial stem and the tibial stem extension of a total knee arthroplasty (TKA), the femoral stem of a total hip arthroplasty (THA), the humeral stem of a total shoulder arthroplasty (TSA), the humeral component of total elbow arthroplasty, and the tibial component of a total ankle arthroplasty.

Figure 39:
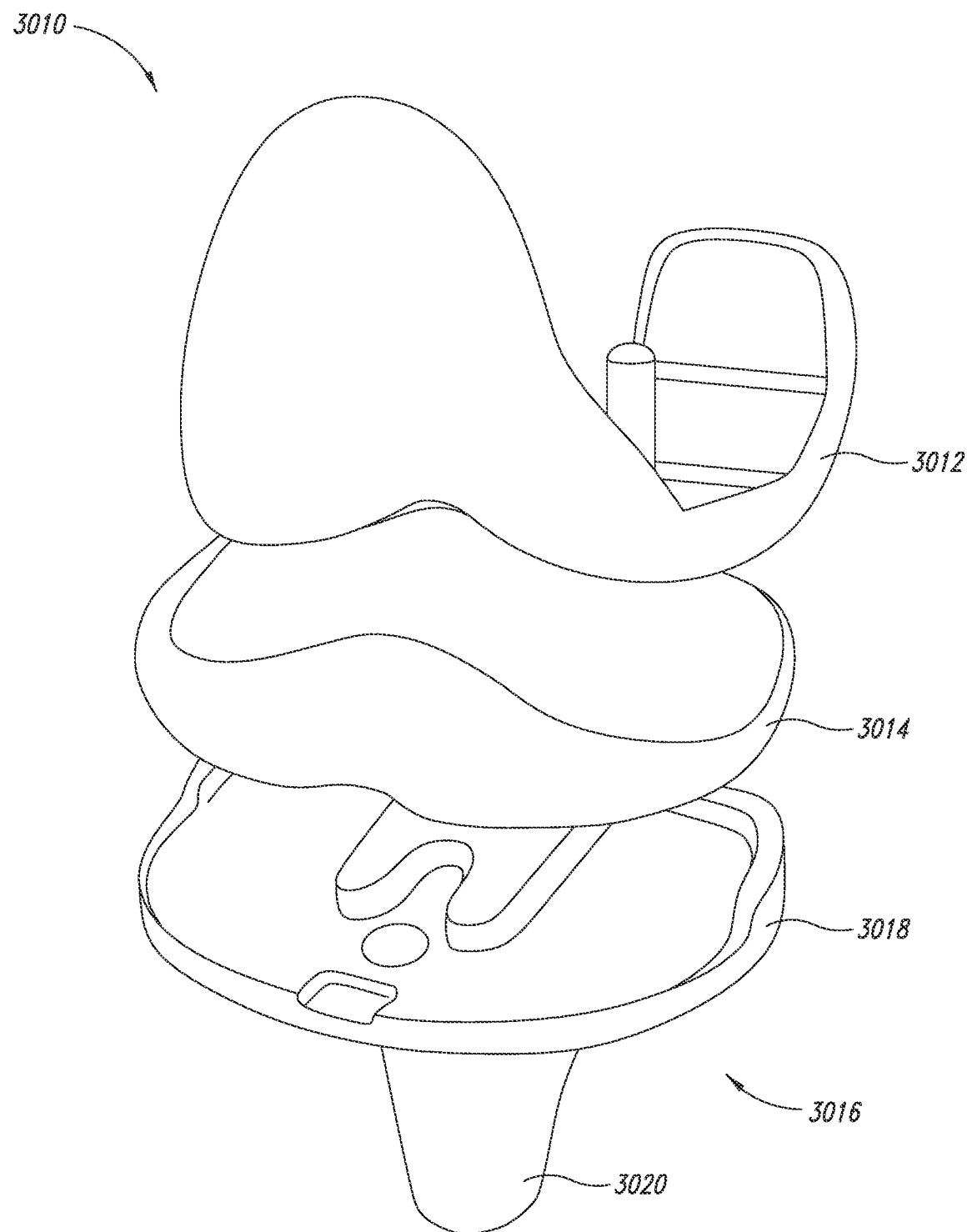
FIG. 39 illustrates components of a currently used total knee arthroscopy system (3010), specifically a femoral component (3012), a tibial insert (3014) and a tibial component (3016), where the tibial component (3016) includes a tibial plate (3018) and a tibial stem (3020).

By way of specific illustration, the typical nomenclature to describe systems for a total knee arthroplasty (TKA) is provided herein with reference to FIG. 39 and FIGS. 40A to 40D. In FIG. 39, a system (3010) for TKA can consist of up to five components: a femoral component (3012), a tibial insert (3014), a tibial component (3016), a tibial extension (not shown in FIG. 39; shown in FIG. 40) and a patella component which is positioned in front of the joint (also omitted from FIG. 39 as well as FIG. 40 for the sake of clarity). The components are designed to work together as a functional unit. The tibial insert (3014) is sometimes called a spacer or an articulating surface. The tibial component (3016) includes a base plate (3018), which is sometimes called a tibial plate, a tibial tray, or a tibial base plate, and a segment that inserts into the marrow cavity of the tibia called the tibial stem (3020). The superior surface of the base plate (3018) contacts and supports the tibial insert (3014). The tibial component may also include a tibial stem extension (not shown in FIG. 39) that attaches to the tibial stem (3020) at its distal end. As shown in FIG. 40, the tibial stem (3020) may be hollow and may terminated with a "female" opening (3022), where this opening/hollow cavity may be positioned to receive a "male" portion of the tibial stem extension (3025) in order to assist in seating the tibial stem extension (3023) into the tibial stem (3020). There are numerous methods of securing the coupling between the tibial stem (3020) and the tibial stem extension (3023) including threading (screwing attachment), specific complimentary coupling attachments and locking screws. While the male coupling part of the tibial stem extension (3025) is contained within the female portion of the tibial stem, the external portion of the tibial stem extension (3024) effectively lengthens the stem portion of the TKA when surgically placed into the tibial marrow cavity and serves to better stabilize the TKA prosthesis.

Figure 40B:
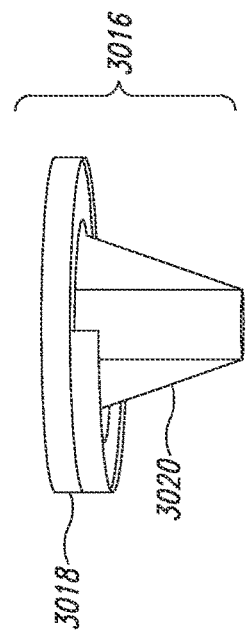
FIG. 40A, FIG. 40B, FIG. 40C and FIG. 40D illustrate exemplary tibial components.
Figure 40D:
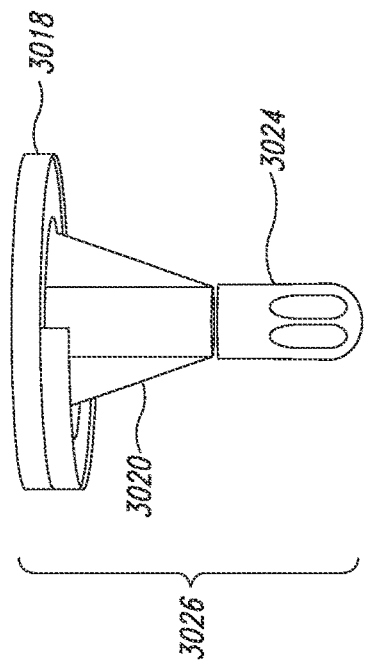
Figure 40A:
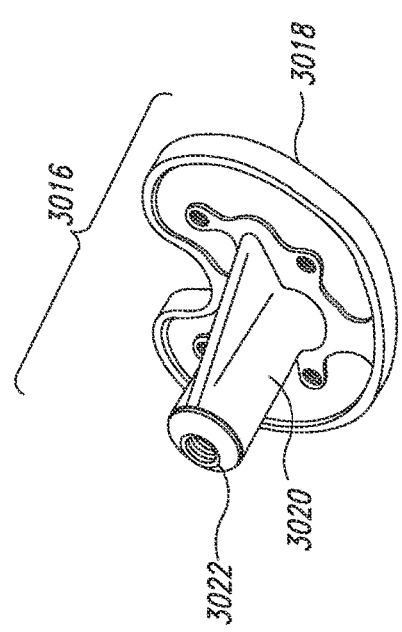
Figure 40C:
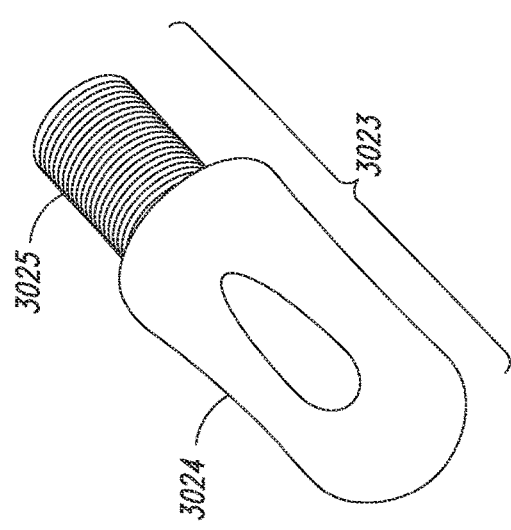

FIG. 40A and FIG. 40B provide two different perspective images of a tibial component (3016), each comprising of a base plate (3018) and a tibial base plate stem (3020). FIG.

40C provides a perspective image of a tibial stem extension (3023). As described above, the tibial stem extension consists of a segment (3025) that inserts into the tibial base stem and a portion which protrudes (3024) to lengthen the overall tibial stem portion of the TKA. FIG. 40D shows the assembled configuration (3026) with the stemmed tibial plate now composed of sections from the base plate stem (3020) and the distal portion of the tibial extension (3024). As described previously, the intelligent implant can be located in the femoral component, the tibial component and/or the spacer, however preferred locations include the tibial stem and the tibial stem extension (as shown in FIGS. 1 and 2).

In some instances, the TJA (e.g. TKA, THA and TSA) may not be stably or anatomically correctly implanted into the patient. It may, for example, demonstrate some degree of misalignment and/or movement relative to the implanted bones and/or the polymeric articular surface, e.g., some degree of wiggle or wobble. This instability or malalignment is, of course, undesirable and can lead to pain, gait/movement problems, physical limitations and patient dysfunction. Poor alignment or instability in the TJA hardware may also lead to bone erosion and accelerated fatigue of the implant components. Left untreated or uncorrected, bone erosion and accelerated fatigue will typically lead to both pain and inflammation. By the time pain and inflammation prompt a TJA patient to seek medical care, the extent of bone erosion and TJA fatigue may leave the health care professional with only one-choice: a highly invasive and expensive surgery with reduced probability of "successful" outcome.

Currently, early identification of subclinical issues is either difficult or impossible since they are often too subtle to be detected on physical exam or demonstratable by radiographic studies. Even if detection were possible, corrective actions would be hampered by the fact that the specific amount movement and/or degree of improper alignment cannot be accurately measured or quantified, making targeted, successful intervention unlikely. The present disclosure provides intelligent implants, devices, systems and methods which provide that the misalignment and/or instability in the TJA hardware can be detected early, before bone erosion and implant fatigue damage has progressed to significant levels. Once misalignment or instability is detected and characterized, the results can be communicated to a health care provider to allow for early treatment and/or more effective treatment of the problem, i.e., the health care provider may take advantage of corrective treatments that are far less invasive, less expensive, and more likely to succeed. The embodiments of the present disclosure address many of the above problems by, (1) identifying the presence of improper alignment and instability through monitoring the patient's daily activity and function via an intelligent implant collecting data under "real world" physical conditions post-operatively, (2) quantifying the specific degree and amount of misalignment or instability identified by such monitoring, (3) using the intelligent implant to identify any negative changes or progression (or positive changes in the event of effective treatment) that occur over time, that therefore allow (4) the design and implementation of specific, pre-emptive, corrective, minimally-invasive measures to address the problems identified. The present disclosure also provides devices and/or methods to address and/or treat the instability and/or misalignment problem. Correcting abnormalities early, prior to the development of significant bone loss, will not only improve the patient's symptoms (pain, impaired ambulation), but also prolong the effective lifespan of the TJA procedure and reduce the need repeat and highly invasive, surgical, corrective procedures.

In one aspect, the present disclosure provides for obtaining data from intelligent implants that documents the degree of misalignment, the anatomic location of the loosening and/or the absolute degree of loosening of the implanted TJA. This precise, site-specific data collected directly from the patient's intelligent TJA implant and the corresponding analyzed data may be used by the health care professional to determine whether, what type, and when an intervention is desired. With minor deficiencies, corrective external bracing, using commercially available joint braces, can be used to restore proper alignment and provide enhanced stability. Determining the correct degree of misalignment and/or the magnitude of instability via the intelligent TJA allows the design of a corrective brace specifically tailored to the patient's deficiency. For lower limb TJA (TKA, THA and ankle arthroplasty), customized orthotics can be utilized for the same purposes. For more severe or advanced misalignment or instability, minimally-invasive corrective measures can be employed. The health care provider may recommend an appropriate intervention to address the instability depending upon whether the TJA component has been cemented into place or is closely fitted into the bone without the use of cement. For example, when the TJA is an uncemented intelligent prosthesis (such as an uncemented TKA or an uncemented THA), and misalignment and/or instability of the TJA is causing pain for the patient, data obtained from the intelligent device can be used to monitor and locate the anatomical location and amount/degree of misalignment or instability. Localized and precise amounts of bone cement can then be injected/applied minimally-invasively to the specific area to correct the abnormality. The patient is monitored by the intelligent TJA peri-procedurally to confirm successful correction and post-procedurally to follow the patient's functional response to treatment. For cemented TJA patients, monitoring data may be used to determine whether the interface between the bone cement and the prosthesis has broken. As with the uncemented TJA, bone cement can be delivered to the correct location in the required amount, using techniques and devices described in greater detail below, to correct the broken cement-bone interface.

In the event that a determination is made that the instability is due to insufficient osteointegration, the present disclosure provides a method for enhancing osteointegration in order to address the TJA instability. Thus, the present disclosure provides methods that include detecting the presence of TJA instability using the intelligent TJA, optionally locating, measuring or otherwise characterizing the TJA instability, and performing a minimally-invasive intervention in order to improve the process of osteointegration at the required sites surrounding the TJA. Such intervention may include using autologous bone graft placement/injection, xenograph bone graft placement/injection, synthetic bone graft placement/injection, bone pastes, injection of bone growth factors (such as Bone Morphogenic Protein or BMP), injection of other growth factors, and methods for locating such therapeutic agents at the site of the TJA installation.

In one aspect, the intelligent implant has generated data indicating that only one or more isolated areas around the TJA is/are loose. Accordingly, the present disclosure provides a method where that/those specific area(s) is/are identified, and autologous, xenographic or synthetic bone graft material (with or without growth factors such as BMP), and/or bone cement or other fixation means is/are directed solely to that/those area(s). In effect, this provides a spot welding approach to addressing the source(s) of instability.

In the event the TJA component is not cemented into place (for example, an uncemented TKA or THA), the present disclosure provides tools that may be used to inject/place autologous, xenographic or synthetic bone graft material (with or without growth factors such as BMP), and/or cement to improve stability. For example, a fenestrated screw or other hollow, boring device may be inserted into a bone, terminating in the space between the uncemented component and the nearby inner surface of the bone. The access thus provided can be used to inject/place autologous, xenographic or synthetic bone graft material (with or without growth factors such as BMP), and/or cement into the space surrounding the uncemented TJA. Cement and/or xenographic or synthetic bone graft material (with or without growth factors such as BMP) may be deposited into this space, in order to fill the space and to secure the tibial component into a permanent position, i.e., a non-moving position with respect to the surround bone.

In one aspect, the present disclosure provides a method that includes detecting the presence of a TJA instability, optionally characterizing that instability, and then intervening in order to stabilize the TJA. In one aspect, the intervention is a method including drilling a hole through the bone cortex surrounding the TJA, and injecting/placing autologous, xenographic or synthetic bone graft material (with or without growth factors such as BMP), and/or cement into a space between the TJA and the surrounding bone.

Optionally, the space between the TJA and the surrounding bone may not be sufficiently large to receive the amount of cement that is desirably injected. In this case, the present disclosure provides a method that include inserting a balloon into the space between the TJA and the surrounding tibia bone, and inflating that balloon to open up additional space between the TJA and the surrounding bone, and then injecting/placing autologous, xenographic or synthetic bone graft material (with or without growth factors such as BMP), and/or cement into the opened space.

In another aspect, the present disclosure provides a method that includes detecting the presence of improper alignment of the TJA prosthetic component using the intelligent implant, optionally characterizing that axis and the degree of misalignment, and then intervening in order to correctly align the prosthetic component. In one aspect, the intervention is a method including drilling a hole through the bone cortex surrounding the TJA, and injecting/placing autologous, xenographic or synthetic bone graft material (with or without growth factors such as BMP), and/or cement into a specified space, in a specified amount, between the TJA and the surrounding tibia bone so to "push" the stem of the TJA in the correct axis to correct the misalignment. The present disclosure also provides a method that includes inserting a balloon into the space between the TJA and the surrounding bone and inflating that balloon to "push" the prosthetic joint stem in the correct axis to correct the misalignment, and then injecting cement into the opened space. The present disclosure also includes the use of a screw, wire, rod or other physical device inserted into the space between the TJA and the surrounding bone to "push" the prosthetic stem in the correct axis, and the correct amount/distance, in order to correct the misalignment, and then injecting/placing autologous, xenographic or synthetic bone graft material (with or without growth factors such as BMP), and/or cement into the opened space to permanently realign the TJA. In the event that osteointegration has already occurred when the misalignment or instability has been detected or is going to be addressed, then the above devices and methods can be used to push the prosthetic stem portion of the device into the correct alignment where it can be permanently embedded correctly through the subsequent application of bone cement, autologous, xenographic or synthetic bone graft material (with or without growth factors such as BMP), or other fixation technique.

Suitable tools and balloons for stabilizing or realigning a TKI according to the present disclosure may be the same or analogous to the tools and/or balloons that are suitable for use in intervertebral disc therapies such as kyphoplasty procedures.

Optionally, in one embodiment, the intelligent implant is interrogated during the procedure used to address the misalignment and/or instability, and based on information obtained from the intelligent implant, the surgeon can optimize the amount and positioning of the cement, xenographic or synthetic bone graft material (with or without growth factors such as BMP) being used to stabilize the implant.

In the event that a determination is made that the instability is due to the presence of a prosthetic joint infection (PJI), the present disclosure provides a method for treating the PJI in order to address the TJA instability. Prosthetic joint infection is a serious complication that occurs in approximately 1% of TJA patients and is frequently caused by skin bacteria (often Staphylococcus epidermidis or *Staphylococcus aureus*). It can be difficult to diagnose and treat due to the indolent nature of the infection and due to the lack of specific signs and symptoms and is therefore often quite advanced by the time it presents clinically. In many cases it can result in failure of the TJA procedure and the need to remove the infected implant. The present disclosure provides methods that include early detection of the presence of PJI using the intelligent TJA thus allowing the healthcare professional to confirm the presence of PJI, determine its location and extent, and perform systemic and/or local therapeutic interventions in order to treat and/or eradicate the infection. Such interventions may include the administration of systemic antibiotics, using localized irrigation of the marrow cavity with antibiotics, the local application of sustained release antibiotic preparations at the site of the infection, the local application of other therapeutic agents, and methods for locating such therapeutic agents at the site of the TJA infection using the devices and techniques described above.

F. Methods and Devices for Adjusting Position of an Artificial Joint

In some instances, the TJA may be stably implanted into the patient, however, the positioning of the TJA is suboptimal. This can occur even after a "successful" implant if the patient loses a great deal of weight or has another joint replaced. Furthermore "perfect" anatomical alignment for a particular patient may not be "ideal" for them as their inherent anatomy may be a few degrees deviated from the normal position. This suboptimal placement of the TJA prosthesis, e.g., TKI, may lead to problems, including pain, distorted gait, difficulty performing certain activities (e.g. climbing stairs, getting out of chairs), weakness, instability and even accelerated wear in all or parts of the TJA prosthesis. By way of illustration, incorrect placement is thought to be a significant contributor to the 20% of patients who report dissatisfaction with their TKA surgery. Data collected from the intelligent TJA prosthesis of the present disclosure can be used to detect problems with placement, alignment and functioning of the TJA prosthesis and be utilized by the healthcare professional to take corrective actions to alleviate symptoms and prevent longer-term sequalae.

In one aspect, the present disclosure provides a series of tamps that can finely adjust the positioning of the TJA within the patient, particularly if the non-optimal positioning is detected early by the intelligent TJA, before substantial osteointegration has taken place. The present disclosure also provides a method of adjusting the position of an implanted TJA to an improved position, which includes using a tamp to adjust the position of the TJA.

In one aspect, the present disclosure provides metal pins and/or K-wires that can be used to adjust the positioning of the TJA within the patient, particularly if the non-optimal positioning is detected early, before substantial osteointegration has taken place. The present disclosure also provides a method of adjusting the position of an implanted TJA to an improved position, which includes using a metal pin or K-wire to adjust the position of the TJA to a position more beneficial to the patient.

In one aspect, the present disclosure provides metal pins and/or K-wires that can be used to adjust the positioning of the TJA within the patient, particularly if the non-optimal positioning is detected early by the intelligent TJA, before substantial osteointegration has taken place. The present disclosure also provides a method of adjusting the position of an implanted TJA to an improved position, which includes using a metal pin or K-wire to adjust the position of the TJA.

In one aspect, the present disclosure provides a "Christmas tree stand" approach, where two, three or more (e.g., 4, 5, 6, 7, 8, 9, 10, 11, 12, 13, 14, 15, 16, 17, 18, 19, 20) screws are inserted into the bone at different locations (e.g. for three screws, at 0°, 120° and 240°) so as to apply pressure to the shaft of the TJA prosthetic stem (or stem extension if present) and adjust/push the TJA into the desired anatomical location. This approach can be used to adjust the positioning of the TJA within the patient, particularly if the non-optimal positioning is detected early, e.g., before clinical symptoms arise, and typically before substantial osteointegration has taken place. The present disclosure also provides a method of adjusting the position of an implanted TJA to an improved position, which includes using this "Christmas tree stand" approach to adjust the position of the TJA. In this approach, a hole is drilled between the outer surface of the bone and the inner surface adjacent to the implant. A screw is then inserted through this hole, until the end of the screw touches the implant. The screw is further inserted, pushing against the implant and causing the implant to tilt slightly. In this way, the position of the implant within the bone is adjusted to the desired location. Additional screws may be used to move the implant, and/or to hold the implant in a desired location.

G. Joint Inserts and Use Thereof

As described previously, the TJA may not be stably or anatomically correctly implanted into the patient due to some degree of misalignment and/or movement relative to the stem component, the polymeric insert or the other articular component. Abnormal movement of the TJA components in contact with the polymeric insert (or the other articular surface) can lead to abnormal wear of the polymer surface, accelerated fatigue of the articular polymers, the generation and liberation of microscopic polymeric fragments into the joint space (which can in turn cause pain and inflammation) and even early failure of the TJA implant itself. Instability, abnormal motion/movement and/or misalignment with respect to the TJA articular surface (i.e. the polymeric insert and the opposing articular surface) clinically manifests itself as pain, inflammation, gait/movement problems, joint instability, joint subluxation, physical limitations and patient dysfunction. By the time pain and inflammation prompt a TJA patient to seek medical care, expensive and invasive replacement surgery may be required.

Currently, early identification of subclinical TJA articular surface issues are either difficult or impossible since they are often too subtle to be detected on physical exam or demonstrable by radiographic studies. Even if detection were possible, corrective actions would be hampered by the fact that the specific amount movement, subluxation, degree of improper alignment, or irregular and accelerated wear cannot be accurately measured or quantified, making targeted, successful intervention unlikely. The present disclosure provides intelligent implants, devices, systems and methods which provide that the misalignment and/or improper movement with respect to the TJA articular surface can be detected early, before polymer erosion has led to permanent problems with the TJA prosthesis. Once misalignment, improper movement, and/or instability is detected and characterized by an intelligent TJA implant, the results can be communicated to a health care provider to allow for early treatment and/or more effective treatment of the problem, i.e., the health care provider may take advantage of corrective treatments that are far less invasive, less expensive, and more likely to succeed. Embodiments of the present disclosure address many of the above problems in several ways, but include non-invasive interventions such as external bracing and orthotics (for lower limb prostheses), as well as less invasive surgical interventions such as the removal of a failing polymeric insert and replacing it with a customized polymeric insert designed to correct the identified problems. Correcting abnormalities early, prior to the development of TJA failure, will not only improve the patient's symptoms (pain, inflammation, impaired joint motion, impaired ambulation), but also prolong the effective lifespan of the TJA procedure and reduce the need for repeat and highly invasive corrective procedures.

Polymeric inserts are used in many TJA applications. In embodiments, the present disclosure provides asymmetrical polymeric inserts for a hip implant, a knee implant, a shoulder implant, an elbow implant and a knee implant. The polymeric insert may be a spacer, an articular spacer or an intraarticular spacer. In one embodiment the spacer is a static spacer. In one embodiment the spacer is an articulating spacer.

Figure 41:
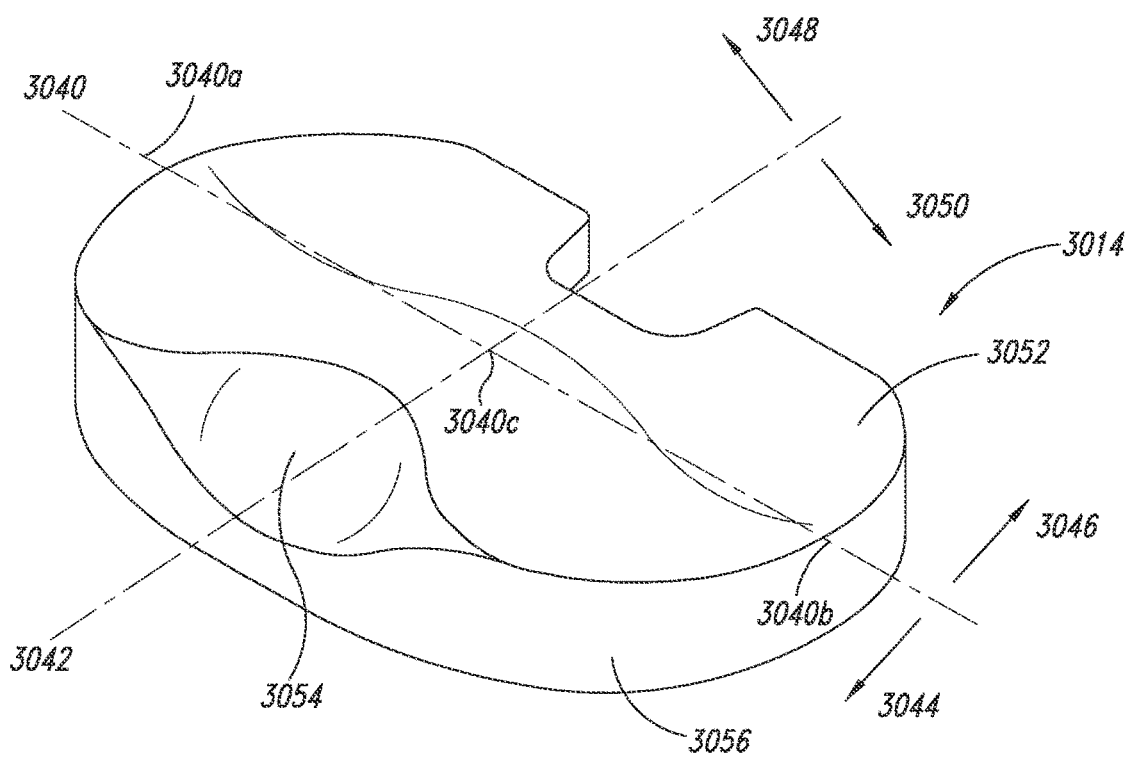
FIG. 41 illustrates a tibial insert.

FIG. 41 provides a specific example of a tibial insert (3014) used in a TKA procedure. In FIG. 41, the tibial insert (3014) is shown to have an axis (3040) that cuts across the longest width (medial-lateral anatomically) of the insert (3014), and extends from the medial edge of the insert at point 3040a to the lateral edge of the insert at point 3040b, and crossing a center line of the insert at point at 3040c, where point 3040c is mid-way between points 3040a and 3040b. In addition, the tibial insert (3014) has an axis (3042) that cuts across the depth (anterior-posterior anatomically) of the insert (3014). Taken together, these two axes (3040) and (3042) divide the tibial insert into four quadrants, when the insert (3014) is viewed from its superior surface (3052), or the surface that contacts the femoral component (3012). The medial-lateral axis (3040) divides the insert (3014) into an anterior side (3044) and a posterior side (3046). The anterior-posterior axis (3042) divides the insert (3014) into a medial side (3048) which will be closest to the recipient's second knee (i.e. the midline), and a lateral side (3046) which will be on the outside of the knee (away from the recipient's second knee; for further clarity, the insert (3014) depicted in FIG. 41 is one located in the left knee of a TKA recipient). As also shown in FIG. 41, the anterior side (3044) of the insert (3014) may have a recess (3054) to accept the patella component (not shown), while the posterior side (3046) often features a "notch" that mimics the anatomy of the tibia. The insert (3014) may also have a sidewall (3056) that extends around the insert (3014).

Figure 42A:
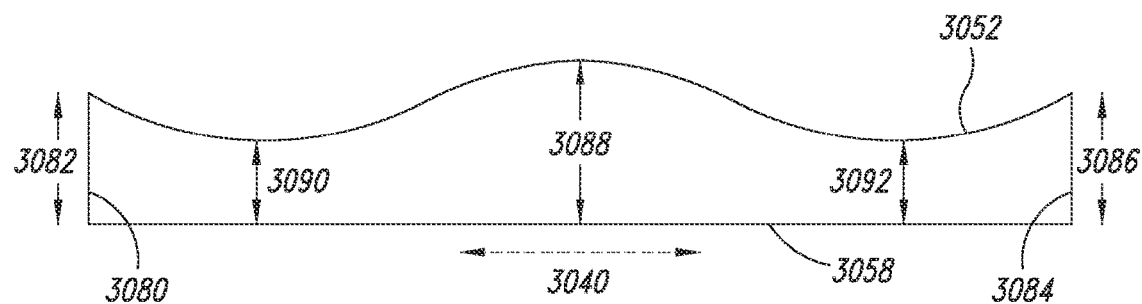
FIG. 42A illustrates a cross-sectional view of the tibial insert of FIG. 41.

FIG. 42A illustrates a cross-section (superior-inferior anatomically) of the tibial insert (3014) of FIG. 41, as viewed along the axis 3040. In the cross-sectional view of FIG. 42A, the insert (3014) is shown to have a top (superior) articular surface (3052) and a bottom (inferior) surface (3058), where the inferior surface (3058) would typically be held in place by the tibial plate (3016) and the superior surface (3052) would be in contact with the femoral head. Also shown in FIG. 42A are the medial edge (3080) which would be at point 3040a in FIG. 41, and the lateral edge (3084) which would be at point 3040b of the insert (3014) also shown in FIG. 41, where the medial edge (3080) has a height (3082) (also referred to as a thickness (3082)) extending from the bottom (inferior) surface (3058) to the top (superior) surface (3052) of the implant, and likewise the lateral edge (3084) has a height (3086) extending from the bottom (inferior) surface (3058) to the top (superior) surface (3052) of the implant. In addition, the insert (3014) has a height (3088) at the midpoint of the insert, i.e., at point 3040c as identified in FIG. 41. In addition, the insert (3014) will have a height (3090) which is the shortest height on the medial side of the insert (3014), and will have a height (3092) which is the shortest height on the lateral side of the insert (3014).

In one aspect, the present disclosure provides a tibial insert having a shortest height (3090) on the medial side of the insert which is not equal to the shortest height (3092) on the lateral side of the insert. In one aspect, the present disclosure provides a tibial insert having a shortest height (3090) on the medial side of the insert which is less than the shortest height (3092) on the lateral side of the insert. In one aspect, the present disclosure provides a tibial insert having a shortest height (3090) on the medial side of the insert which is greater than the shortest height (3092) on the lateral side of the insert. The term least thickness may be used in lieu of shortest height.

Figure 42B:
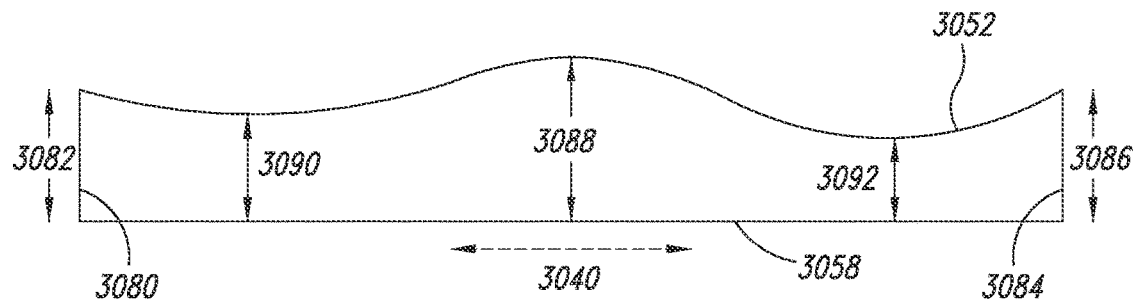
FIG. 42B illustrates a deviation in the cross-sectional view of FIG. 42A.

For example, in embodiments, the present disclosure provides a tibial insert for an implantable TKA prosthesis, where the tibial insert is about 1, 2, 3, 4, 5, 6, 7, 8, 9, or 10 mm thicker (higher) on the medial side of the implant, as compared to the lateral side. Such an embodiment is illustrated in FIG. 42B, where the thickness (3090) on the medial side of the insert (14) is shown to be greater than the thickness (3092) on the lateral side of the insert (3014). This configuration could be desirable, for example, in a patient experience medial knee instability where the prosthesis exhibits some degree of undesirable movement or subluxation towards the midline. After using the intelligent implant to determine the anatomical location, direction and amount/ degree of movement leading to the medial instability, a customized tibial insert could be created with a higher medial minimum thickness and a lower lateral minimum thickness to correct the abnormal movement and instability. Thus, rather than replacing the entire joint, the knee could be opened surgically, the ineffective tibial insert removed, and replaced with a superior (for that patient), customized tibial insert. Early detection by the implanted sensors would allow correction prior to significant bone loss or implant damage requiring highly invasive TKA revision surgery.

As another example, in embodiments, the present disclosure provides a tibial insert for an implantable TKA prosthesis, where the tibial insert is about 1, 2, 3, 4, 5, 6, 7, 8, 9, or, 10 mm thicker (higher) on the lateral side of the implant, as compared to the medial side. This design would be used as described above, but in patients experiencing abnormal lateral movement and instability.

Figure 43:
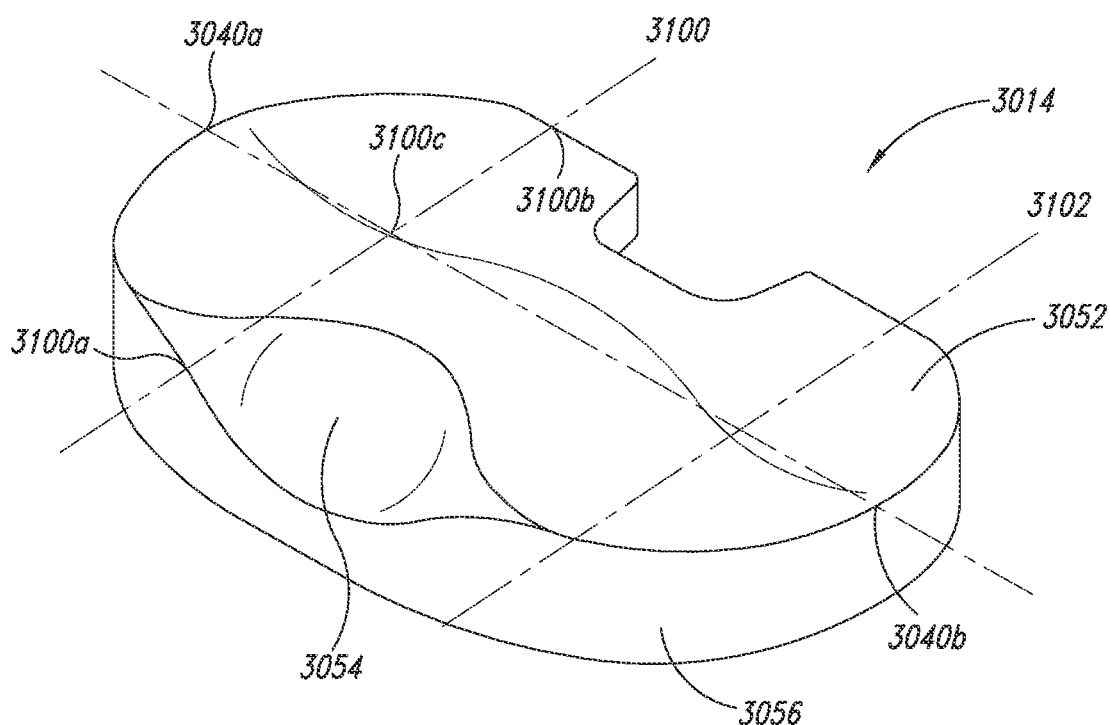
FIG. 43 illustrates a tibial insert.

FIG. 43 provides an additional perspective illustration of a tibial insert (3014). In FIG. 43, the tibial insert (3014) is shown to have two axes (3100) and (3102) that cut across the thinnest portion of the medial and lateral sides, respectively, of the insert (3014), each running in an anterior-posterior direction. Axis 3100 may be further characterized as having a point 3100a located at the anterior edge of the insert (3104), a point 3100b located at the posterior edge of the insert (3104) and a center point (mid-point) located at position 3100c which is mid-way between points 3100a and 3100b.

Figure 44A:
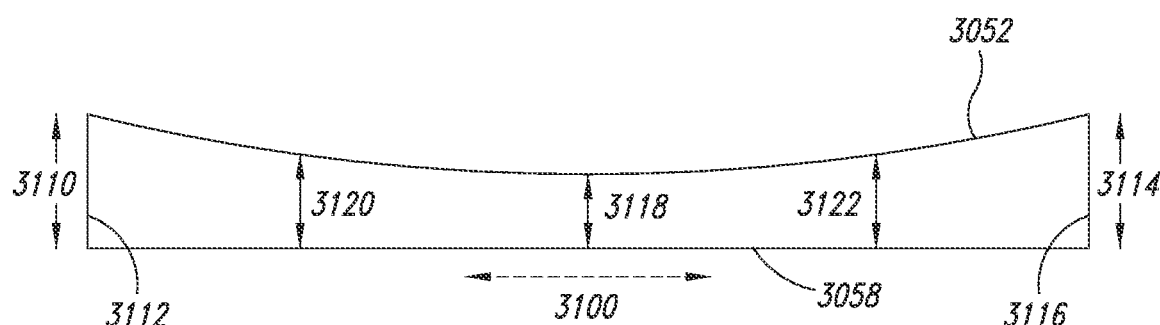
FIG. 44A illustrates a cross-sectional view of the tibial insert of FIG. 43.

FIG. 44A shows a cross-section of the insert (3014) of FIG. 43, as viewed along the line 3100. Thus, in FIG. 44A, the insert (3014) has an anterior edge (3112) located at position 3100a in FIG. 43, having a height (also known as thickness) (3110) and a posterior edge (3116) located as position 3100b in FIG. 43, having a height (3114) where a height is measured as the distance of the edge 3110 or 3114 extending from the top surface (3052) to the bottom surface (3058) of the insert (3014). In addition, the insert (3014) has a height (3118) at a center point located at the intersection of axes (3040) and (3100), i.e., position 3100c in FIG. 43. On either side off this centerpoint, the insert will have an average height (3120) on the anterior side, and an average height (3122) on the posterior side, respectively, of the insert (3014). The average height 3120 is 50% of the combined heights 3100 and 3118, while the average height 3122 is 50% of the combined heights 3114 and 3118.

In one aspect, the present disclosure provides a tibial insert having an average height (3120) on the anterior side of the insert which is not equal to the average height (3122) on the posterior side of the insert. In one aspect, the present disclosure provides a tibial insert having an average height (3120) on the anterior side of the insert which is less than the average height (3122) on the posterior side of the insert. In one aspect, the present disclosure provides a tibial insert having an average height (3120) on the medial side of the insert which is greater than the average height (3122) on the lateral side of the insert. The term least thickness may be used in lieu of height.

Figure 44B:
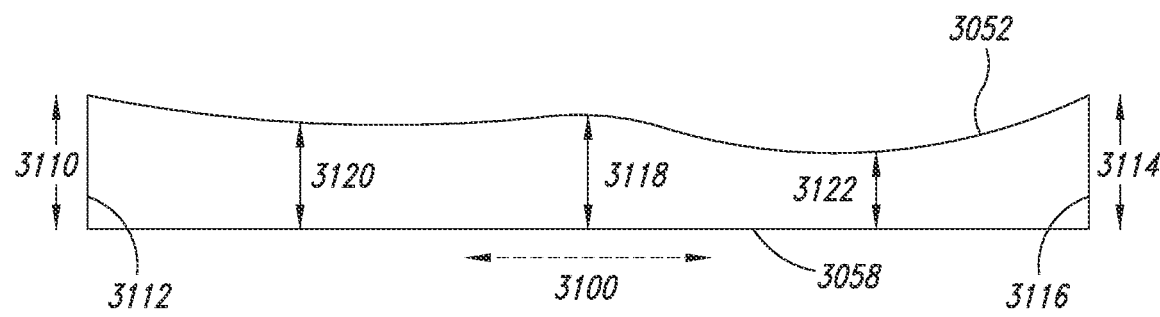
FIG. 44B illustrates a deviation in the cross-sectional view of the FIG. 44A.

For example, in embodiments, the present disclosure provides a tibial insert for an implantable knee prosthesis, where the medial side of the tibial insert has an average thickness (3120) on its anterior portion which is about 1, 2, 3, 4, 5, 6, 7, 8, 9, or, 10 mm greater than the average thickness (3122) on the posterior portion of the medial side. Such an embodiment is illustrated in FIG. 44B, where the thickness (3120) on the anterior side of the insert (14) is shown to be greater than the thickness (3122) on the posterior side of the insert (3014). This design would be used as described previously, but in patients experiencing abnormal anterior movement and instability.

As another example, in embodiments, the present disclosure provides a tibial insert for an implantable knee prosthesis, where the medial side of the tibial insert has an average thickness (3120) on its anterior portion which is about 1, 2, 3, 4, 5, 6, 7, 8, 9, or, 10 mm less than the average thickness (3122) on the posterior portion of the medial side.

This design would be used as described previously, but in patients experiencing abnormal posterior movement and instability.

As another example, in embodiments, the present disclosure provides a tibial insert for an implantable knee prosthesis, where the lateral side of the tibial insert has an average thickness (3120) on its anterior portion which is about 1, 2, 3, 4, 5, 6, 7, 8, 9, or, 10 mm greater than the average thickness (3122) on the posterior portion of the lateral side of the implant.

As yet another example, in embodiments, the present disclosure provides a tibial insert for an implantable knee prosthesis, where the lateral side of the tibial insert has an average thickness (3120) on its anterior portion which is about 1, 2, 3, 4, 5, 6, 7, 8, 9, or, 10 mm less than the average thickness (3122) on the posterior portion of the lateral side of the implant.

In another embodiment, the present disclosure provide a tibial insert for an implantable knee prosthesis, and a TKA system comprising a tibial insert, where the tibial insert is about 1, 2, 3, 4, 5, 6, 7, 8, 9, or, 10 mm thicker on the medial, lateral, anterior and/or posterior side of the implant. Thus, the present disclosure provides that each of the four quadrants of a tibial inset, i.e., the anterior and posterior portions of the medial side of the implant, and the anterior and posterior portions of the lateral side of the implant, may have a unique height. Abnormal movement, instability and subluxation of the TKA joint can occur in any direction and the embodiments described above can be combined to design a tibial insert capable of correcting the undesirable movement.

Figure 45:
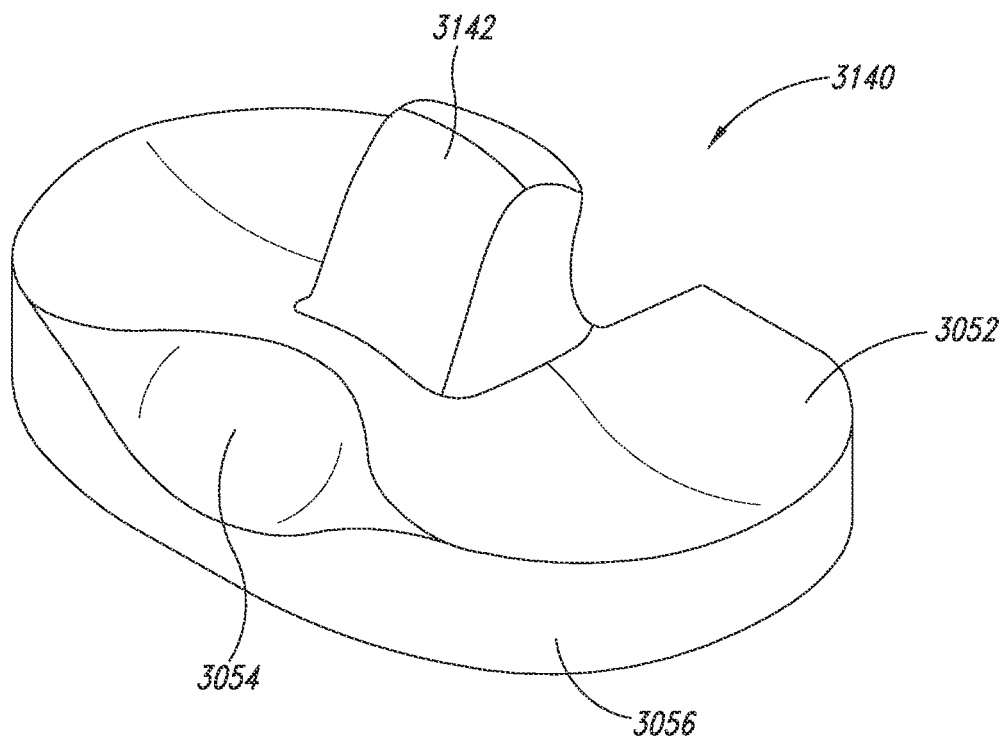
FIG. 45 illustrates a tibial insert with a horn that extends into a femoral component.
Figure 46:
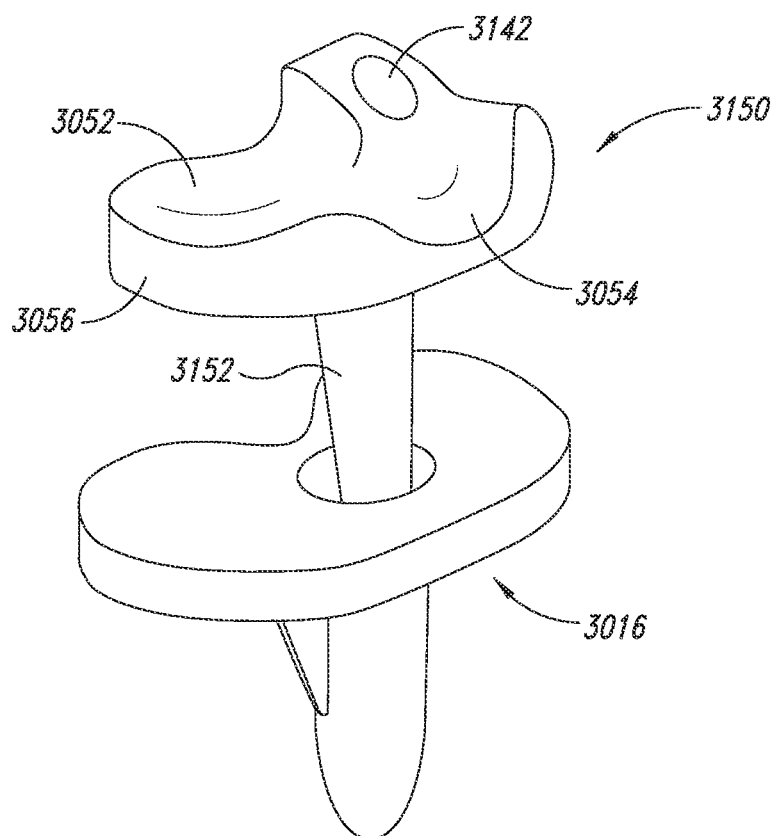
FIG. 46 illustrates a tibial insert with a spike that extends into a tibial component.

In one embodiment, the present disclosure provides a tibial insert that has been customized to the particular needs of a patient. These needs may be determined using the implanted sensors and associated analysis provided herein. Also, the tibial insert of the present disclosure may be formed into shapes other than that shown in FIG. 39. For example, as shown in FIG. 45, the tibial insert 3140 of the present disclosure may have a horn 3142 that can extend into a femoral component, where the tibial insert 3140 will also have a space 3054 to fit a patella implant, a top surface 3052 which articulates with the femoral component, and a side 3056. Alternatively, or additionally as illustrated in FIG. 46, the tibial insert 3150 may include a spike 3152 that may extend into a tibial component 3016, where the insert 3150 as shown in FIG. 46 also has a top surface 3052, a space 3054 for a patella implant, a side surface 3056 and a hole 3142.

While the descriptions and examples provided above are specific to TKA embodiments, as described previously, many other total joint arthroplasty (TJA) products also feature a polymeric insert. While the exact anatomy will differ for hip (THA), shoulder (TSA), elbow arthroplasty and ankle arthroplasty, the same principles apply: (1) the intelligent implant is utilized to identify the location, direction and extent of the abnormal movement, instability or subluxation, (2) a customized polymeric insert, which may also be referred to as a spacer or an articular spacer or intraarticular spacer, can be designed and created to minimize, resist and/or eliminate the observed direction of abnormal movement, instability or subluxation (3) the existing, ineffective polymeric insert is then surgically removed, and (4) the customized polymeric insert is implanted in its place to reduces, resist or eliminates the undesirable movement, instability and/or subluxation. Instituted early enough, these embodiments can prevent the development of irreparable damage to the TJA or the surrounding bone tissue to prolong the effective lifespan of the TJA and reduce the need for invasive, expensive, revision surgery.

The TJA polymeric insert according to the present disclosure may be made by any suitable technique. Exemplary techniques include 3-D printing, also known as additive manufacturing, or by molding, or by machining such as computer numerical control (CNC) machining.

The TJA polymeric insert of the present disclosure may be composed of any suitable material. Exemplary suitable materials include polyethylene such as high molecular weight polyethylene and ultra-high molecular weight polyethylene, or polyether ether ketone (PEEK).

The following are exemplary numbered embodiments of the present disclosure.

1. A tibial insert for an implantable knee prosthesis, comprising a tibial insert that is 1, 2, 3, 4, 5, 6, 7, 8, 9, or, 10 mm thicker on the medial side of the implant, as compared to the lateral side.

2. A tibial insert for an implantable knee prosthesis, comprising a tibial insert that is 1, 2, 3, 4, 5, 6, 7, 8, 9, or, 10 mm thicker on the lateral side of the implant, as compared to the medial side.

3. A tibial insert for an implantable knee prosthesis, comprising a tibial insert that is 1, 2, 3, 4, 5, 6, 7, 8, 9, or, 10 mm thicker on the anterior side of the implant, as compared to the posterior side.

4. A tibial insert for an implantable knee prosthesis, comprising a tibial insert that is 1, 2, 3, 4, 5, 6, 7, 8, 9, or, 10 mm thicker on the posterior side of the implant, as compared to the anterior side.

5. A tibial insert/articular spacer/for an implantable knee prosthesis, comprising a tibial insert that is 1, 2, 3, 4, 5, 6, 7, 8, 9, or, 10 mm thicker on the medial, lateral, anterior and/or posterior side of the implant.

6. The tibial insert according to any one of embodiments 1-5, wherein said tibial insert is composed of polyethylene, or polyetheretherketone (PEEK).

7. The tibial insert according to any one of embodiments 1-6 wherein said tibial insert is customized to a patient.

8. The tibial insert according to any one of embodiments 1 to 7 wherein said insert is manufactured by 3-D printing, or, by molding.

When the tibial insert is described as having a thickness on a medial, lateral, anterior and/or posterior side of the implant, this description is made in reference to when the insert is positioned adjacent to the implant within the patient, where the medial, lateral, anterior and/or posterior sides of the implant corresponds to the medial, lateral, anterior and/or posterior sides, respectively, of the insert that sits adjacent to the implant.

The following are exemplary numbered embodiments of the present disclosure.

9. A tibial insert for an implantable knee prosthesis, comprising a tibial insert that is 1-10 mm thicker, e.g., 1, 2, 3, 4, 5, 6, 7, 8, 9, or, 10 mm thicker on a medial side of the insert, as compared to a lateral side of the insert.

10. A tibial insert for an implantable knee prosthesis, comprising a tibial insert that is 1-10 mm thicker, e.g., 1, 2, 3, 4, 5, 6, 7, 8, 9, or, 10 mm thicker on a lateral side of the insert, as compared to a medial side of the insert.

11. A tibial insert for an implantable knee prosthesis, comprising a tibial insert that is 1-10 mm thicker, e.g., 1, 2, 3, 4, 5, 6, 7, 8, 9, or, 10 mm thicker on an anterior side of the insert, as compared to a posterior side of the insert.

12. A tibial insert for an implantable knee prosthesis, comprising a tibial insert that is 1-10 mm thicker, e.g., 1, 2, 3, 4, 5, 6, 7, 8, 9, or, 10 mm thicker on a posterior side of the insert, as compared to an anterior side of the insert.

13. A tibial insert or articular spacer for an implantable knee prosthesis, comprising a tibial insert that is 1-10 mm thicker, e.g., 1, 2, 3, 4, 5, 6, 7, 8, 9, or, 10 mm thicker on one of a medial, lateral, anterior and/or posterior side of the insert compared to a corresponding side of the insert, where medial and lateral are corresponding sides and anterior and posterior are corresponding sides.

14. The tibial insert according to any one of embodiments 9-13, wherein said tibial insert is composed of polyethylene, or polyetheretherketone (PEEK).

15. The tibial insert according to any one of embodiments 9-14 wherein said tibial insert is customized to a patient.

16. The tibial insert according to any one of embodiments 9-15 wherein said insert is manufactured by 3-D printing, or, by molding.

H. Clinical Solutions and Products

Through signal processing techniques of accelerometer and gyroscopic sensors, the absolute length of motion associated with core lower limb gait or upper limb movement, macroscopic instability, and microscopic instability can be calculated. In some instances, the ability to resolve differences and/or the presence of these abnormal motions is enhanced by looking at an individual's kinematic motion relative to (1) a population of other individuals stratified for common factors such as, but not limited to, age, sex, age, body mass index (BMI), bone density and/or (2) their own motion at known dates post joint implant.

With respect to macroscopic instability, it is understood that the absolute abnormal motion in the 5 mm to 10 cm range may be correlated with clinical data and further sub-ranges may be used to identify sub-clinical and clinically significant abnormal motion. Whereas sub-clinical abnormal motion may be watched for further change, clinically significant abnormal motion and instability will necessitate intervention to resolve patient symptoms. The intervention may take the form of the patient being provided with external support agents such as braces, custom shoes, and/or orthodics to provide the joint with additional stability. Pharmacologic therapy may be used to address symptoms of pain and inflammation of the joint. The clinician may also prescribe physical therapy in lieu of, or in concert with, these devices to further enhance surrounding musculoskeletal structures to alleviate the issue.

With respect to microscopic instability, it is understood that absolute abnormal motion in the 0.1 mm to 2 cm range may be correlated with clinical data and further sub-ranges may be used to identify sub-clinical and clinically significant abnormal motion. Whereas sub-clinical abnormal motion may be watched for further change, clinically significant abnormal motion and instability will necessitate intervention to resolve patient symptoms. As described above, the intervention may take the form of the patient receiving a custom polymer insert designed to re-establish proper motion of the joint and contact with the opposing articulating surface. As opposed to letting the joint degrade to a point that a complete revision is necessary, this solution presents the opportunity for earlier intervention with a less invasive procedure without the need to remove and replace the cemented (or uncemented) metal, prosthetic components. Resolving the microscopic instability may also take the form of techniques to stabilize the TJA metallic components implanted within the adjacent bone. One example of such a procedure involves placing the patient under sedation (conscious or full), and using 3 or more k-wires placed using imaging modalities such as bi-plane fluoroscopy, ultrasound, or other methods known to those skilled in the art through the skin, muscle, cortical bone, and cancellous bone until they contact the TJA stem and/or distal surface of the TJA component, the TJA component may be re-positioned into the proper plane within the bone. Electrodes may also be attached to the k-wires to insure neural structures are not negatively impacted during the k-wire insertion process. Once the k-wires have been manipulated to re-position the TJA component, fenestrated screws may be advanced over the k-wire, engaged in the bone for purchase and in contact with the TJA component (typically the stem containing the intelligent implant). In some cases, prior to insertion of the fenestrated screw, the proximal surface of the fenestrated screw can be attached to an external conduit capable of delivering a flowable material such as bone cement, biologic agents and growth factors (such as BM P), bone allograft material (autologous or xenographic), synthetic bone graft material, or other material to facilitate further stabilization of the TJA component and associated stem within the bone. It is also understood adjustments to both the polymer insert and the other TJA components may be needed to resolve the microinstability.

In one embodiment, the present disclosure provides a method for determining a condition, either a clinical condition or a subclinical condition, in a patient having an implanted artificial joint, comprising a) analyzing movement of an implanted artificial joint, and b) comparing said movement vs. previous/standardized norms. The method of the present disclosure also provides that the implanted artificial joint is referring to an implanted intelligent prosthesis as described herein, where the prosthesis is implanted in a bone (e.g., a tibia) adjacent to a joint (e.g., a knee joint). The movement of the implanted artificial joint may be analyzed by making measurements using a sensor coupled to the implanted artificial joint during a monitoring session wherein the artificial joint moves, where the measurements provide monitoring-session-data that may undergo processing to provide information about the movement, e.g., motion modes and optionally additional metric values. Optionally, the sensor may be an accelerometer, i.e., one or more accelerometers. Optionally, the movement of the implanted artificial joint is relative to the environment of the patient, e.g., the patient's residence, such as when the patient sits down, stands up, or walks across the floor. These movements may be analyzed based upon data obtained during one or more monitoring sessions, to thereby provide an initial description of the condition of the implant. Subsequent movements may then be analyzed based upon data obtained during one or more monitoring sessions, to thereby provide a subsequent description of the condition of the implant, where the subsequent description is compared to the initial description (also referred to as the previous/standardized norms) to see if there has been a change in the condition of the implant, and to provide information about the nature of that change. For example, the present disclosure provides a method for determining joint loosening in a patient having an implanted artificial joint, comprising a) analyzing movement of an implanted artificial joint, and b) comparing said movement vs. previous/standardized norms. For example, the present disclosure provides a method for determining loosening of an intelligent prosthesis that has been implanted in a patient, comprising a) analyzing movement of an implanted prosthesis, and b) comparing said movement vs. previous/standardized norms The following are exemplary embodiments of the present disclosure:

1) A method for identifying a clinical or subclinical condition associated with an implant in a patient, the method comprising:
    a) monitoring a first motion of the implant during a first monitoring session using a sensor which is directly coupled to the implant, to provide a first monitoring-session data for the first motion;
    b) monitoring a second motion of the implant during a second monitoring session using the sensor, to provide a second monitoring-session-data for the second motion; and
    c) comparing the first monitoring-session data or a product thereof to the second monitoring-session-data or a product thereof, to provide a comparison that is indicative of a clinical or subclinical condition associated with the implant.
2) The method of embodiment 1 wherein the clinical or subclinical condition is a loosening of the implant. The loosening may be motion of prosthesis within the surrounding bone or cement, e.g., the implant becomes separated from the host bone due, e.g., to periprosthetic lucency or periprosthetic osteolysis.
3) The method of embodiment 1 wherein the clinical or subclinical condition is a malalignment, which may refer to sub-optimal positioning of a prosthetic component, or a realignment of the implant, which may refer to a change over time in alignment of prosthetic component.
4) The method of embodiment 1 wherein the clinical or subclinical condition is deformation of the implant, where the deformation maybe a wearing down of the implant.
5) The method of embodiment 1 wherein the patient is asymptomatic for the condition, and the comparison of the first and second data or products thereof indicate that the condition has occurred between the first and second monitoring sessions.
6) The method of embodiment 1 wherein the patient is asymptomatic for loosening of the implant, and the comparison of the first and second data or products thereof indicate that the implant has loosened between the first and second monitoring sessions.
7) The method of embodiment 1 wherein the patient is asymptomatic for realignment of the implant, and comparison of the first and second data or products thereof indicate that the implant has changed alignment between the first and second monitoring sessions.
8) The method of embodiment 1 wherein the patient is asymptomatic for deformation of the implant, and comparison of the first and second data or products thereof indicate that the implant has deformed between the first and second monitoring sessions.
9) A method for treating a clinical or subclinical condition associated with an implant in a patient, comprising:
    a) identifying an implant in a patient, where the implant has a clinical or subclinical condition; and
    b) attaching corrective external bracing to patient to restore proper alignment and/or enhanced stability to the implant.
10) The method of embodiment 9 wherein the corrective external bracing has been specifically tailored to the patient and the subclinical condition.
11) A method for treating a clinical or subclinical condition associated with an implant in a patient, comprising:
    a) identifying an implant in a patient, where the implant has a clinical or subclinical condition; and
    b) contacting the implant with a fixation system to retard progression of the subclinical condition.
12) The method of embodiment 11 wherein the fixation system comprises hardware selected from a K-wire, pin, screw, plate and intramedullary device.
13) The method of embodiment 11 wherein a screw is located through a bone that holds the implant, where a terminus of the screw pushes against a surface of the implant to retard movement of the implant, where a screw is selected from one, two, three, four, five, six, seven, eight, nine, ten, eleven, twelve, thirteen, fourteen, fifteen, sixteen, seventeen, eighteen, nineteen and twenty screws.
14) The method of embodiment 11 wherein the fixation system comprises bone cement.
15) A method for treating a clinical or subclinical condition associated with an implant in a patient, comprising:
    a) identifying an implant in a patient, where the implant has a clinical or subclinical condition; and
    b) contacting the implant with a tamp, where the contacting changes a location of the implant within the patient.
16) The method of embodiment 15 wherein the subclinical condition is a realignment of the implant.
17) A method for treating a clinical or subclinical condition associated with an implant in a patient, comprising:
    a) identifying an implant in a patient, where the implant has a clinical or subclinical condition; and
    b) implanting an insert adjacent to a component of the implant, where the insert modifies forces acting on the component of the implant.
18) The method of embodiment 17 wherein the insert is a tibial insert.
19) The method of embodiment 17 wherein the insert is a tibial insert having (i) a lateral side with a minimum thickness and (ii) a medial side with a minimum thickness that is non-identical to the minimum thickness of the lateral side.
20) A method for treating a clinical or subclinical condition associated with an implant in a patient, comprising:
    a) identifying an implant in a patient, where the implant has a clinical or subclinical condition; and
    b) delivering a pro-osteointegration agent to a location surrounding the implant.
21) The method of embodiment 20 wherein the pro-osteointegration agent is selected from autologous bone graft, xenograph bone graft, synthetic bone graft, bone pastes, bone growth factor, and growth factor.
22) A method for treating a clinical or subclinical condition associated with an implant in a patient, comprising:
    a) identifying an implant in a patient, where the implant has a clinical or subclinical condition; and
    b) delivering an anti-bacterial agent to a location surrounding the implant.
23) The method of embodiment 22 wherein the anti-bacterial agent is compounded in a sustained release form.
24) The method of any of embodiments 1-23 wherein the implant is an intelligent implant.
25) The method of embodiments 1-23 wherein the implant is selected from a knee implant, a hip implant and a shoulder implant.
26) The method of any of embodiments 1-23 wherein the product of the monitoring-session data comprises a motion mode.

27) The method of any of embodiments 1-23 wherein the product of the monitoring-session data comprises a motion mode, and a status of the implant is determined from the motion mode.
28) The method of any of embodiments 1-23 wherein the product of the monitoring-session data comprises a motion mode, and a status of the patient is determined from the motion mode.
29) The method of embodiments 1-23 wherein the implant has been located within the patient for at least 10 weeks prior to the first monitoring session.
30) The method of embodiments 1-23 wherein the implant has changed alignment over a period of at least 2 weeks.
31) The method of embodiments 1-23 wherein the implant has loosened over a period of at least two weeks.
32) The method of embodiments 1-23 wherein the implant has deformed over a period of at least two weeks.
33) The method of embodiments 1-23 wherein the implant comprises a control circuit configured to cause the sensor to generate a sensor signal at a frequency that is related to a telemedicine code for the clinical or subclinical condition, and the sensor signal is generated at the frequency.
34) The method of embodiments 1-23 wherein the implant comprises a control circuit configured to cause the sensor to generate a sensor signal at a frequency that allows a doctor to qualify for payment under a telemedicine insurance code, and the sensor signal is generated at the frequency.
35) The method of embodiments 1-23 wherein the implant comprises a control circuit configured to cause the sensor to generate a sensor signal at a frequency that allows a doctor to qualify for full payment under a telemedicine insurance code, and the sensor signal is generated at the frequency.
36) The method of embodiments 1-23 further comprising generating a sensor signal that is related to the implant at a frequency that allows (i) a doctor to qualify for full payment available under a telemedicine insurance code, or (ii) a doctor to qualify for payment available under a telemedicine insurance code.
37) A method comprising:
  a) providing an intelligent prosthesis implanted in a bone adjacent to a joint of a patient, where an accelerometer is contained within the intelligent prosthesis, and where the accelerometer is positioned within the bone;
  b) moving the implanted intelligent prosthesis relative to an external environment wherein the patient is located, where the implanted intelligent prosthesis is moved during a first monitoring session;
  c) making first measurements with the accelerometer during the first monitoring session, where the first measurements provide first monitoring-session-data or a product thereof which identifies a status of the implanted intelligent prosthesis at a time of the first measurements.
38) The method of embodiment 37 wherein the accelerometer is a plurality of accelerometers.
39) The method of embodiment 37 wherein the accelerometer is selected from a 1-axis accelerometer, a 2-axis accelerometer and a 3-axis accelerometer.
40) The method of embodiment 37 wherein the accelerometer operates in a broadband mode.
41) The method of embodiment 37 wherein the bone is a tibia.
42) The method of embodiment 37 wherein the accelerometer is located in a tibial extension of the intelligent prosthesis.
43) The method of embodiment 37 wherein the implanted intelligent prosthesis is moved relative to the external environment without an impact force being applied to the patient or the intelligent prosthesis during the first monitoring session.
44) The method of embodiment 37 wherein the external environment comprises a residence of the patient.
45) The method of embodiment 37 wherein the external environment comprises an operating room wherein the intelligent prosthesis has been implanted into the patient, where the first monitoring session optionally occurs while the intelligent prosthesis is being implanted into the patient, and/or the first monitoring session optionally occurs after the intelligent prothesis has been implanted into the patient.
46) The method of embodiment 37 wherein the status of the implanted intelligent prosthesis is a characterization of the looseness of the implanted intelligent prosthesis within the bone.
47) The method of embodiment 37 wherein the status of the implanted intelligent prosthesis is a characterization of the alignment of the implanted intelligent prosthesis within the bone.
48) The method of embodiment 37 wherein the status of the implanted intelligent prosthesis is a characterization of the wear of the implanted intelligent prosthesis.
49) The method of embodiment 37 wherein the status of the implanted intelligent prosthesis is a characterization of bacterial infection of a region within the bone adjacent to the implanted intelligent prosthesis.
50) The method of embodiment 37 wherein the status of the implanted intelligent prosthesis indicates a subclinical condition.
51) The method of embodiment 37 wherein step b) is repeated after a waiting period, where the repeat of step b) comprises moving the implanted intelligent prosthesis relative to an external environment wherein the patient is located, where the implanted intelligent prosthesis is moved during a second monitoring session, and wherein second measurements are made with the accelerometer during the second monitoring session, where the second measurements provide second monitoring-session-data or a product thereof which identifies a status of the implanted of the implanted intelligent prosthesis at the time of the second measurements.
52) The method of embodiment 37 wherein step b) is repeated a plurality of times, the plurality of times separated from one another by identical or non-identical waiting periods, where the repeating of step b) comprises moving the implanted intelligent prosthesis relative to an external environment wherein the patient is located, where the implanted intelligent prosthesis is moved during a plurality of monitoring sessions, and wherein measurements are made with the accelerometer during each of the plurality of monitoring sessions, where the measurements provide a plurality of monitoring-session-data or products thereof, each of which monitoring-session data or product thereof identifies a status of the implanted intelligent prosthesis at the time of the measurements.
53) The method of embodiment 37 wherein step b) is repeated a plurality of times, the plurality of times separated from one another by identical or non-identical waiting periods, where the repeating of step b) comprises moving the implanted intelligent prosthesis relative to an external environment wherein the patient is located, where the implanted intelligent prosthesis is moved during a plurality of monitoring sessions, and wherein measurements are made with the accelerometer during each of the plurality of monitoring sessions, where the measurements provide a plurality of monitoring-session-data or products thereof, each of which identifies a status of the implanted of the implanted intelligent prosthesis at the time of the measurements; where the plurality of monitoring-session data taken together indicate a change in the status of the implanted intelligent prosthesis during the time when the plurality of monitoring sessions occurred.
54) The method of embodiment 53 wherein the change in the status is indicative of a healing of bone tissue surrounding the implanted intelligent prosthesis.
55) The method of embodiment 53 wherein the change in the status is indicative of an infection of the tissue surrounding the implanted prosthesis.
56) The method of embodiment 53 wherein the change in the status is indicative of a loosening of the implanted intelligent prothesis within the bone.
57) The method of embodiment 53 wherein the change in status is indicative of wear of the implanted intelligent prosthesis.
58) The method of embodiment 53 wherein the change in status is indicative of deformation of the implanted intelligent prosthesis.
59) The method of embodiment 53 wherein the change in status is indicative of malalignment of the implanted intelligent prosthesis.
60) The method of embodiment 53 wherein the change in status is indicative of a change in alignment of the implanted intelligent prosthesis.
61) The method of embodiment 53 wherein the change in status is indicative of bone erosion of the bone adjacent to the implanted intelligent prosthesis.
62) The method of embodiment 53 wherein the change in status is indicative of a subclinical condition.
63) The method of embodiment 53 wherein the change in status is indicative of a clinical condition.
64) The method of embodiment 53 wherein step b) is repeated 2 to 14 times over a 2 to 4 week period.
65) The method of embodiment 53 wherein step b) is repeated 2-30 times, e.g., 2 or 3 or 4 or 5 or 6 or 7 or 8 or 9 or 10 or 11 or 12 or 13 or 14 times over a 2 week period.
66) The method of embodiment 53 wherein step b) is repeated on a daily basis.
67) The method of any of embodiments 1-66 wherein the condition is a subclinical condition and the patient is asymptomatic for the condition of the implant.

Thus, in one embodiment the present disclosure provides a method that includes providing an intelligent prosthesis implanted in a bone adjacent to a joint of a patient (step a), where an accelerometer is contained within the intelligent prosthesis, and where the accelerometer is positioned within the bone. This implanted intelligent prosthesis is then moved relative to an external environment wherein the patient is located (step b), where the patient's residence or an operating room where the prosthesis has been implanted are two exemplary external environments, i.e., environments external to the patient. The movement may be, e.g., at least an inch, or at least 2, or 3, or 4, or 5, or 6, or 7, or 8, or 9, or 10, or 11, or 12 inches. The implanted intelligent prosthesis is moved during a first monitoring session. First measurements are made with the accelerometer during the first monitoring session (step c), where the first measurements provide first monitoring-session-data or a product thereof. This data or product thereof provides or identifies a status or condition of the implanted intelligent prosthesis at a time of the first measurements. For example, the status may be a certain looseness (or lack of looseness) in the prosthesis as it is seated in the bone of the patient. As another example, the status may be a certain alignment of the prosthesis within the bone of the patient. This information may provide a baseline status for the prosthesis within the patient, where subsequent monitoring sessions may be performed after a waiting period to obtain subsequent monitoring-session-data or a product thereof, which may provide or identify a status or condition of the implanted prosthesis at the time when the subsequent monitoring sessions are performed. The waiting period may be, e.g., 23 hours, so that the monitoring sessions are performed on a daily basis. However, the waiting period may be more or less than 23 hours. For example, a waiting period may be shorter than 23 hours, e.g., on the scale of 1-10 hours, or 11-22 hours, or may be longer than 23 hours, e.g., 2-14 days, or 1-4 weeks, or 1-6 months. Generally, in order to identify the condition while it is still a sub-clinical condition, the waiting period may be relatively short, e.g., the monitoring sessions may be performed on a daily basis.

Optionally, in the method, the method and/or the implant used in the method may be further described by one or more of: the accelerometer is a plurality of accelerometers; the accelerometer is selected from a 1-axis accelerometer, a 2-axis accelerometer and a 3-axis accelerometer; the accelerometer operates in a broadband mode; the bone is a tibia and the sensor is located within a tibial extension of the tibial intelligent prosthesis; the implanted intelligent prosthesis is moved relative to the external environment without an impact force being applied to either the patient or the intelligent prosthesis during the first monitoring session, in other words, nothing external to the patient causes a movement of the intelligent implant; the external environment comprises a residence of the patient; the external environment comprises an operating room wherein the intelligent prosthesis has been implanted into the patient; the status of the implanted intelligent prosthesis is a characterization of the looseness of the implanted intelligent prosthesis within the bone; the status of the implanted intelligent prosthesis is a characterization of the alignment of the implanted intelligent prosthesis within the bone; the status of the implanted intelligent prosthesis is a characterization of the wear of the implanted intelligent prosthesis; the status of the implanted intelligent prosthesis is a characterization of bacterial infection of a region within the bone adjacent to the implanted intelligent prosthesis; the status of the implanted intelligent prosthesis indicates a subclinical condition.

As mentioned, step b) may repeated after a waiting period, where the repeat of step b) comprises moving the implanted intelligent prosthesis relative to an external environment wherein the patient is located, where the implanted intelligent prosthesis is moved during a second monitoring session, and wherein second measurements are made with the accelerometer during the second monitoring session, where the second measurements provide second monitoring-session-data or a product thereof which identifies a status of the implanted of the implanted intelligent prosthesis at the time of the second measurements.

As mentioned, step b) may be repeated a plurality of times, the plurality of times separated from one another by identical or non-identical waiting periods, where the repeating of step b) comprises moving the implanted intelligent prosthesis relative to an external environment wherein the patient is located, where the implanted intelligent prosthesis is moved during a plurality of monitoring sessions, and wherein measurements are made with the accelerometer during each of the plurality of monitoring sessions, where the measurements provide a plurality of monitoring-session-data or products thereof, each of which identifies a status of the implanted of the implanted intelligent prosthesis at the time of the measurements.

As mentioned, step b) may be repeated a plurality of times, the plurality of times separated from one another by identical or non-identical waiting periods, where the repeating of step b) comprises moving the implanted intelligent prosthesis relative to an external environment wherein the patient is located, where the implanted intelligent prosthesis is moved during a plurality of monitoring sessions, and wherein measurements are made with the accelerometer during each of the plurality of monitoring sessions, where the measurements provide a plurality of monitoring-session-data or products thereof, each of which identifies a status of the implanted of the implanted intelligent prosthesis at the time of the measurements; wherein the plurality is optionally selected from 2 to 20 monitoring sessions, and where the plurality of monitoring-session data taken together indicate a change in the status of the implanted intelligent prosthesis during the time when the plurality of monitoring sessions occurred.

The foregoing methods, e.g., methods of embodiments 1-67, may identify a problem with an intelligent implanted prosthesis, e.g., a clinical or subclinical condition such as loosening of the implant, change in alignment of the implant and/or deformation of the implant.

In one embodiment of each of the foregoing methods, e.g., the methods of embodiments 1-67, the implant is an implantable medical device, the device comprising: at least one sensor configured to generate a sensor signal; and a control circuit configured to cause the at least one sensor to generate the sensor signal at a frequency that is related to a telemedicine code. The telemedicine code may indicate the clinical or subclinical condition associated with the implanted medical device in the patient.

In one embodiment of each of the foregoing methods, e.g., the methods of embodiments 1-67, the implant is an implantable medical device, the device comprising at least one sensor configured to generate a sensor signal; and a control circuit configured to cause the at least one sensor to generate the sensor signal at a frequency that allows a doctor to qualify for payment under a telemedicine insurance code.

In one embodiment in each of the foregoing methods, e.g., the methods of embodiments 1-67, the implant is an implantable medical device, the device comprising at least one sensor configured to generate a sensor signal; and a control circuit configured to cause the at least one sensor to generate the sensor signal at a frequency that allows a doctor to qualify for full payment under a telemedicine insurance code.

The foregoing methods, e.g., the methods of embodiments 1-67, may identify a problem with an intelligent implanted prosthesis, e.g., a clinical or subclinical condition such as loosening of the implant, change in alignment of the implant and/or deformation of the implant. In addition to identifying the problem, each method may include generation of a telemedicine code as descried herein. For example, in one embodiment of each of the foregoing methods, the method further comprises generating a sensor signal that is related to the implanted medical device at a frequency that allows a doctor to qualify for full payment available under a telemedicine insurance code. As another example, in one embodiment of each of the foregoing methods, the method further comprises generating a sensor signal that is related to the implanted medical device at a frequency that allows a doctor to qualify for full payment available under a telemedicine insurance code.

For example, the present disclosure provides a method for identifying a clinical or subclinical condition associated with an implant in a patient, the method comprising: monitoring a first motion of the implant during a first monitoring session using a sensor which is directly coupled to the implant, to provide a first data description of the first motion; monitoring a second motion of the implant during a second monitoring session using the sensor, to provide a second data description of the second motion; comparing the first and second data descriptions to identify a clinical or subclinical condition associated with the implant; and generating a sensor signal that is related to the implant at a frequency that allows a doctor to qualify for full payment available under a telemedicine insurance code.

The foregoing methods, e.g., the methods of embodiments 1-67 may identify a problem with an intelligent implanted prosthesis, e.g., a clinical or subclinical condition such as loosening of the implant, change in alignment of the implant and/or deformation of the implant. The foregoing methods make use of an intelligent implant having a sensor, where a sensor refers to one or more sensors, and likewise refers to at least one sensor. The intelligent implant may have additional features as disclosed herein.

For example, the intelligent implant may further comprise a control circuit configured to cause the sensor, or another sensor which is a component of the implant, to generate a sensor signal at a frequency that allows a doctor to qualify for payment under a telemedicine insurance code.

As another example, the intelligent implant may be described as comprising a housing; and an implanted circuit disposed in the housing, where the circuit is configured to (i) generate at least one first signal representative of a movement; (ii) determine whether the signal meets at least one first criterion; and (iii) send the signal to a remote location in response to determining that the signal meets the at least one first criterion, as described herein. The intelligent implant or a component thereon, e.g., the implanted circuit disposed in the housing of the intelligent implant, may be further described by one or more of the following: the housing includes a tibial extension; the movement includes a movement of the patient; the movement includes the patient walking; the at least one first criterion includes that the signal represents the movement for at least a threshold duration; the at least one first criterion includes that the signal represents the movement for at least a threshold number of events; the movement includes the patient walking, and the at least one first criterion includes that the signal represents the movement for at least a threshold number of steps taken by the patient; the implanted circuit is further configured to determine whether the movement meets at least one second criterion before determining whether the signal meets the at least one first criterion, and to determine whether the signal meets the at least one first criterion in response to determining that the movement meets the second criterion, particularly wherein the at least one second criterion includes that the movement is the patient walking; the implanted circuit is further configured to determine, in response to the signal, whether the movement meets at least one second criterion before determining whether the signal meets the at least one first criterion, and to determine whether the signal meets the at least one first criterion in response to determining that the movement meets the second criterion; the implanted circuit is further configured to determine, in response to the signal, whether the movement meets at least one second criterion, and to cease generating the signal in response to determining that the movement does not meet the at least one second criterion; the implanted circuit is further configured to determine, in response to the signal, whether the movement meets at least one second criterion, and to cease generating the signal before determining whether the signal meets the at least one first criterion in response to determining that the movement does not meet the at least one second criterion; the implanted circuit is further configured to store the signal in response to determining that the signal meets the at least one first criterion, and to send the stored signal to the remote location; the implanted circuit is further configured to encrypt the signal before sending the signal to the remote location; the implanted circuit is further configured to encode the signal before sending the signal to the remote location; the implanted circuit is further configured to generate a message that includes the signal; and wherein sending the signal includes sending the message; and the implanted circuit is further configured to generate a data packet that includes the signal; and wherein sending the message includes sending the data packet to the remote location.

In additional embodiments, the present disclosure provides a method comprising generating a sensor signal in response to a movement of a patient in which an intelligent prosthesis is implanted. The following are exemplary of such methods of the present disclosure:

A method comprising: generating a sensor signal in response to a movement of a patient in which an intelligent prosthesis is implanted; and transmitting the sensor signal to a remote location, wherein the sensor signal identifies a clinical or subclinical condition associated with the implanted intelligent prosthesis, particularly where the patient is asymptomatic for the condition.

A method comprising: generating a sensor signal in response to a movement of a patient in which an intelligent prosthesis is implanted; sampling the sensor signal; and transmitting the samples to a remote location, wherein the sensor signal identifies a clinical or subclinical condition associated with the implanted intelligent prosthesis, particularly where the patient is asymptomatic for the condition.

A method comprising: generating a sensor signal in response to a movement of a patient in which an intelligent prosthesis is implanted; determining whether the sensor signal represents a qualified event; and transmitting the signal to a remote location in response to determining that the sensor signal represents a qualified event, wherein the sensor signal identifies a clinical or subclinical condition associated with the implanted intelligent prosthesis, particularly where the patient is asymptomatic for the condition.

A method comprising: generating a sensor signal in response to a movement of a patient in which an intelligent prosthesis is implanted; receiving a polling signal from a remote location; and transmitting the sensor signal to the remote location in response to the polling signal, wherein the sensor signal identifies a clinical or subclinical condition associated with the implanted intelligent prosthesis, particularly where the patient is asymptomatic for the condition.

A method comprising: generating a sensor signal in response to a movement of a patient in which an intelligent prosthesis is implanted; generating a message that includes the sensor signal or data representative of the sensor signal; and transmitting the message to a remote location, wherein the sensor signal identifies a clinical or subclinical condition associated with the implanted intelligent prosthesis, particularly where the patient is asymptomatic for the condition.

A method comprising: generating a sensor signal in response to a movement of a patient in which an intelligent prosthesis is implanted; generating a data packet that includes the sensor signal or data representative of the sensor signal; and transmitting the data packet to a remote location, wherein the sensor signal identifies a clinical or subclinical condition associated with the implanted intelligent prosthesis, particularly where the patient is asymptomatic for the condition.

A method comprising: generating a sensor signal in response to a movement of a patient in which an intelligent prosthesis is implanted; encrypting at least a portion of the sensor signal or data representative of the sensor signal; and transmitting the encrypted sensor signal to a remote location, wherein the sensor signal identifies a clinical or subclinical condition associated with the implanted intelligent prosthesis, particularly where the patient is asymptomatic for the condition.

A method comprising: generating a sensor signal in response to a movement of a patient in which an intelligent prosthesis is implanted; encoding at least a portion of the sensor signal or data representative of the sensor signal; and transmitting the encoded sensor signal to a remote location, wherein the sensor signal identifies a clinical or subclinical condition associated with the implanted intelligent prosthesis, particularly where the patient is asymptomatic for the condition.

A method comprising: generating a sensor signal in response to a movement of a patient in which an intelligent prosthesis is implanted; transmitting the sensor signal to a remote location; and entering an implantable circuit associated with the prosthesis into a lower-power mode after transmitting the sensor signal, wherein the sensor signal identifies a clinical or subclinical condition associated with the implanted intelligent prosthesis, particularly where the patient is asymptomatic for the condition.

In additional embodiments, the present disclosure provides a method comprising generating a sensor signal and/or receiving a sensor signal from an implanted intelligent prosthesis. The following are exemplary of such methods of the present disclosure, where the sensor signal may be within a data packet.

A method comprising: generating a first sensor signal in response to a movement of a patient in which an intelligent prosthesis is implanted; transmitting the first sensor signal to a remote location; entering at least one component of an implantable circuit associated with the prosthesis into a lower-power mode after transmitting the sensor signal; and generating a second sensor signal in response to a movement of the patient after an elapse of a low-power-mode time for which the implantable circuit is configured, wherein the sensor signal identifies a clinical or subclinical condition associated with the implanted intelligent prosthesis, particularly where the patient is asymptomatic for the condition.

A method comprising: receiving a sensor signal from an intelligent prosthesis implanted in a patient; and transmitting the received sensor signal to a destination, wherein the sensor signal identifies a clinical or subclinical condition associated with the implanted intelligent prosthesis, particularly where the patient is asymptomatic for the condition.

A method comprising: sending an inquiry to an intelligent prosthesis implanted in a patient; receiving a sensor signal from the intelligent prosthesis after sending the inquiry; and transmitting the received sensor signal to a destination, wherein the sensor signal identifies a clinical or subclinical condition associated with the implanted intelligent prosthesis, particularly where the patient is asymptomatic for the condition.

A method comprising: receiving a sensor signal and at least one identifier from an intelligent prosthesis implanted in a patient; determining whether the identifier is correct; and transmitting the received sensor signal to a destination in response to determining that the identifier is correct, wherein the sensor signal identifies a clinical or subclinical condition associated with the implanted intelligent prosthesis, particularly where the patient is asymptomatic for the condition.

A method comprising: receiving a message including a sensor signal from an intelligent prosthesis implanted in a patient; decrypting at least a portion of the message; and transmitting the decrypted message to a destination, wherein the sensor signal identifies a clinical or subclinical condition associated with the implanted intelligent prosthesis, particularly where the patient is asymptomatic for the condition.

A method comprising: receiving a message including a sensor signal from an intelligent prosthesis implanted in a patient; decoding at least a portion of the message; and transmitting the decoded message to a destination, wherein the sensor signal identifies a clinical or subclinical condition associated with the implanted intelligent prosthesis, particularly where the patient is asymptomatic for the condition.

A method comprising: receiving a message including a sensor signal from an intelligent prosthesis implanted in a patient; encoding at least a portion of the message; and transmitting the encoded message to a destination, wherein the sensor signal identifies a clinical or subclinical condition associated with the implanted intelligent prosthesis, particularly where the patient is asymptomatic for the condition.

A method comprising: receiving a message including a sensor signal from an intelligent prosthesis implanted in a patient; encrypting at least a portion of the message; and transmitting the encrypted message to a destination, wherein the sensor signal identifies a clinical or subclinical condition associated with the implanted intelligent prosthesis, particularly where the patient is asymptomatic for the condition.

A method comprising: receiving a data packet including a sensor signal from an intelligent prosthesis implanted in a patient; decrypting at least a portion of the data packet; and transmitting the decrypted data packet to a destination, wherein the sensor signal identifies a clinical or subclinical condition associated with the implanted intelligent prosthesis, particularly where the patient is asymptomatic for the condition.

A method comprising: receiving a data packet including a sensor signal from an intelligent prosthesis implanted in a patient; decoding at least a portion of the data packet; and transmitting the decoded data packet to a destination, wherein the sensor signal identifies a clinical or subclinical condition associated with the implanted intelligent prosthesis, particularly where the patient is asymptomatic for the condition.

A method comprising: receiving a data packet including a sensor signal from an intelligent prosthesis implanted in a patient; encoding at least a portion of the data packet; and transmitting the encoded data packet to a destination, wherein the sensor signal identifies a clinical or subclinical condition associated with the implanted intelligent prosthesis, particularly where the patient is asymptomatic for the condition.

A method comprising: receiving a data packet including a sensor signal from an intelligent prosthesis implanted in a subject; encrypting at least a portion of the data packet; and transmitting the encrypted data packet to a destination, wherein the sensor signal identifies a clinical or subclinical condition associated with the implanted intelligent prosthesis, particularly where the patient is asymptomatic for the condition.

A method comprising: receiving a sensor signal from an intelligent prosthesis implanted in a patient; decrypting at least a portion of the sensor signal; and transmitting the decrypted sensor signal to a destination, wherein the sensor signal identifies a clinical or subclinical condition associated with the implanted intelligent prosthesis, particularly where the patient is asymptomatic for the condition.

A method comprising: receiving a sensor signal from an intelligent prosthesis implanted in a patient; decoding at least a portion of the sensor signal; and transmitting the decoded sensor signal to a destination, wherein the sensor signal identifies a clinical or subclinical condition associated with the implanted intelligent prosthesis, particularly where the patient is asymptomatic for the condition.

A method comprising receiving a sensor signal from an intelligent prosthesis implanted in a patient; encoding at least a portion of the sensor signal; and transmitting the encoded sensor signal to a destination, wherein the sensor signal identifies a clinical or subclinical condition associated with the implanted intelligent prosthesis, particularly where the patient is asymptomatic for the condition.

A method comprising: receiving a sensor signal from an intelligent prosthesis implanted in a patient; encrypting at least a portion of the sensor signal; and transmitting the encrypted sensor signal to a destination, wherein the sensor signal identifies a clinical or subclinical condition associated with the implanted intelligent prosthesis, particularly where the patient is asymptomatic for the condition.

In addition, the present disclosure provides a method for identifying a clinical or subclinical condition associated with an implant in a patient, such as a looseness of the implant, or a malalignment of the implant. The method includes monitoring a first motion of the implant during a first monitoring session using a sensor which is directly coupled to the implant. The first motion may be, e.g., a movement of the implant relative to the environment within which the patient having the implant is disposed. The monitoring provides a first monitoring-session data or a product thereof, for the first motion. The monitoring is carried out by a monitoring-session-data collection, analysis, and status-reporting system implemented as a component of one or more computer systems, each computer system having one or more processors, one or more memories, one or more network connections, and access to one or more mass-storage devices, as described herein. As also described herein, the monitoring may include: receiving monitoring-session-data, optionally including acceleration data generated by one or more sensors within or proximal to a prosthesis attached to or implanted within a patient, from an external monitoring-session-data source; storing the received monitoring-session-data in one or more of the one or more memories and one or more mass-storage devices; determining component trajectories representing motion modes, and optionally representing additional metric values, from the monitoring session data; determining at least one of a prosthesis status and a patient status from the motion modes and optionally from the additional metric value; distributing the determined prosthesis status and/or patient status to target computer systems through the network connections; and when indicated by the determined prosthesis status and/or patient status, distributing one or more alarms and events to target computer systems through the network connections.

The following Examples are offered by way of illustration and not by way of limitation.

EXAMPLES

Example 1

Surgical Method for Replacement of a Tibial Insert

Once a decision to change the polymeric insert is made, the patient is prepared for surgery. This includes not only medical clearance but evaluation of the kinematic data to determine the direction, amount and pattern of abnormal motion and instability. The data obtained from the patient's intelligent implant will then be used to determine the specific characteristics (as described previously) of the polyethylene insert so as to resist or eliminate the abnormal motion or instability observed in the patient. This would include polymeric inserts of increased size and constraint and/or offset designs to adjust coronal alignment as determined by the intelligent implant joint movement analysis.

For example, in a TKA patient, a new incision is made through the previous incision site and dissection is continued to the level of the extensor mechanism. The arthrotomy is performed and the proximal tibia is exposed. Maneuvers are then performed to place the tibia in a forward position so as to permit exchange of the tibial tray. The existing, ineffective, tibial insert is removed, and a customized tibial insert is implanted in its place. Trial reductions are then performed, and best fit is determined. The selection of the correct tibial insert is made not only by the surgeon based upon the clinical feel and stability of the TKA containing the new tibial insert, but is also informed by data obtained from kinematic analysis performed intraoperatively by the intelligent TKA. Several different tibial inserts might be tested before determining which one best eliminates the abnormal movement and/or instability. The new, preferred tibial insert is then placed into the tibial tray, standard closure is performed, and post-operative rehabilitation is initiated.

Example 2

Surgical Method for Realignment of a Misaligned Implanted Artificial Joint Using a Filler Traditional methods of TJA malalignment involved either prosthesis retention until failure or either partial or complete revision. These revisions result in not only a major invasive procedure that is not only costly, but can also lead to increased complications such as bone loss, decreased performance, infection and poor results compared to a primary Total Joint Replacement.

Intraoperative malalignment of a TJA implant can be achieved with prosthesis retention through an intraoperative osteotomy procedure. Joint kinematics obtained from the intelligent TJA are reviewed preoperatively and a decision is made on the direction and degree of prosthesis adjustment required. The adjustment begins by making a small osteotomy around the medial and/or the lateral aspect of the misaligned TJA component (typically the stem of the prosthesis). A series of tamps are then inserted via the osteotomy and into contact with the TJA component. The tamps are carefully advanced in order to adjust the prosthesis alignment to the desired "new" location and intraoperative kinematics are performed to confirm placement and ensure adequate correction. A small boney window is then made, and either liquid bone cement, bone allograft material (autologous or xenographic), synthetic bone graft material, or other filler material is then injected into the space between the implant and the bone to solidify the prosthesis in its new position. Standard closure and post-operative rehabilitation is then initiated.

The devices, methods, systems etc. of the present disclosure have been described broadly and generically herein. Each of the narrower species and subgeneric groupings falling within the generic disclosure also form part of the present disclosure. This includes the generic description of the devices, methods, systems etc. of the present disclosure with a proviso or negative limitation removing any subject matter from the genus, regardless of whether or not the excised material is specifically recited herein.

The following are some exemplary embodiments of the present disclosure, numbered for convenience:

1. A tibial insert for a implantable knee prosthesis, comprising a tibial insert that is 1, 2, 3, 4, 5, 6, 7, 8, 9, or, 10 mm thicker on the medial side of the implant, as compared to the lateral side.

2. A tibial insert for a implantable knee prosthesis, comprising a tibial insert that is 1, 2, 3, 4, 5, 6, 7, 8, 9, or, 10 mm thicker on the lateral side of the implant, as compared to the medial side.

3. A tibial insert for a implantable knee prosthesis, comprising a tibial insert that is 1, 2, 3, 4, 5, 6, 7, 8, 9, or, 10 mm thicker on the anterior side of the implant, as compared to the posterior side.

4. A tibial insert for a implantable knee prosthesis, comprising a tibial insert that is 1, 2, 3, 4, 5, 6, 7, 8, 9, or, 10 mm thicker on the posterior side of the implant, as compared to the anterior side.

5. A tibial insert/articular spacer/for a implantable knee prosthesis, comprising a tibial insert that is 1, 2, 3, 4, 5, 6, 7, 8, 9, or, 10 mm thicker on the medial, lateral, anterior and/or posterior side of the implant.

6. The tibial insert according to any one of embodiments 1-5, wherein said tibial insert is composed of polyethylene, or polyetheretherketone (PEEK).

7. The tibial insert according to any one of embodiments 1-6 wherein said tibial insert is customized to a patient.

8. The tibial insert according to any one of embodiments 1 to 7 wherein said insert is manufactured by 3-D printing, or, by molding.

In the embodiments 1-8, which are directed to a tibial insert for an implantable knee prosthesis, the insert will have a medial side, a lateral side, an anterior side and a posterior side. The embodiments provide for asymmetry in the thickness of the tibial insert, such that the insert is thicker at a location on one side of the insert than it is at an equivalent location at the opposing side of the insert, e.g., the center of the medial side of the insert as compared to the center of the lateral side of the insert, or the center of the anterior side of the insert as compared to the center of the posterior side of the insert. This asymmetry can, e.g., compensate for malalignment in positioning of the implanted knee prosthesis, such that forces are better balanced.

9. An implantable medical device, comprising:
   a circuit configured to be fixedly attached to an implantable prosthetic device;
   a power component; and
   a device configured to uncouple the circuit from the power component.

10. An implantable medical device, comprising:
a circuit configured to be fixedly attached to an implantable prosthetic device;
a battery; and
a fuse coupled between the circuit and the battery.

11. A method, comprising electrically opening a fuse that is disposed between a circuit and a battery, at least the fuse and the circuit being disposed on an implanted prosthetic device.

12. An implantable medical device, comprising:
at least one sensor configured to generate a sensor signal; and
a control circuit configured to cause the at least one sensor to generate the sensor signal at a frequency that is related to a telemedicine code.

13. An implantable medical device, comprising:
at least one sensor configured to generate a sensor signal; and
a control circuit configured to cause the at least one sensor to generate the sensor signal at a frequency that allows a doctor to qualify for payment under a telemedicine insurance code.

14. An implantable medical device, comprising:
at least one sensor configured to generate a sensor signal; and
a control circuit configured to cause the at least one sensor to generate the sensor signal at a frequency that allows a doctor to qualify for full payment under a telemedicine insurance code.

15. A method, comprising, generating a sensor signal that is related to an implanted medical device at a frequency that allows a doctor to qualify for payment available under a telemedicine insurance code.

16. A method, comprising, generating a sensor signal that is related to an implanted medical device at a frequency that allows a doctor to qualify for full payment available under a telemedicine insurance code.

17. An implantable prosthesis, comprising:
a housing; and
an implantable circuit disposed in the housing and configured
to generate at least one first signal representative of a movement;
to determine whether the signal meets at least one first criterion; and
to send the signal to a remote location in response to determining that the signal meets the at least one first criterion.

18. A base station, comprising:
a housing; and
a base-station circuit disposed in the housing and configured
to receive, from an implantable prosthesis, at least first signal representative of a movement;
to send the at least one first signal to a destination;
to receive at least one second signal from a source; and
to send the at least one second signal to the implantable prosthesis.

19. A method, comprising opening a fuse disposed on an implantable prosthesis between a power source and an implantable circuit in response to a current through the fuse exceeding an overcurrent threshold.

20. A method, comprising opening a fuse disposed on an implantable prosthesis between a power source and an implantable circuit in response to a current through the fuse exceeding an overcurrent threshold for at least a threshold time.

21. A method, comprising opening a fuse disposed on an implantable prosthesis between a power source and an implantable circuit in response to a voltage across the fuse exceeding an overvoltage threshold.

22. A method, comprising opening a fuse disposed on an implantable prosthesis between a power source and an implantable circuit in response to a voltage across the fuse exceeding an overvoltage threshold for at least a threshold time.

23. A method, comprising opening a fuse disposed on an implantable prosthesis between a power source and an implantable circuit in response to a temperature exceeds an overtemperature threshold.

24. A method, comprising opening a fuse disposed on an implantable prosthesis between a power source and an implantable circuit in response to a temperature exceeding an overtemperature threshold for at least a threshold length of time.

25. A method, comprising:
generating a sensor signal in response to a movement of a subject in which a prosthesis is implanted; and
transmitting the sensor signal to a remote location.

26. A method, comprising:
generating a sensor signal in response to a movement of a subject in which a prosthesis is implanted;
sampling the sensor signal; and
transmitting the samples to a remote location.

27. A method, comprising:
generating a sensor signal in response to a movement of a subject in which a prosthesis is implanted;
determining whether the sensor signal represents a qualified event; and
transmitting the signal to a remote location in response to determining that the sensor signal represents a qualified event.

28. A method, comprising:
generating a sensor signal in response to a movement of a subject in which a prosthesis is implanted;
receiving a polling signal from a remote location; and
transmitting the sensor signal to the remote location in response to the polling signal.

29. A method, comprising:
generating a sensor signal in response to a movement of a subject in which a prosthesis is implanted;
generating a message that includes the sensor signal or data representative of the sensor signal; and
transmitting the message to a remote location.

30. A method, comprising:
generating a sensor signal in response to a movement of a subject in which a prosthesis is implanted;
generating a data packet that includes the sensor signal or data representative of the sensor signal; and
transmitting the data packet to a remote location.

31. A method, comprising:
generating a sensor signal in response to a movement of a subject in which a prosthesis is implanted;
encrypting at least a portion of the sensor signal or data representative of the sensor signal; and
transmitting the encrypted sensor signal to a remote location.

32. A method, comprising:
generating a sensor signal in response to a movement of a subject in which a prosthesis is implanted;
encoding at least a portion of the sensor signal or data representative of the sensor signal; and
transmitting the encoded sensor signal to a remote location.

33. A method, comprising:
generating a sensor signal in response to a movement of a subject in which a prosthesis is implanted;
transmitting the sensor signal to a remote location; and
entering an implantable circuit associated with the prosthesis into a lower-power mode after transmitting the sensor signal.

34. A method, comprising:
generating a first sensor signal in response to a movement of a subject in which a prosthesis is implanted;
transmitting the first sensor signal to a remote location;
entering at least one component of an implantable circuit associated with the prosthesis into a lower-power mode after transmitting the sensor signal; and
generating a second sensor signal in response to a movement of the subject after an elapse of a low-power-mode time for which the implantable circuit is configured.

35. A method, comprising:
receiving a sensor signal from a prosthesis implanted in a subject; and
transmitting the received sensor signal to a destination.

36. A method, comprising:
sending an inquiry to a prosthesis implanted in a subject
receiving a sensor signal from a prosthesis after sending the inquiry; and
transmitting the received sensor signal to a destination.

37. A method, comprising:
receiving a sensor signal and at least one identifier from a prosthesis implanted in a subject;
determining whether the identifier is correct; and
transmitting the received sensor signal to a destination in response to determining that the identifier is correct.

38. A method, comprising:
receiving a message including a sensor signal from a prosthesis implanted in a subject;
decrypting at least a portion of the message; and
transmitting the decrypted message to a destination.

39. A method, comprising:
receiving a message including a sensor signal from a prosthesis implanted in a subject;
decoding at least a portion of the message; and
transmitting the decoded message to a destination.

40. A method, comprising:
receiving a message including a sensor signal from a prosthesis implanted in a subject;
encoding at least a portion of the message; and
transmitting the encoded message to a destination.

41. A method, comprising:
receiving a message including a sensor signal from a prosthesis implanted in a subject;
encrypting at least a portion of the message; and
transmitting the encrypted message to a destination.

42. A method, comprising:
receiving a data packet including a sensor signal from a prosthesis implanted in a subject;
decrypting at least a portion of the data packet; and
transmitting the decrypted data packet to a destination.

43. A method, comprising:
receiving a data packet including a sensor signal from a prosthesis implanted in a subject;
decoding at least a portion of the data packet; and
transmitting the decoded data packet to a destination.

44. A method, comprising:
receiving a data packet including a sensor signal from a prosthesis implanted in a subject;
encoding at least a portion of the data packet; and
transmitting the encoded data packet to a destination.

45. A method, comprising:
receiving a data packet including a sensor signal from a prosthesis implanted in a subject;
encrypting at least a portion of the data packet; and
transmitting the encrypted data packet to a destination.

46. A method, comprising:
receiving a sensor signal from a prosthesis implanted in a subject;
decrypting at least a portion of the sensor signal; and
transmitting the decrypted sensor signal to a destination.

47. A method, comprising:
receiving a sensor signal from a prosthesis implanted in a subject;
decoding at least a portion of the sensor signal; and
transmitting the decoded sensor signal to a destination.

48. A method, comprising:
receiving a sensor signal from a prosthesis implanted in a subject;
encoding at least a portion of the sensor signal; and
transmitting the encoded sensor signal to a destination.

49. A method, comprising:
receiving a sensor signal from a prosthesis implanted in a subject;
encrypting at least a portion of the sensor signal; and
transmitting the encrypted sensor signal to a destination.

50. An implantable circuit for an implantable prosthesis.

51. An implantable prosthesis including an implantable circuit.

52. An implantable prosthesis including a fuse.

53. A base station for communication with an implantable prosthesis.

54. A monitoring-session-data collection, analysis, and status-reporting system implemented as a component of one or more computer systems, each computer system having one or more processors, one or more memories, one or more network connections, and access to one or more mass-storage devices, the one or more the monitoring-session-data collection, data-analysis, and status-reporting system comprising:
a monitoring-session-data-receiving component that receives monitoring-session-data, including acceleration data generated by sensors within or proximal to a prosthesis attached or implanted within a patient, from an external monitoring-session-data source and that stores the received monitoring-session-data in one or more of the one or more memories and one or more mass-storage devices;
a monitoring-session-data-processing component that prepares the monitoring-session-data for processing, determines component trajectories representing motion modes and additional metric values from the monitoring-session-data; and
a monitoring-session-data-analysis component that determines a prosthesis status and a patient status from the motion modes and additional metric values, distributes the determined prosthesis status and patient status to target computer systems through the network connections, and when indicated by the determined prosthesis status and patient status, distributes one or more alarms and events to target computer systems through the network connections.

55. The monitoring-session-data collection, analysis, and status-reporting system of embodiment 54 wherein the monitoring-session-data includes:
- a patient identifier;
- a device identifier;
- a timestamp;
- device-configuration data; and
- an ordered set of data.

56. The monitoring-session-data collection, analysis, and status-reporting system of embodiment 55 wherein the ordered set of data comprises one of:
- a time sequence of data vectors, each data vector including numerical values related to linear-accelerations with respect to three coordinate axes of an internal device coordinate system; and
- a time sequence of data vectors, each data vector including numerical values related to linear-accelerations with respect to three coordinate axes of a first internal device coordinate system and including numerical values related to angular velocities, numerical values related to angular velocities relative to the first internal device coordinate system or to a second internal device coordinate system.

57. The monitoring-session-data collection, analysis, and status-reporting system of embodiment 54 wherein the monitoring-session-data-processing component prepares the monitoring-session-data for processing by:
- receiving a time sequence of data vectors, each data vector including three numerical values related to linear-accelerations in the directions of three coordinate axes of a first internal device coordinate system and including three numerical values related to angular velocities about each axis of the first or a second internal device coordinate system;
- when rescaling of the data-vector sequence is needed, rescaling the numerical values of the data vectors;
- when normalization of the data-vector sequence is needed, normalizing the numerical values of the data vectors;
- when transformation of one or more of the numerical values related to linear-acceleration and the numerical values related to angular velocities is needed to relate the numerical values related to linear-acceleration and the numerical values related to angular velocities to a common internal coordinate system, transforming one or more of the numerical values related to linear-acceleration and the numerical values related to angular velocities to relate to the common internal coordinate system; and
- when the time sequence of data vectors needs to be synchronized with respect to a fixed-interval time sequence, synchronizing the data vectors with respect to a fixed-interval time sequence.

58. The monitoring-session-data collection, analysis, and status-reporting system of embodiment 54 wherein the monitoring-session-data-processing component determines component trajectories representing motion modes and additional metric values from the monitoring-session-data by:
- orienting the prepared monitoring-session-data, comprising data vectors, each data vector including three numerical values related to linear-accelerations in the directions of three coordinate axes of an internal device coordinate system and including three numerical values related to angular velocities about each axis of the internal device coordinate system, with respect to a natural coordinate system;
- bandpass filtering the oriented data vectors to obtain a set of data vectors for each of multiple frequencies, including a normal-motion frequency;
- determining, from the data vectors for each of the non-normal-motion frequencies, a spatial amplitude in each of the coordinate-axis directions of the natural coordinate system;
- determining, from a basis trajectory for the patient and the data vectors for the normal-motion frequency, a spatial amplitude in each of the coordinate-axis directions of the natural coordinate system; and
- determining, from the basis trajectory for the patient and the data vectors for the normal-motion frequency, current normal-motion characteristics.

59. The monitoring-session-data collection, analysis, and status-reporting system of embodiment 58 wherein determining, from the data vectors for a frequency, a spatial amplitude in each of the coordinate-axis directions of the natural coordinate system further comprises:
- generating a spatial trajectory from the data vectors;
- projecting the spatial frequency onto each of the coordinate axes; and
- determining the lengths of the protections of the spatial frequency onto each of the coordinate axes.

60. The monitoring-session-data collection, analysis, and status-reporting system of embodiment 54 wherein the monitoring-session-data-analysis component determines a prosthesis status and a patient status from the motion modes and additional metric values by:
- submitting the motion modes and additional metric values to a decision tree that generates a diagnosis-and-suggestions report; and
- packaging the diagnosis-and-suggestions report together with amplitudes generated for the motion modes, metrics generated from a normal-motion-frequency trajectory and a base trajectory, and additional metric values to generate one or both of an output report and output data values that characterize the prosthesis status and the patient status.

61. The monitoring-session-data collection, analysis, and status-reporting system of embodiment 54 wherein the monitoring-session-data-analysis component wherein the one or more alarms and events distributed to target computer systems include:
- an alarm that notifies a medical practitioner or medical facility of the need, by the patient, of immediate assistance or intervention; and
- an event that indicates additional services and/or equipment needed by the patient that may be handled by various external computer systems to automatically provide the additional services and/or equipment to the patient or inform the patient of the additional services and/or equipment and provide the patient with information regarding procurement of the additional services and/or equipment.

62. A method, carried out by a monitoring-session-data collection, analysis, and status-reporting system implemented as a component of one or more computer systems, each computer system having one or more processors, one or more memories, one or more network connections, and access to one or more mass-storage devices, the method comprising:
- receiving monitoring-session-data, including acceleration data generated by sensors within or proximal to a prosthesis attached or implanted within a patient, from an external monitoring-session-data source;

storing the received monitoring-session-data in one or more of the one or more memories and one or more mass-storage devices;

determining a prosthesis status and a patient status from the motion modes and additional metric values, distributing the determined prosthesis status and patient status to target computer systems through the network connections, and when indicated by the determined prosthesis status and patient status, distributing one or more alarms and events to target computer systems through the network connections.

63. The method of embodiment 62 wherein determining a prosthesis status and a patient status from the motion modes and additional metric values further comprises:

preparing the monitoring-session-data for processing, determines component trajectories representing motion modes and additional metric values from the monitoring-session-data;

submitting the motion modes and additional metric values to a decision tree that generates a diagnosis-and-suggestions report; and packaging the diagnosis-and-suggestions report together with amplitudes generated for the motion modes, metrics generated from a normal-motion-frequency trajectory and a base trajectory, and additional metric values to generate one or both of an output report and output data values that characterize the prosthesis status and the patient status.

64. The method of embodiment 62 wherein preparing the monitoring-session-data for processing further comprises receiving a time sequence of data vectors, each data vector including three numerical values related to linear-accelerations in the directions of three coordinate axes of a first internal device coordinate system and including three numerical values related to angular velocities about each axis of the first or a second internal device coordinate system;

when rescaling of the data-vector sequence is needed, rescaling the numerical values of the data vectors;

when normalization of the data-vector sequence is needed, normalizing the numerical values of the data vectors;

when transformation of one or more of the numerical values related to linear-acceleration and the numerical values related to angular velocities is needed to relate the numerical values related to linear-acceleration and the numerical values related to angular velocities to a common internal coordinate system, transforming one or more of the numerical values related to linear-acceleration and the numerical values related to angular velocities to relate to the common internal coordinate system; and when the time sequence of data vectors needs to be synchronized with respect to a fixed-interval time sequence, synchronizing the data vectors with respect to a fixed-interval time sequence.

65. The method of embodiment 62 wherein determining component trajectories representing motion modes and additional metric values from the monitoring-session-data by:

orienting the prepared monitoring-session-data, comprising data vectors, each data vector including three numerical values related to linear-accelerations in the directions of three coordinate axes of an internal device coordinate system and including three numerical values related to angular velocities about each axis of the internal device coordinate system, with respect to a natural coordinate system;

bandpass filtering the oriented data vectors to obtain a set of data vectors for each of multiple frequencies, including a normal-motion frequency;

determining, from the data vectors for each of the non-normal-motion frequencies, a spatial amplitude in each of the coordinate-axis directions of the natural coordinate system;

determining, from a basis trajectory for the patient and the data vectors for the normal-motion frequency, a spatial amplitude in each of the coordinate-axis directions of the natural coordinate system; and determining, from the basis trajectory for the patient and the data vectors for the normal-motion frequency, current normal-motion characteristics.

66. The method of embodiment 54 wherein determining, from the data vectors for a frequency, a spatial amplitude in each of the coordinate-axis directions of the natural coordinate system further comprises:

generating a spatial trajectory from the data vectors;

projecting the spatial frequency onto each of the coordinate axes; and determining the lengths of the protections of the spatial frequency onto each of the coordinate axes.

67. The method of embodiment 54 wherein determining a prosthesis status and a patient status from the motion modes and additional metric values further comprises:

submitting the motion modes and additional metric values to a decision tree that generates a diagnosis-and-suggestions report; and packaging the diagnosis-and-suggestions report together with amplitudes generated for the motion modes, metrics generated from a normal-motion-frequency trajectory and a base trajectory, and additional metric values to generate one or both of an output report and output data values that characterize the prosthesis status and the patient status.

68. The method of embodiment 54 wherein the one or more alarms and events distributed to target computer systems include:

an alarm that notifies a medical practitioner or medical facility of the need, by the patient, of immediate assistance or intervention; and an event that indicates additional services and/or equipment needed by the patient that may be handled by various external computer systems to automatically provide the additional services and/or equipment to the patient or inform the patient of the additional services and/or equipment and provide the patient with information regarding procurement of the additional services and/or equipment.

69. A physical data-storage device encoded with computer instructions that, when executed by one or more processors within one or more computer systems of a monitoring-session-data collection, analysis, and status-reporting system, each computer system having one or more processors, one or more memories, one or more network connections, and access to one or more mass-storage devices, control the monitoring-session-data collection, analysis, and status-reporting system to:

receive monitoring-session-data, including acceleration data generated by sensors within or proximal to a prosthesis attached or implanted within a patient, from an external monitoring-session-data source.

70. A method for determining joint loosening in a patient having an implanted artificial joint, comprising a) analyzing movement of an implanted artificial joint, and b) comparing said movement vs. previous/standardized norms.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the present disclosure are described in terms of Markush groups, it is intended, and those skilled in the art will recognize, that the present disclosure embraces and is also thereby described in terms of any individual member and any subgroup of members of the Markush group, and Applicants reserve the right to revise the application or claims to refer specifically to any individual member or any subgroup of members of the Markush group.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents, i.e., one or more, unless the content and context clearly dictates otherwise. For example, the term "a sensor" refers to one or more sensors, and the term "a medical device comprising a sensor" is a reference to a medical device that includes at least one sensor, where the medical device comprising a sensor may have, for example, 1 sensor, 2 sensors, 3 sensors, 4 sensors, 5 sensors, 6 sensors, 7 sensors, 8 sensors, 9 sensors, 10 sensors, or more than 10 sensors. A plurality of sensors refers to more than one sensor. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Any headings used within this document are only being utilized to expedite its review by the reader, and should not be construed as limiting the disclosure, invention or claims in any manner. Thus, the headings and Abstract of the Disclosure provided herein are for convenience only and do not interpret the scope or meaning of the embodiments.

Where a range of values is provided herein, it is understood that each intervening value, to the tenth of the unit of the lower limit unless the context clearly dictates otherwise, between the upper and lower limit of that range and any other stated or intervening value in that stated range is encompassed within the disclosure, invention or claims. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the present disclosure. The publications discussed above and throughout the text are provided solely for their disclosure prior to the filing date of the present application. Nothing herein is to be construed as an admission that the inventors are not entitled to antedate any referenced publication by virtue of prior invention.

All patents, publications, scientific articles, web sites, and other documents and materials referenced or mentioned herein are indicative of the levels of skill of those skilled in the art to which the disclosure pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Furthermore, the written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

As mentioned above, in the following claims, the terms used should not be construed to limit the claims to the specific embodiments disclosed in the specification and the claims, but should be construed to include all possible embodiments along with the full scope of equivalents to which such claims are entitled. For example, described embodiments with one or more omitted components or steps can be additional embodiments contemplated and covered by this application. Further in example, such additional embodiments can be the flow diagrams 1120 (FIG. 122), 1160 (FIG. 123), and 1190 (FIG. 124) with one or more steps omitted. Similarly, described embodiments with one or more added components or steps can be additional embodiments contemplated and covered by this application. Further in example, such additional embodiments can be the flow diagrams 1120 (FIG. 122), 1160 (FIG. 123), and 1190 (FIG. 124) with one or more steps added. And described embodiments with one or more omitted components or steps and one or more additional components or steps can be additional embodiments contemplated and covered by this application. Further in example, such additional embodiments can be the flow diagrams 1120 (FIG. 122), 1160 (FIG. 123), and 1190 (FIG. 124) with one or more steps omitted and one or more steps added. Accordingly, the claims are not limited by the disclosure.

What is claimed is:

1. A method for identifying a clinical or subclinical condition associated with an implant in a patient, the method comprising:
   a. monitoring a first motion of the implant during a first monitoring session based on a first sensor signal generated by a sensor which is directly coupled to the implant, to provide a first monitoring-session data for the first motion comprising a first motion mode derived from a filtered first sensor signal;
   b. monitoring a second motion of the implant during a second monitoring session based on a second sensor signal generated by the sensor, to provide a second monitoring-session data for the second motion comprising a second motion mode derived from a filtered second sensor signal; and
   c. comparing the first motion mode to the second motion mode, to provide a comparison that is indicative of a clinical or subclinical condition associated with the implant.

2. The method of claim 1 wherein the clinical or subclinical condition is a loosening of the implant, optionally due to periprosthetic lucency or periprosthetic osteolysis.

3. The method of claim 1 wherein the clinical or subclinical condition is a malalignment or a realignment of the implant.

4. The method of claim 1 wherein the clinical or subclinical condition is deformation of the implant.

5. The method of claim 1 wherein the patient is asymptomatic for the condition, and the comparison of the first motion mode and second motion mode indicates that the condition has occurred between the first and second monitoring sessions.

6. The method of claim 1 wherein the patient is asymptomatic for loosening of the implant, and the comparison of the first motion mode and second motion mode indicates that the implant has loosened between the first and second monitoring sessions.

7. The method of claim 1 wherein the patient is asymptomatic for realignment of the implant, and comparison of the first motion mode and second motion mode indicates that the implant has changed alignment between the first and second monitoring sessions.

8. The method of claim 1 wherein the patient is asymptomatic for deformation of the implant, and comparison of the first motion mode and second motion mode indicates that the implant has deformed between the first and second monitoring sessions.

9. The method of claim 1 wherein the implant is an intelligent implant.

10. The method of claim 1 wherein the implant is selected from a knee implant, a hip implant and a shoulder implant.

11. The method of claim 1 wherein the comparison is indicative of a status of the patient.

12. The method of claim 1 wherein the implant has been located within the patient for at least 10 weeks prior to the first monitoring session.

13. The method of claim 1 wherein the implant has changed alignment over a period of at least 2 weeks.

14. The method of claim 1 wherein the implant has loosened over a period of at least two weeks.

15. The method of claim 1 wherein the implant has deformed over a period of at least two weeks.

16. The method of claim 1 further comprising monitoring a plurality of subsequent motions of the implant during a corresponding plurality of subsequent monitoring sessions using the sensor, to provide a corresponding plurality of subsequent monitoring-session-data, wherein the first monitoring session, the second monitoring session, and the plurality of subsequent monitoring sessions occur over a time period, wherein the total number of monitoring sessions over the time period corresponds to a frequency that is related to a telemedicine code for the clinical or subclinical condition.

17. The method of claim 1 further comprising monitoring a plurality of subsequent motions of the implant during a corresponding plurality of subsequent monitoring sessions using the sensor, to provide a corresponding plurality of subsequent monitoring-session-data, wherein the first monitoring session, the second monitoring session, and the plurality of subsequent monitoring sessions occur over a time period, wherein the total number of monitoring sessions over the time period corresponds to a frequency that allows a doctor to qualify for payment under a telemedicine insurance code.

18. The method of claim 1 further comprising monitoring a plurality of subsequent motions of the implant during a corresponding plurality of subsequent monitoring sessions using the sensor, to provide a corresponding plurality of subsequent monitoring-session-data, wherein the first monitoring session, the second monitoring session, and the plurality of subsequent monitoring sessions occur over a time period, wherein the total number of monitoring sessions over the time period corresponds to a frequency that allows a doctor to qualify for full payment under a telemedicine insurance code.

19. The method of claim 1, wherein:
the first motion mode is a first gait-frequency motion mode derived by filtering the first sensor signal to obtain a gait-frequency representation of the first sensor signal; and
the second motion mode is a second gait-frequency motion mode derived by filtering the second sensor signal to obtain a gait-frequency representation of the second sensor signal.

20. The method of claim 19, wherein:
the sensor has a three-dimensional coordinate system;
the first gait-frequency motion mode is based on an amplitude associated with each of the three dimensions of the coordinate system; and
the second gait-frequency motion mode is based on an amplitude associated with each of the three dimensions of the coordinate system.

21. The method of claim 1, wherein:
the first motion mode is a first non-gait-frequency motion mode derived by filtering the first sensor signal to obtain a non-gait-frequency representation of the first sensor signal; and
the second motion mode is a second non-gait-frequency filtered representation of the second sensor signal derived by filtering the second sensor signal to obtain a non-gait-frequency representation of the second sensor signal.

22. The method of claim 21, wherein:
the sensor has a three-dimensional coordinate system;
the first non-gait-frequency motion mode is represented by an amplitude associated with each of the three dimensions of the coordinate system; and
the second non-gait-frequency motion mode is represented by an amplitude associated with each of the three dimensions of the coordinate system.

23. The method of claim 1, wherein:
the first monitoring-session data for the first motion further comprises at least one first discontinuity motion mode based on a detection of a discontinuity in the first sensor signal; and
the second monitoring-session data for the second motion further comprises at least one second discontinuity motion mode based on a detection of a discontinuity in the second sensor signal.

\* \* \* \* \*